US011554042B2

United States Patent
Oberkircher et al.

(10) Patent No.: US 11,554,042 B2
(45) Date of Patent: Jan. 17, 2023

(54) METHOD AND APPARATUS FOR SUBRETINAL ADMINISTRATION OF THERAPEUTIC AGENT

(71) Applicant: Gyroscope Therapeutics Limited, London (GB)

(72) Inventors: Brendan J. Oberkircher, Cincinnati, OH (US); Daniel W. Price, Loveland, OH (US); Michael F. Keane, Downingtown, PA (US); Saeed Sokhanvar, Belmont, MA (US); Daniel J. Yasevac, Somerville, MA (US); Michel G. Bruehwiler, Newton, MA (US); Leah R. Soffer, Somerville, MA (US); Isaac J. Khan, Bridgewater, NJ (US); Benjamin L. Ko, Cincinnati, OH (US); Christopher D. Riemann, Cincinnati, OH (US); Nathan D. Grubbs, West Chester, OH (US)

(73) Assignee: Gyroscope Therapeutics Limited, London (GB)

( * ) Notice: Subject to any disclaimer, the term of this patent is extended or adjusted under 35 U.S.C. 154(b) by 280 days.

(21) Appl. No.: 16/184,212

(22) Filed: Nov. 8, 2018

(65) Prior Publication Data
US 2019/0142634 A1    May 16, 2019

Related U.S. Application Data

(63) Continuation of application No. 14/619,256, filed on Feb. 11, 2015, now Pat. No. 10,226,379.
(Continued)

(51) Int. Cl.
*A61F 9/00* (2006.01)
*A61M 5/158* (2006.01)

(52) U.S. Cl.
CPC .......... *A61F 9/0017* (2013.01); *A61F 9/0008* (2013.01); *A61M 5/158* (2013.01);
(Continued)

(58) Field of Classification Search
CPC ...... A61F 9/0017; A61F 9/0008; A61F 9/007; A61M 25/0068; A61M 25/006007;
(Continued)

(56) References Cited

U.S. PATENT DOCUMENTS

| 5,409,457 A | 4/1995 | del Cerro et al. |
| 5,860,986 A | 1/1999 | Reich et al. |

(Continued)

FOREIGN PATENT DOCUMENTS

| WO | WO 2015/187629 A1 | 12/2015 |
| WO | WO 2017/042584 A1 | 3/2017 |

OTHER PUBLICATIONS

Gallab, et. al, Development of a Spherical Model with a 3D Microchannel: An Application to Glaucoma Surgery, Aug. 30, 2019. Micromachines, 10(5), p. 297. (Year: 2019).*
(Continued)

*Primary Examiner* — Emily L Schmidt
(74) *Attorney, Agent, or Firm* — Frost Brown Todd LLP

(57) ABSTRACT

An apparatus for delivering therapeutic agent to an eye comprises a body, a cannula, a hollow needle, and an actuation assembly. The cannula extends distally from the body and is sized and configured to be insertable between a choroid and a sclera of a patient's eye. The actuation assembly is operable to actuate the needle relative to the cannula to thereby drive a distal portion of the needle along an exit axis that is obliquely oriented relative to the longitudinal axis of the cannula. The cannula may be inserted through a sclerotomy incision to position a distal end of the cannula at a posterior region of the eye, between the choroid
(Continued)

and sclera. The needle may be advanced through the choroid to deliver the therapeutic agent adjacent to the potential space between the neurosensory retina and the retinal pigment epithelium layer, adjacent to the area of geographic atrophy.

20 Claims, 84 Drawing Sheets

Related U.S. Application Data

(60) Provisional application No. 62/104,295, filed on Jan. 16, 2015, provisional application No. 62/049,128, filed on Sep. 11, 2014, provisional application No. 62/049,089, filed on Sep. 11, 2014, provisional application No. 62/049,100, filed on Sep. 11, 2014, provisional application No. 62/049,056, filed on Sep. 11, 2014, provisional application No. 61/938,956, filed on Feb. 12, 2014.

(52) U.S. Cl.
CPC .............. *A61M 2005/1585* (2013.01); *A61M 2210/0612* (2013.01)

(58) Field of Classification Search
CPC ........ A61M 25/071; A61M 2210/0612; A61N 5/1017; A61B 17/0218; A61B 17/0469; A61B 17/3423; A61B 2017/345
See application file for complete search history.

(56) References Cited

U.S. PATENT DOCUMENTS

| | | | |
|---|---|---|---|
| 5,964,740 A | 10/1999 | Ouchi | |
| 6,143,004 A | 11/2000 | Davis et al. | |
| 6,162,197 A | 12/2000 | Mohammad | |
| 6,190,353 B1 | 2/2001 | Makower et al. | |
| 6,283,951 B1* | 9/2001 | Flaherty | A61B 17/11 604/164.11 |
| 6,299,603 B1* | 10/2001 | Hecker | A61F 9/007 604/181 |
| 6,368,315 B1 | 4/2002 | Gillis et al. | |
| 6,413,245 B1 | 7/2002 | Yaacobi et al. | |
| 6,761,724 B1 | 7/2004 | Zrenner et al. | |
| 6,824,532 B2 | 11/2004 | Gillis et al. | |
| 7,189,245 B2 | 3/2007 | Kaplan | |
| 7,207,980 B2 | 4/2007 | Christian et al. | |
| 7,413,734 B2 | 8/2008 | Mistry et al. | |
| 8,197,435 B2 | 6/2012 | Prausnitz et al. | |
| 8,425,473 B2 | 4/2013 | Ho et al. | |
| 8,808,225 B2 | 8/2014 | Prausnitz et al. | |
| 10,226,379 B2 | 3/2019 | Oberkircher et al. | |
| 10,668,258 B1* | 6/2020 | Calhoun | A61M 25/09 |
| 2002/0133184 A1* | 9/2002 | LoRusso | A61M 1/008 606/167 |
| 2002/0143302 A1 | 10/2002 | Hinchliffe et al. | |
| 2004/0039253 A1 | 2/2004 | Peyman et al. | |
| 2004/0138562 A1 | 7/2004 | Makower et al. | |
| 2004/0199130 A1* | 10/2004 | Chornenky | A61K 31/205 604/289 |
| 2005/0143363 A1 | 6/2005 | de Juan et al. | |
| 2005/0266047 A1* | 12/2005 | Tu | A61F 9/0017 424/427 |
| 2006/0025720 A1 | 2/2006 | Sawa et al. | |
| 2006/0047250 A1 | 3/2006 | Hickingbotham et al. | |
| 2006/0293647 A1 | 12/2006 | McRae et al. | |
| 2008/0004596 A1 | 1/2008 | Yun et al. | |
| 2008/0058704 A1 | 3/2008 | Hee et al. | |
| 2008/0161845 A1* | 7/2008 | Murakami | A61B 17/3417 606/185 |
| 2008/0281292 A1 | 11/2008 | Hickingbotham et al. | |
| 2010/0004499 A1 | 1/2010 | Brigatti et al. | |
| 2010/0042118 A1 | 2/2010 | Garrison et al. | |
| 2010/0173866 A1* | 7/2010 | Hee | A61F 9/0017 514/54 |
| 2010/0191176 A1* | 7/2010 | Ho et al. | A61F 9/007 604/22 |
| 2010/0222802 A1* | 9/2010 | Gillespie, Jr. | A61F 2/2481 606/192 |
| 2010/0305514 A1 | 12/2010 | Valenti et al. | |
| 2011/0207987 A1* | 8/2011 | DiCarlo | A61N 5/1017 600/3 |
| 2012/0071832 A1 | 3/2012 | Bunch | |
| 2012/0191064 A1* | 7/2012 | Conston | A61F 9/00727 604/506 |
| 2012/0271272 A1 | 10/2012 | Hammack et al. | |
| 2012/0323220 A1 | 12/2012 | Mackay, II et al. | |
| 2013/0103026 A1 | 4/2013 | Kleshinski et al. | |
| 2013/0211379 A1 | 8/2013 | Clair et al. | |
| 2013/0216623 A1 | 8/2013 | Yamamoto et al. | |
| 2013/0245600 A1 | 9/2013 | Yamamoto et al. | |
| 2013/0253402 A1* | 9/2013 | Badawi | A61F 9/00781 604/8 |
| 2014/0121641 A1 | 5/2014 | Fischell et al. | |
| 2015/0209180 A1 | 7/2015 | Prausnitz et al. | |
| 2015/0223977 A1 | 8/2015 | Oberkircher et al. | |
| 2015/0258120 A1 | 9/2015 | Zarnitsyn | |
| 2015/0351958 A1 | 12/2015 | Contiliano et al. | |
| 2015/0351959 A1 | 12/2015 | Clem et al. | |
| 2016/0074211 A1 | 3/2016 | Ko et al. | |
| 2016/0074212 A1 | 3/2016 | Price et al. | |
| 2016/0074217 A1 | 3/2016 | Price et al. | |
| 2016/0081849 A1 | 3/2016 | Tsai et al. | |
| 2016/0143776 A1* | 5/2016 | Rotenstreich | A61F 9/00836 604/21 |
| 2017/0095369 A1 | 4/2017 | Andino et al. | |
| 2017/0333416 A1 | 11/2017 | Zarnitsyn et al. | |
| 2018/0042765 A1 | 2/2018 | Noronha et al. | |
| 2018/0153579 A1* | 6/2018 | Ueda | A61M 5/32 |
| 2018/0200108 A1* | 7/2018 | Price | A61F 9/00736 |

OTHER PUBLICATIONS

International Search Report and Written Opinion dated Jun. 7, 2017 for International Application No. PCT/US2017/021508, 12 pages.
International Preliminary Report on Patentability dated Sep. 11, 2018 for International Application No. PCT/US2017/021508, 8 pages.
U.S. Appl. No. 62/305,767, filed Mar. 9, 2016.
International Search Report and Written Opinion re Application No. PCT/US2015/015362, dated Aug. 27, 2015.
Chinese Office Action dated Jun. 5, 2018 for Application No. 201580008275.2, 8 pages.
U.S. Appl. No. 61/938,956, filed Feb. 12, 2014.
U.S. Appl. No. 62/049,056, filed Sep. 11, 2014.
U.S. Appl. No. 62/049,089, filed Sep. 11, 2014.
U.S. Appl. No. 62/049,100, filed Sep. 11, 2014.
U.S. Appl. No. 62/049,128, filed Sep. 11, 2014.
U.S. Appl. No. 62/104,295, filed Jan. 16, 2015.
Kang, Se Woong, et al. "A new instrument for drainage or injection of fluid within subretinal space." *Retina* 23.5 (2003): 661-666.
Komaromy, András M., et al. "Application of a new subretinal injection device in the dog." *Cell transplantation* 15.6 (2006): 511-519.
Olsen, Timothy W., et al. "Cannulation of the suprachoroidal space: a novel drug delivery methodology to the posterior segment." *American journal of ophthalmology* 142.5 (2006): 777-787.
Patel, S. R., et al. "Intraocular Pharmacokinetics of Suprachoroidal Drug Delivery Administered Using Hollow Microneedles." *Investigative Ophthalmology & Visual Science* 51.13 (2010): 3796-3796.
Patel, S., et al. "Suprachoroidal Drug Delivery Using Microneedles." *Investigative Ophthalmology & Visual Science* 49.13 (2008): 5006-5006.
Patel, Samirkumar R., et al. "Suprachoroidal drug delivery to the back of the eye using hollow microneedles." *Pharmaceutical research* 28.1 (2011): 166-176.

(56) References Cited

OTHER PUBLICATIONS

Peden, M. C., et al. "Safety Study of Ab-Externo AAV Gene Therapy Delivery to the Subretinal and Suprachoroidal Space Using a 250 Micron Flexible Microcatheter." *Investigative Ophthalmology & Visual Science* 50.13 (2009): 1450-1450.
Schanze, Thomas, et al. "Implantation and testing of subretinal film electrodes in domestic pigs." *Experimental eye research* 82.2 (2006): 332-340.
Soni, M. H., and A. K. Tyagi. "Induction of Choroidal Detachment: A New Surgical Technique for Choroidal Biopsy." *Investigative Ophthalmology & Visual Science* 46.13 (2005): 5438-5438.
Chinese Office Action dated Feb. 14, 2019 for Application No. 201580008275.2, 6 pages.
European Communication dated Mar. 7, 2019 for Application No. 15708368.4, 6 pages.
European Communication dated May 19, 2020 for Application No. 15708368.4, 4 pages.
Japanese Office Action dated Nov. 7, 2018 for Application No. 2016-552291, 3 pages.
Japanese Office Action dated Aug. 11, 2020 for Application No. 2019-111845, 6 pages.
Extended European Search Report dated Mar. 3, 2021, for Application No. 20200019.6, 9 pages.
Chinese Office Action dated Jun. 3, 2021, for Application No. 201911066539.6, 12 pages.
U.S. Appl. No. 17/346,654, entitled "Method and Apparatus for Suprachoroidal Administration of Therapeutic Agent," filed Jun. 14, 2021.
U.S. Pat. Pub. No. 2019/0142635 May 16, 2019 Oberkircher et al.
U.S. Pat. No. 10,226,379 Mar. 12, 2019 Oberkircher et al.

* cited by examiner

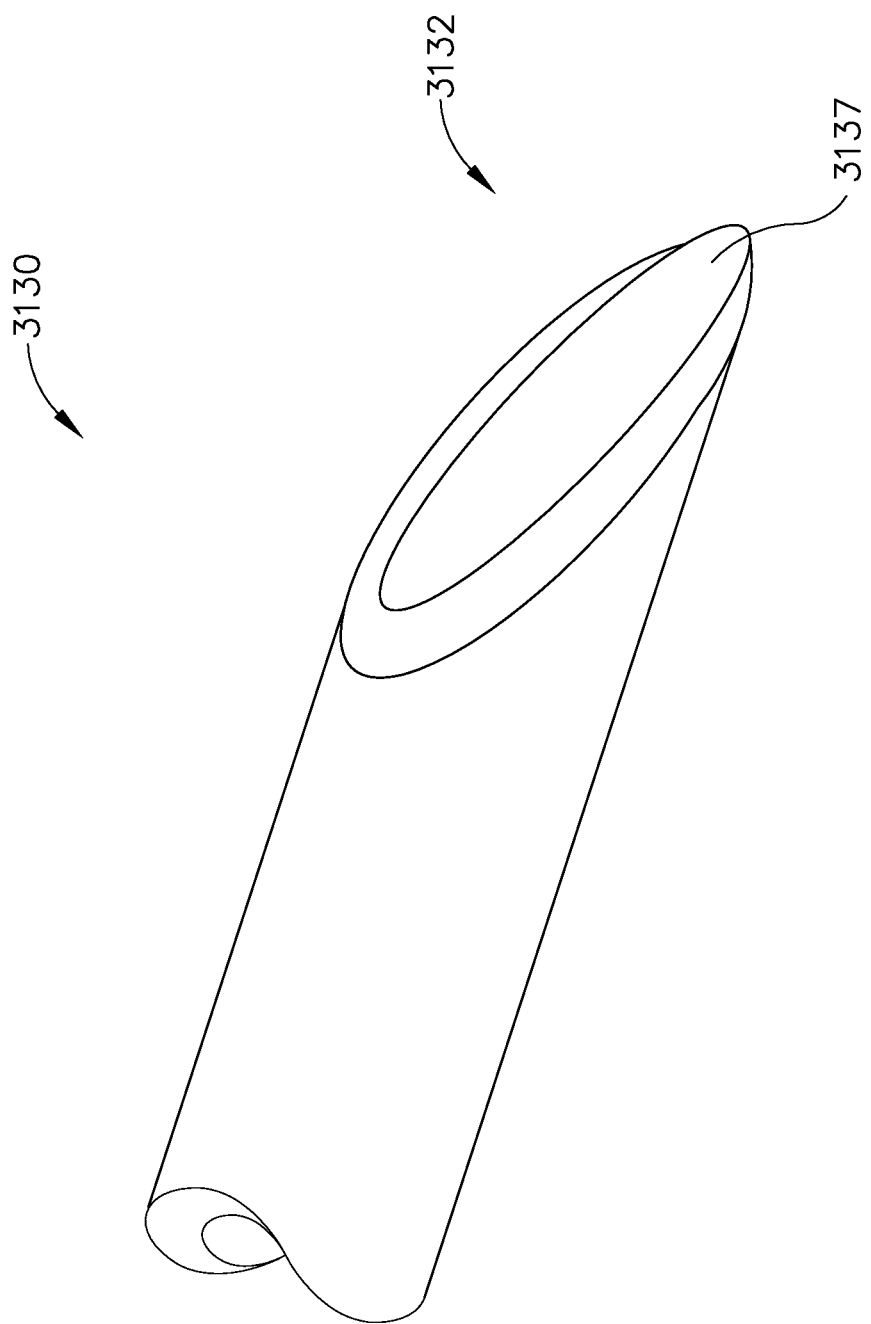

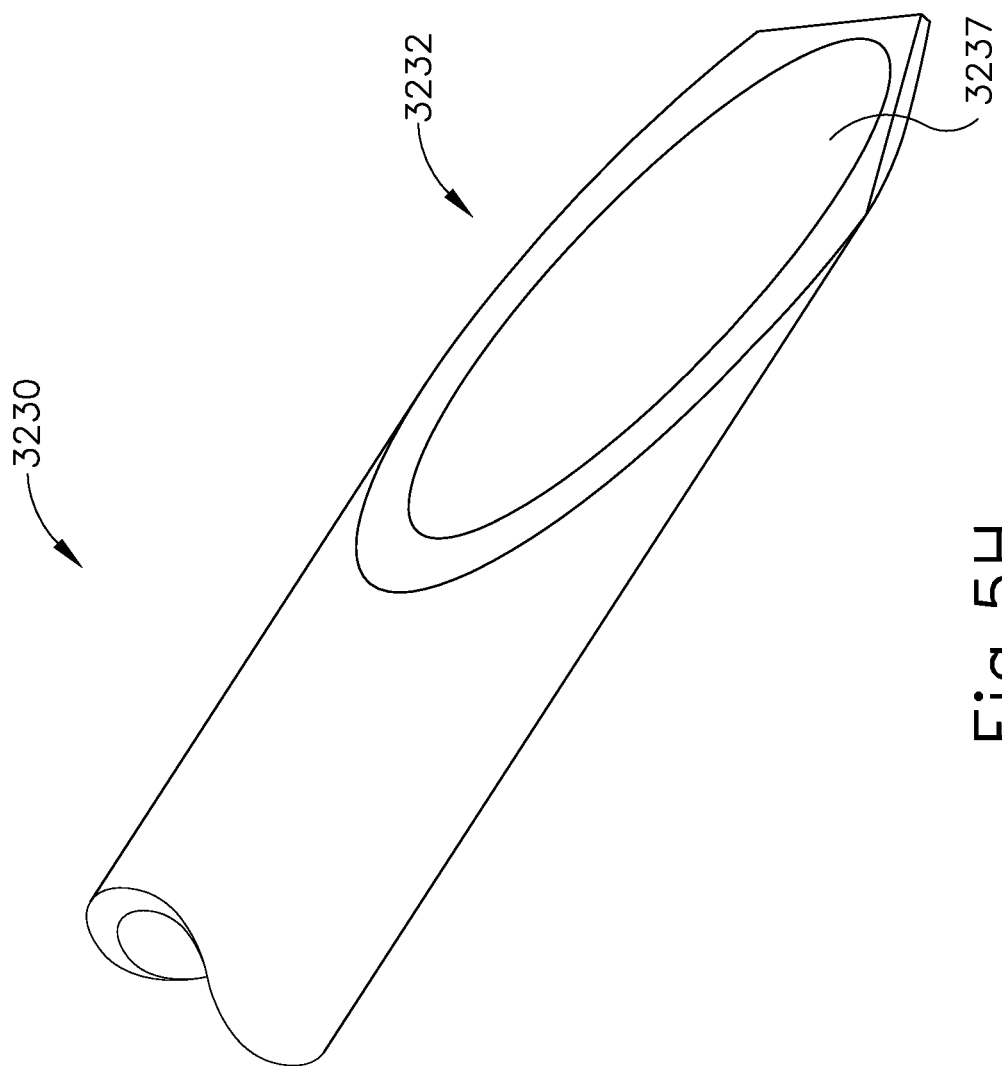

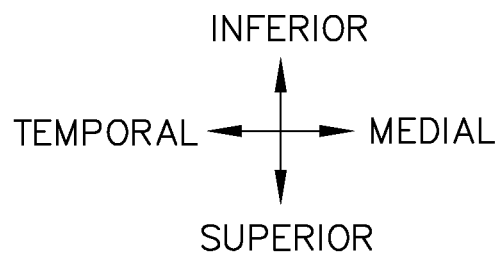
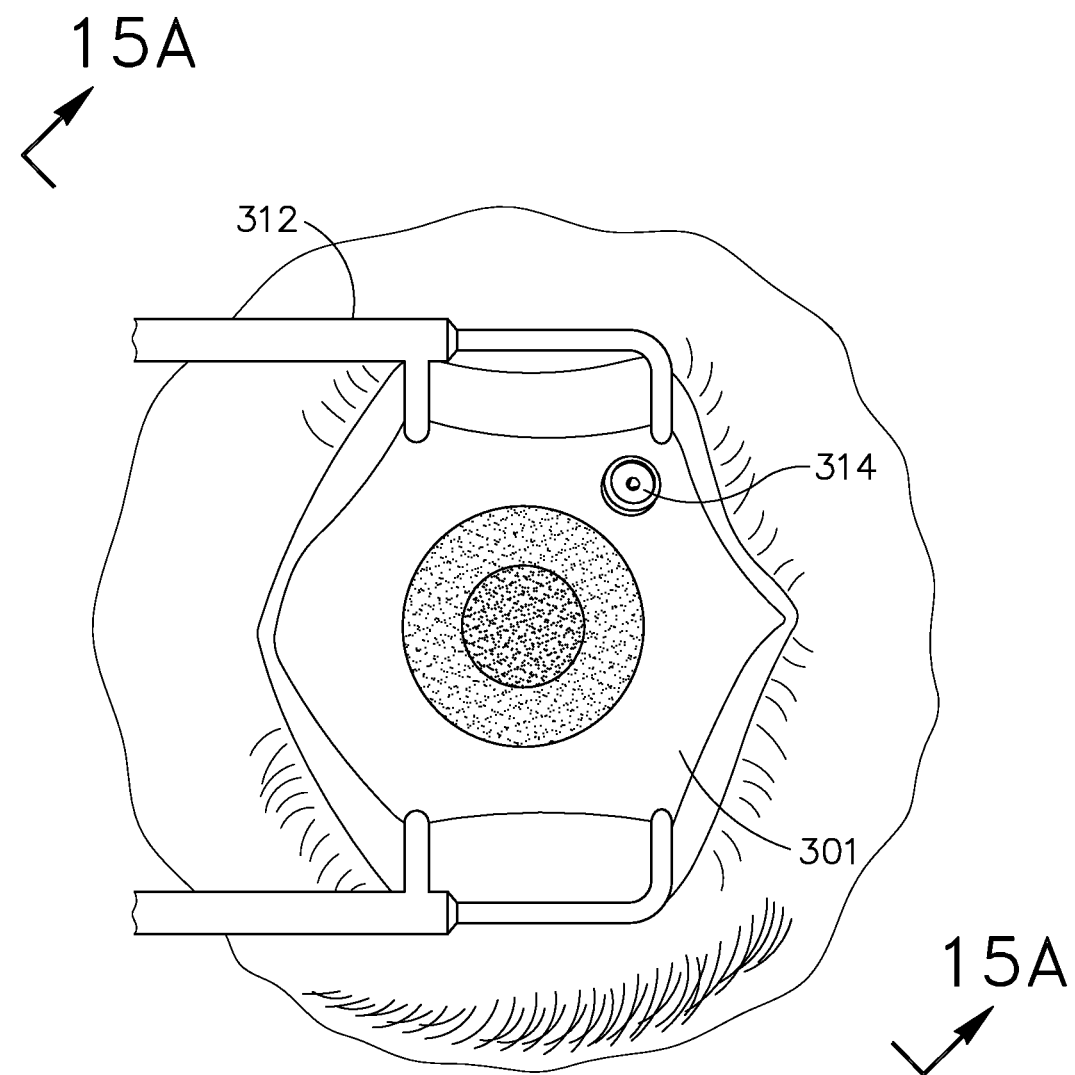
Fig.14A

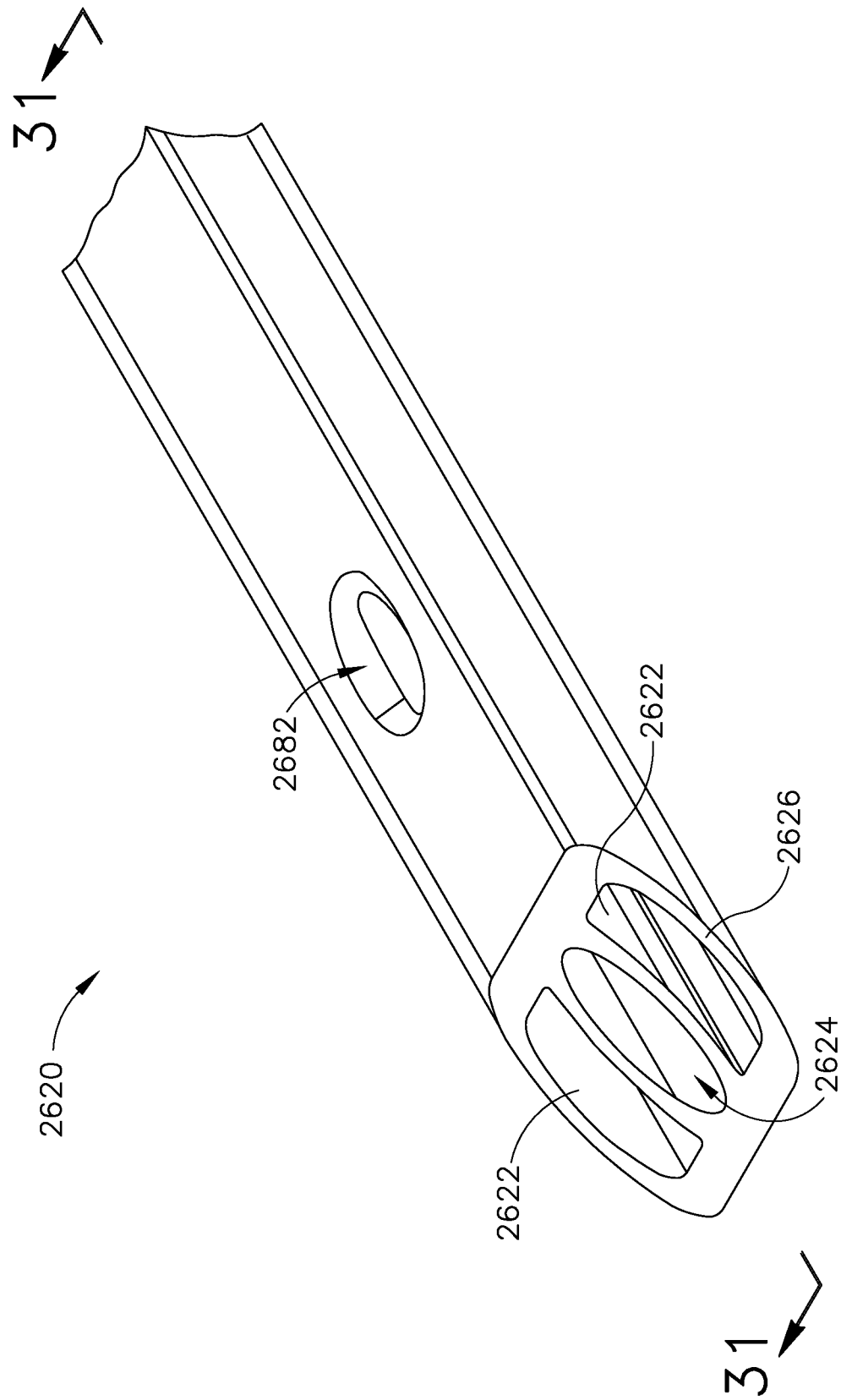

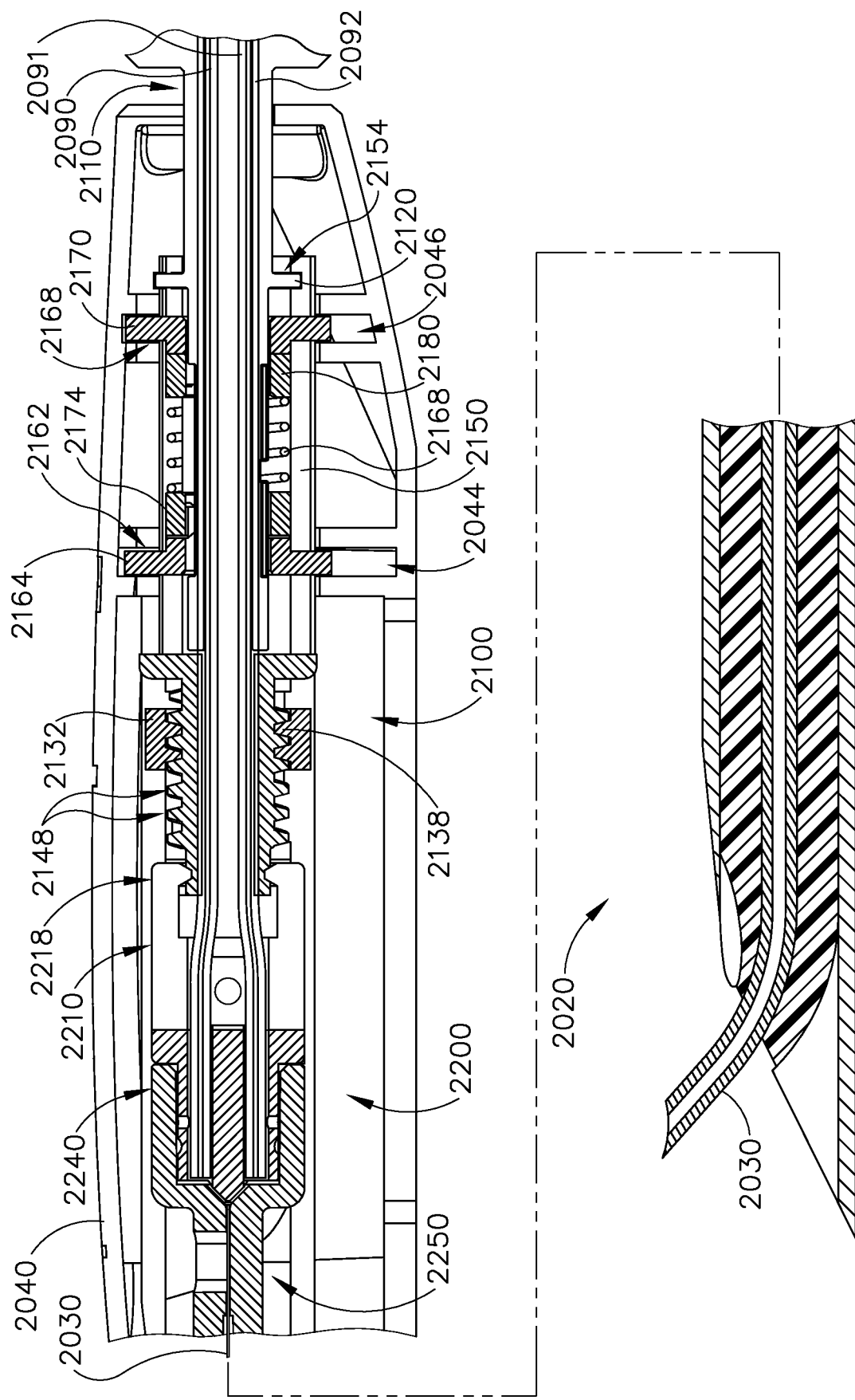

METHOD AND APPARATUS FOR SUBRETINAL ADMINISTRATION OF THERAPEUTIC AGENT

This application is a continuation of U.S. patent application Ser. No. 14/619,256, entitled "Method and Apparatus for Subretinal Administration of Therapeutic Agent," filed Feb. 11, 2015, published as U.S. Pub. No. 2015/0223977 on Aug. 13, 2015.

PRIORITY

U.S. patent application Ser. No. 14/619,256 claims priority to U.S. Provisional Patent Application No. 61/938,956, entitled "Suprachoroidal Approach," filed Feb. 12, 2014, the disclosure of which is incorporated by reference herein.

U.S. patent application Ser. No. 14/619,256 also claims priority to U.S. Provisional Patent Application No. 62/049,056, entitled "Suprachoroidal Injector Design," filed Sep. 11, 2014, the disclosure of which is incorporated by reference herein.

U.S. patent application Ser. No. 14/619,256 also claims priority to U.S. Provisional Patent Application No. 62/049,089, entitled "Suprachoroidal Suture Measurement Template," filed Sep. 11, 2014, the disclosure of which is incorporated by reference herein.

U.S. patent application Ser. No. 14/619,256 also claims priority to U.S. Provisional Patent Application No. 62/049,100, entitled "Suprachoroidal Procedure Method," filed Sep. 11, 2014, the disclosure of which is incorporated by reference herein.

U.S. patent application Ser. No. 14/619,256 also claims priority to U.S. Provisional Patent Application No. 62/049,128, entitled "Suprachoroidal Manual Advance Injector and Third Arm," filed Sep. 11, 2014, the disclosure of which is incorporated by reference herein.

U.S. patent application Ser. No. 14/619,256 also claims priority to U.S. Provisional Patent App. No. 62/104,295, entitled "Method and Apparatus for Suprachoroidal Administration of Therapeutic Agent," filed Jan. 16, 2015, the disclosure of which is incorporated by reference herein.

JOINT RESEARCH STATEMENT

Subject matter disclosed in this application was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties to the joint research agreement include Ethicon Endo-Surgery, Inc. and Janssen Research & Development, LLC.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and in some cases may disappear as well. It may therefore be desirable to provide treatment for macular degeneration in order to prevent or reverse the loss of vision caused by macular degeneration. In some cases it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

SUMMARY OF THE INVENTION

A first embodiment of the invention includes an apparatus for delivering therapeutic agent to an eye. The apparatus comprises a body, a cannula, a hollow needle, and an actuation assembly. The cannula extends distally from the body. The cannula is sized and configured to be insertable between a choroid and a sclera of a patient's eye. The cannula defines a longitudinal axis. The needle is slidable relative to the cannula. The actuation assembly is operable to actuate the needle relative to the cannula to thereby drive a distal portion of the needle along an exit axis that is obliquely oriented relative to the longitudinal axis of the cannula.

In some versions of the first embodiment, the actuation assembly includes an actuation member that is movable relative to the body to actuate the needle.

In some versions of the first embodiment where the actuation member is movable relative to the body to actuate the needle, the actuation member is translatable relative to the body to actuate the needle.

In some versions of the first embodiment where the actuation member is movable relative to the body to actuate the needle, the actuation member is rotatable relative to the body to actuate the needle.

In some versions of the first embodiment where the actuation member is rotatable relative to the body to actuate the needle, the actuation assembly includes a threaded member that is associated with the actuation member. The threaded member is configured to engage a threaded bore in the body to actuate the needle when the actuation member is rotated relative to the body.

In some versions of the first embodiment, the needle includes a sharp distal tip.

In some versions of the first embodiment where the needle includes a sharp distal tip, the sharp distal tip of the needle comprises a first bevel, a second bevel, and a third bevel. The first bevel, second bevel, and third bevel are each oriented obliquely relative to each other.

In some versions of the first embodiment, the exit axis is oriented at an angle between approximately 5° and approximately 30° relative to the longitudinal axis of the cannula.

In some versions of the first embodiment, the exit axis is oriented at an angle between approximately 7° and approximately 9° relative to the longitudinal axis of the cannula.

In some versions of the first embodiment, the needle includes a blunt distal tip.

In some versions of the first embodiment, the cannula includes a beveled distal end. The beveled distal end has a bevel angle, wherein the bevel angle is between approximately 10° and approximately 30°.

In some versions of the first embodiment, the cannula defines a plurality of lumens extending longitudinally through the length of the cannula. At least one lumen of the plurality of lumens is configured to slidably receive the needle.

In some versions of the first embodiment, the cannula has a bending stiffness between $0.7 \times 10^{-6}$ Nm$^2$ and $11.1 \times 10^{-6}$ Nm$^2$.

In some versions of the first embodiment, the cannula has a bending stiffness between $2.0 \times 10^{-6}$ Nm$^2$ and $6.0 \times 10^{-6}$ Nm$^2$.

In some versions of the first embodiment, the apparatus further comprise a valve assembly. The valve assembly is operable to provide a fluid coupling between a fluid source and the needle. The valve assembly is configured to translate with the needle relative to the body.

A second embodiment of the invention includes a method for use of a surgical instrument. The surgical instrument comprises a cannula and a hollow needle that is movable relative to the cannula. The method comprises performing a sclerotomy by forming an incision in the eye of the patient, wherein the incision extends through a sclera layer of the eye to provide access to a suprachoroidal space of the eye. The method further comprises inserting the cannula through the sclerotomy. The method further comprises advancing the cannula between the choroid and the sclera to position the distal end of the cannula at a posterior region of the suprachoroidal space. The method further comprises advancing the needle relative to the cannula and through the choroid and into the subretinal space, without perforating the retina. The method further comprises delivering a therapeutic agent into the subretinal space via the advanced needle.

In some versions of the second embodiment, the method further comprises delivering a leading bleb of fluid via the advanced needle before delivering the therapeutic agent via the advanced needle.

In some versions of the second embodiment, the method further comprises attaching a suture loop to an eye of a patent. The act of attaching the suture loop includes threading a suture through at least a portion of the eye (e.g., the sclera) of the patient to form at least one loop defined by the suture. The act of inserting the cannula comprises passing the cannula through the suture loop.

A third embodiment of the invention includes a method of suprachoroidially administering a therapeutic solution to an eye of a patient. The method comprises threading a suture through at least a portion of the eye (e.g., the sclera) of the patient to form at least one loop defined by the suture. The method further comprises incising at least a portion of the eye (e.g., the sclera) to provide access to the choroid of the eye. The method further comprises guiding a cannula through the at least one loop defined by the suture and into an incision created by incising at least a portion of the eye (e.g., the sclera). The method further comprises advancing a needle through the cannula to penetrate through the choroid and administer the therapeutic solution.

In some versions of the third embodiment, the method further comprises guiding the cannula to an injection site by direct visualization through the pupil.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 5G depicts a detailed perspective view of the distal end of yet another exemplary alternative needle for use with the instrument of FIG. 1;

FIG. 5H depicts a detailed perspective view of the distal end of yet another exemplary alternative needle for use with the instrument of FIG. 1;

FIG. 5I depicts a detailed perspective view of the distal end of yet another exemplary alternative needle for use with the instrument of FIG. 1;

FIG. 14A depicts a top plan view of an eye of a patient, with surrounding structures of the eye immobilized and a chandelier installed;

FIG. 30 depicts a perspective view of the distal end of an exemplary alternative cannula for use with the instrument of FIG. 1;

FIG. 45C depicts a partial, cross-sectional side view of the instrument of FIG. 34, with the cross-section taken along line 35-35 of FIG. 34 and the drive assembly of FIG. 38 in a second partially actuated state;

Figure 1:
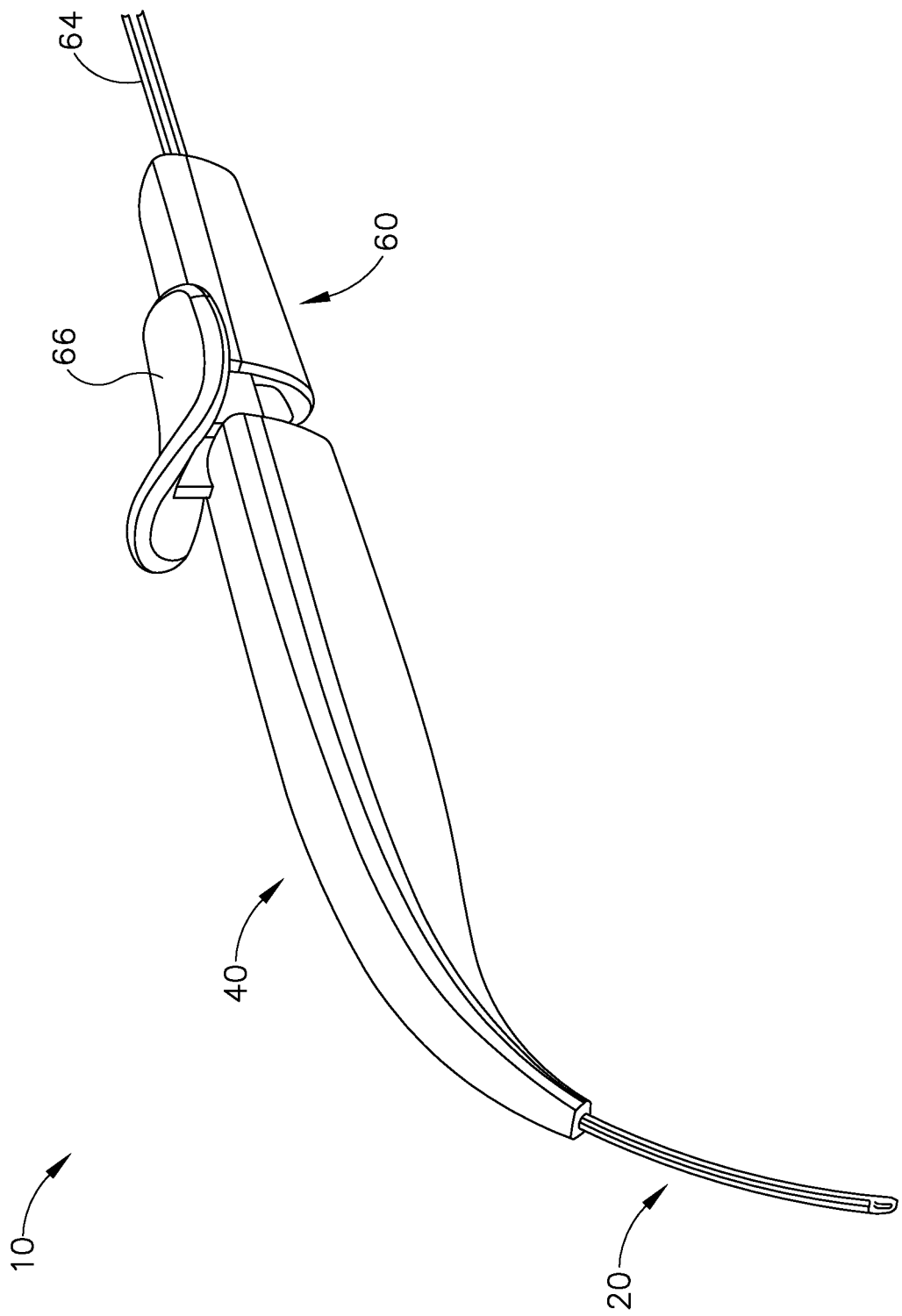
FIG. 1 depicts a perspective view of an exemplary instrument for suprachoroidal administration of a therapeutic agent.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Instrument with Slider Articulation Feature

Figure 2:
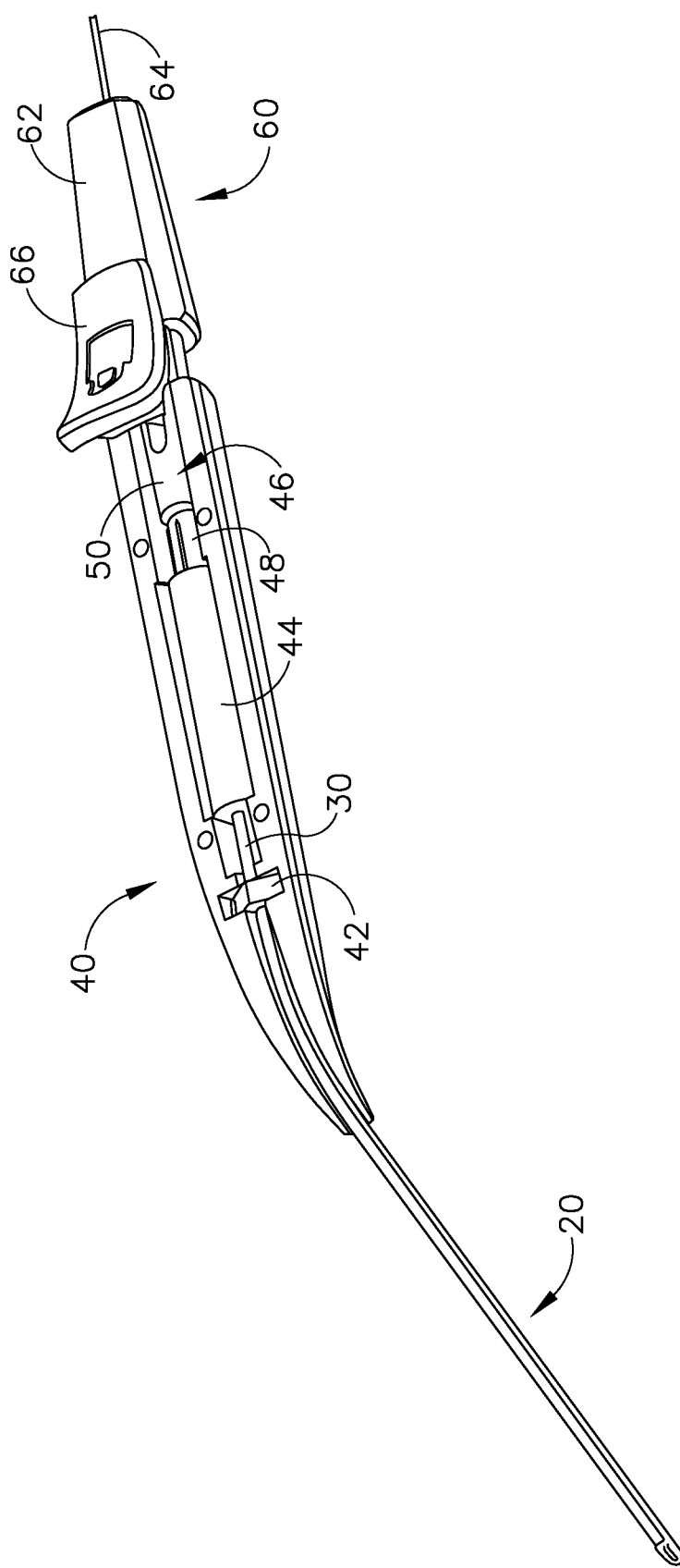
FIG. 2 depicts another perspective view of the instrument of FIG. 1, with a portion of a body removed.

FIGS. 1 and 2 show an exemplary instrument (10) that is configured for use in a procedure for the suprachoroidal administration of a therapeutic agent to an eye of a patient. Instrument (10) comprises a flexible cannula (20), a body (40), and a slidable (60). Cannula (20) extends distally from body (40) and has a generally rectangular cross section. Cannula (20) is generally configured to support a needle (30) that is slidable within cannula (20), as will be described in greater detail below.

In the present example, cannula (20) comprises a flexible material such as Polyether block amide (PEBA), which may be manufactured under the trade name PEBAX. Of course, any other suitable material or combination of materials may be used. Also in the present example, cannula (20) has a cross-sectional profile dimension of approximately 2.0 mm by 0.8 mm, with a length of approximately 80 mm. Alternatively, any other suitable dimensions may be used.

As will be described in greater detail below, cannula (20) is flexible enough to conform to specific structures and contours of the patient's eye, yet cannula (20) has sufficient column strength to permit advancement of cannula (20) between the sclera and choroid of patient's eye without buckling. Several factors may contribute to suitable flexibility of cannula (20). For instance, the durometer of the material used to construct cannula (20) at least partially characterizes the flexibility of cannula (20). By way of example only, the material that is used to form cannula (20) may have a shore hardness of approximately 27D, approximately 33D, approximately 42D, approximately 46D, or any other suitable shore hardness. It should be understood that the shore hardness may fall within the range of approximately 27D to approximately 46D; or more particularly within the range of approximately 33D to approximately 46D; or more particularly within the range of approximately 40D to approximately 45D. The particular cross-sectional shape of cannula (20) may also at least partially characterize the flexibility of cannula (20). Additionally, the stiffness of needle (30) disposed within cannula (20) may at least partially characterize the flexibility of cannula (20).

In the present example, the flexibility of cannula (20) may be quantified by calculating a bending stiffness for cannula (20). Bending stiffness is calculated by the product of the elastic modulus and the area moment of inertia. By way of example only, one exemplary material that may be used to form cannula (20) may have a shore hardness of D27, an elastic modulus (E) of $1.2 \times 10^7$ N/m$^2$, and an area moment of inertia ($I_x$) of $5.52 \times 10^{-14}$ m$^4$, providing a calculated bending stiffness about the x-axis at $0.7 \times 10^{-6}$ Nm$^2$. Another exemplary material that may be used to form cannula (20) may have a shore hardness of D33, an elastic modulus (E) of $2.1 \times 10^7$ N/m$^2$, and an area moment of inertia ($I_x$) of $5.52 \times 10^{-14}$ m$^4$, providing a calculated bending stiffness about the x-axis at $1.2 \times 10^{-6}$ Nm$^2$. Another exemplary material that may be used to form cannula (20) may have a shore hardness of D42, an elastic modulus (E) of $7.7 \times 10^7$ N/m$^2$, and an area moment of inertia ($I_x$) of $5.52 \times 10^{-14}$ m$^4$, providing a calculated bending stiffness about the x-axis at $4.3 \times 10^{-6}$ Nm$^2$. Another exemplary material that may be used to form cannula (20) may have a shore hardness of D46, an elastic modulus (E) of $17.0 \times 10^7$ N/m$^2$, and an area moment of inertia ($I_x$) of $5.52 \times 10^{-14}$ m$^4$, providing a calculated bending stiffness about the x-axis at $9.4 \times 10^{-6}$ Nm$^2$. Thus, by way of example only, the bending stiffness of cannula (20) may fall within the range of approximately $0.7 \times 10^{-6}$ Nm$^2$ to approximately $9.4 \times 10^{-6}$ Nm$^2$; or more particularly within the range of approximately $1.2 \times 10^{-6}$ Nm$^2$ to approximately $9.4 \times 10^{-6}$ Nm$^2$; or more particularly within the range of approximately $2.0 \times 10^{-6}$ Nm$^2$ to approximately $7.5 \times 10^{-6}$ Nm$^2$; or more particularly within the range of approximately $2.0 \times 10^{-6}$ Nm$^2$ to approximately $6.0 \times 10^{-6}$ Nm$^2$; or more particularly within the range of approximately $3.0 \times 10^{-6}$ Nm$^2$ to approximately $5.0 \times 10^{-6}$ Nm$^2$; or more particularly within the range of approximately $4.0 \times 10^{-6}$ Nm$^2$ to approximately $5.0 \times 10^{-6}$ Nm$^2$.

In the present example, the flexibility of cannula (20) may also be quantified by the following formula:

$$\delta = FL^3/48EI \quad (1)$$

In the above equation, bending stiffness (EI) is calculated experimentally by deflecting cannula (20) having a fixed span (L) a set distance to yield a predetermined amount of deflection δ). The amount of force (F) required for such a deflection may then be recorded. For instance, when using such a method cannula (20) may have a span of 0.06 m and may be deflected for a given distance. By way of example only, one exemplary material that may be used to form cannula (20) may require a force of 0.0188 N to achieve a deflection of 0.0155 m, providing a calculated bending stiffness about the x-axis of $5.5 \times 10^{-6}$ Nm$^2$. In another exemplary material that may be used to form cannula (20) may require a force of 0.0205 N to achieve a deflection of 0.0135 m, providing a calculated bending stiffness about the x-axis of $6.8 \times 10^{-6}$ Nm$^2$. In still another exemplary material that may be used to form cannula (20) may require a force of 0.0199 N to achieve a deflection of 0.0099 m, providing a calculated bending stiffness about the x-axis of $9.1 \times 10^{-6}$ Nm$^2$. In yet another exemplary material that may be used to form cannula (20) may require a force of 0.0241 N to achieve a deflection of 0.0061 m, providing a calculated bending stiffness about the x-axis of $1.8 \times 10^{-6}$ Nm$^2$. In yet another exemplary material that may be used to form cannula (20) may require a force of 0.0190 N to achieve a deflection 0.0081 m, providing a calculated bending stiffness about the x-axis of $1.0 \times 10^{-6}$ Nm$^2$. In yet another exemplary material that may be used to form cannula (20) may require a force of 0.0215 N to achieve a deflection of 0.0114 m, providing a calculated bending stiffness about the x-axis of $8.4 \times 10^{-6}$ Nm$^2$. In yet another exemplary material that may be used to form cannula (20) may require a force of 0.0193 N to achieve a deflection of 0.0170 m, providing a calculated bending stiffness about the x-axis of $5.1 \times 10^{-6}$ Nm$^2$. In yet another exemplary material that may be used to form cannula (20) may require a force of 0.0224 N to achieve a deflection of 0.0152 m, providing a calculated bending stiffness about the x-axis of $6.6 \times 10^{-6}$ Nm$^2$. In yet another exemplary material that may be used to form cannula (20) may require a force of 0.0183 N to achieve a deflection of 0.0119 m, providing a calculated bending stiffness about the x-axis of $6.9 \times 10^{-6}$ Nm$^2$. In yet another exemplary material that may be used to form cannula (20) may require a force of 0.0233 N to achieve a deflection of 0.0147 m, providing a calculated bending stiffness about the x-axis of $7.1 \times 10^{-6}$ Nm$^2$. In yet another exemplary material that may be used to form cannula (20) may require a force of 0.0192 N to achieve a deflection of 0.0122, providing a calculated bending stiffness about the x-axis of $7.1 \times 10^{-6}$ Nm$^2$. In yet another exemplary material that may be used to form cannula (20) may require a force of 0.0201 N to achieve a deflection of 0.0201, providing a calculated bending stiffness about the x-axis of $4.5 \times 10^{-6}$ Nm$^2$. Thus, by way of example only, the bending stiffness of cannula (20) may fall within the range of approximately $1.0 \times 10^{-6}$ Nm$^2$ to approximately $9.1 \times 10^{-6}$ Nm$^2$. It should be understood that in other examples, the bending stiffness of cannula may fall within the range of approximately $0.7 \times 10^{-6}$ Nm$^2$ to approximately $11.1 \times 10^{-6}$ Nm$^2$; or more particularly within the range of approximately $2.0 \times 10^{-6}$ Nm$^2$ to approximately $6.0 \times 10^{-6}$ Nm$^2$.

Needle (30) may have a bending stiffness that differs from the bending stiffness of cannula (20). By way of example only, needle (30) may be formed of a nitinol material that has an elastic modulus (E) of $7.9 \times 10^{10}$ N/m$^2$, and an area moment of inertia ($I_x$) of $2.12 \times 10^{-17}$ m$^4$, providing a calculated bending stiffness about the x-axis at $1.7 \times 10^{-6}$ Nm$^2$. By way of further example only, the bending stiffness of needle (30) may fall within the range of approximately $0.5 \times 10^{-6}$ Nm$^2$ to approximately $2.5 \times^{-6}$ Nm$^2$; or more particularly within the range of approximately $0.75 \times 10^{-6}$ Nm$^2$ to approximately $2.0 \times 10^{-6}$ Nm$^2$; or more particularly within the range of approximately $1.25 \times 10^{-6}$ Nm$^2$ to approximately $1.75 \times 10^{-6}$ Nm$^2$.

Figure 3:
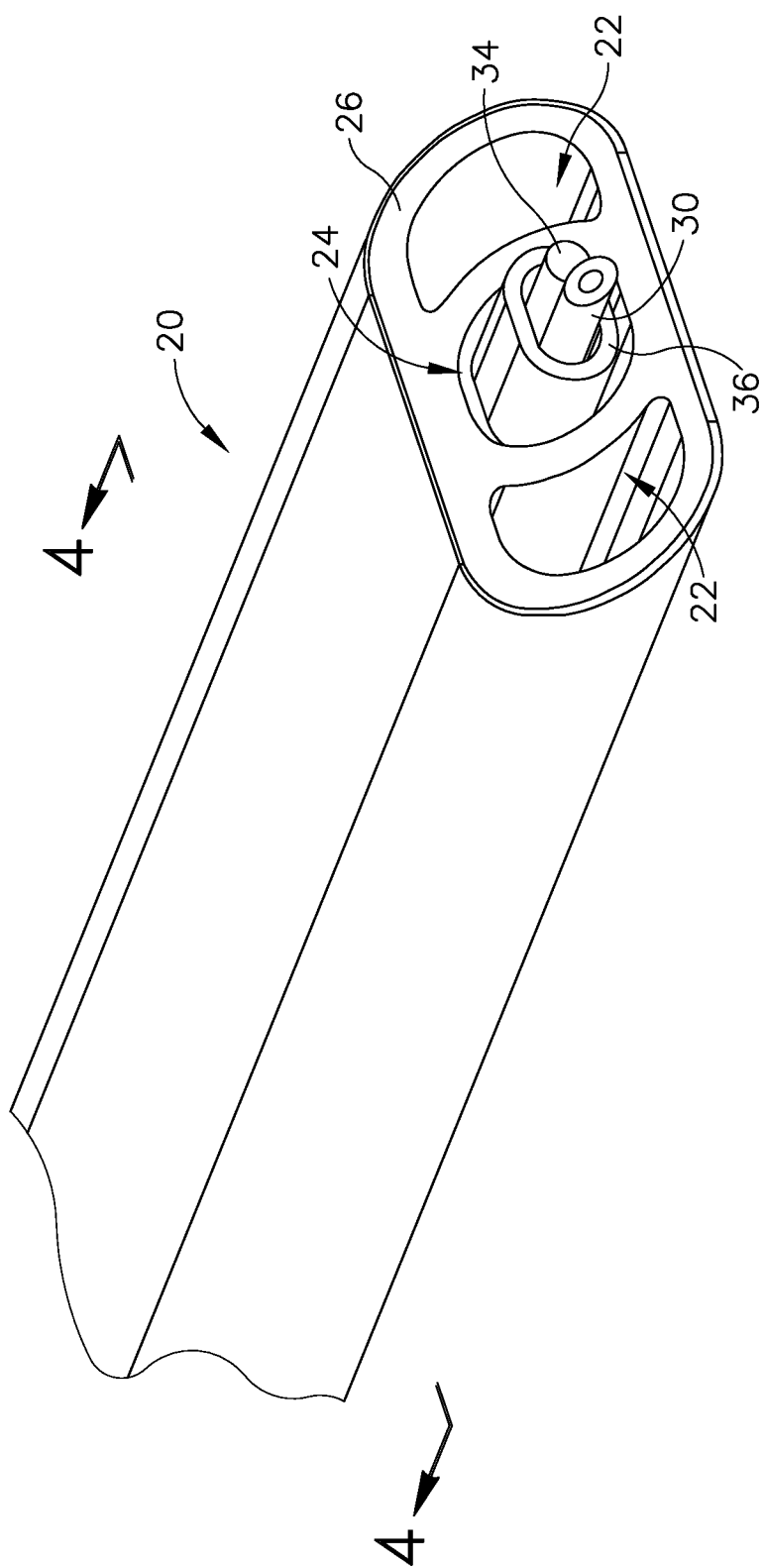
FIG. 3 depicts a detailed view of the distal end of a cannula of the instrument of FIG. 1.
Figure 4:
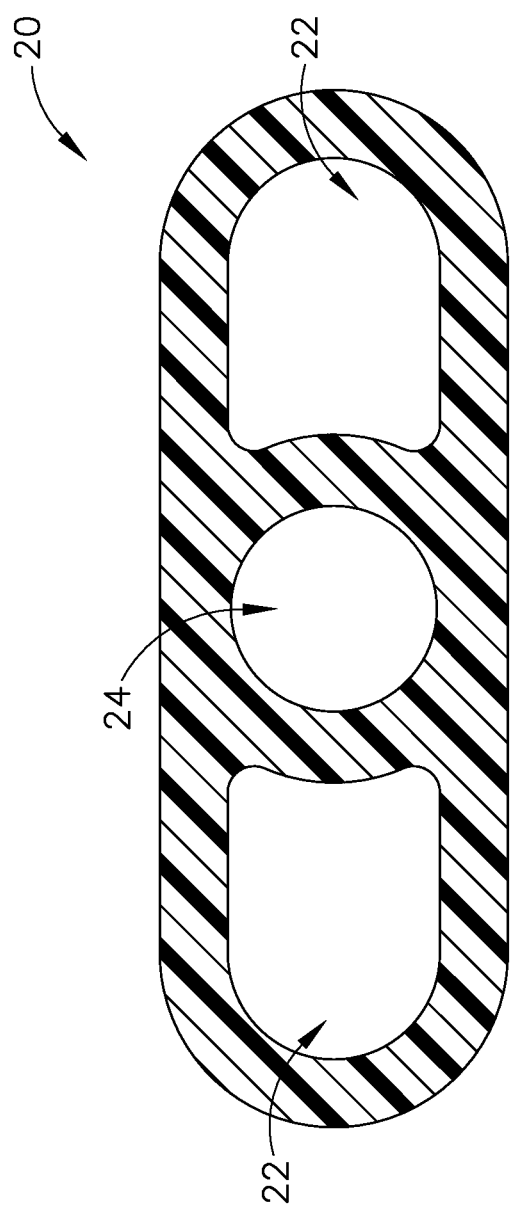
FIG. 4 depicts a cross-sectional view of the cannula of FIG. 3, with the cross-section taken along line 4-4 of FIG. 3.

As can be seen in FIGS. 3 and 4, cannula (20) has a generally rectangular cross-sectional shape and includes a pair of opposing rounded sides and a pair of opposing flat sides adjacent to the rounded sides. In some examples such a rectangular shape may prevent cannula (20) from rotating as it is inserted into a patient's eye. As will be understood, such a feature may be desirable such that needle (30) may exit from cannula (20) in a predictable direction. In other examples, cannula (20) may have any other suitable cross-sectional shape that may generally prevent rotation as will be apparent to those of ordinary skill in the art in view of the teachings herein.

Cannula (20) defines three lumens (22, 24) extending longitudinally through cannula (20) and terminating at a beveled distal end (26). In particular, lumens (22, 24) comprise two side lumens (22) and a single central lumen (24). Side lumens (22) contribute to the flexibility of cannula (20). Although side lumens (22) are shown as being open at beveled distal end (26), it should be understood that in some examples, side lumens (22) may optionally be closed at beveled distal end (26). As will be described in greater detail below, central lumen (24) is configured to receive needle (30) and an optical fiber (34).

Beveled distal end (26) is generally beveled to provide separation between the sclera and choroid layers to enable cannula (20) to be advanced between such layers while not inflicting trauma to the sclera or choroid layers. In the present example, beveled distal end (26) is beveled at an angle of approximately 15° relative to the longitudinal axis of cannula (20) in the present example. In other examples, beveled distal end (26) may have a bevel angle within the range of approximately 5° to approximately 50°; or more particularly within the range of approximately 5° to approximately 40°; or more particularly within the range of approximately 10° to approximately 30°; or more particularly within the range of approximately 10° to approximately 20°.

As described above, needle (30) and optical fiber (34) are disposed within central lumen (24). In particular, needle (30) is slidably disposed within central lumen (24) such that needle (30) may be advanced distally from beveled distal end (26). Optical fiber (34) of the present example is fixedly secured within central lumen (24), although in other examples optical fiber (34) may be slidable relative to beveled distal end (26) similar to needle (30).

Both needle (30) and optical fiber (34) pass through a guide member (36) that is disposed within central lumen (24). Guide member (36) is configured to direct needle (30) as needle (30) is advanced distally relative to beveled distal end (26). In particular, guide member (36) of the present example is configured to direct needle (30) along the longitudinal axis of cannula (20) such that needle (30) is advanced obliquely relative beveled distal end (26). Alternatively, guide member (36) may be configured in other examples to direct needle (30) along a path separate from the longitudinal axis of cannula (20). For instance, guide member (36) of such an example may include a curved channel (not shown) that may impose a curve on needle (30) as it is advanced through guide member (36). Needle (30) may then be advanced along a path that is oriented at an oblique angle relative to the longitudinal axis of cannula (20). By way of example only, guide member (36) may urge needle (30) to exit cannula (20) along a path that is oriented at an angle of approximately 7° to approximately 9° relative to the longitudinal axis of cannula (20). By way of further example only, guide member (36) may urge needle (30) to exit cannula (20) along a path that is oriented at an angle within the range of approximately 5° to approximately 30° relative to the longitudinal axis of cannula (20); or more particularly within the range of approximately 5° to approximately 20° relative to the longitudinal axis of cannula (20); or more particularly within the range of approximately 5° to approximately 10° relative to the longitudinal axis of cannula (20). Although guide member (36) is shown as a separate member relative to cannula (20), it should be understood that in other examples guide member (36) may be integral to cannula (20).

Needle (30) of the present example comprises a nitinol hypodermic needle that is sized to deliver the therapeutic agent while being small enough to create self sealing wounds as needle (30) penetrates tissue structures of the patient's eye, as will be described in greater detail below. By way of example only, needle (30) may be 35 gauge with a 100 μm inner diameter, although other suitable sizes may be used. For instance, the outer diameter of needle (30) may fall within the range of 27 gauge to 45 gauge; or more particularly within the range of 30 gauge to 42 gauge; or more particularly within the range of 32 gauge to 39 gauge. As another merely illustrative example, the inner diameter of needle (30) may fall within the range of approximately 50 μm to approximately 200 μm; or more particularly within the range of approximately 50 μm to approximately 150 μm; or more particularly within the range of approximately 75 μm to approximately 125 μm.

Figure 5A:
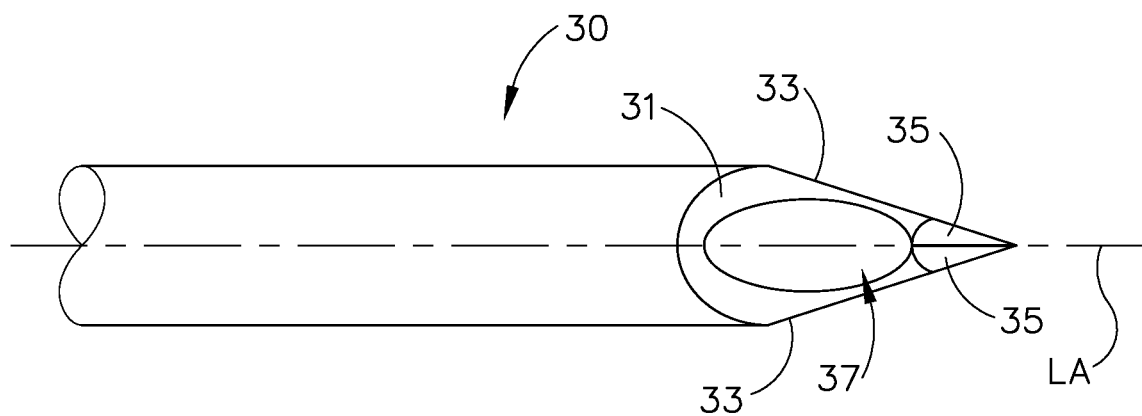
FIG. 5A depicts a detailed perspective view of the distal end of a needle of the instrument of FIG. 1.
Figure 5B:
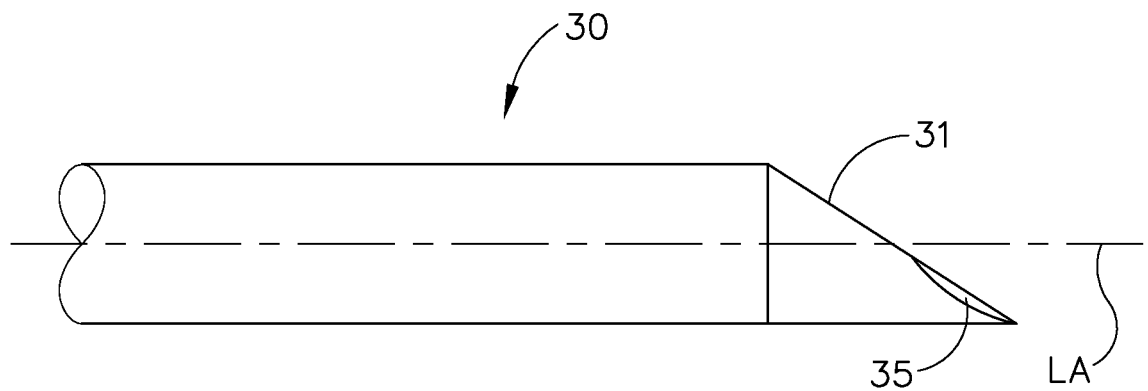
FIG. 5B depicts a detailed elevational view of the distal end of a needle of the instrument of FIG. 1.

As can best be seen in FIGS. 5A and 5B, needle (30) has a sharp distal end. Distal end (32) of the present example is a tri-bevel configuration. In particular, several bevels (31, 33, 35) converge with each other to form the distal end. The distal end (32) is formed by first grinding or laser cutting a first bevel (31) in needle (30), at an oblique angle relative to the longitudinal axis (LA) of needle (30). By way of example only, first bevel (31) may be oriented at an angle of approximately 30° relative to the longitudinal axis (LA) of needle (30). Next a pair of laterally opposing second bevels (33) are ground or laser cut into needle (30) at an oblique angle relative to the longitudinal axis (LA) of needle (30). By way of example only, second bevels (33) may each be oriented at an angle of approximately 35° relative to the longitudinal axis (LA) of needle (30).

Finally, a pair of third bevels (35) are ground or laser cut into needle (30) at an oblique angle relative to first bevel (31) and relative to and second bevels (33). Second bevels (33) and third bevels (35) are cut such that they are cut into a portion of first bevel (31), while leaving at least a portion of first bevel (31) intact. Bevels (31, 33, 35) all converge at the distal end of needle to form a sharp tip. Because needle (30) is a hypodermic needle, bevels (31, 33, 35) intersect with an opening (37) in the distal end of needle (30). As can be seen, opening (37) tapers as bevels (31, 33, 35) intersect with opening (37), thus forming an additional cutting edge to further increase the sharpness of needle (30). Although needle (30) is shown as having a particular number and arrangement of bevels (31, 33, 35), in other examples distal end (32) may include any other suitable number of bevels. For instance, distal end (32) may include a single bevel, two bevels, or more than three bevels. By way of further example only, distal end (32) may include a bevel formed at an angle that falls within the range of approximately 5° and approximately 50°; or more particularly within the range of approximately 15° and approximately 40°; or more particularly within the range of approximately 15° and approximately 30°; or alternatively within the range of approximately 25° and approximately 35°.

Figure 5C:
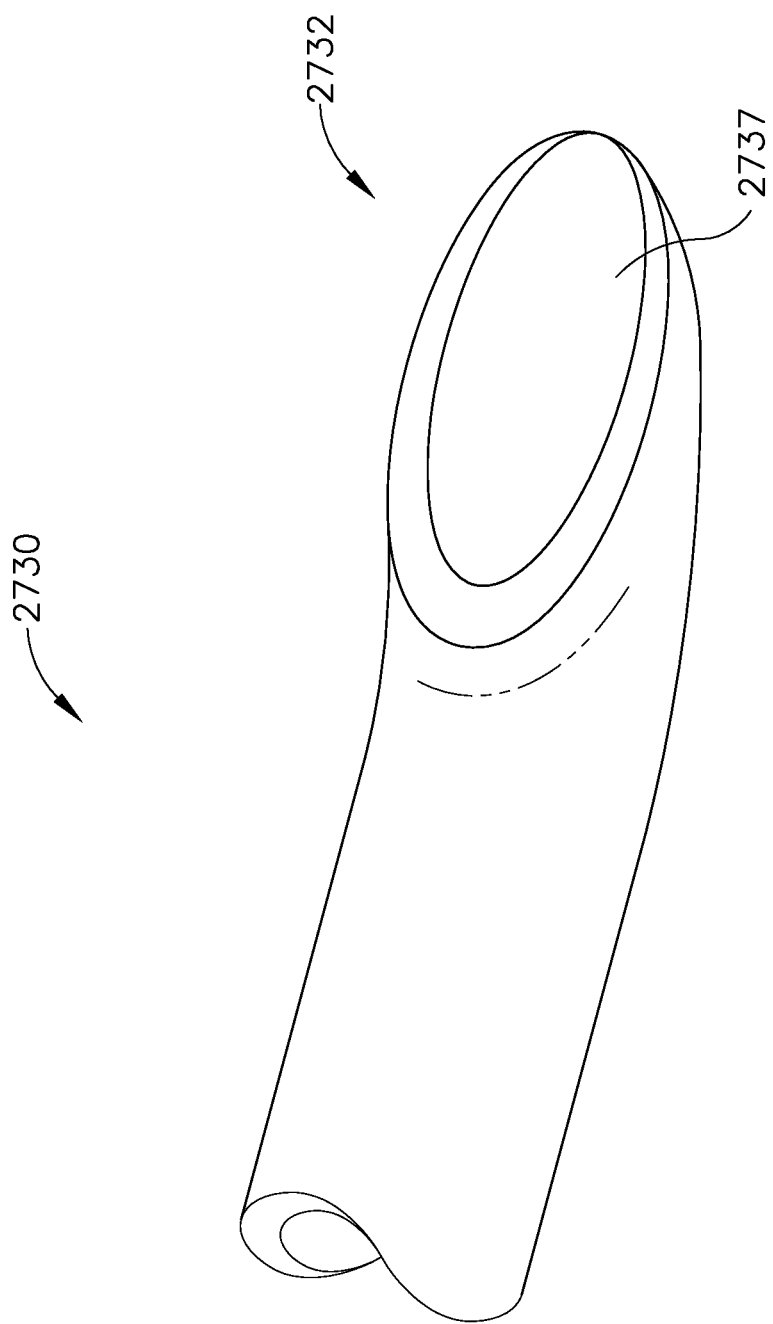
FIG. 5C depicts a detailed perspective view of the distal end of an exemplary alternative needle for use with the instrument of FIG. 1.

FIGS. 5C-5I show several merely exemplary alternative needles (2730, 2830, 2930, 3030, 3130, 3230, 3330, 3430) that may be used with instrument (10) in place of needle (30). As can be seen in FIG. 5C, one merely exemplary alternative needle (2730) may be a Touhy needle (2730).

Needle (2730) includes a sharp distal end (2732), which is slightly curved. Needle (2730) further includes an opening (2737) in distal end (2732). Opening (2737) is cut in needle (2730) at an angle to provide sharpness to distal end (2732).

Figure 5D:
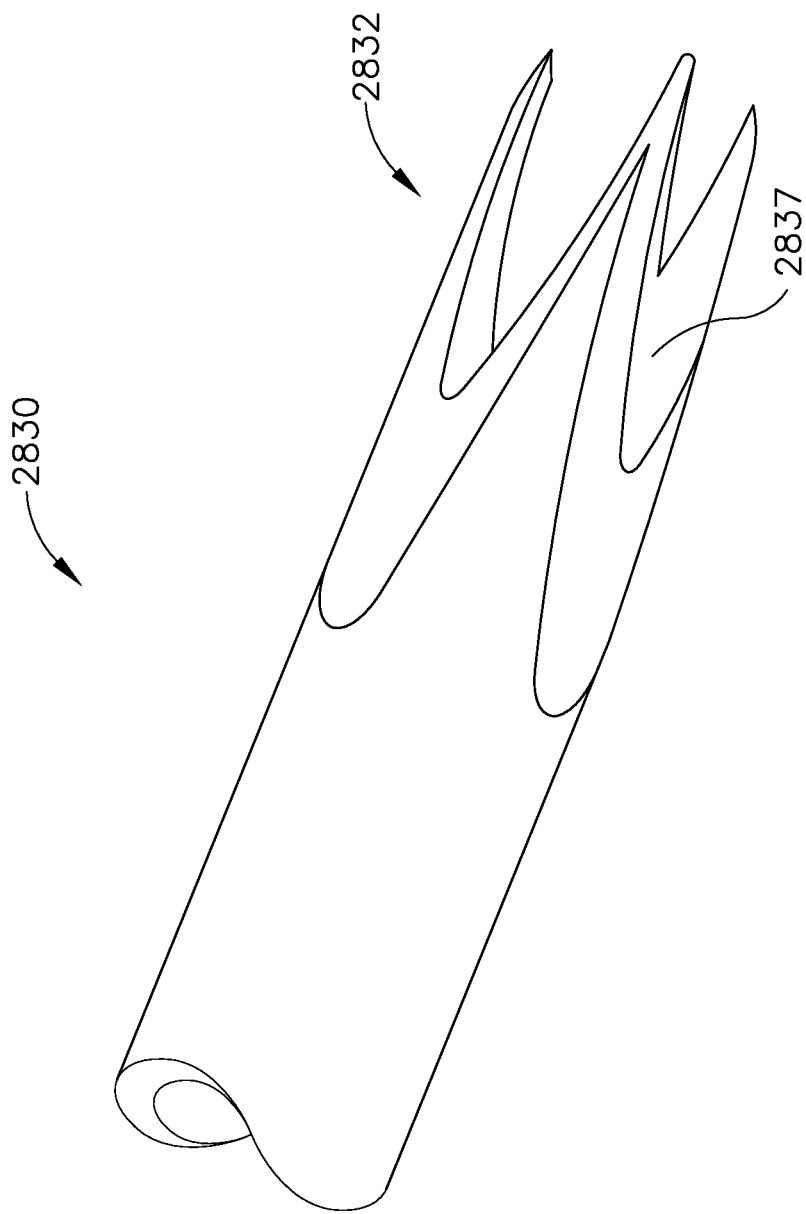
FIG. 5D depicts a detailed perspective view of the distal end of another exemplary alternative needle for use with the instrument of FIG. 1.

FIG. 5D shows another exemplary alternative needle (2830) that may be used with instrument (10) in place of needle (30). Needle (2830) is substantially the same as needle (30) described above, except needle (2830) is a Franseen needle (2830). As can be seen, needle (2830) comprises a sharp distal tip (2832) having four separate sharp points. Each sharp point is oriented relative to the others in a symmetrical pattern. A parabolic beveled region is disposed between each sharp point. The beveled regions together with each sharp point define an opening (2837) for fluid delivery.

Figure 5E:
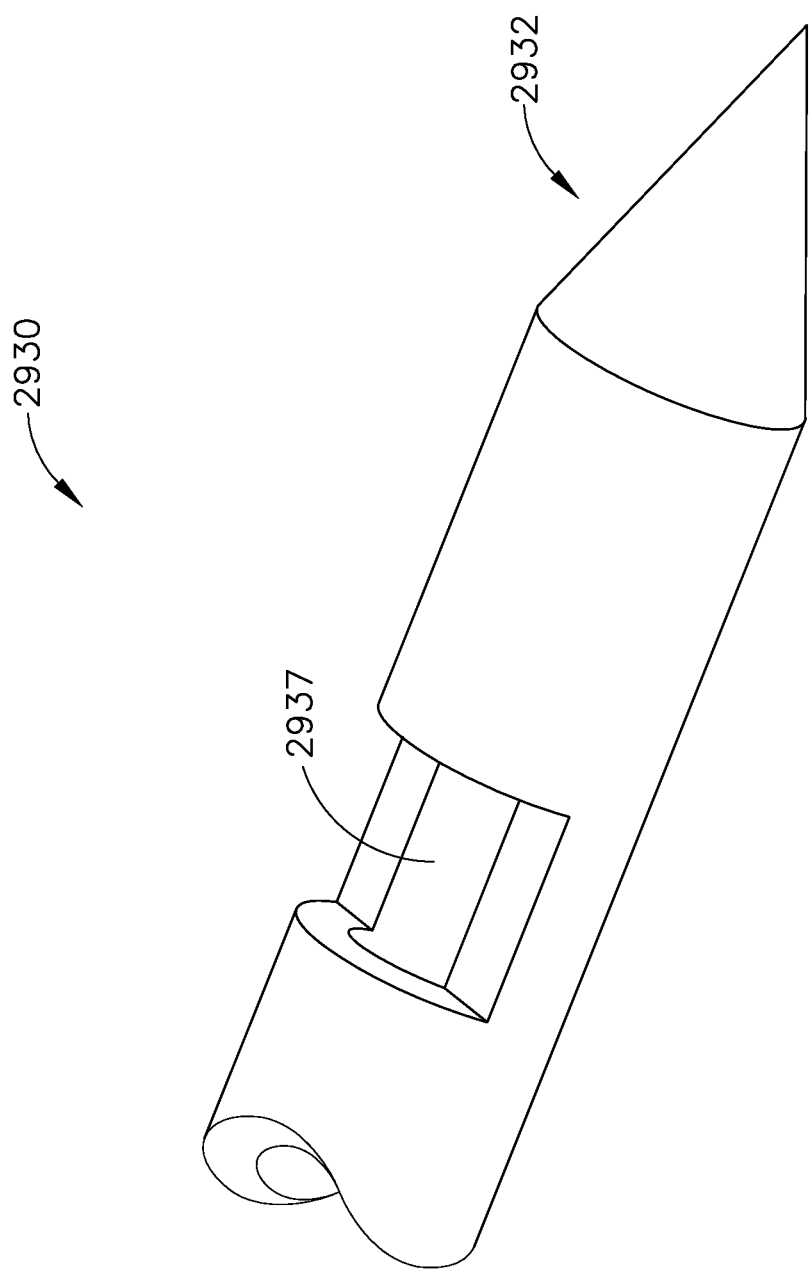
FIG. 5E depicts a detailed perspective view of the distal end of still another exemplary alternative needle for use with the instrument of FIG. 1.

FIG. 5E shows still another alternative needle (2930) that may be used with instrument (10) in place of needle (30). Needle (2930) is substantially the same as needle (30) described above, except needle (2930) is a Whitacre needle (2830). As can be seen, needle (2930) comprises a sharp conical distal tip (2932) with a lateral opening (2937) disposed proximal to distal tip (2937). Distal tip (2932) may be beveled at any suitable angle for piercing tissue, similar to bevel angles described above. Opening (2937) may be any suitable distance proximal to distal tip (2932).

Figure 5F:
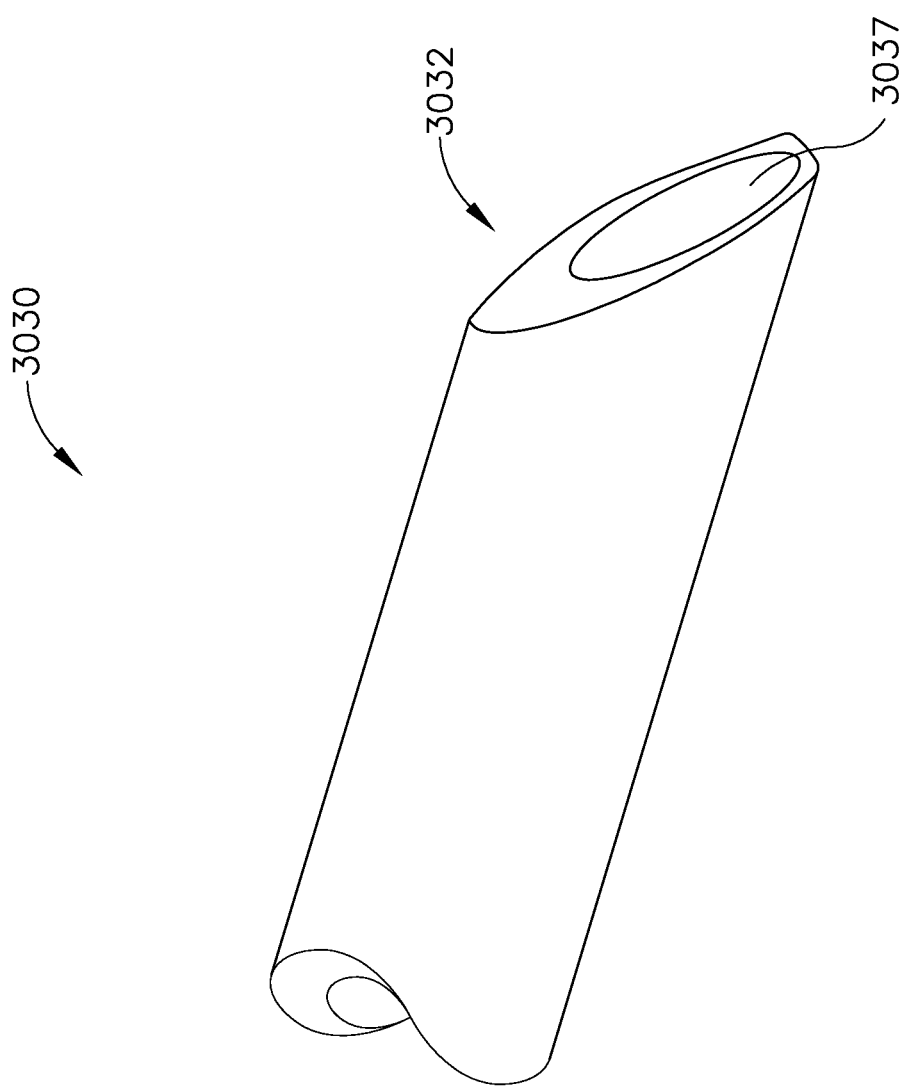
FIG. 5F depicts a detailed perspective view of the distal end of yet another exemplary alternative needle for use with the instrument of FIG. 1.
Figure 51:
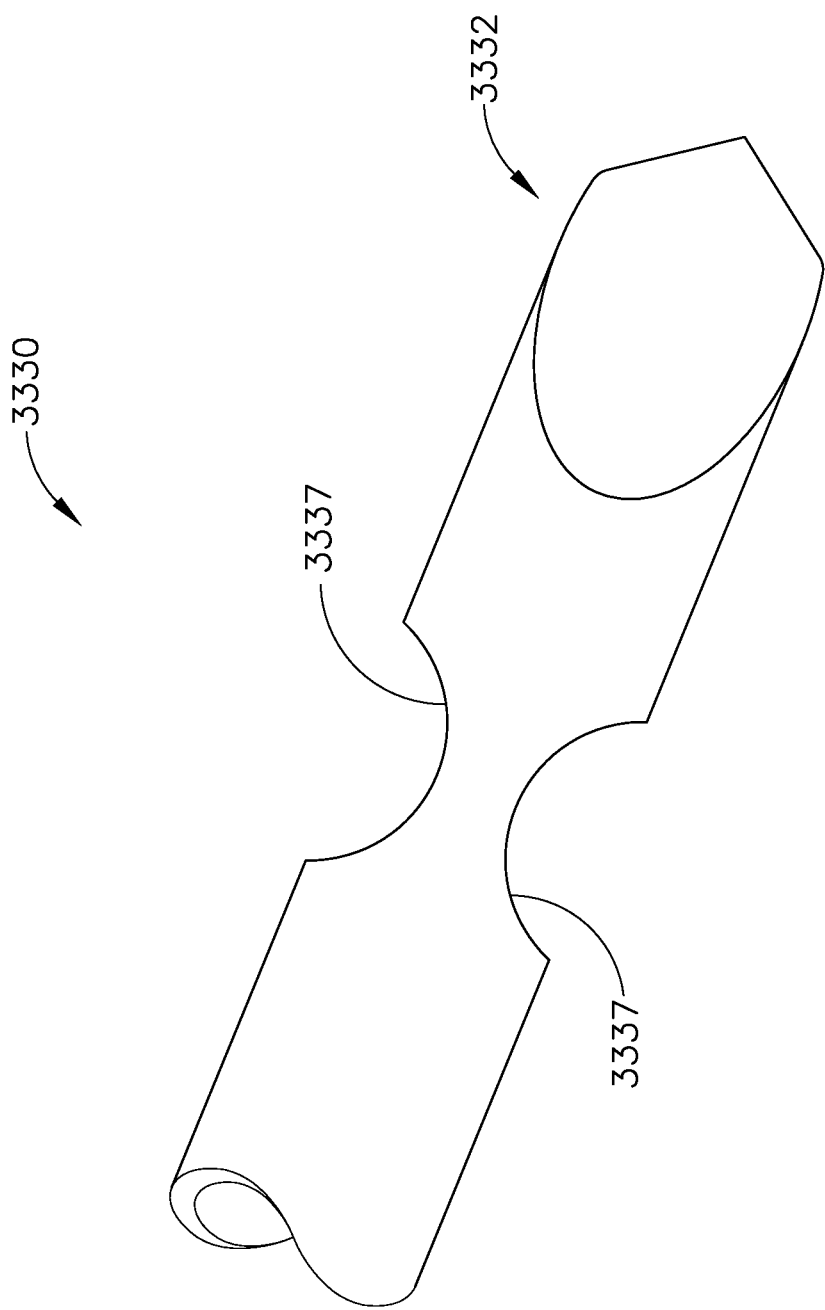

FIG. 5F shows yet another alternative needle (3030) that may be used with instrument (10) in place of needle (30). Needle (3030) is substantially the same as needle (30) described above, except needle (3030) is a Cournand needle (3030). As can be seen, needle (3030) comprises a sharp distal tip (3032) with an opening (3037) defined by a beveled edge. The beveled edge forms two distinct beveled faces—a proximal face and a distal face. Each beveled face has a different bevel angle. For instance, the proximal face is beveled at a generally small angle relative to the longitudinal axis of needle (3030), while the distal face is beveled at a generally large angle relative to the longitudinal axis of needle (3030). It should be understood that the faces may be beveled at any suitable angle as will be apparent to those of ordinary skill in the art in view of the teachings herein.

FIG. 5G shows yet another alternative needle (3130) that may be used with instrument (10) in place of needle (30). Needle (3130) is substantially the same as needle (30) described above, except needle (3130) is a Mengini needle (3130). As can be seen, needle (3130) comprises a sharp distal tip (3132) with an opening (3137) defined by a beveled edge. The beveled edge includes a bevel angle that continuously adjusts from one end of the beveled edge to the other. For instance, the beveled edge initially cuts needle (3130) along a plane that is perpendicular to the longitudinal axis of needle (3130). As the beveled edge extends downwardly, the beveled edge cuts needle (3130) at a plane that is increasingly parallel with the longitudinal axis of needle (3130).

FIG. 5H shows yet another alternative needle (3230) that may be used with instrument (10) in place of needle (30). Needle (3230) is substantially the same as needle (30) described above, except needle (3230) is a back cut bevel needle (3230). As can be seen, needle (3230) comprises a sharp distal tip (3232) with an opening (3237) defined by a top bevel face. Distal tip (3232) also includes two opposing bevel faces on the underside of needle (3230), which intersect with the tip bevel face to thereby form sharp distal tip (3232).

FIG. 5I shows yet another alternative needle (3330) that may be used with instrument (10) in place of needle (30). Needle (3330) is substantially the same as needle (30) described above, except needle (3330) is a Dos Santos needle (3330). As can be seen, needle (3330) comprises a sharp distal tip (3332) with a flat bevel. Needle (3330) further includes two openings (3337) disposed proximal distal tip (3337), which are configured to communicate fluid from needle (3330). The bevel may be beveled at any suitable angle for piercing tissue, similarly to bevel angles described above. Openings (3337) may be any suitable distance proximally from distal tip (3332) as will be apparent to those of ordinary skill in the art in view of the teachings herein.

Optical fiber (34) of the present example is a single fiber optic strand of fused silica with a polyimide cladding. Although optical fiber (34) is described herein as being a single fiber optic strand, it should be understood that in other examples, optical fiber (34) may be comprised of a plurality of fibers. Moreover, optical fiber (34) may be comprised of any suitable material such as sapphire or fluoride glasses, plastics, and/or any other suitable material(s). As will be described in greater detail below, optical fiber (34) is generally configured to illuminate the area immediately in front of needle (30) to assist the positioning of needle (30) and/or cannula (20) within the eye of a patient. It should be understood that optical fiber (34) is merely optional and in other examples optical fiber (34) may simply be omitted.

Referring back to FIGS. 1-2, body (40) is generally shaped as an elongate rectangle with a curved distal end. The particular shape of body (40) that is shown is configured to be grasped by an operator. Alternatively, body (40) may be mounted on a support device or robotic arm for ease of positioning instrument (10), as will be described in greater detail below.

As can best be seen in FIG. 2, an interior of body (40) includes a cannula attachment member (42), a bushing (44), and a needle advancement member (46). Cannula attachment member (42) fixedly secures a proximal end of cannula (20) to body (40), such that cannula (20) cannot rotate or translate relative to body (40). As described above, needle (30) is slidably disposed within cannula (20). A proximal portion of needle (30) extends through body (40), through bushing (44), and terminates within advancement member (46). Bushing (44) is configured to isolate needle (30) from the rest of body (40). In some examples, bushing (44) may be magnetized to permit selective attachment of busing (44) to a support device or any other ferromagnetic surface.

Needle advancement member (46) comprises a bushing engagement portion (48) and a body engagement portion (50). Bushing engagement portion (48) slidably engages with the proximal end of bushing (44) to locate bushing engagement portion (48) relative to bushing (44). Body engagement portion (50) slidably engages with the inside of body (40) to locate advancement member (46) relative to body (40). Body engagement portion (50) further extends through the proximal end of body (40) to attach to actuation assembly (60), as will be described in greater detail below. Body (40) and advancement member (46) may further include one or more sets of complementary features that are configured to prevent advancement member (46) from rotating relative to body (40) yet permit advancement member (46) to translate relative to body (40). Such complementary features may include a key and keyway, pin and slot, hex features, etc.

In the present example, body engagement portion (50) includes a fluid coupling member (not shown) that is disposed within body engagement portion (50). In particular, bushing engagement portion (48) may be hollow or include a lumen such that needle (30) may extend proximally through bushing engagement portion (48) to the fluid coupling member of body engagement portion (50). As will be described in greater detail below, the fluid coupling member of body engagement portion (50) couples needle (30) to a supply tube (64) such that supply tube (64) is in fluid communication with the lumen of needle (30). Additionally, the fluid coupling member of body engagement portion (50) couples needle (30) to body engagement portion (50) such that needle (30) may be advanced through body (40) and cannula (20). By way of example only, the fluid coupling member may comprise a feature that is overmolded about the proximal end of needle, with the feature being secured to body engagement portion via threading, interference fitting, welding, adhesive, etc. Various suitable forms that a fluid coupling member may take will be apparent to those of ordinary skill in the art in view of the teachings herein.

Actuation assembly (60) includes an actuation member (62) and a locking member (66). Actuation member (62) is secured to the proximal end of body engagement portion (50) of advancement member (46). In the present example, actuation member (62) is integral with body engagement portion (50) of advancement member (46), although advancement member (46) and body engagement portion (50) may be coupled by any other suitable means. The shape of actuation member (62) is configured for grasping by an operator. As will be described in greater detail below, actuation member (62) is configured to translate relative to body (40) to actuate advancement member (46) within body (40) to thereby advance needle (30) distally through cannula (20). As will also be described in greater detail below, actuation member (62) may additionally be rotated relative to body (40) in some versions.

In the present example, actuation member (62) includes a lumen (not shown) extending longitudinally though actuation member (62). The lumen of actuation member (62) is configured to receive supply tube (64). In particular, supply tube (64) connects to the fluid coupling member of body engagement portion (50), extends proximally through body engagement portion (50), proximally through actuation member (62), and proximally out through the proximal end of actuation member (62). Thus, supply tube (64) defines a conduit through actuation member (62) to needle (30) such that fluid may be injected via supply tube (64) through needle (30) to an injection site. In the present example, the proximal end of supply tube (64) connects to a fluid source such as a syringe, an automated or semi-automated injector, or any other suitable fluid source. It should be understood that the proximal end of supply tube (64) may include a luer fitting and/or any other suitable kind of fitting to enable supply tube (64) to be releasably coupled with a fluid source.

Locking member (66) is removably attachable to body engagement portion (50), between body (40) and actuation member (62). As will be described in greater detail below, locking member (66) fills a space between body (40) and actuation member (62) to prevent actuation member (62) from being advanced distally relative to body (40). However, locking member (66) can be removed to selectively permit actuation member (62) to be advanced distally relative to body (40).

Figure 6:
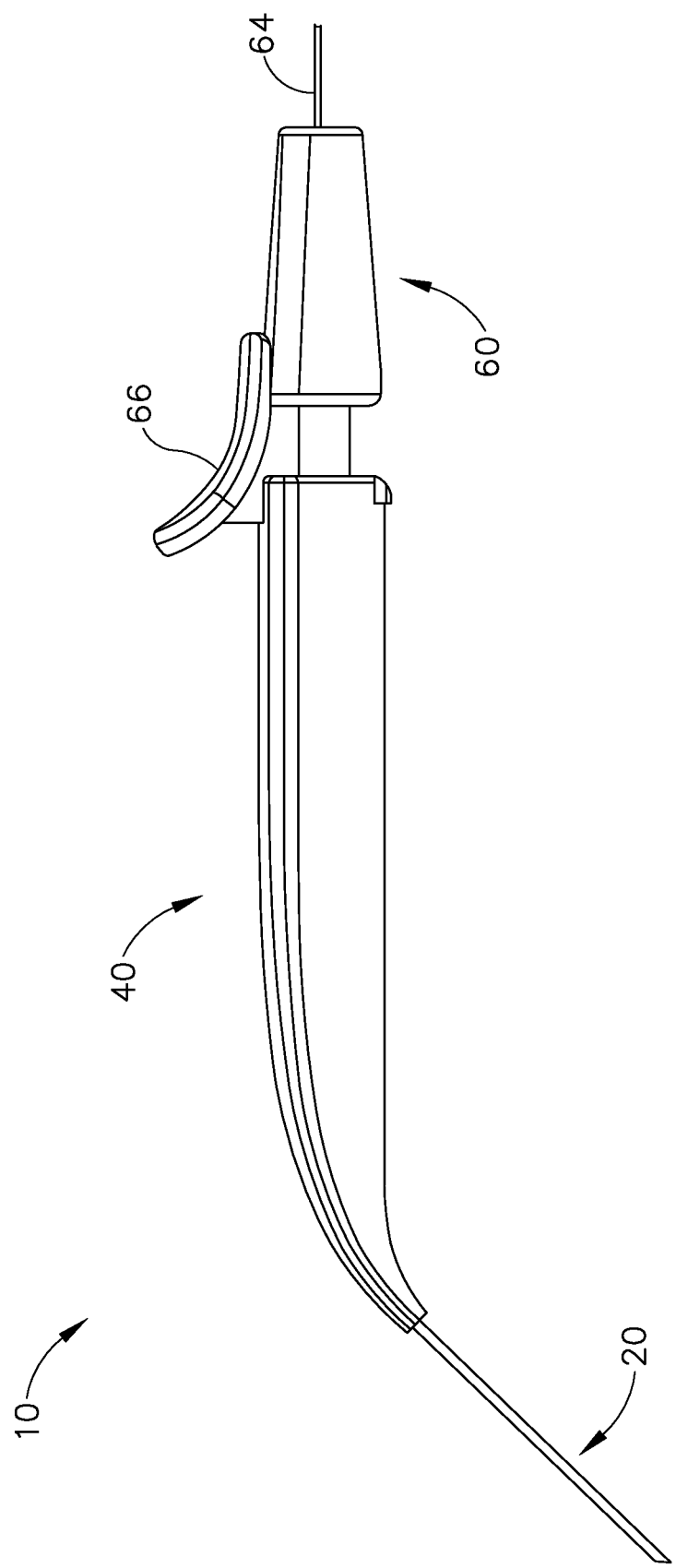
FIG. 6 depicts a side elevational view of the instrument of FIG. 1.
Figure 7:
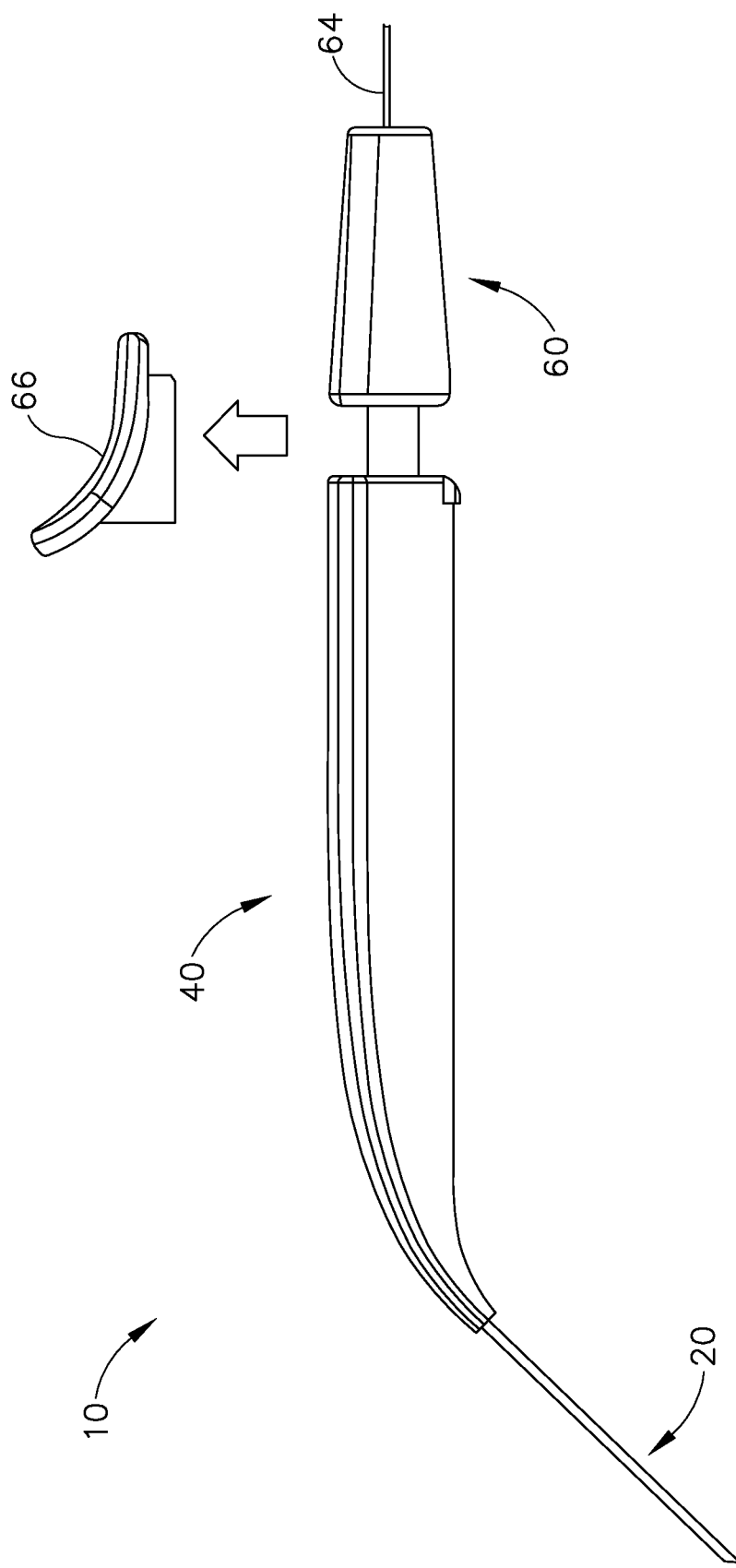
FIG. 7 depicts another side elevational view of the instrument of FIG. 1, with a locking member removed.
Figure 8:
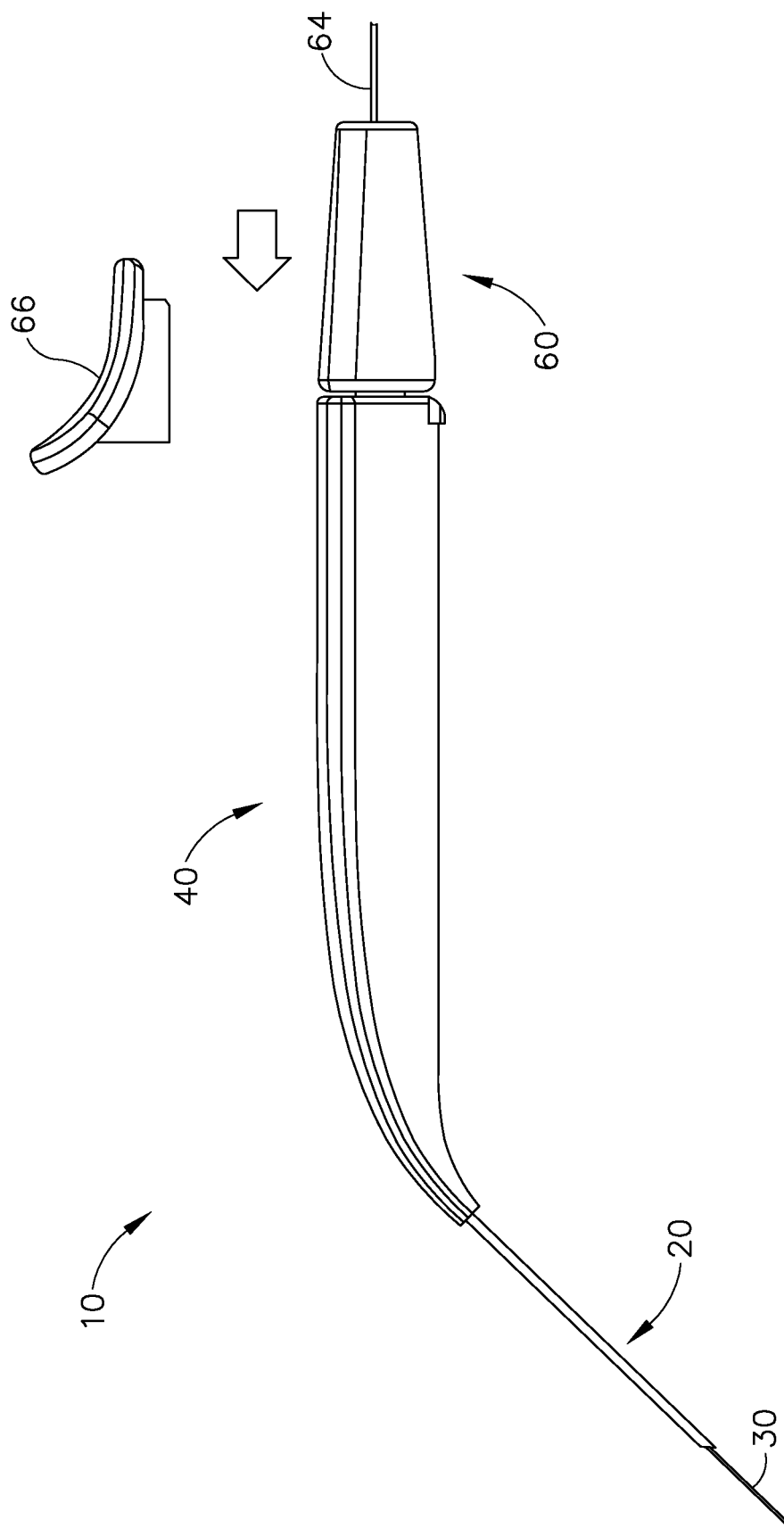
FIG. 8 depicts another side elevational view of the instrument of FIG. 1, with an actuation member advanced distally to extend the needle distally from the cannula.
Figure 9:
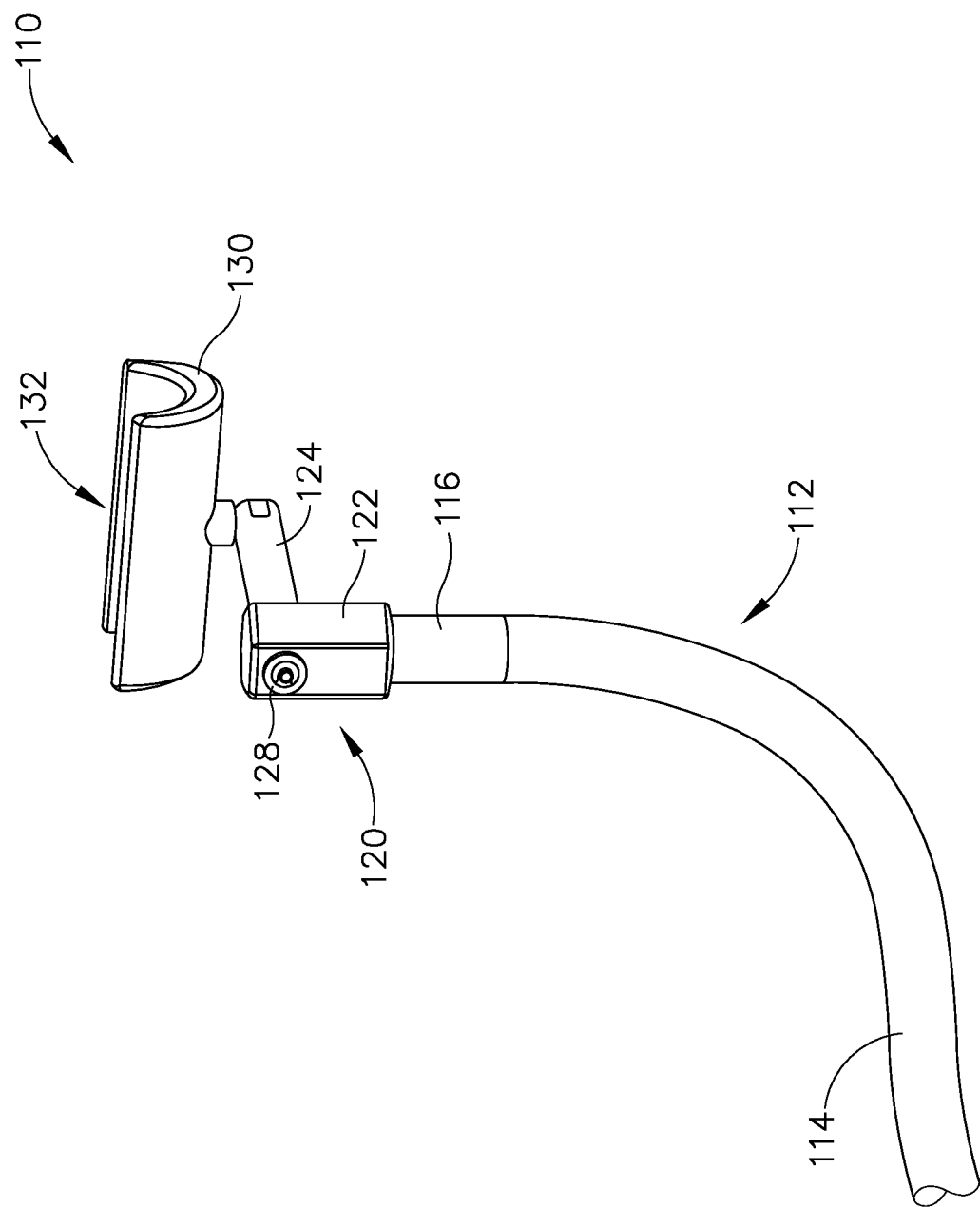
FIG. 9 depicts a perspective view of an exemplary support assembly for use with the instrument of FIG. 1.
Figure 10:
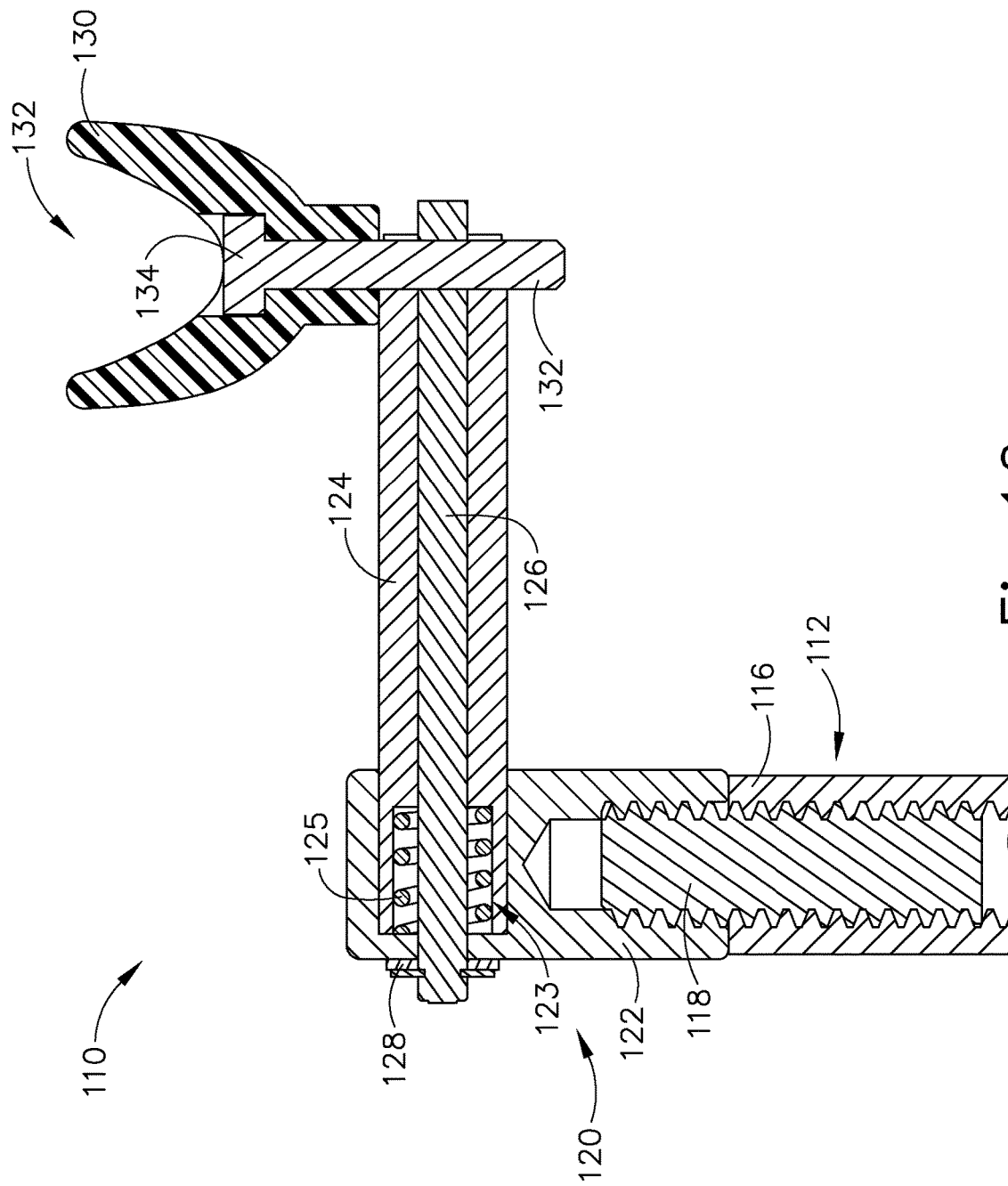
FIG. 10 depicts a cross-sectional view of the support assembly of FIG. 9.

FIGS. 6-8 show an exemplary actuation of instrument (10). In particular, as can be seen in FIG. 6, needle (30) is initially retracted into cannula (20) and locking member (66) is positioned between body (40) and actuation member (62), thereby preventing advancement of actuation member (62). With instrument (10) in this configuration, cannula (20) may be positioned within an eye of a patient as will be described in greater detail below.

Once cannula (20) is positioned within an eye of a patient, an operator may desire to advance needle (30) relative to cannula (20). To advance needle (30), an operator may first remove locking member (66) by pulling locking member (66) away from instrument (10), as can be seen in FIG. 7. Once locking member (66) is removed, actuation member (62) may be moved or translated relative to body (40) to advance needle (30) relative to cannula (20). Actuation member (62) of the present example is only configured to translate needle (30) and not rotate needle (30). In other examples, it may be desirable to rotate needle (30). Accordingly, alternative examples may include features in actuation member (62) to rotate and translate needle (30).

In the present example, advancement of actuation member (62) into contact with body (40) as shown in FIG. 8 corresponds to advancement of needle (30) to a position relative to cannula (20) to a predetermined amount of penetration within an eye of a patient. In other words, instrument (10) is configured such that an operator only has to advance actuation member (62) into contact with body (40) to properly position needle (30) within an eye of a patient. In some examples, the predetermined amount of advancement of needle (30) relative to cannula (20) is between approximately 0.25 mm to approximately 10 mm; or more particularly within the range of approximately 0.1 mm to approximately 10 mm; or more particularly within the range of approximately 2 mm to approximately 6 mm; or more particularly to approximately 4 mm. In other examples, contact between actuation member (62) and body (40) may have no particular significance besides the maximum advancement of needle (30) relative to cannula (20). Instead, instrument (10) may be equipped with certain tactile feedback features to indicate to an operator when needle (30) has been advanced to certain predetermined distances relative to cannula (20). Accordingly, an operator may determine the desired depth of penetration of needle (30) into a patient's eye based on direct visualization of indicia on instrument and/or based on tactile feedback from instrument (10). Of course, such tactile feedback features may be combined with the present example, as will be apparent to those of ordinary skill in the art in view of the teachings herein.

II. Exemplary Support Assembly

FIGS. 9-12 show an exemplary support assembly (110) that may be used to provide structural support for instrument (10) described above. Support assembly (110) is generally configured to provide a selectively movable support surface upon which an operator may removably couple instrument (10). Support assembly (110) comprises a flex arm (112) and a rotation assembly (120). Flex arm (112) is comprised of a generally malleable material such that an operator may bend flex arm (112) as desired to a position that may be maintained by flex arm (112) after the bending force is removed. By way of example only, flex arm (112) may comprise a solid malleable tube such as a malleable plastic or metal rod. In other examples, flex arm (112) may be comprised of a hollow coil of metal or plastic. Of course, flex arm (112) may be comprised of any other suitable material or may have any other suitable configuration as will be apparent to those of ordinary skill in the art in view of the teachings herein.

Regardless of the particular construction of flex arm (112), flex arm (112) comprises a bottom end (114) and a top end (116). Although not shown, it should be understood that in some examples bottom end (114) may include a clamp, bracket, or other attachment feature that may permit support assembly (110) to be attached to a surgical table or other structures used in surgical procedures. By way of example only, bottom end (114) may include one or more features that are configured to selectively secure bottom end (114) to a conventional wrist rest that is used for ophthalmic surgery.

Top end (116) is fixedly secured to rotation assembly (120). As can best be seen in FIG. 10, top end (116) of flex arm (112) is fixedly secured to rotation assembly (120) by a threaded stud (118). In particular, threaded stud (118) engages threads cut into the inner diameters of a base (122) of rotation assembly (120) and top end (116) of flex arm (112). In the present example, base (122) is configured to rotate relative to flex arm (112) and threaded stud (118). Alternatively, base (122) may merely be fastened to flex arm (112) without the capacity to rotate relative to flex arm (112). Base (122) is configured to receive a clamping sleeve (124) and tie rod (126). In particular, clamping sleeve (124) is configured to receive tie rod (126) to generally permit clamping sleeve (124) to maintain an orthogonal position relative to top end (116) of flex arm (112), yet also permit clamping sleeve (124) to rotate about the longitudinal axis of clamping sleeve (124). As can be seen, clamping sleeve (124) includes a bore (123) that is configured to receive a spring (125). Spring (125) generates a compressive force between a washer (128) and a bore (not shown) on opposing ends of tie rod (126) by forcing clamping sleeve (124) away from base (122), as will be described in greater detail below.

Rotation assembly (120) further includes a cradle (130) that is supported by a dowel (132). Dowel (132) extends through bores (not shown) in clamping sleeve (124) and tie rod (126). Tie rod (126) together with spring (125) places clamping sleeve (124) and dowel (132) in compression. This compressive force is strong enough to generally maintain the position of compression sleeve (124) and dowel (132), yet weak enough to permit compression sleeve (124) and/or dowel (132) to rotate when acted upon by an operator. Cradle (130) includes an indentation (132) that is configured to receive instrument (10) described above. Additionally, cradle (130) includes a magnet (134) embedded in cradle (130) adjacent to indentation (132). In examples of instrument (10) that are equipped with a magnetic bushing similar to busing (44) described above, magnet (134) may function to removably couple instrument (10) to cradle (130).

Figure 11:
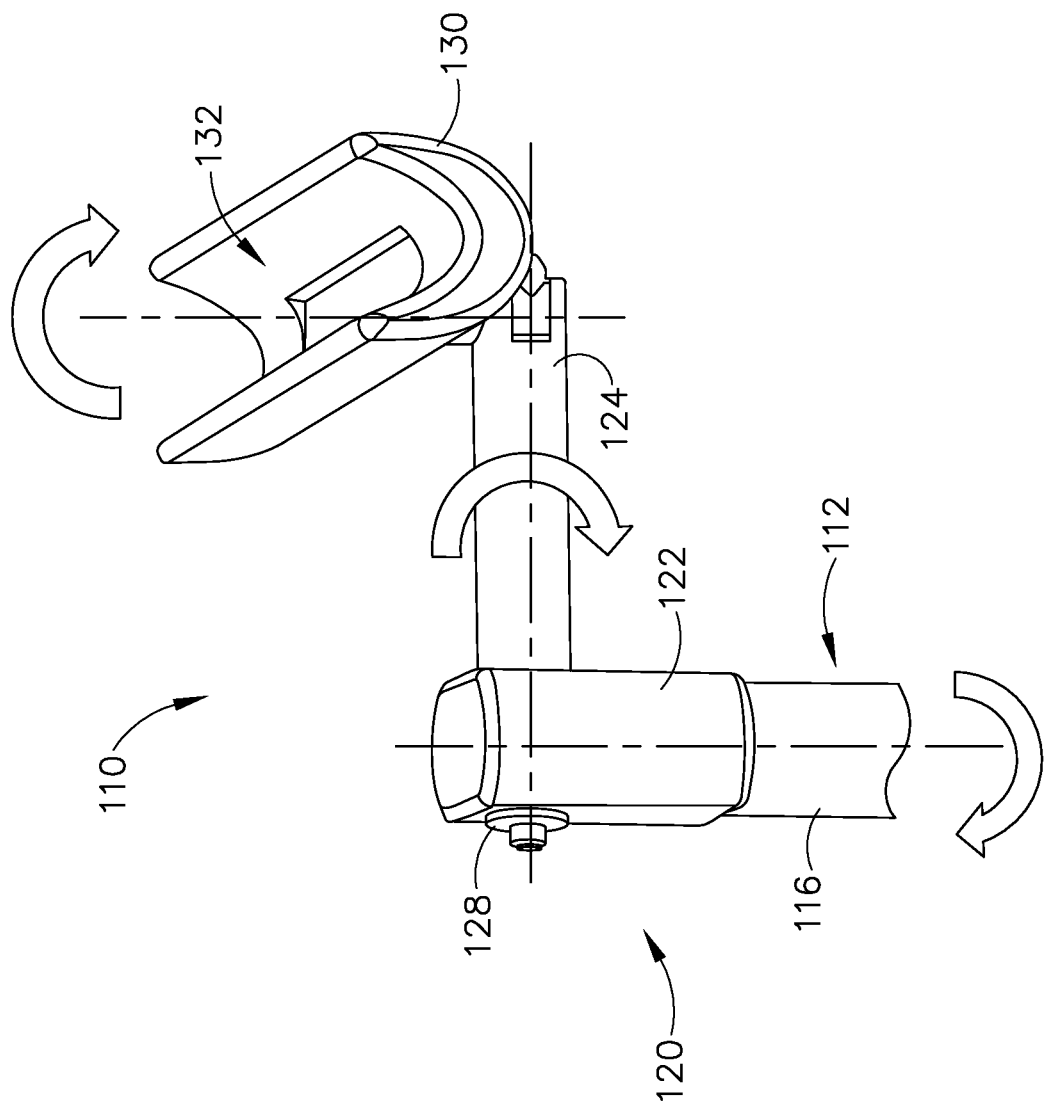
FIG. 11 depicts another perspective view of the support assembly of FIG. 9, showing various axes of movement.

In an exemplary use of support assembly (110), components of support assembly (110) may be rotated about the axes shown in phantom lines in FIG. 11. In particular, support assembly (110) may be manipulated to orbit cradle (130) about the longitudinal axis of flex arm (112). Likewise, support assembly (110) may be manipulated to orbit cradle (130) about the longitudinal axis of clamping sleeve (124). Finally, support assembly (110) may be manipulated to rotate cradle (130) about the longitudinal axis of dowel (132). The rotatability of components of support assembly (110), along with the malleability of flex arm (112), permit cradle (130) to be moved to a variety of desired positions relative to a patient.

Figure 12:
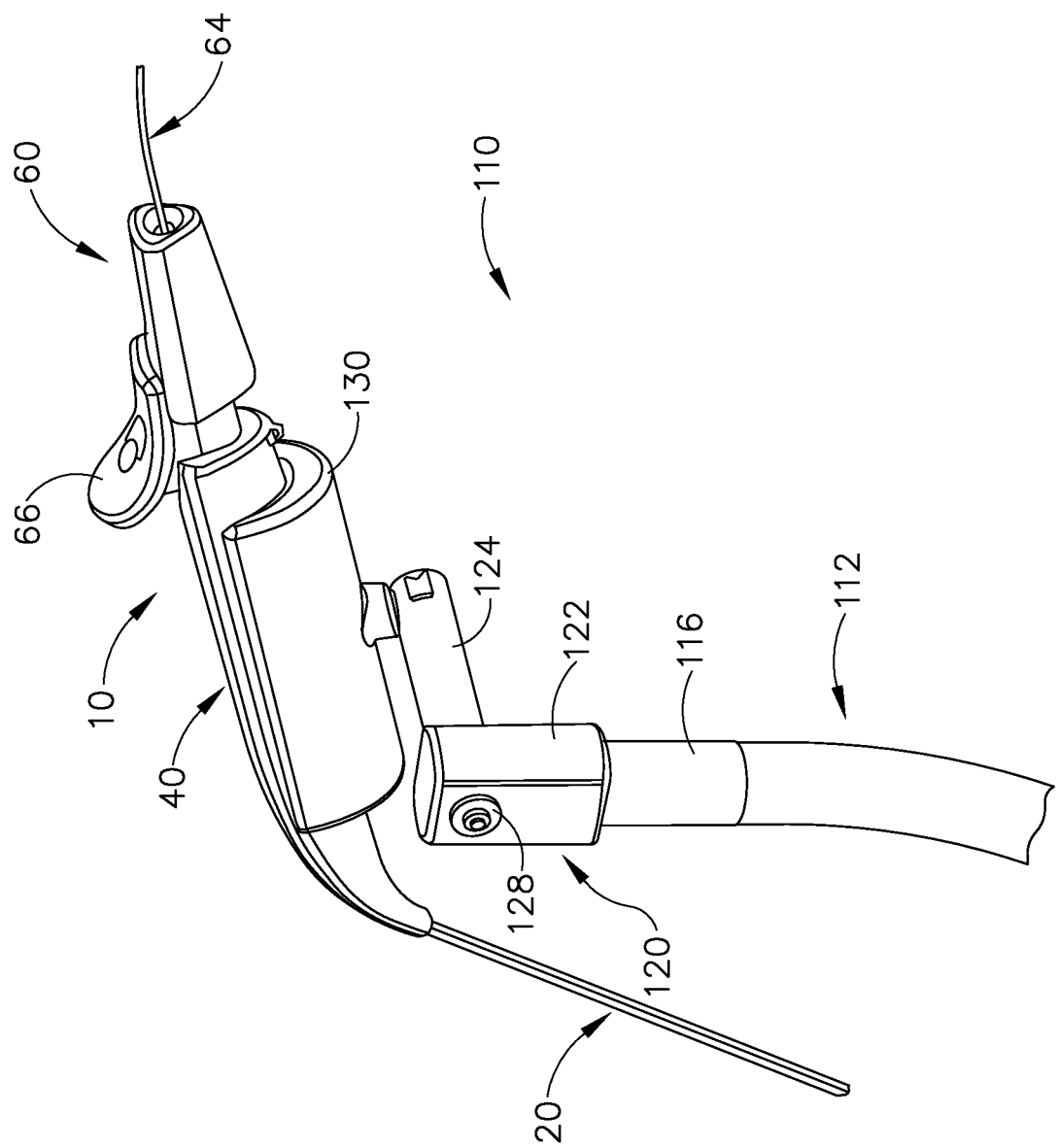
FIG. 12 depicts another perspective view of the support assembly of FIG. 9, with the instrument of FIG. 1 disposed in a cradle of the support assembly.

In one merely exemplary use, cradle (130) may first be moved into a desired position relative to a patient. Next, instrument (10) may be placed into cradle (130) as shown in FIG. 12. Alternatively, in another exemplary use, instrument (10) may first be placed in cradle (130) and then cradle (130) may be moved along with instrument (10). Other suitable ways in which support assembly (110) may be used in combination with instrument (10) will be apparent to those of ordinary skill in the art in view of the teachings herein.

III. Exemplary Suture Measurement Template

Figure 13:
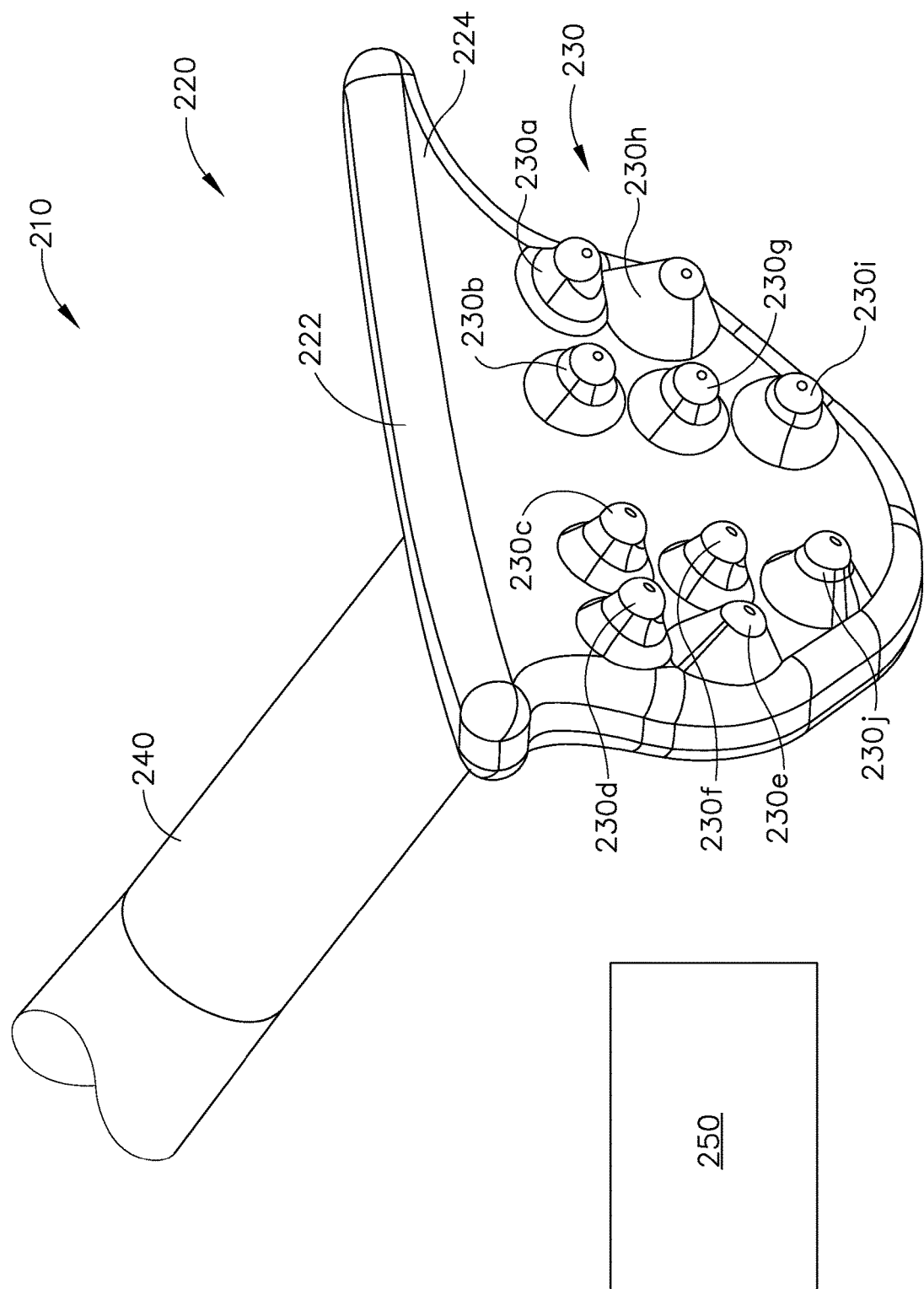
FIG. 13 depicts a perspective view of an exemplary suture measurement template for use in an exemplary method for the suprachoroidal administration of a therapeutic agent.

FIG. 13 shows an exemplary suture measurement template (210) for use in a method for suprachoroidal delivery of a therapeutic agent, as will be described in greater detail below. Generally, template (210) is configured to be pressed against an eye of a patient to stamp a particular pattern of pigment onto the patient's eye. It should be understood that reference herein to pressing template (210) against an eye of a patent may include, but is not necessarily limited to, pressing template (210) directly against the sclera (304) surface (e.g., after the conjunctiva has been taken down or otherwise displaced). Template (210) comprises a rigid body (220) and a rigid shaft (240). As will be described in greater detail below, body (220) is generally contoured to correspond to the curvature of a patient's eye such that body (220) may be pressed or placed onto at least a portion of the patient's eye. Body (220) comprises an upper guide portion (222) and a plurality of protrusions (230) extending distally from an eye face (224) of body (220).

Upper guide portion (222) is generally semi-circular in shape and is disposed at the top of body (220). The semi-circular shape of upper guide portion (222) has a radius that corresponds to the curvature of the limbus of a patient's eye. In other words, upper guide portion (222) curves proximally along a first radius corresponding to a radius of curvature of a patient's eyeball; and downwardly (toward the longitudinal axis of shaft (240)) along a second radius corresponding to a radius of curvature of the limbus of the patient's eye. As will be described in greater detail below, upper guide portion (222) may be used to properly locate template (210) relative to the limbus of the patient's eye. Accordingly, any pigmentation that may be deposited onto a patient's eye by template may be positioned relative to the limbus of the patient's eye.

Protrusions (230) are spaced a predetermined distance from upper guide portion (222). In particular, protrusions (230) form a pattern that may correspond to relevant marks for use during the method described below. Protrusions (230) of the present example comprise four suture loop protrusions (230a-230h) and two sclerotomy protrusions (230i, 230j). Suture loop protrusions (230a-320h) and sclerotomy protrusions (230i, 230j) extend outwardly from body (220) an equal distance such that protrusions (230) collectively maintain the curvature defined by body (220). In other words, the tips of protrusions (230a-230j) all lie along a curved plane that is defined by a radius of curvature complementing the radius of curvature of the patient's eyeball. The tips of protrusions (230a-230j) are rounded and atraumatic such that protrusions (230a-230j) may be pressed against the eye without damaging the sclera or other portions of the patient's eye.

Shaft (240) extends proximally from body (220). Shaft (240) is configured to permit an operator to grasp template (210) and manipulate body (220). In the present example, shaft (240) is integral with body (220). In other examples, shaft (240) may be selectively attachable to body by a mechanical fastening means such as a threaded coupling or a mechanical snap fit, etc. In some versions, an operator may be presented with a kit comprising a shaft (240) and a plurality of bodies (220). The bodies (220) may have different curvatures to correspond with different eyeballs having different radii of curvature. The operator may thus select an appropriate body (220) from the kit based on the anatomy of the particular patient before the operator; and the operator may then secure the selected body (220) to the shaft (240). Although not shown, it should be understood that the proximal end of shaft (240) may additionally include a t-grip, knob, or other gripping feature to permit an operator to more readily grip shaft (240).

In an exemplary use, suture loop protrusions (232) and sclerotomy protrusions (234) each correspond to a particular portion of the method described below. In particular, prior to, or during the method described below, an operator may coat protrusions (230) with a biocompatible pigment or ink by pressing protrusions (230) onto a pigment or ink pad (250), by brushing the pigment or ink onto protrusions (230), or by otherwise applying the pigment or ink to protrusions (230). Once protrusions (230) have received the pigment or ink, an operator may mark an eye of a patent by pressing protrusions (230) of template (210) onto the eye of the patient, as will be described in greater detail below. Once template (210) is removed from an eye of a patient, the pigment from protrusions may remain adhered to the eye to mark particular points of interest, as will be described in greater detail below.

IV. Exemplary Method for Suprachoroidal Delivery of Therapeutic Agent

FIGS. 14A-17C show an exemplary procedure for suprachoroidal delivery of therapeutic agent using instrument (10) described above. By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

Figure 14B:
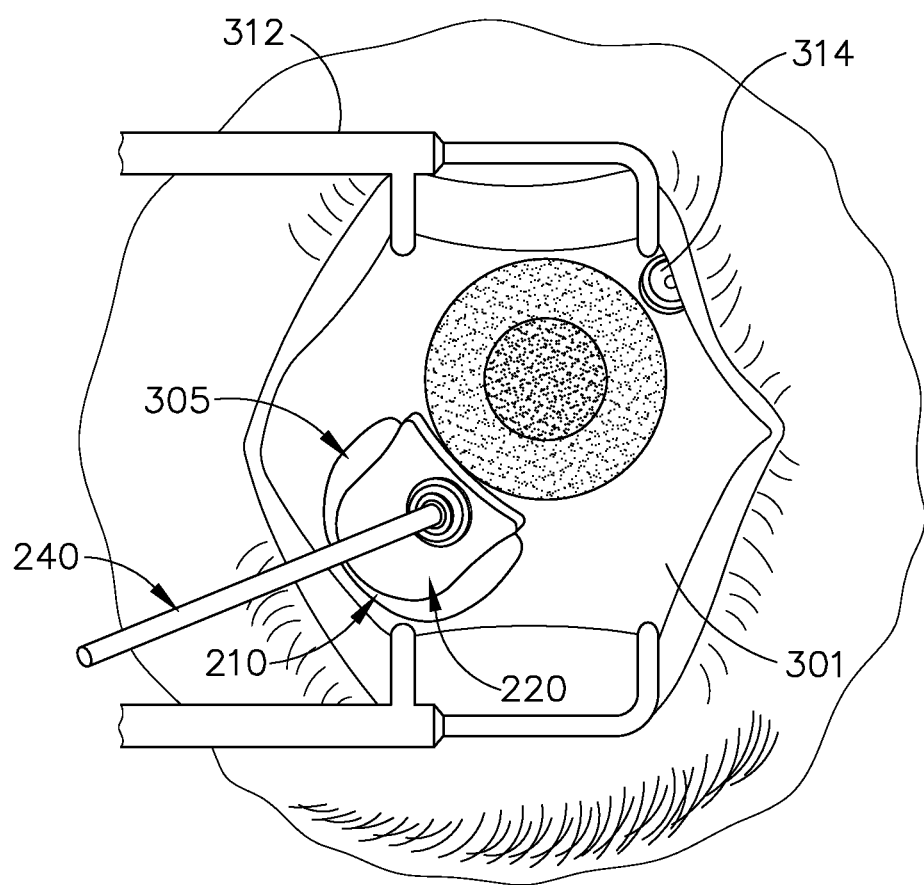
FIG. 14B depicts a top plan view of the eye of FIG. 14A, with the template of FIG. 13 disposed on the eye.
Figure 15A:
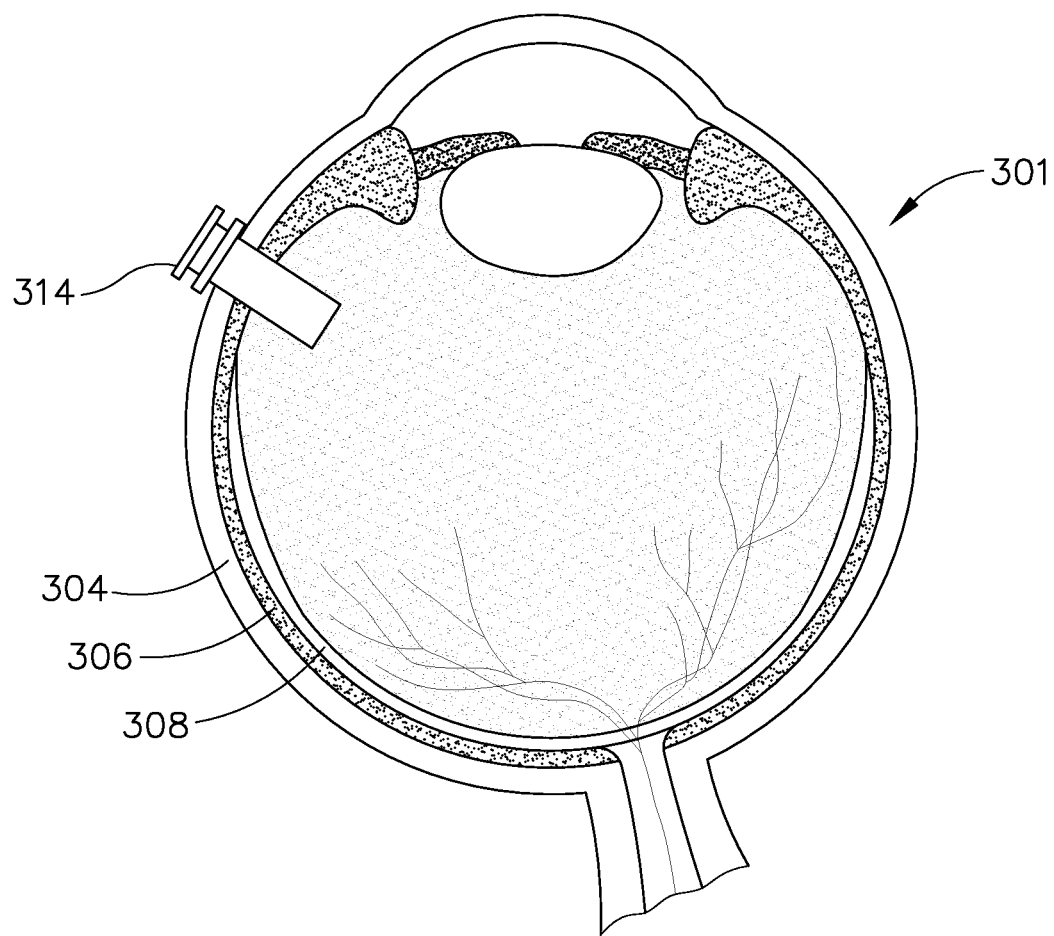
FIG. 15A depicts a cross-sectional view of the eye of FIG. 14A, with the cross-section taken about line 15A-15A of FIG. 14A.
Figure 15B:
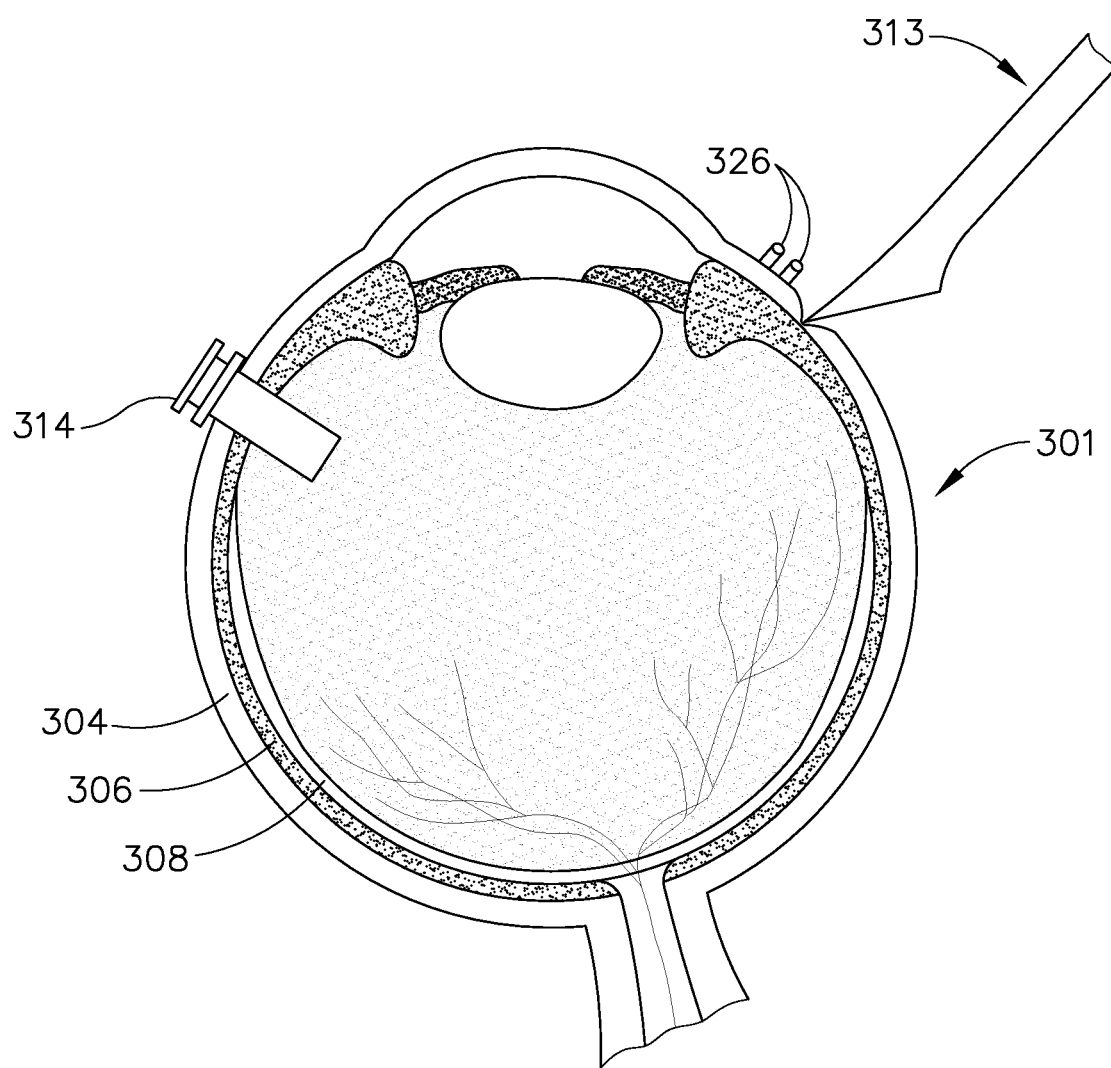
FIG. 15B depicts a cross-sectional view of the eye of FIG. 14A, with the cross-section taken about line 15B-15B of FIG. 14E.

As can be seen in FIG. 14A, the procedure begins by an operator immobilizing tissue surrounding a patient's eye (301) (e.g., the eyelids) using a speculum (312), and/or any other instrument suitable for immobilization. While is immobilization described herein with reference to tissue surrounding eye (301), it should be understood that eye (301) itself may remain free to move. Once the tissue surrounding eye (301) has been immobilized, an eye chandelier port (314) is inserted into eye (301) to provide intraocular illumination when the interior of eye (301) is viewed through the pupil. In the present example, eye chandelier port (314) is positioned in the inferior medial quadrant such that a superior temporal quadrant sclerotomy may be preformed. As can be seen in FIG. 15A, eye chandelier port (314) is positioned to direct light onto the interior of eye (314) to illuminate at least a portion of the retina (e.g., including at least a portion of the macula). As will be understood, such illumination corresponds to an area of eye (301) that is being targeted for delivery of therapeutic agent. In the present example, only chandelier port (314) is inserted at this stage, without yet inserting an optical fiber (315) into port (314). In some other versions, an optical fiber (315) may be inserted into chandelier port (314) at this stage. In either case, a microscope may optionally be utilized to visually inspect the eye to confirm proper positioning of eye chandelier port (314) relative to the target site. In some examples, the target region may be identified by a relative lack of retinal pigmentation. Although FIG. 14A shows a particular positioning of eye chandelier port (314), it should be understood that eye chandelier port (314) may have any other positioning as will be apparent to those of ordinary skill in the art in view of the teachings herein.

Figure 14C:
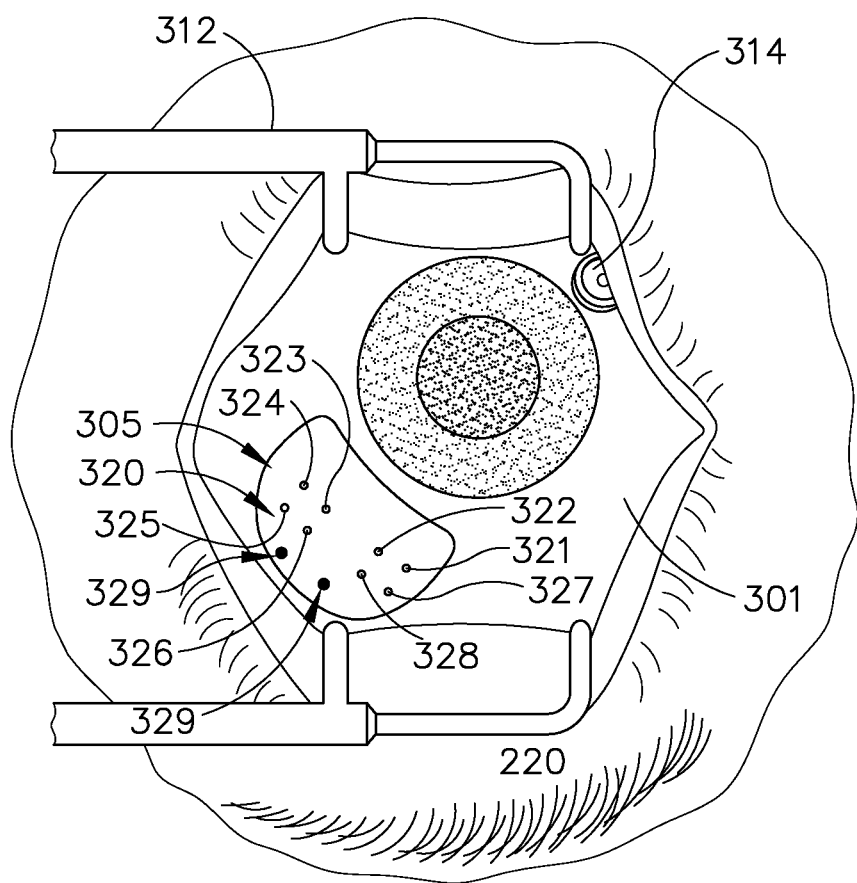
FIG. 14C depicts a top plan view of the eye of FIG. 14A, with a plurality of markers disposed on the eye.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. Template (210), described above, may then be used to mark eye (301). As can be seen in FIG. 14B template (210) is positioned to align with the limbus of eye (301). An operator may apply a light force to template (210) to apply pigment to eye (301). Template (210) is then removed, leaving pigment adhered to the exposed surface (305) of the sclera (304) to provide a visual guide (320) for an operator, as can be seen in FIG. 14C. An operator may then use visual guide (320) to attach a suture loop assembly (330) and to perform a sclerotomy. Visual guide (320) comprises a set of suture loop markers (321, 322, 323, 324, 325, 326, 327) and a pair of sclerotomy markers (329).

Figure 14D:
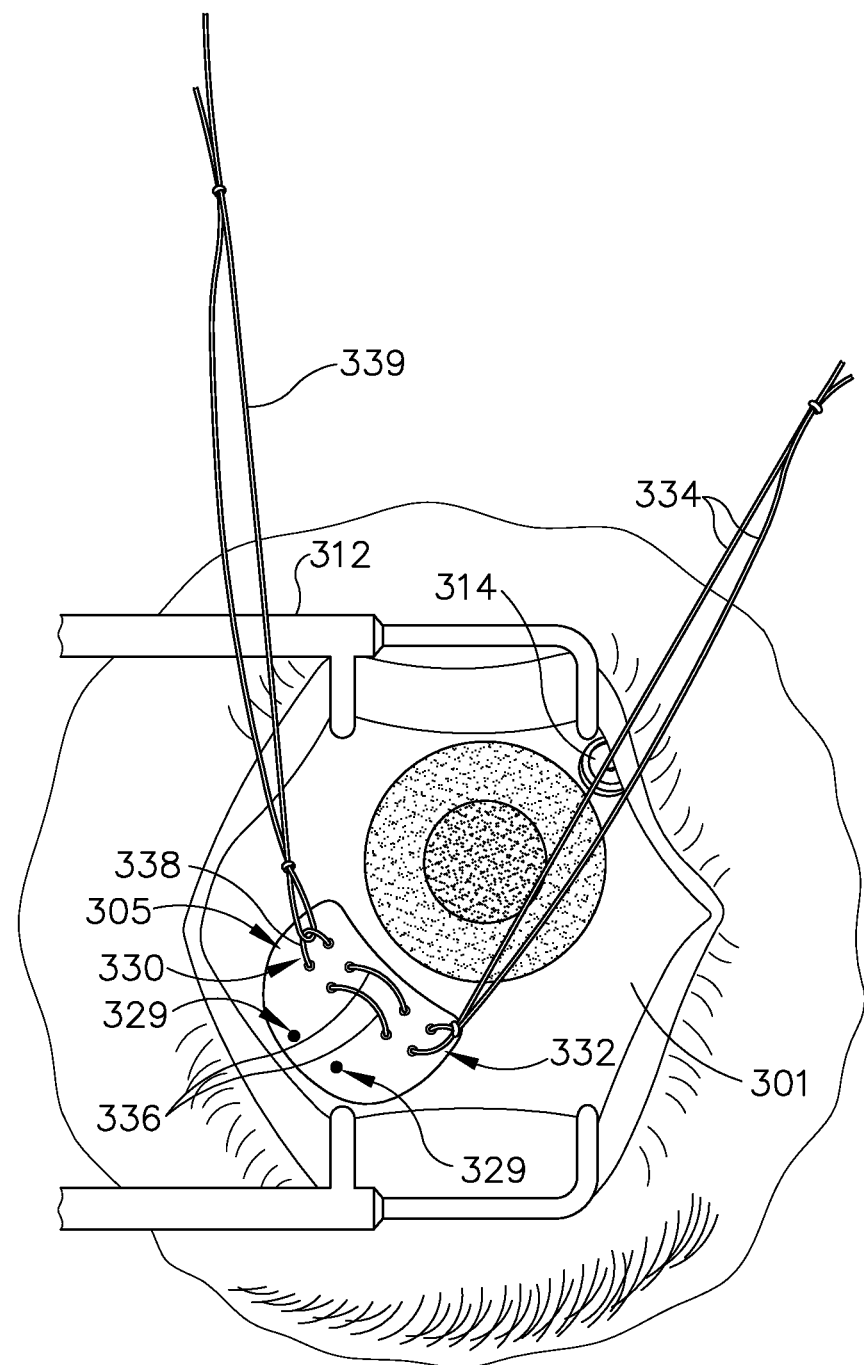
FIG. 14D depicts a top plan view of the eye of FIG. 14A, with a suture loop attached to the eye.
Figure 16A:
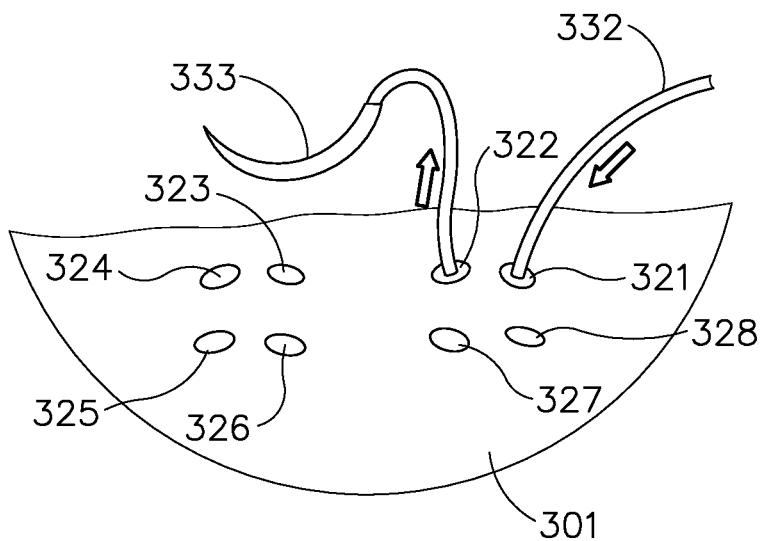
FIG. 16A depicts a detailed perspective view of the eye of FIG. 14A, with a suture being initially threaded through the eye.

FIG. 14D shows a completed suture loop assembly (330). As will be described in greater detail below, suture loop assembly (330) is generally configured to guide cannula (20) of instrument (10) through a sclerotomy and into eye (301). FIGS. 16A-16E show an exemplary procedure for attaching suture loop assembly (330) such as the suture loop assembly (330) that is shown in FIG. 14D. In particular, as can be seen in FIG. 16A, a suture (332) is threaded through eye (301) at a first suture loop marker (321), using a curved needle (333). Suture (332) is then directed out of eye (301) through a second suture loop marker (322). This anchors suture (332) between first suture loop marker (321) and second suture loop marker (322). Suture (332) is then similarly anchored between third and fourth suture loop markers (323, 324), fifth and sixth suture loop markers (325, 326), and seventh and eighth suture loop markers (327, 328).

Figure 16B:
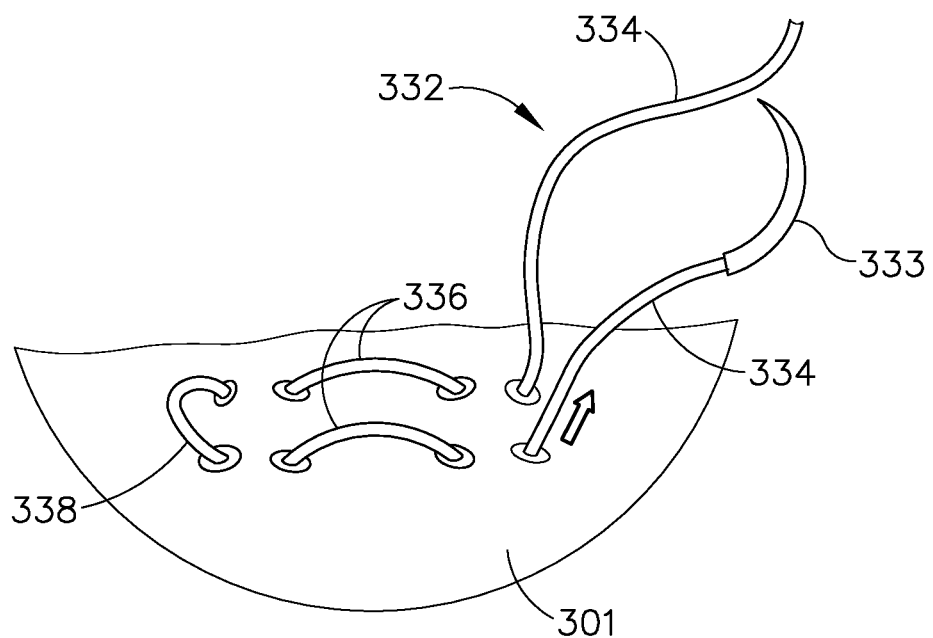
FIG. 16B depicts a detailed perspective view of the eye and suture of FIG. 16A, with the suture being further threaded through the sclera of the eye to form a loop.
Figure 16C:
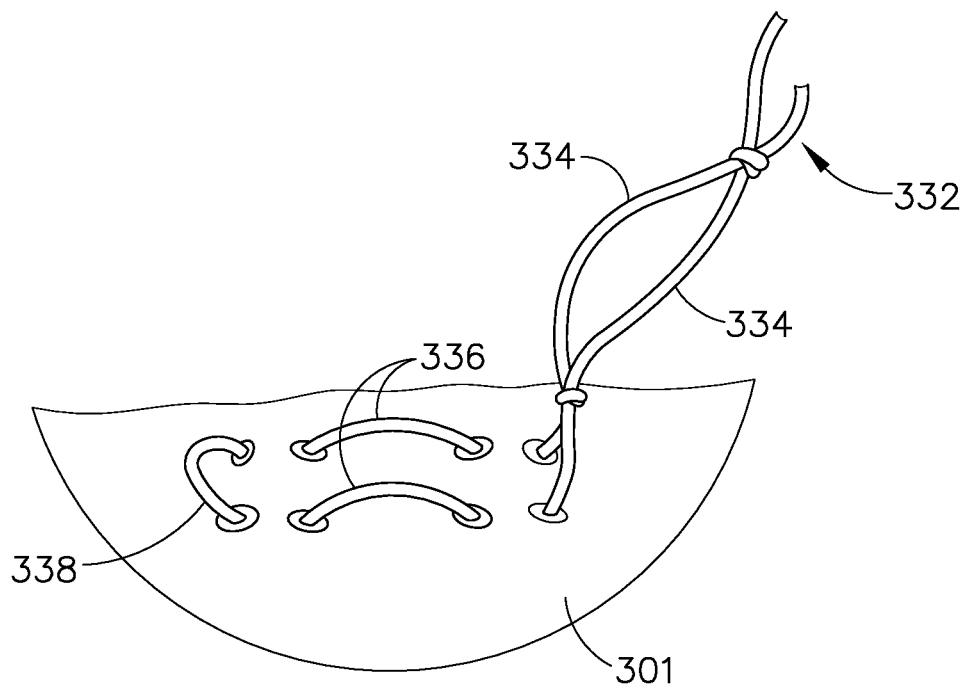
FIG. 16C depicts a detailed perspective view of the eye and suture of FIG. 16A, with a two loose ends of the suture being tied together.
Figure 16D:
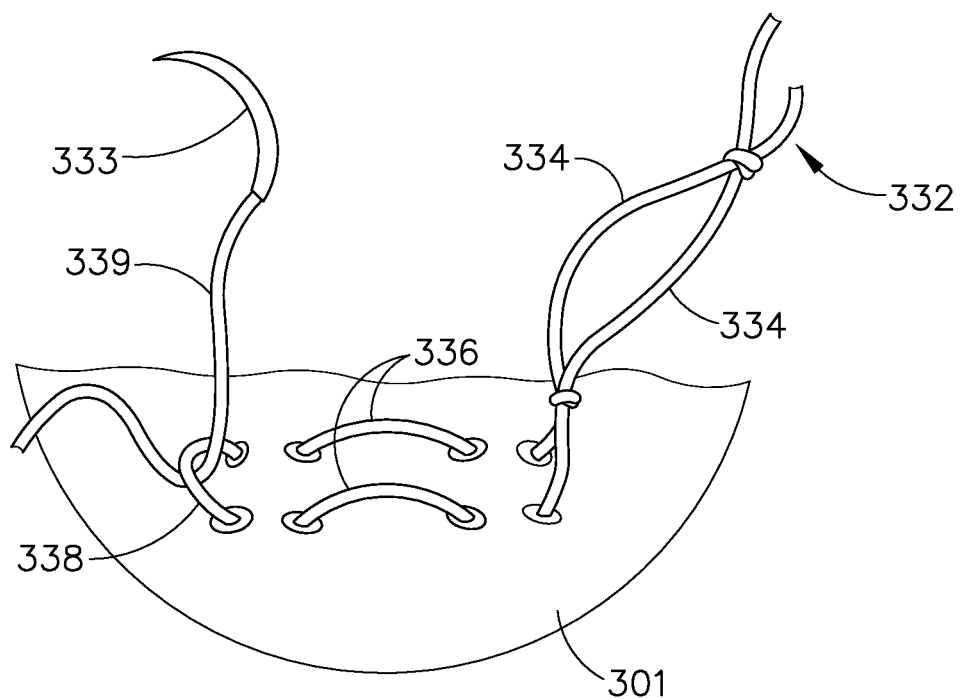
FIG. 16D depicts a detailed perspective view of the eye and suture of FIG. 16A, with a second suture being attached to the suture loop of FIG. 16B.
Figure 16E:
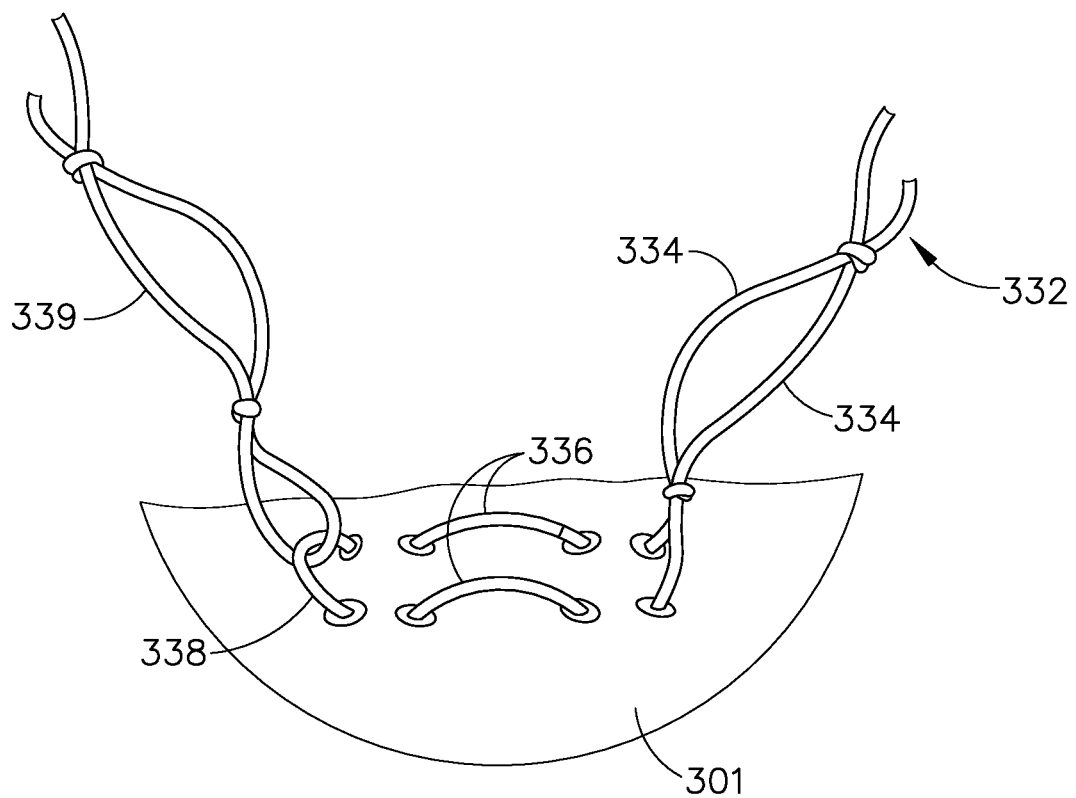
FIG. 16E depicts a detailed perspective view of the eye and suture of FIG. 16A, with the second suture of FIG. 16D cut and tied to the suture loop of FIG. 16B.

With suture (332) anchored as described above, suture (332) forms the configuration shown in FIG. 16B. As can be seen, suture (332) is configured to form two loose ends (334), two guide loops (336) and one return loop (338). Loose ends (334) may be tied together to permit an operator to grip loose ends (334), as can be seen in FIG. 16C. Similarly, return loop (338) may be used to attach a second suture (339) to permit an operator to grip return loop (338), as seen in FIGS. 16D and 16E. It should be understood that loose ends (334) and second suture (339) may be used to assist in stabilizing eye (301) throughout the procedure. Alternatively, loose ends (334) and second suture (339) may be simply positioned or tied off away from eye (301). As will be described in greater detail below, guide loops (336) may be used to guide cannula (20) of instrument (10) through the sclerotomy and to thereby help to ensure a tangential entry angle of cannula (20) as cannula (20) enters through the sclerotomy into the suprachoroidal space, thereby reducing the risk of cannula (20) inflicting trauma on the choroid (306).

Figure 14E:
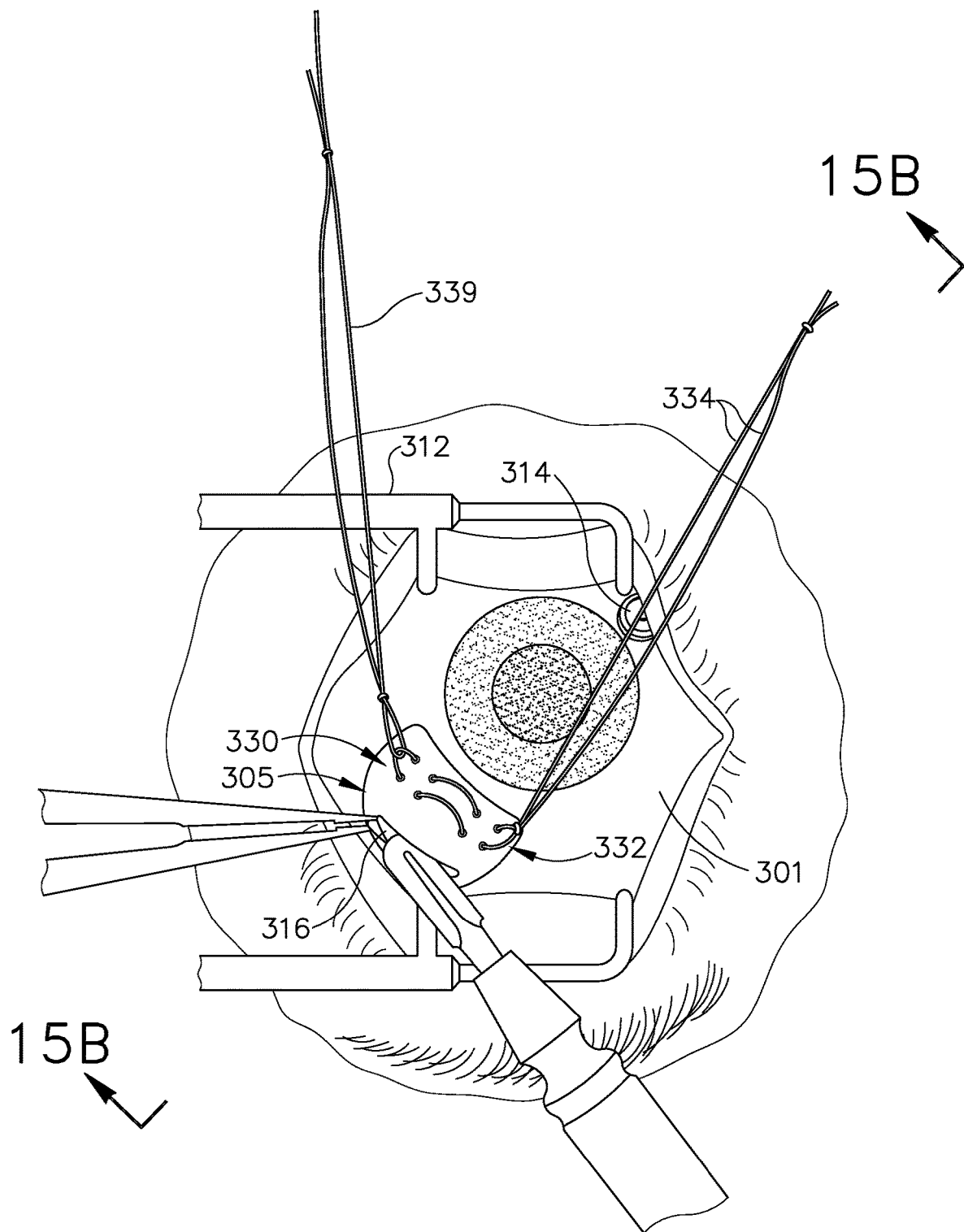
FIG. 14E depicts a top plan view of the eye of FIG. 14A, with a sclerotomy being performed.

Once suture loop assembly (330) has been attached to eye (301), a sclerotomy may be performed on eye (301). As seen in FIG. 14E, eye (301) is cut between sclerotomy markers (329) using a conventional scalpel (313) or other suitable cutting instrument. Although sclerotomy markers (329) are shown as comprising two discrete dots, it should be understood that in other examples, markers (329) may comprise any other type of markings such as a solid, dotted or dashed line. The sclerotomy procedure forms a small incision (316) through sclera (304) of eye (301). As can best be seen in FIG. 15B, the sclerotomy is preformed with particular care to avoid penetration of the choroid (306). Thus, the sclerotomy procedure provides access to the space between sclera (304) and choroid (306). Once incision (316) is made in eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 14F:
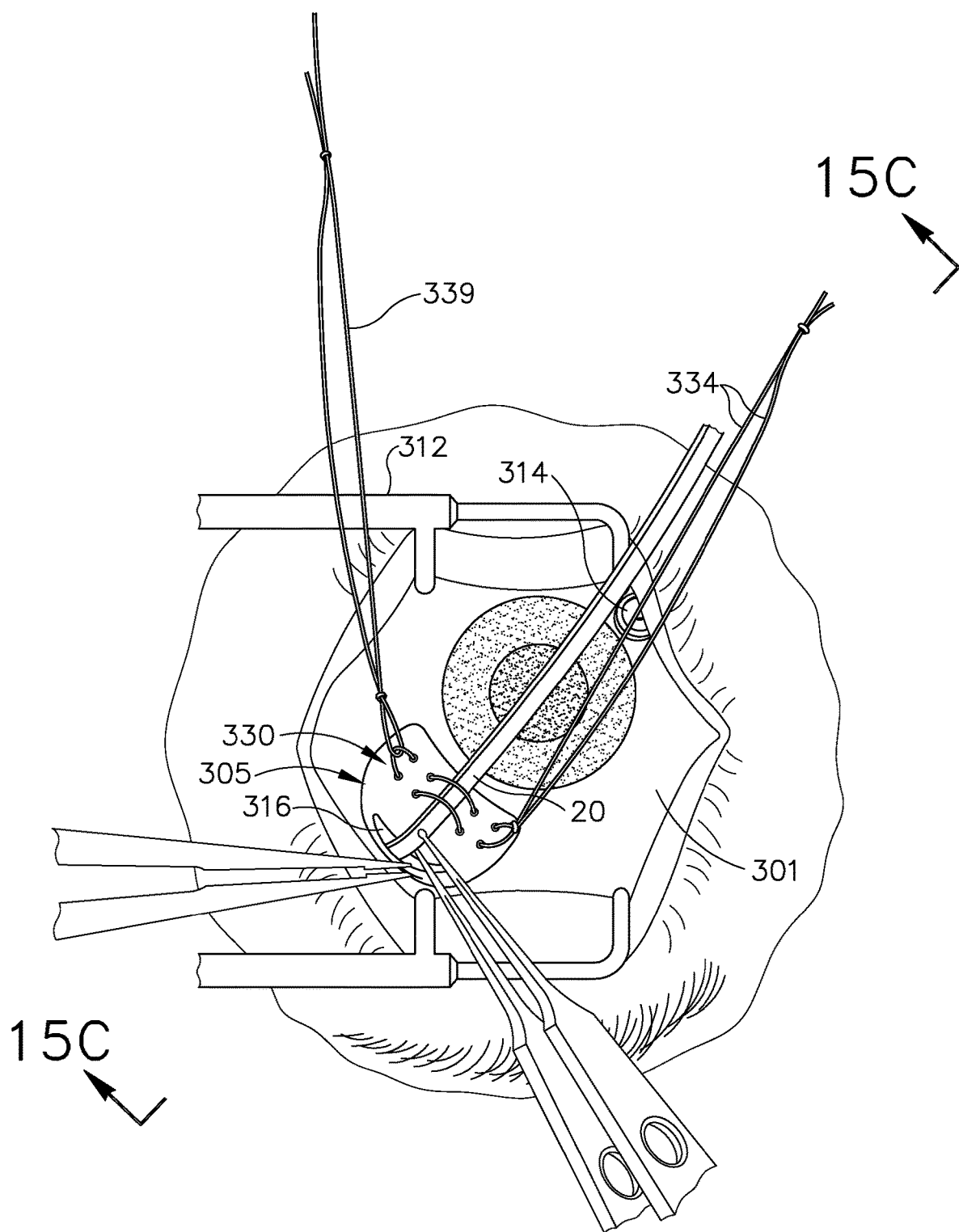
FIG. 14F depicts a top plan view of the eye of FIG. 14A, with the instrument of FIG. 1 being inserted through the sclerotomy opening and in between the sclera and choroid of the eye.

With the sclerotomy procedure performed, an operator may insert cannula (20) of instrument (10) through incision (316) and into the space between sclera (304) and choroid (306). As can be seen in FIG. 14F, cannula (20) is directed through guide loops (336) of suture loop assembly (330) and into incision (316). As described above, guide loops (336) may stabilize cannula (20). Additionally, guide loops (336) maintain cannula (20) in a generally tangential orientation relative to incision (316). Such tangential orientation may reduce trauma as cannula (20) is guided through incision (316) to stabilize cannula (20) and to prevent damage to surrounding tissue. As cannula (20) is inserted into incision (316) through guide loops (336), an operator may use forceps or other instruments to further guide cannula (20) along an atraumatic path. Of course, use of forceps or other instruments is merely optional, and may be omitted in some examples. Although not shown, it should be understood that in some examples cannula (20) may include one or more markers on the surface of cannula (20) to indicate various depths of insertion. While merely optional, such markers may be desirable to aid an operator in identifying the proper depth of insertion as cannula (20) is guided along an atraumatic path. For instance, the operator may visually observe the position of such markers in relation to guide loops (336) and/or in relation to incision (316) as an indication of the depth to which cannula (20) is inserted in eye (301). By way of example only, one such marker may correspond to an approximately 6 mm depth of insertion of cannula (20).

Once cannula (20) is at least partially inserted into eye (301), an operator may insert an optical fiber (315) into eye chandelier port (314) the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (20) may optionally be made at this point to ensure proper positioning relative to the area of geographic atrophy of retina (308). In some instances, the operator may wish to rotate the eye (301), such as by pulling on sutures (334, 339), to direct the pupil of the eye (301) toward the operator in order to optimize visualization of the interior of the eye (301) via the pupil.

Figure 14G:
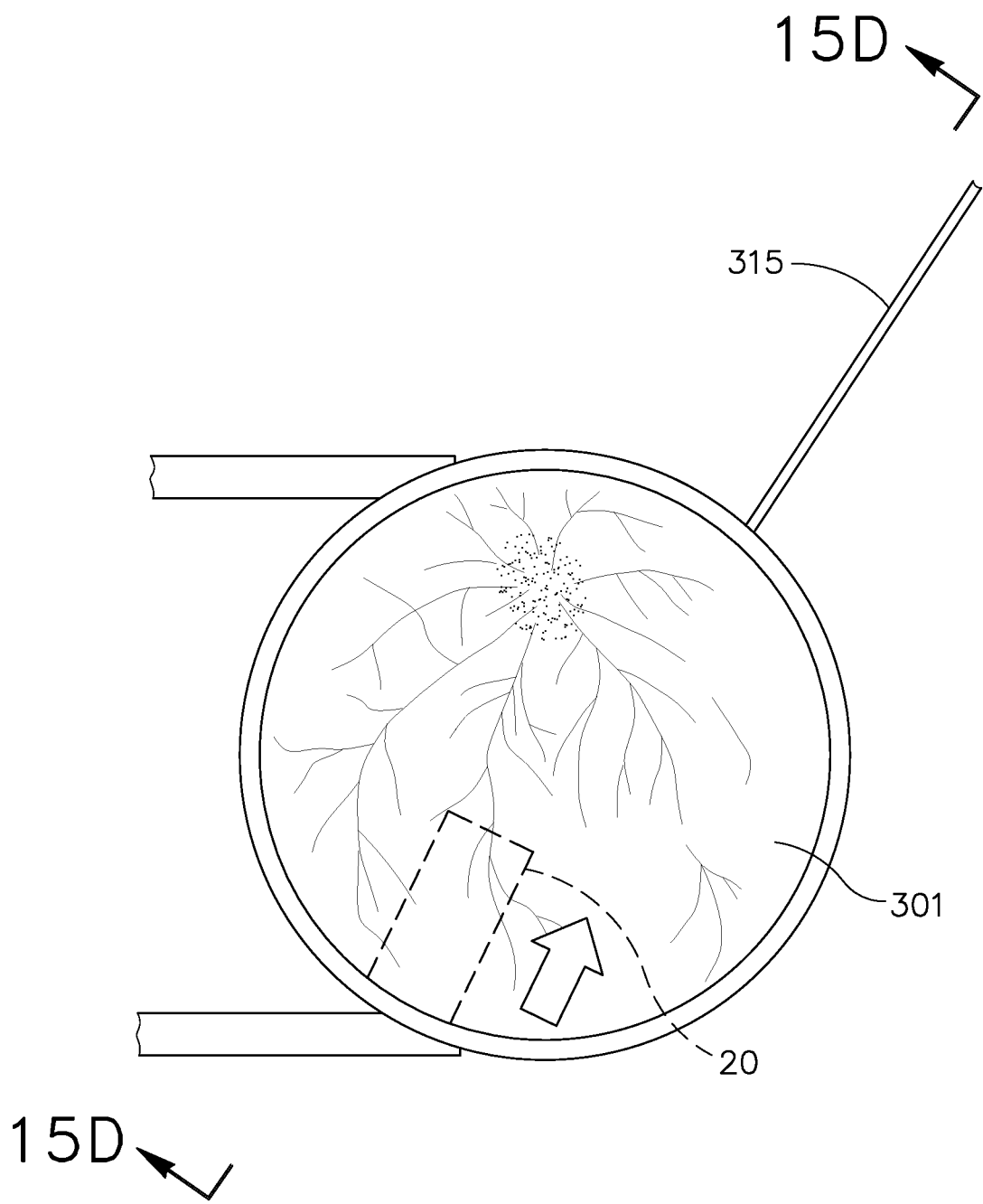
FIG. 14G depicts a top plan view of the eye of FIG. 14A, with the instrument of FIG. 1 under direct visualization at the back of the eye, between the sclera and choroid.
Figure 15C:
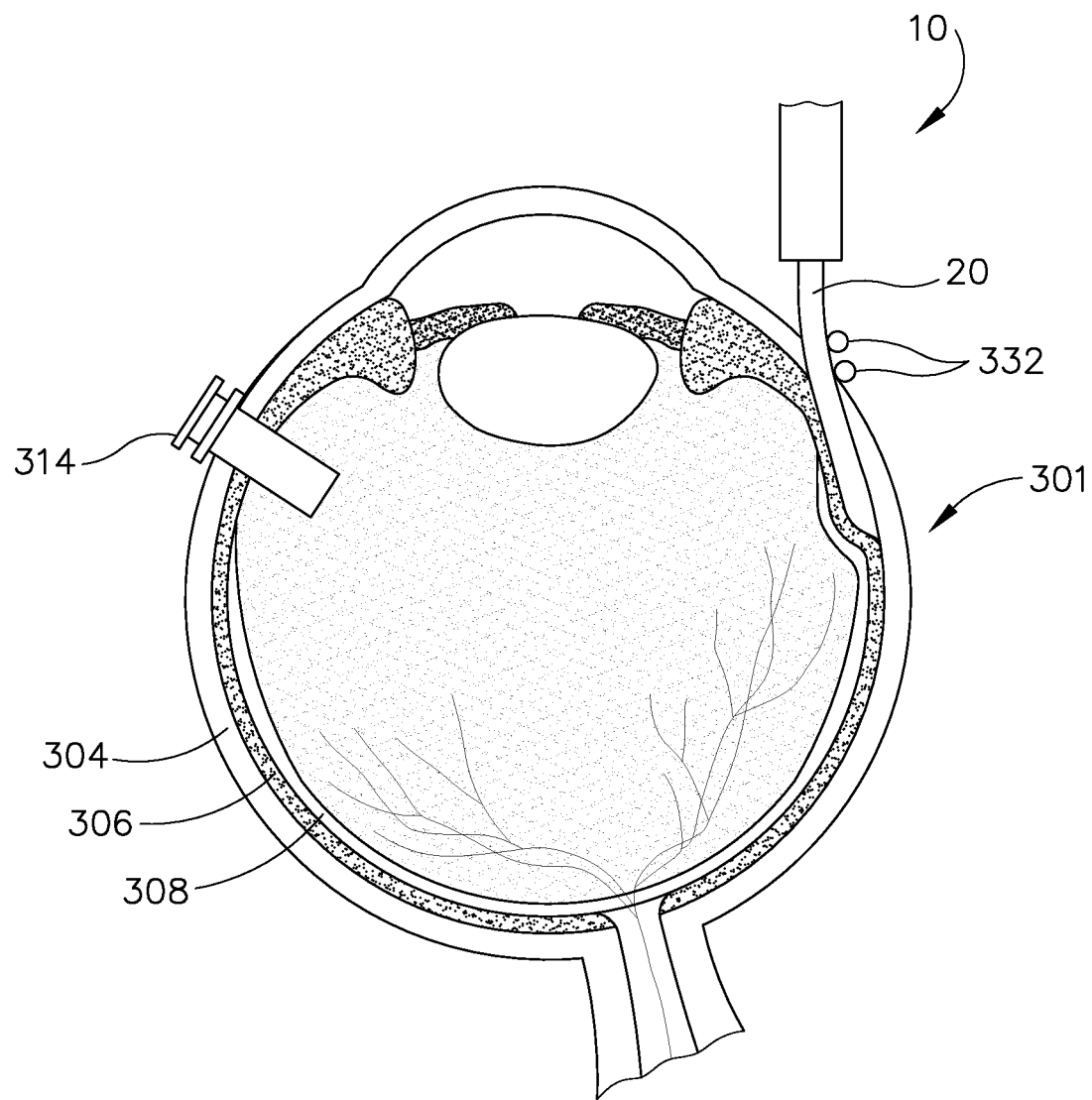
FIG. 15C depicts a cross-sectional view of the eye of FIG. 14A, with the cross-section taken about line 15C-15C of FIG. 14F.
Figure 15D:
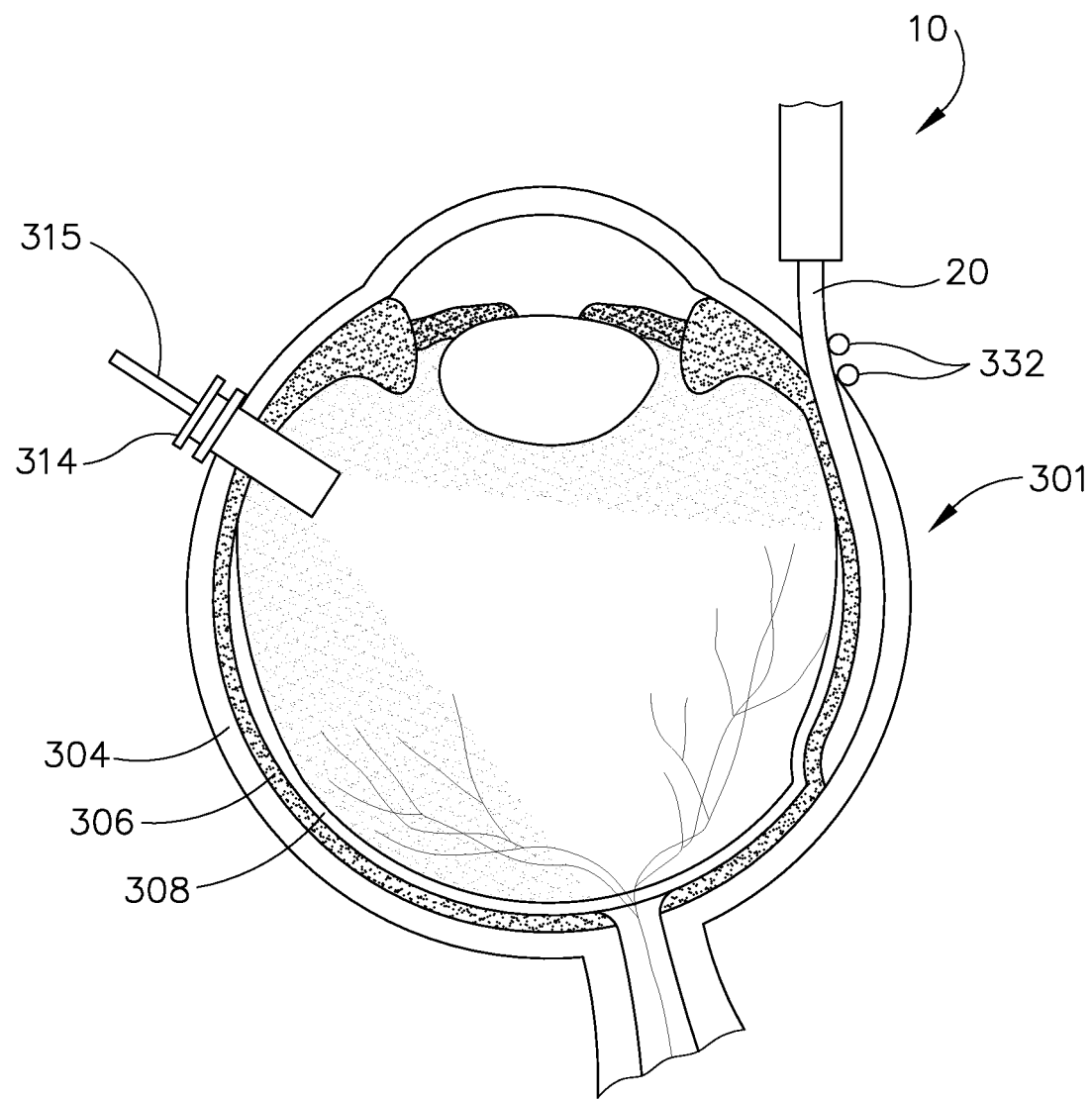
FIG. 15D depicts a cross-sectional view of the eye of FIG. 14A, with the cross-section taken about line 15D-15D of FIG. 14G.
Figure 15E:
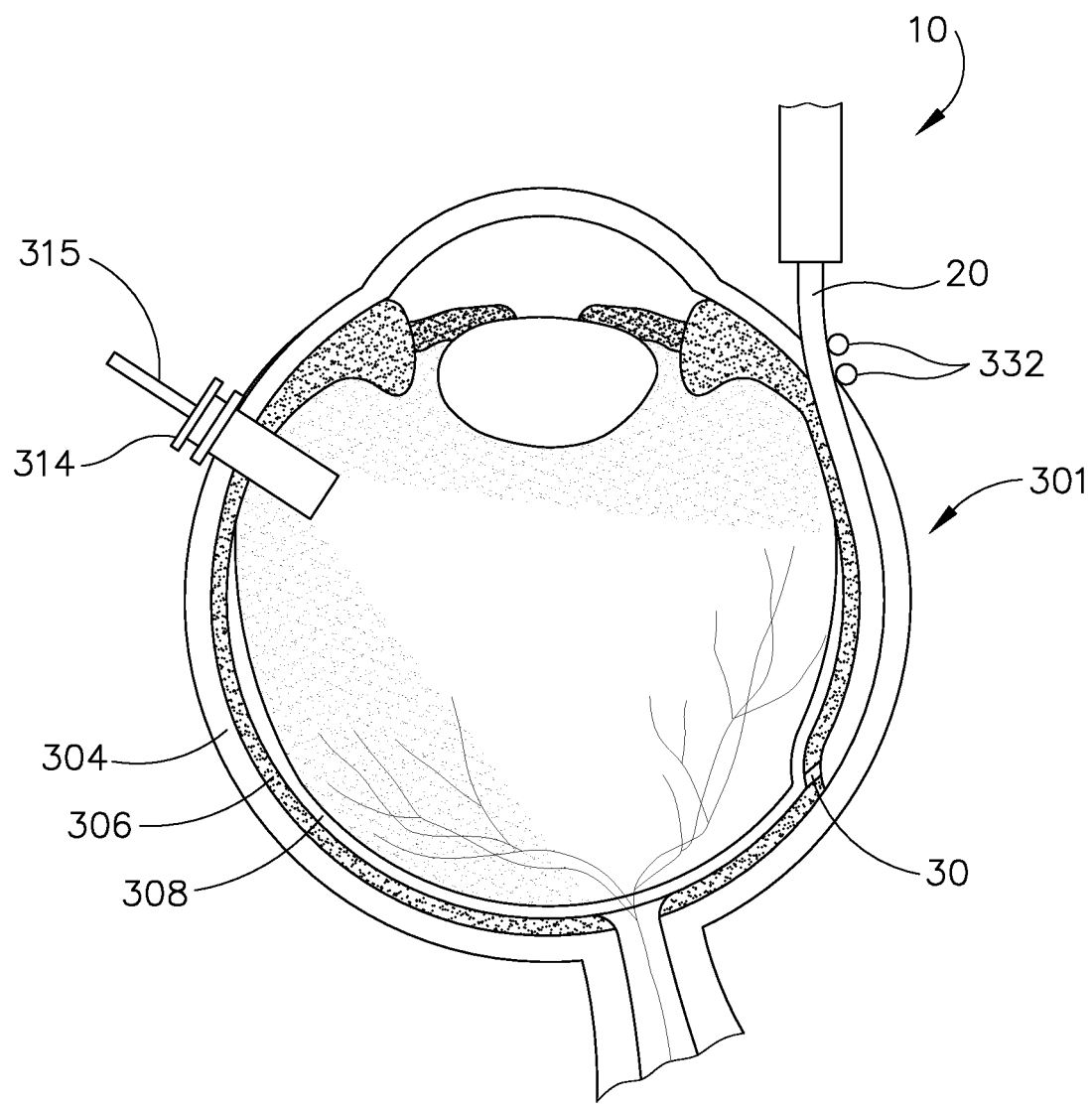
FIG. 15E depicts a cross-sectional view of the eye of FIG. 14A, with the cross-section taken about line 15E-15E of FIG. 14H.

FIGS. 14G and 15C-15D show cannula (20) as it is guided between sclera (304) and choroid (306) to the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. FIG. 14G shows eye (301) under direct visualization through a microscope directed through the pupil of eye (301), with illumination provided through fiber (315) and port (314). As can be seen, cannula (20) is at least partially visible through a retina (308) and choroid (306) of eye (301). Thus, an operator may track cannula (20) as it is advanced through eye (301) from the position shown in FIG. 15C to the position shown in 15D. Such tracking may be enhanced in versions where an optical fiber (34) is used to emit visible light through the distal end of cannula (20).

Figure 14H:
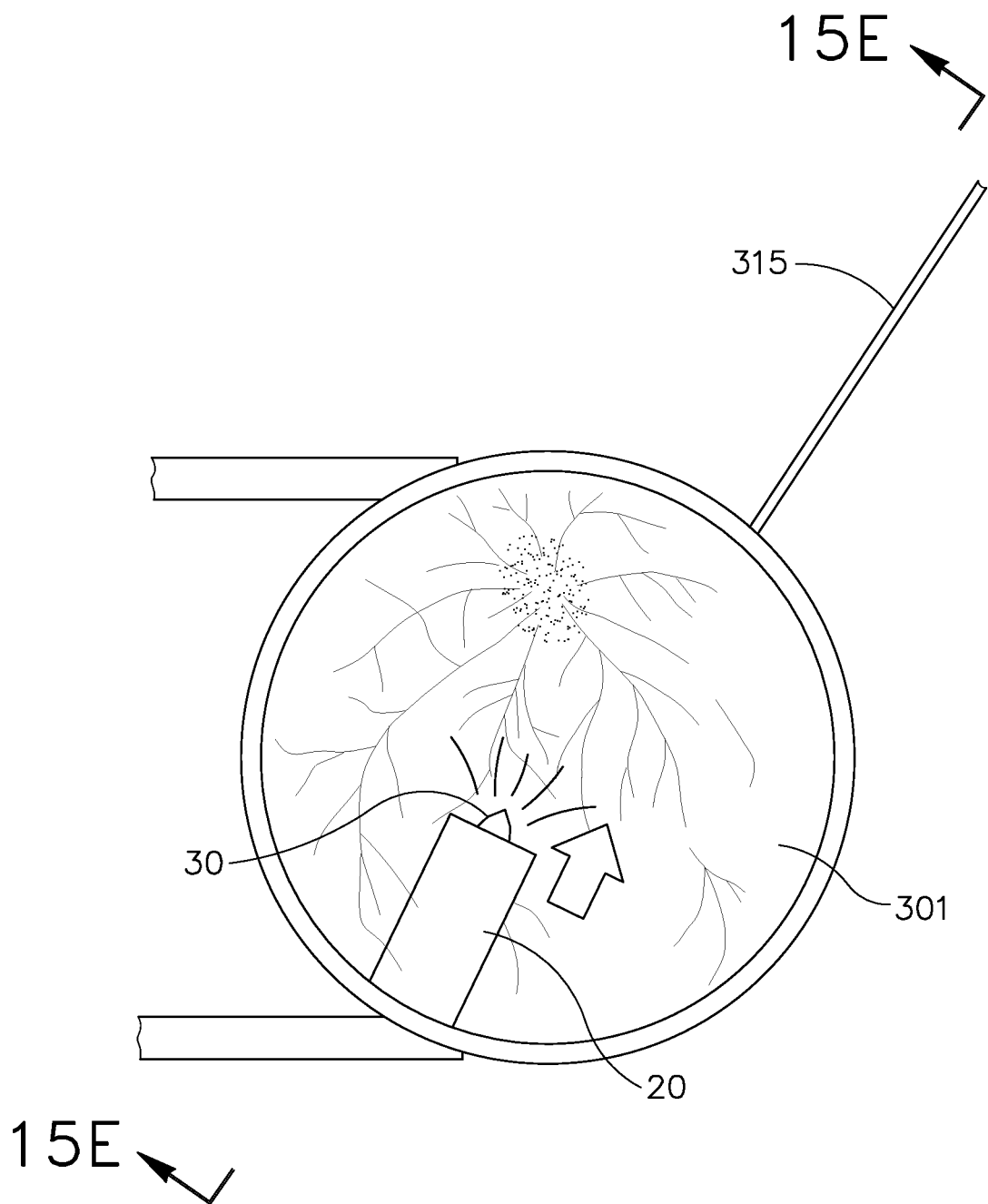
FIG. 14H depicts a top plan view of the eye of FIG. 14A, with the needle of the instrument of FIG. 1 being advanced under direct visualization at the back of the eye, pressing against the outer surface of the choroid causing the choroid to 'tent'.

Once cannula (20) has been advanced to the delivery site as shown in FIG. 15D, an operator may advance needle (30) of instrument (10) as described above with respect to FIGS. 6-8. As can be seen in FIGS. 14H-14I, 15E, and 17A, needle (30) is advanced relative to cannula (20) such that needle (30) pierces through choroid (306) without penetrating retina (308). Immediately prior to penetrating choroid (306), needle (30) may appear under direct visualization as "tenting" the surface of choroid (306), as can be seen in FIG. 14H. In other words, needle (30) may deform choroid (306) by pushing upwardly on choroid, providing an appearance similar to a tent pole deforming the roof of a tent. Such a visual phenomenon may be used by an operator to identify whether choroid (306) is about to be pierced and the location of any eventual piercing. The particular amount of needle (30) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, a merely exemplary range of needle (30) advancement may be between approximately 0.25 mm and approximately 10 mm; or more particularly between approximately 2 mm and approximately 6 mm.

Figure 14I:
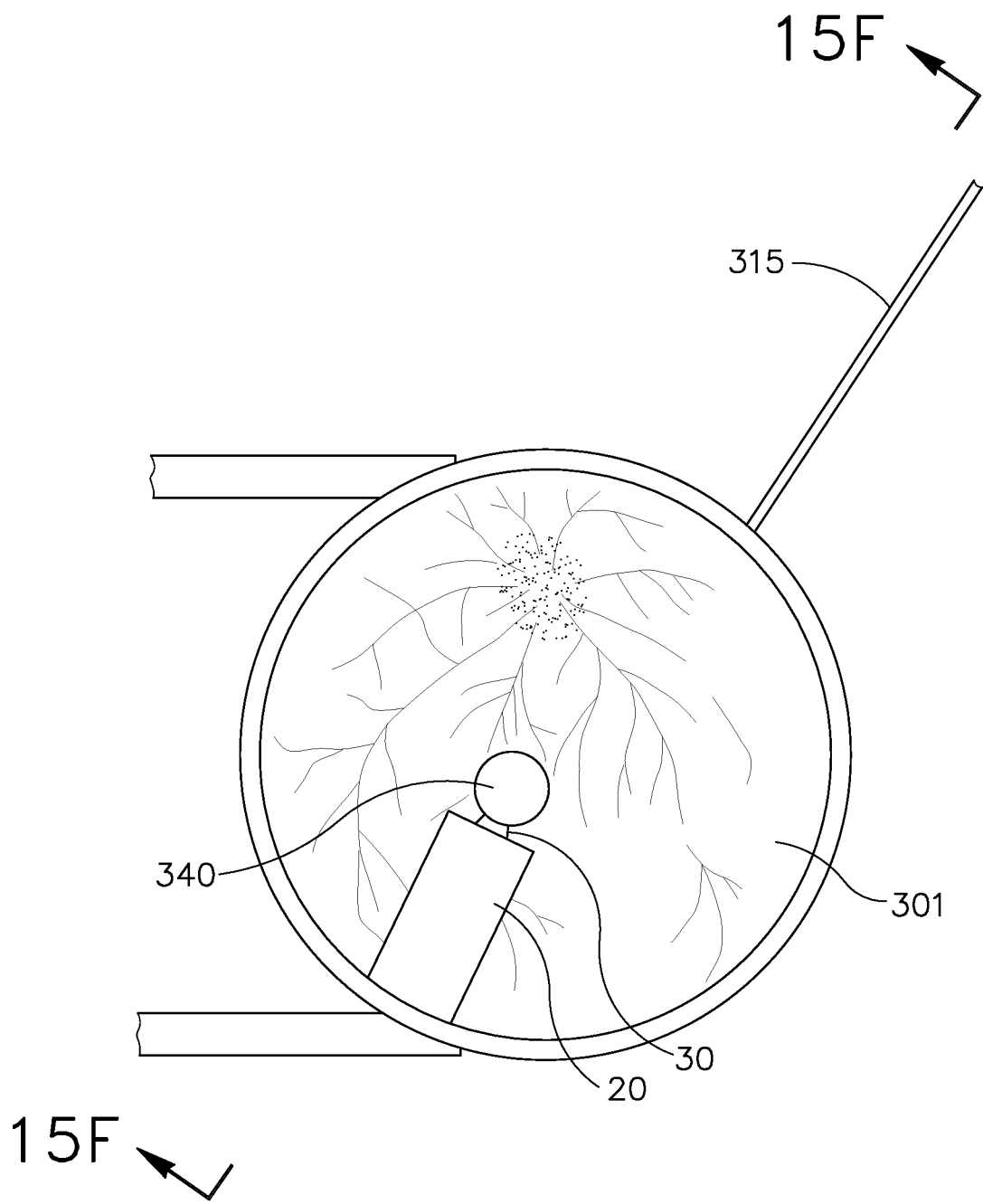
FIG. 14I depicts a top plan view of the eye of FIG. 14A, with the needle dispensing a leading bleb under direct visualization at the back of the eye, the needle between the sclera and choroid, and the leading bleb in the sub retinal space between the choroid and a retina.
Figure 15F:
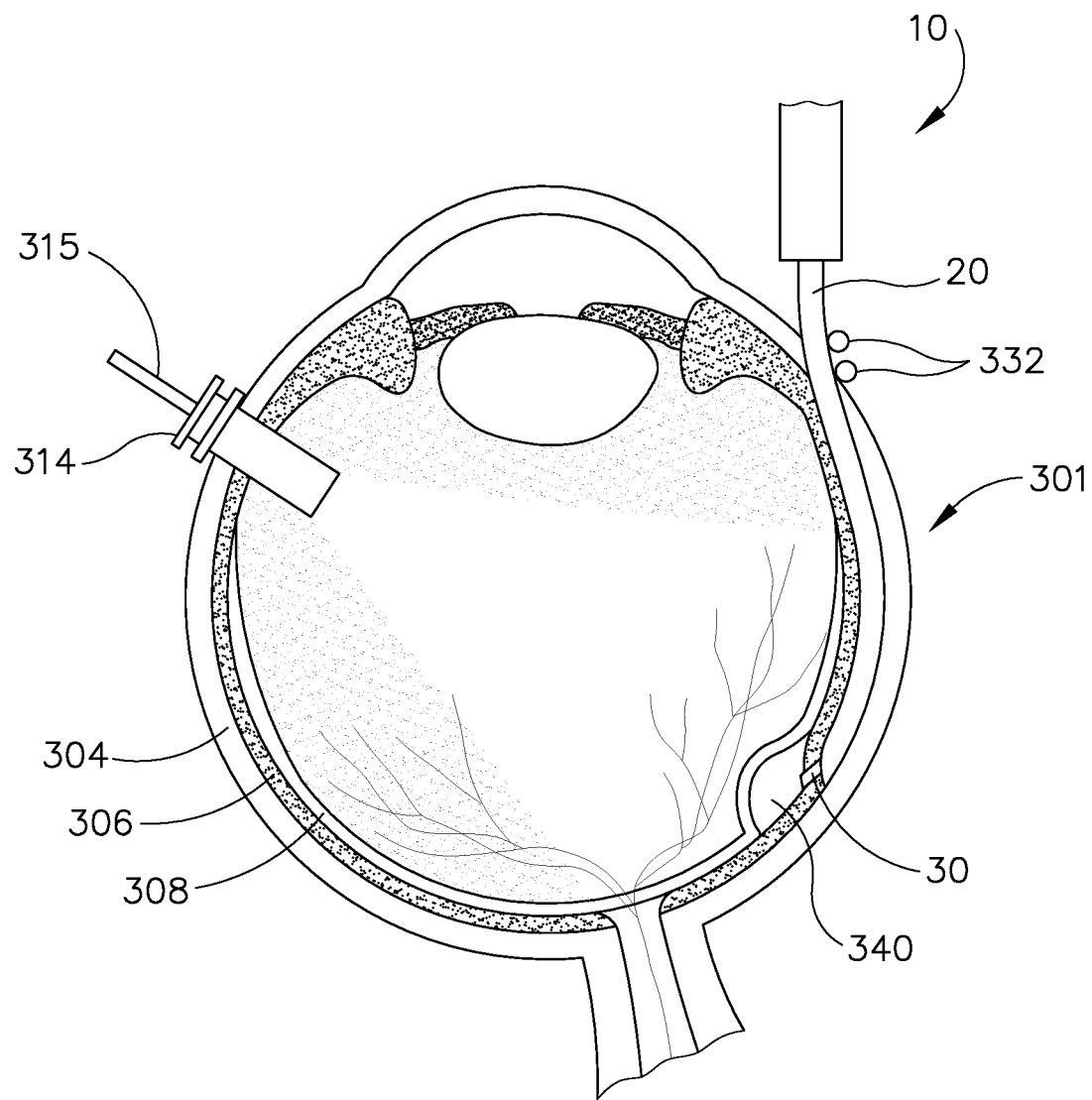
FIG. 15F depicts a cross-sectional view of the eye of FIG. 14A, with the cross-section taken about line 15F-15F of FIG. 14I.
Figure 17A:
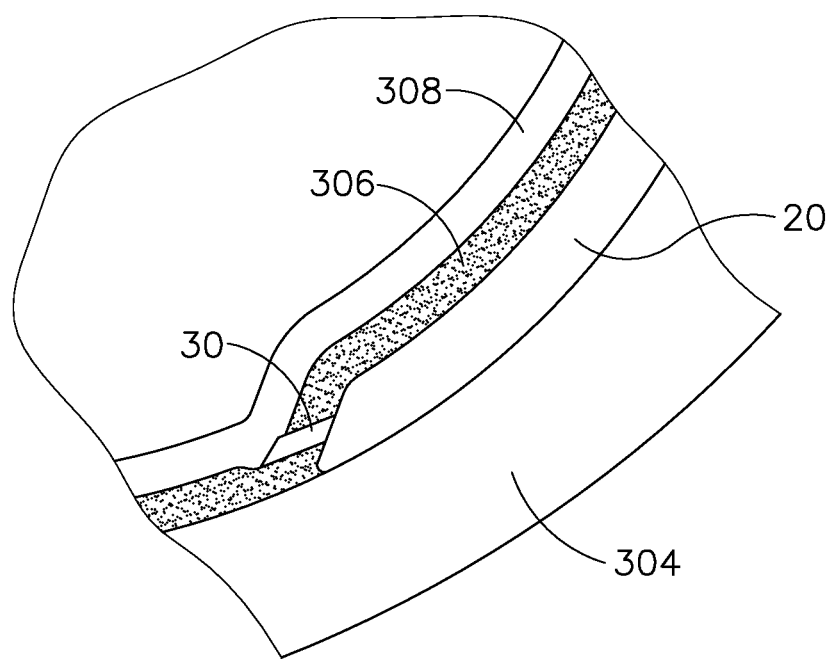
FIG. 17A depicts a detailed cross-sectional view of the eye of FIG. 14A depicted in the state shown in FIG. 15E.
Figure 17B:
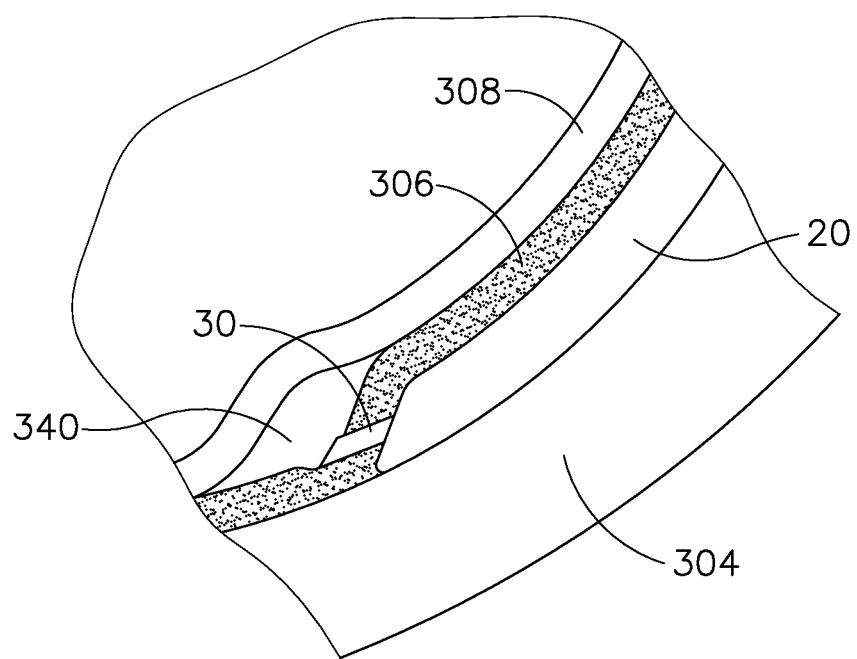
FIG. 17B depicts a detailed cross-sectional view of the eye of FIG. 14A depicted in the state shown in FIG. 15F.

In the present example, after the operator has confirmed that needle (30) has been properly advanced by visualizing the tenting effect described above, the operator infuses a balanced salt solution (BSS) or other similar solution as needle (30) is advanced relative to cannula (20). Such a BSS solution may form a leading bleb (340) ahead of needle (30) as needle (30) is advanced through choroid (306). Leading bleb (340) may be desirable for two reasons. First, as shown in FIGS. 14I, 15F, and 17B, leading bleb (340) may provide a further visual indicator to an operator to indicate when needle (30) is properly positioned at the delivery site. Second, leading bleb (340) may provide a barrier between needle (30) and retina (308) once needle (30) has penetrated choroid (306). Such a barrier may push the retinal wall outwardly (as is best seen in FIGS. 15F and 17B), thereby minimizing the risk of retinal perforation as needle (30) is advanced to the delivery site. In some versions, a foot pedal is actuated in order to drive leading bleb (340) out from needle (30). Alternatively, other suitable features that may be used to drive leading bleb (340) out from needle (30) will be apparent to those of ordinary skill in the art in view of the teachings herein.

Once an operator visualizes leading bleb (340), an operator may cease infusion of BSS, leaving a pocket of fluid as can be seen in FIGS. 14I, 15F, and 17B. Next, a therapeutic agent (341) may be infused by actuating a syringe or other fluid delivery device as described above with respect to instrument (10). The particular therapeutic agent (341) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, and/or any other suitable therapeutic agent as will be apparent to those of ordinary skill in the art in view of the teachings herein. By way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein.

Figure 14J:
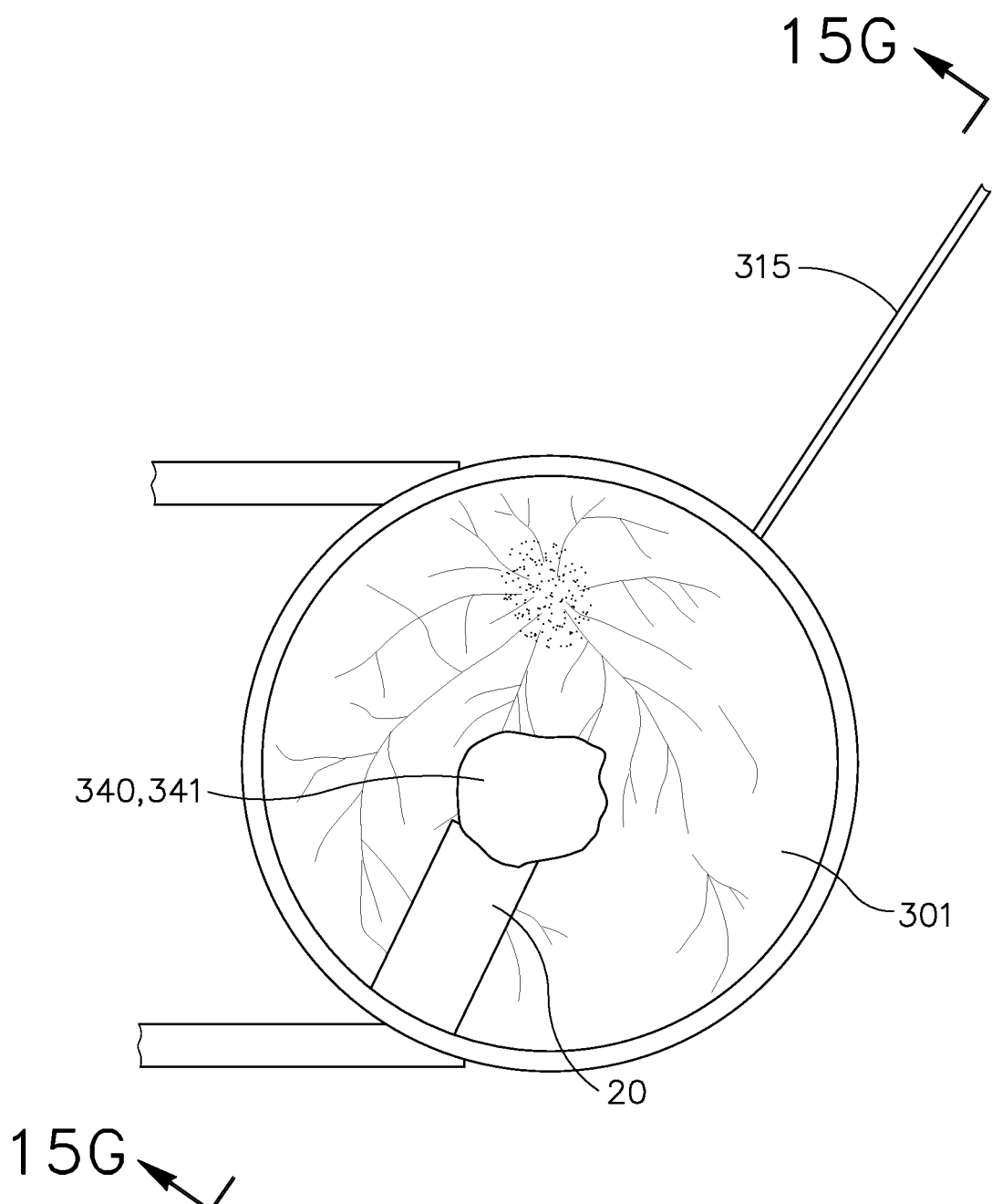
FIG. 14J depicts a top plan view of the eye of FIG. 14A, with the needle dispensing a therapeutic agent to the eye at the back of the eye, between the sclera and choroid.
Figure 15G:
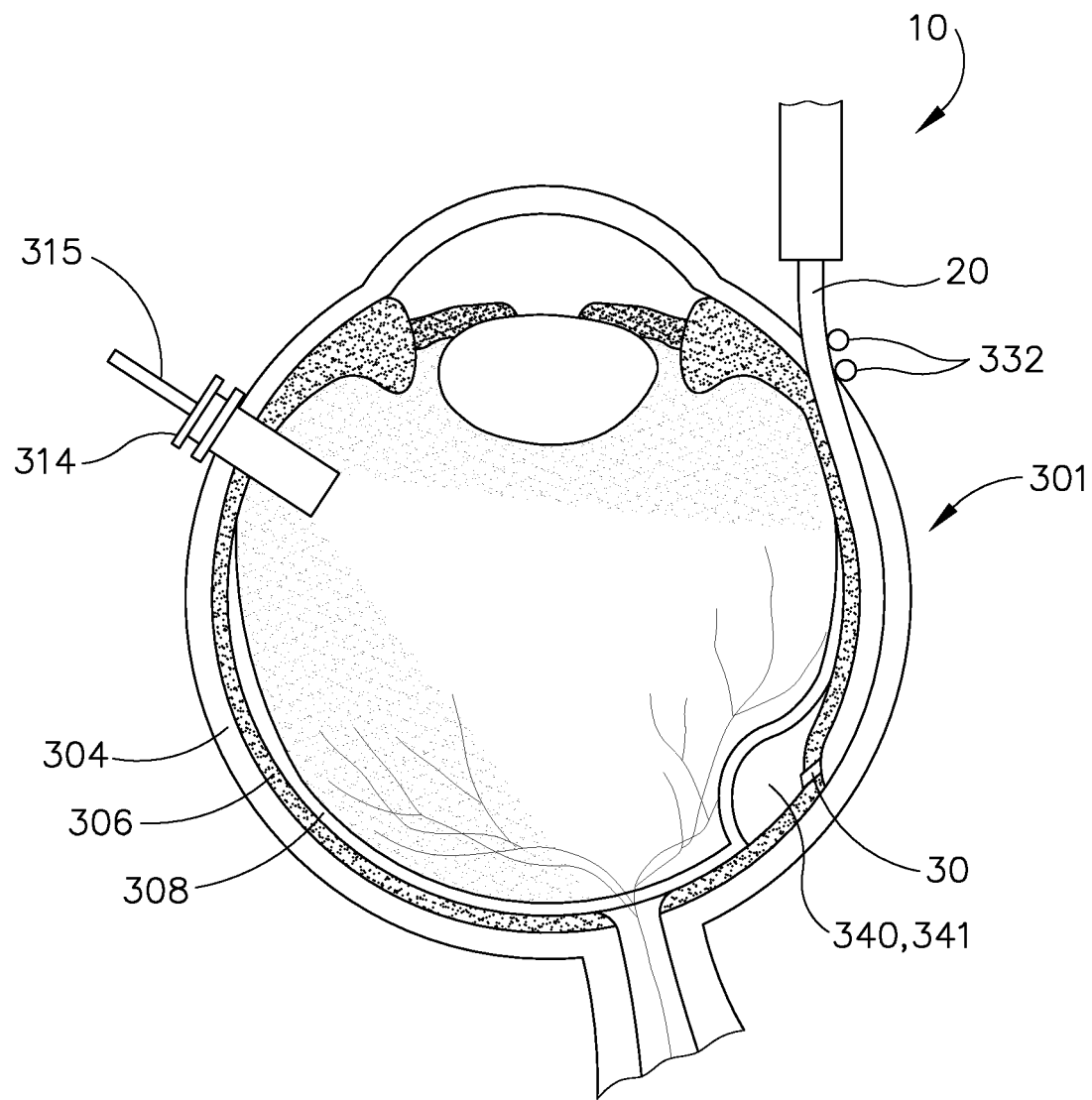
FIG. 15G depicts a cross-sectional view of the eye of FIG. 14A, with the cross-section taken about line 15G-15G of FIG. 14J.
Figure 17C:
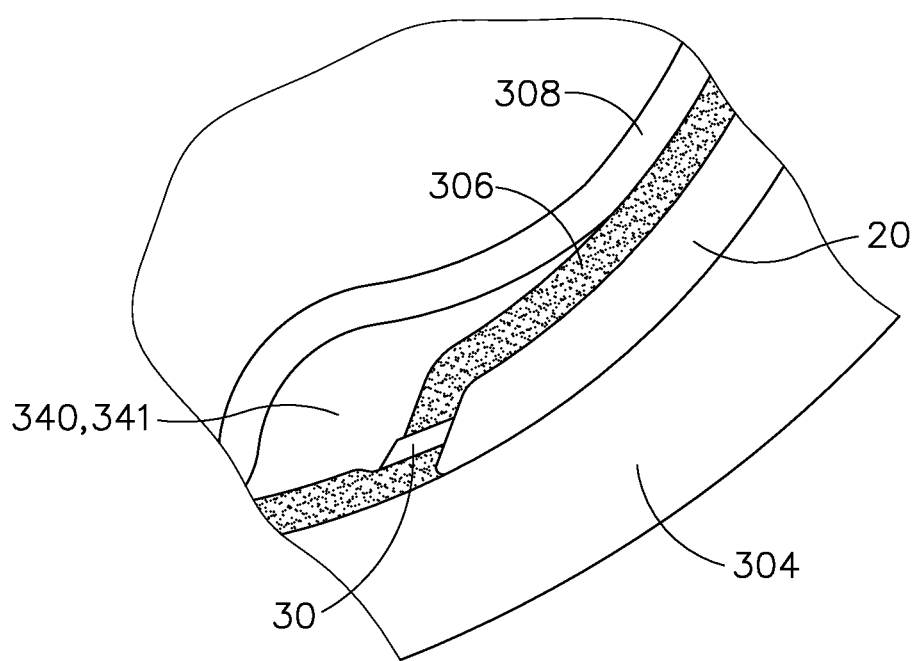
FIG. 17C depicts a detailed cross-sectional view of the eye of FIG. 14A depicted in the state shown in FIG. 15G.

In the present example, the amount of therapeutic agent (341) that is ultimately delivered to the delivery site is approximately 50 µL, although any other suitable amount may be delivered. In some versions, a foot pedal is actuated in order to drive agent (341) out from needle (30). Alternatively, other suitable features that may be used to drive agent (341) out from needle (30) will be apparent to those of ordinary skill in the art in view of the teachings herein. Delivery of therapeutic agent (341) may be visualized by an expansion of the pocket of fluid (340, 341) as can be seen in FIGS. 14J, 15G, and 17C. As shown, therapeutic agent (341) essentially mixes with the fluid of leading bleb (340) as therapeutic agent (341) is injected into the surprachoroidal space.

Once delivery is complete, needle (20) may be retracted by sliding actuation assembly (60) proximally relative to body (40); and cannula (30) may then be withdrawn from eye (301). It should be understood that because of the size of needle (20), the site where needle (20) penetrated through choroid (306) is self sealing, such that no further steps need be taken to seal the delivery site through choroid (306). Suture loop assembly (330) and chandelier (314) may be removed, and incision (316) in the sclera (304) may be closed using any suitable conventional techniques.

As noted above, the foregoing procedure may be carried out to treat a patient having macular degeneration. In some such instances, the therapeutic agent (341) that is delivered by needle (20) may comprise cells that are derived from postpartum umbilicus and placenta. As noted above, and by way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (20) may be used to deliver any other suitable substance or substances, in addition to or in lieu of those described in U.S. Pat. No. 7,413,734 and/or elsewhere herein. By way of example only, therapeutic agent (341) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

V. Exemplary Alternative Instruments and Features

In some examples, it may be desirable to vary certain components or features of the instruments described herein. For instance, it may be desirable to utilize instruments similar to instrument (10) with alternative mechanisms to actuate needle (30). Yet in other examples, it may be desirable to utilize instruments similar to instrument (10) equipped with different cannula (20) or needle (30) geometries. Instruments having the above referenced variations may be desirable for different surgical procedures, or surgical procedures similar to the procedure discussed above, to engage tissue structures of having varying physical properties. While certain examples of variations are described herein, it should be understood that the instruments described herein may include any other alternative features as will be apparent to those of ordinary skill in the art in view of the teachings herein.

A. Exemplary Alternative Instrument with Rotatable Actuation Feature

FIGS. 18-21 show an exemplary alternative instrument (410) that is similar to instrument (10) described above. It should be understood that instrument (410) may be readily used in place of instrument (10) to perform the medical procedure described above. It should also be understood that except as otherwise described herein, instrument (410) of this example is substantially the same as instrument (10) described above. Similar to instrument (10), instrument (410) comprises a cannula (420), a body (440), and an actuation assembly (460). Cannula (420) is substantially the same as cannula (20) described above, such that the particular details of cannula (420) will not be described further. Body (440) is also substantially the same as body (40) described above, except body (440) is configured with a more compact form factor. Accordingly, further details of body (440) will not be described herein.

Figure 18:
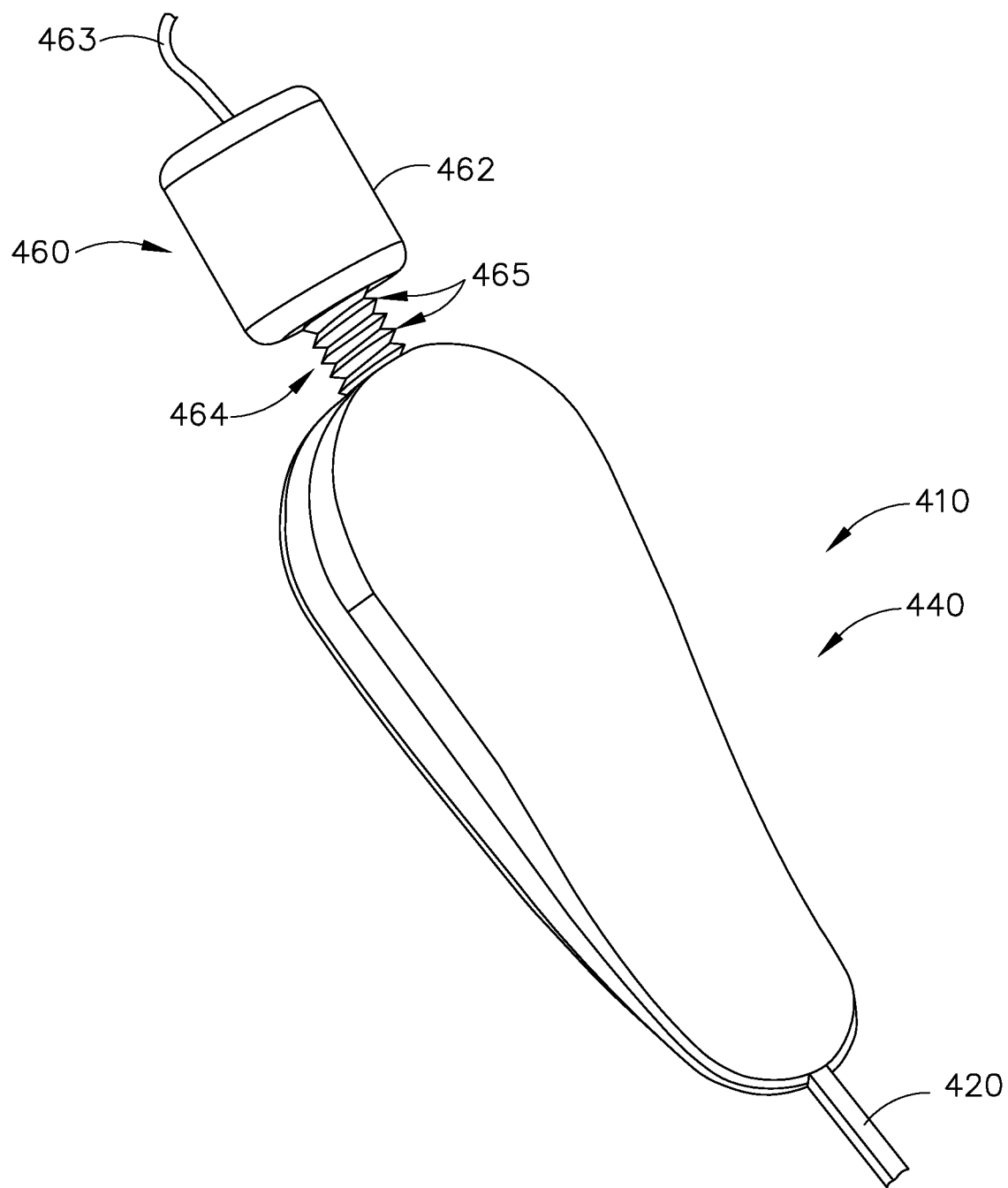
FIG. 18 depicts a perspective view of an exemplary alternative instrument for suprachoroidal administration of a therapeutic agent.
Figure 19:
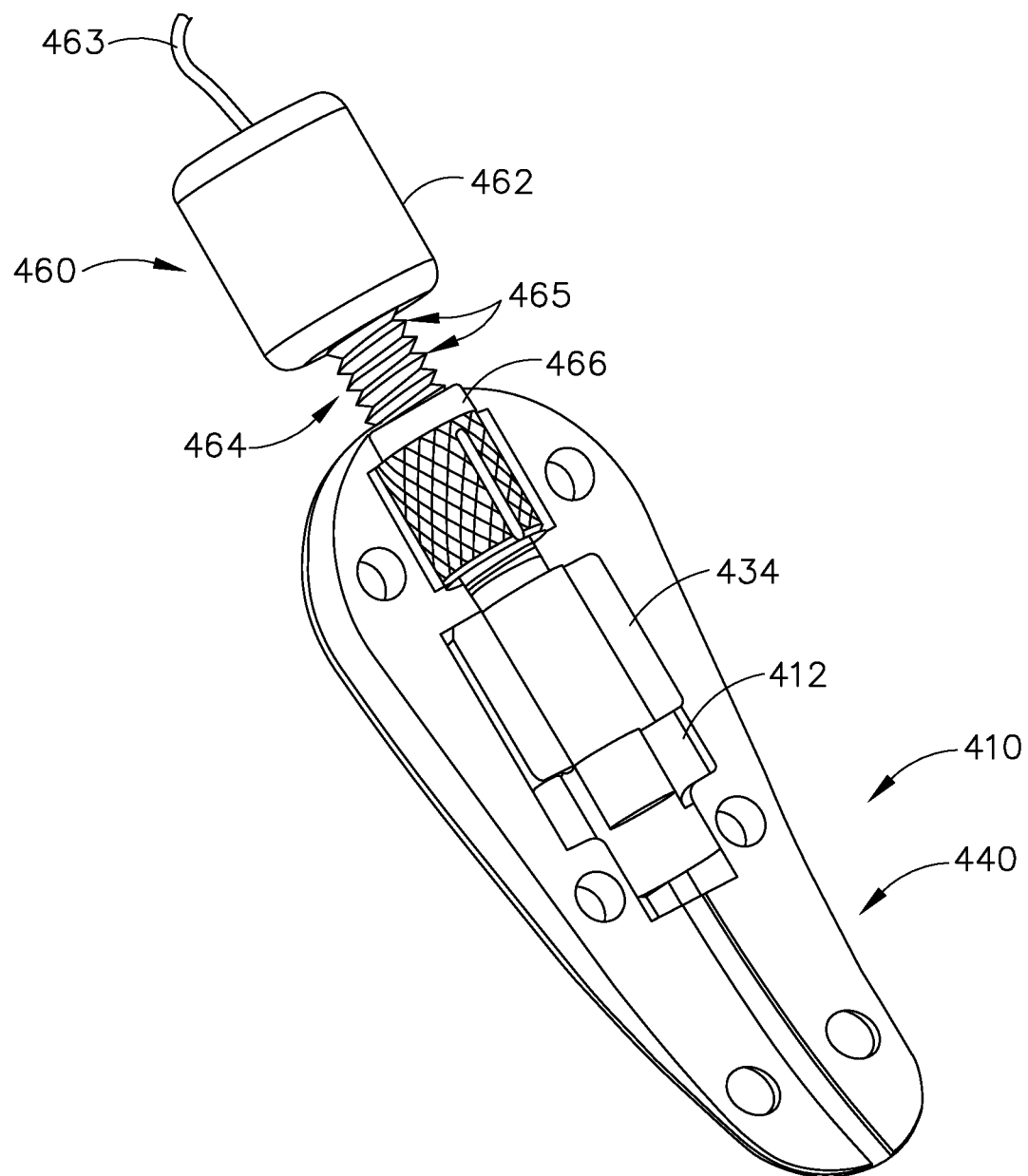
FIG. 19 depicts another perspective view of the instrument of FIG. 18, with a portion of a body removed.

The primary difference between instrument (10) and instrument (410) is that actuation assembly (460) of instrument (410) is rotatable instead of slidable. As can be seen in FIGS. 18 and 19, actuation assembly (460) includes a rotary actuation member (462), a threaded member (464) and a threaded receiving member (466). Actuation member (462) is generally cylindrical and is configured to be grasped by an operator's fingers. Additionally, in some examples, actuation member (462) may include a rubberized surface, knurling, ridges, and/or other features configured to enhance the gripability of actuation member (462). A fluid supply tube (463) passes through a central bore (not shown) formed through actuation member (462) and is coupled with the proximal end of needle (430). Thus, fluid supply tube (463) may be used to supply a therapeutic agent and/or other fluids to needle (430). Fluid supply tube (463) is not secured to actuation member (462) or threaded member (464), such that fluid supply tube (463) will not rotate or become twisted when actuation member (462) and threaded member (464) are rotated.

Threaded member (464) extends distally from actuation member (462) and includes threading (465) on the exterior of threaded member (464). Threaded member (464) has a length suitable to actuate a needle (430) a predetermined length when threaded member (464) is rotated relative to receiving member (466) by actuation member (462), as will be described in greater detail below. The length of threaded member (464) is further suitable to extend through threaded receiving member (466) to engage a needle body (434) on the proximal end of needle (430). Needle body (434) is slidable on a track (412) disposed within body (410). As will be described in greater detail below, needle body (434) together with track (412) generally defines the range of motion of needle (430). Needle body (434) is fixedly secured to the proximal end of needle (430) and is rotatably secured to the distal end of threaded member (464). Thus, needle body (434) translates with threaded member (464) relative to body (440) yet needle body (434) does not rotate with threaded member (464) relative to body (440).

Threaded receiving member (466) is fixedly secured within body (440) and is generally configured to receive threaded member (464). Threaded receiving member (466) is generally cylindrical with a threaded bore (not shown) extending through threaded receiving member (466). The exterior of threaded receiving member (466) may include a knurled surface to maintain the position of threaded receiving member (466) relative to body (440). Of course, knurled surface is merely optional and in other examples, threaded receiving member (466) may be secured within body (440) by mechanical fastening mechanisms, adhesive bonding, and/or other structures or techniques.

The threaded bore of threaded receiving member (466) includes threading that is complementary to threading (465) on the exterior of threaded member (464). Thus, threaded receiving member (466) is configured to receive threaded member (464) such that threaded member (464) may be advanced distally or proximally by turning threaded member (464) in a given direction. In other words, threaded member (464) may serve as a translating lead screw while threaded receiving member (466) serves as a stationary nut.

Figure 21:
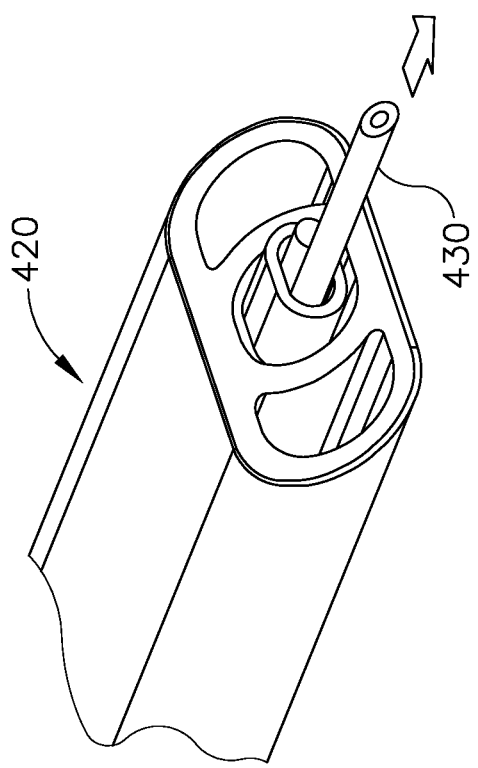
FIG. 21 depicts a perspective view of the distal end of a cannula of the instrument of FIG. 18, with a needle actuated relative to the cannula.
Figure 20:
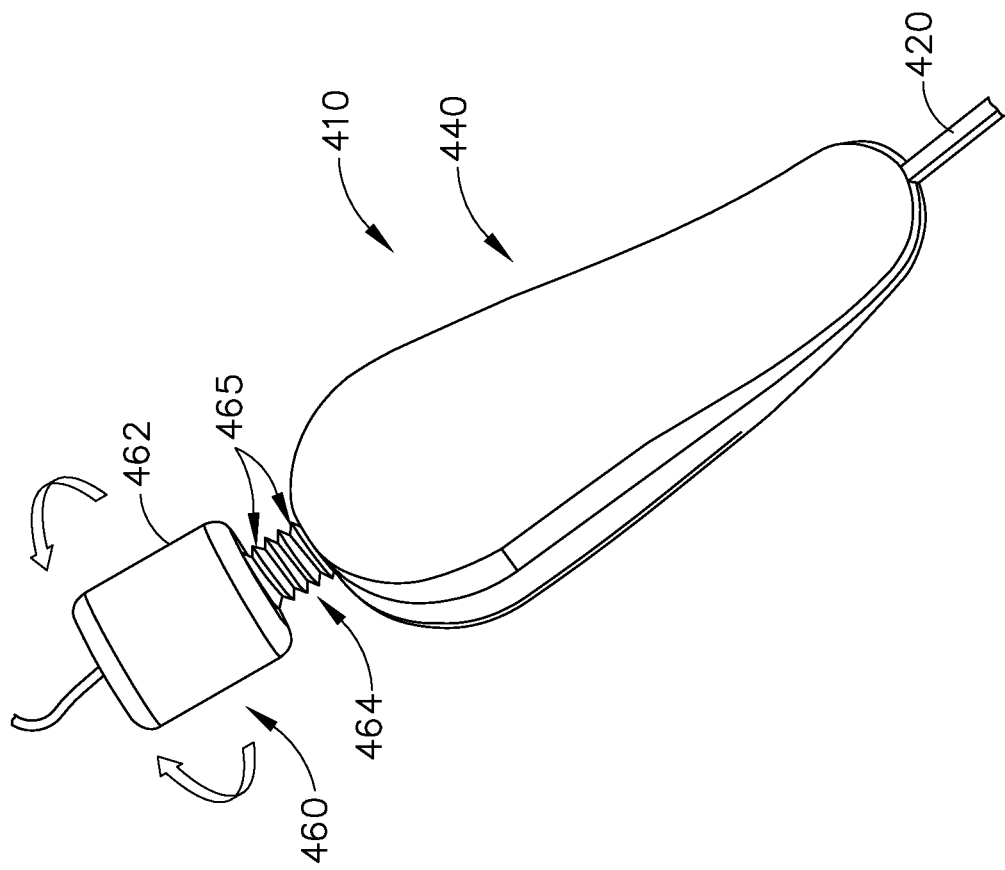
FIG. 20 depicts another perspective view of the instrument of FIG. 18, with an actuation member being actuated.

In an exemplary mode of operation, as can be seen in FIGS. 20 and 21, needle (430) is generally advanced relative to cannula (420) by an operator rotating actuation member (462). In particular, rotation of actuation member (462) causes threaded member (464) to correspondingly rotate. Rotation of threaded member (464) relative to threaded receiving member (466) causes threaded member (464) to translate relative to body (410) because threaded receiving member (466) is fixed relative to body (410). As threaded member (464) translates, threaded member (464) pushes needle body (434) distally along track (412). Distal movement of needle body (434) in turn leads to distal movement of needle (430) relative to body (410) and cannula (420).

An operator may continue to rotate actuation member (462) until needle (430) has been advanced a desired amount relative to cannula (420). Alternatively, if an operator continues to rotate actuation member (462) indefinitely, further rotation will eventually be prevented by needle body (434) reaching the distal end of track (412). The operator may then deliver fluid and/or a therapeutic agent via needle (430). An operator may then desire to retract needle (430). At such a point an operator may simply reverse the rotation of actuation member (462). Reversal of rotation of actuation member (462) causes threaded member (464) to translate proximally relative to body (410). This in turn causes needle body (434) to retract proximally relative to body (410); and needle (430) to retract proximally relative to cannula (420). In some versions, instrument (410) includes a resilient member providing a proximal bias to needle (430), thereby further assisting in retraction of needle (430) relative to cannula (420).

B. Exemplary Alternative Cannula

Figure 22:
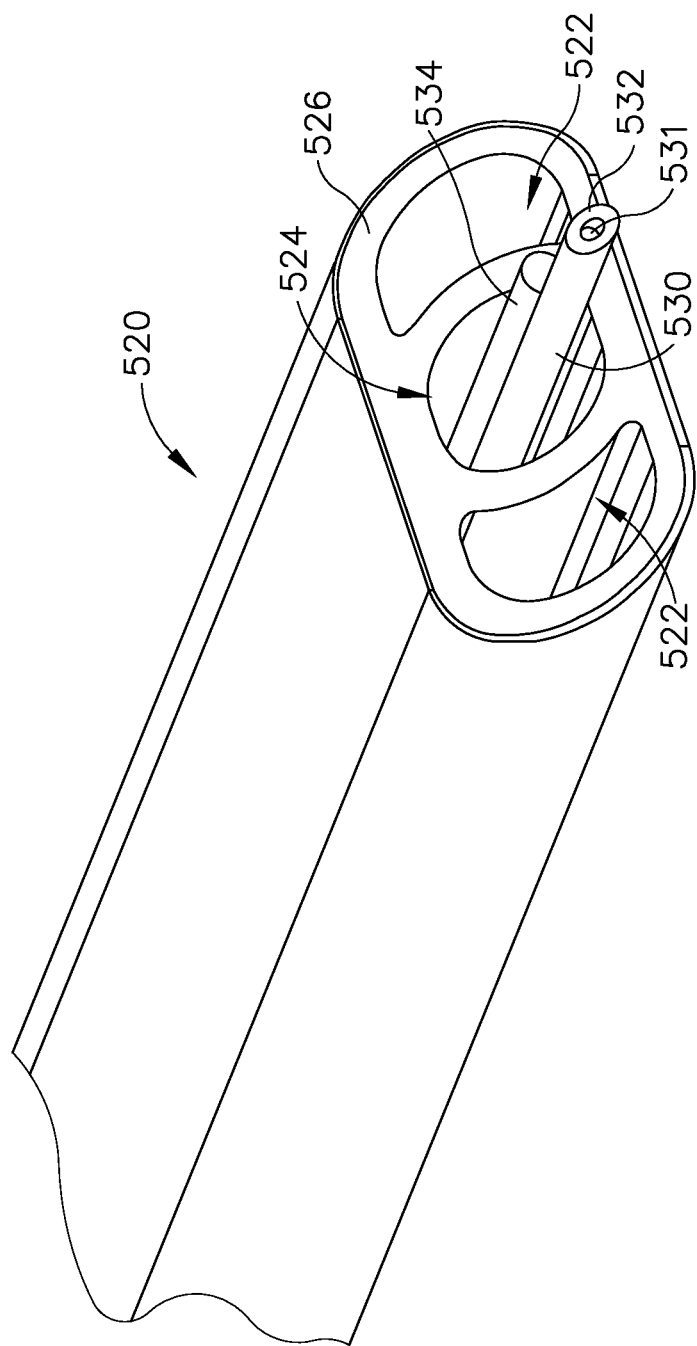
FIG. 22 depicts a perspective view of the distal end of an exemplary alternative cannula for use with the instrument of FIG. 1.
Figure 23:
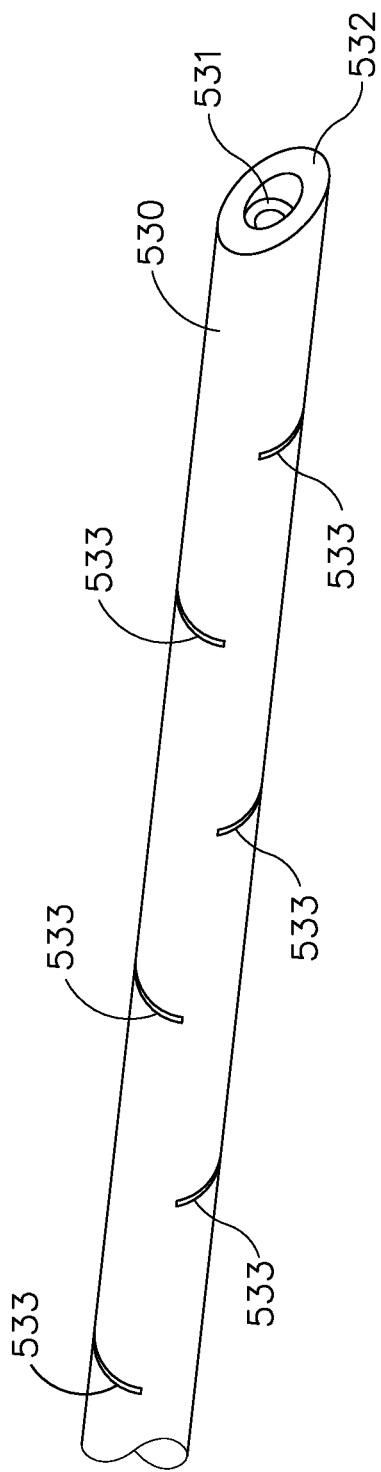
FIG. 23 depicts a perspective view of the distal end of a needle of the cannula of FIG. 22.

FIGS. 22 and 23 show an exemplary alternative cannula (520) for use with instruments (10, 410) described above. Cannula (520) is substantially the same as cannula (20) described above. For instance, like with cannula (20), cannula (520) is flexible enough to conform to the specific structures and contours of a patient's eye, yet cannula (520) is rigid enough to permit advancement without buckling. As can be seen in FIG. 22, cannula (520), like cannula (20), comprises three lumens (522, 524) extending longitudinally through cannula (520) and terminating at a beveled distal end (526). Lumens (522, 524) and beveled distal end (526) are substantially the same as lumens (22, 24) and beveled distal end (26), described above, such that the particular details of these elements will not be described herein.

Cannula (520) of the present example includes a needle (530) and an optical fiber (534). Optical fiber (534) is substantially the same as optical fiber (34), described above, such that the particular details of optical fiber (534) will not be repeated here. Needle (530) is similar to needle (30) described above, except needle (530) of the present example comprises features to enhance the flexibility of needle (530). In particular, as can best be seen in FIG. 23, needle (530) comprises an inner liner (531), a sharp distal end (532), and a series of alternating slits (533) in the outer surface of needle (530). Inner liner (531) comprises a polyimide or other similar material. Inner liner (531) is generally operable to seal needle (530) relative to slits (533).

Sharp distal end (532) is similar to sharp distal end (32) described above, except sharp distal end (532) comprises a single bevel configuration. In particular, sharp distal end (532) is shown as having a single 45° bevel relative to the longitudinal axis of needle (530). Like with sharp distal end (32), sharp distal end (532) may be formed by grinding or laser cutting. It should be understood that although a 45° bevel is shown, any other suitable bevel angle may be used. For instance, in some examples the bevel angle may range from 25° to 50° relative to the longitudinal axis of needle.

Slits (533) are arranged in an alternating pattern along the top and bottom of needle (530). In particular, slits (533) are constructed by transversely laser cutting each slit approximately half way through needle (530) from either the top or the bottom of needle (530). Each slit (533) is in a spaced apart relationship relative to another subsequent slit (533). Although a particular spacing is shown, it should be understood that any suitable spacing may be used. For instance, slits (533) of the present example are configured to enhance the flexibility of needle (530) to permit needle (530) to be bendable away from a straight longitudinal axis of needle (530). Accordingly, in other examples, needle (530) may be equipped with a greater number of slits (533) being oriented more closely together to increase the bendability of needle (530). Still in other examples, needle (530) may include fewer slits (533) being oriented further apart to increase the stiffness or decrease the bendability of needle (530). Of course, any other suitable configuration of slits (533) may be used as will be apparent to those of ordinary skill in the art in view of the teachings herein. It should also be understood that guide member (36) is omitted from this example, though guide member (36) may instead be included if desired.

Figure 24:
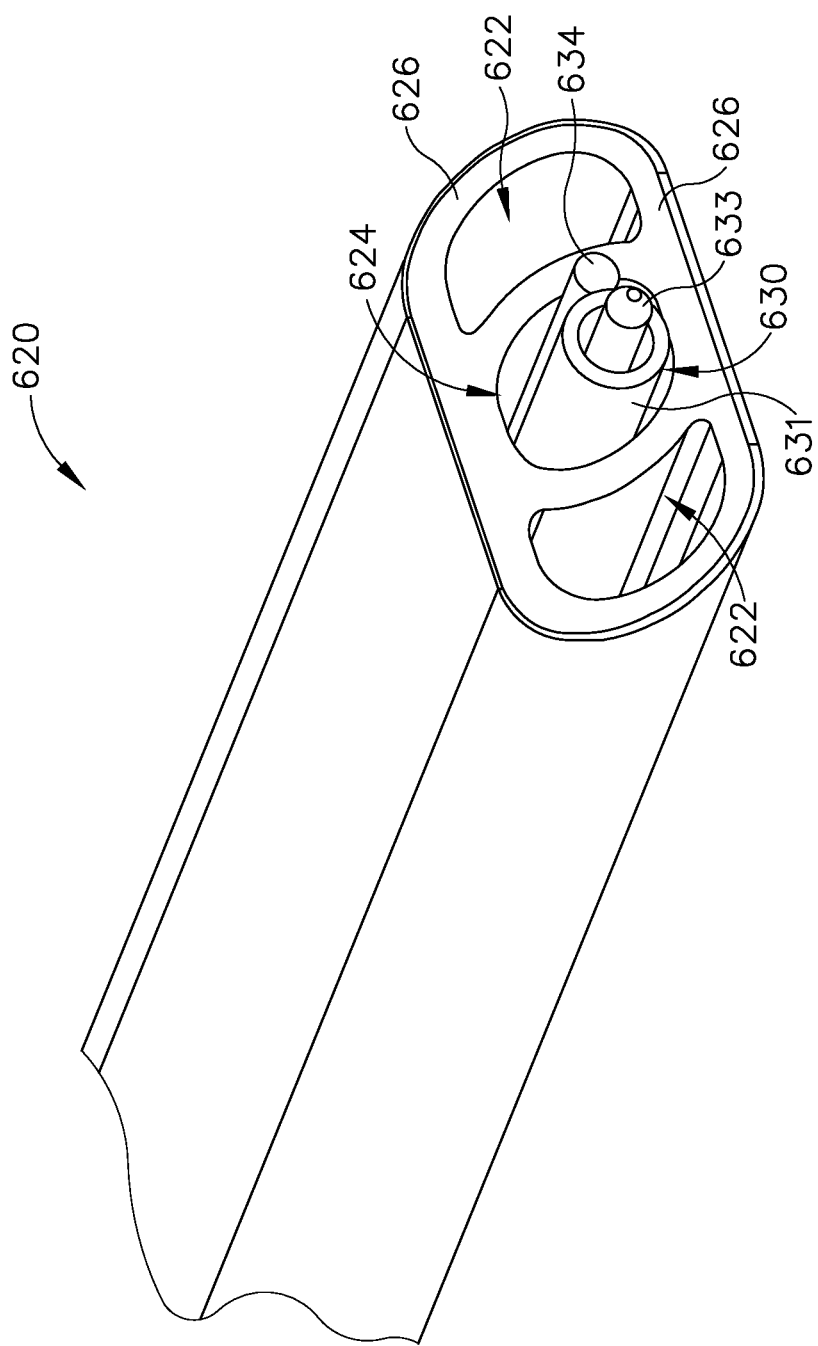
FIG. 24 depicts a perspective view of the distal end of another exemplary alternative cannula for use with the instrument of FIG. 1.
Figure 25:
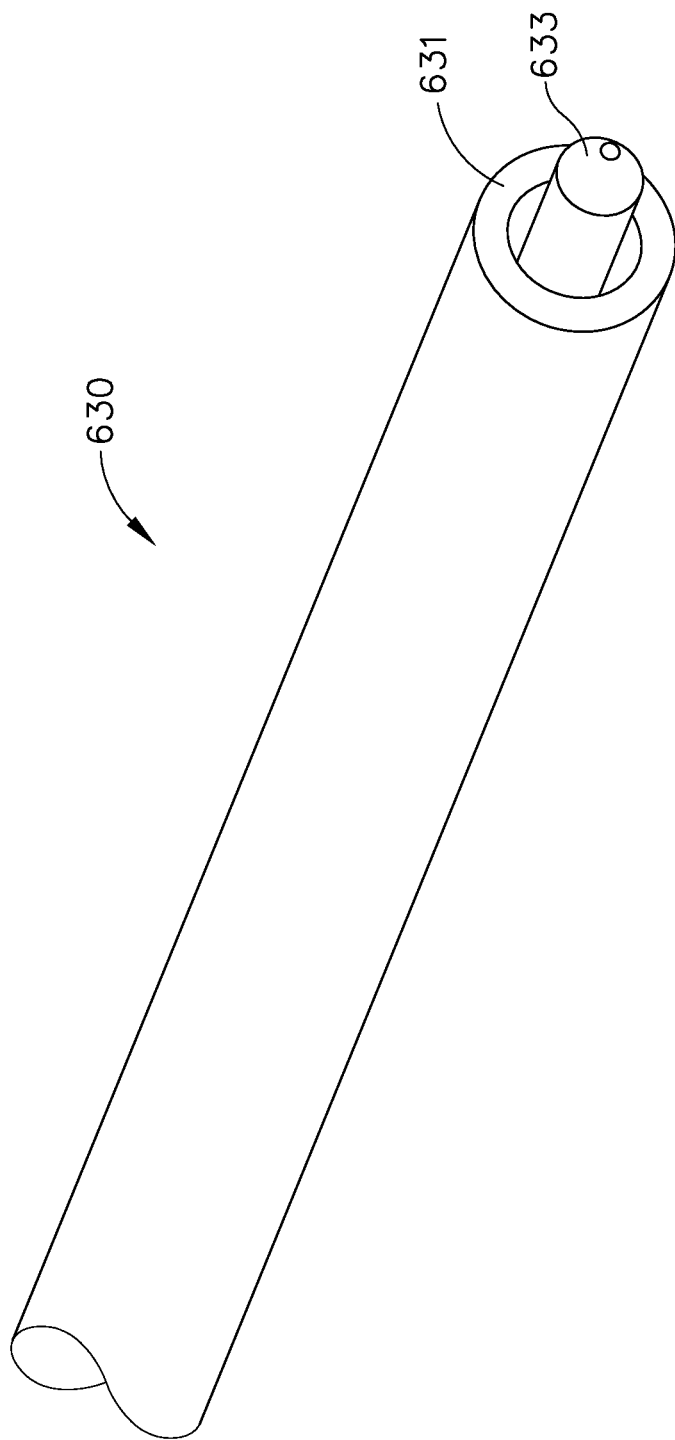
FIG. 25 depicts a perspective view of the distal end of a needle of the cannula of FIG. 24.

FIGS. 24 and 25 show still another alternative cannula (620) for use with instruments (10, 410) described above. Cannula (620) is substantially the same as cannula (20) described above. For instance, like with cannula (20), cannula (620) is flexible enough to conform to the specific structures and contours of a patient's eye, yet cannula (620) is rigid enough to permit advancement without buckling. As can be seen in FIG. 22, cannula (620), like cannula (20), comprises three lumens (622, 624) extending longitudinally through cannula (620) and terminating at a beveled distal end (626). Lumens (622, 624) and beveled distal end (626) are substantially the same as lumens (22, 24) and beveled distal end (26), described above, such that the particular details of these elements will not be repeated herein.

Cannula (620) of the present example includes a needle (630) and an optical fiber (634). Optical fiber (634) is substantially the same as optical fiber (34), described above, such that the particular details of optical fiber (634) will not be repeated here. Needle (630) is similar to needle (30) described above, except needle (630) of the present example comprises a needle cannula (631) and an inner core wire (633). In particular, as can best be seen in FIG. 25, inner core wire (633) is longitudinally disposed within needle cannula (631). Needle cannula (631) of the present example is an elongate hollow tube comprising plastic such as polycarbonate, polypropylene, and/or any other suitable material(s). The inner diameter of needle cannula (631) is configured to provide space for inner core wire (633) and to provide additional clearance for fluid flow. Thus, it should be understood that needle cannula (631) is configured to deliver fluid to the delivery site described above.

Inner core wire (633) comprises a wire consisting of stainless steel, nitinol, or etc. Inner core wire (633) of the present example has an outer diameter of approximately 1.3 µm, although any other suitable diameter may be used. Inner core wire (633) includes a sharp distal tip (632). Unlike sharp distal tips (32, 532) described above, sharp distal tip (632) of the present example is conical in shape such that sharp distal tip (632) tapers to a point that is located on the central longitudinal axis of inner core wire (633). Sharp distal tip (632) may taper at any suitable slope as will be apparent to those of ordinary skill in the art in view of the teachings herein.

In an exemplary use, needle cannula (631) and inner core wire (633) are advanced simultaneously to pierce tissue. In particular, inner core wire (633) may lead needle cannula (631), with tip (632) being positioned distally relative to the distal end of needle cannula (631), as both needle cannula (631) and inner core wire (633) are advanced relative to cannula (620). Because inner core wire (633) leads needle cannula (631), inner core wire (633) may contact tissue first and begin to penetrate via sharp distal tip (632). As both needle cannula (631) and inner core wire (633) are advanced further, needle cannula (631) may begin to penetrate the tissue through an opening created by sharp distal tip (632). Needle cannula (631) may then deliver fluid through the tissue as described above.

Although needle cannula (631) and inner core wire (633) are described herein as being advanced simultaneously, it should be understood that in other examples needle cannula (631) and inner core wire (633) may be advanced separately. For instance, in one merely exemplary mode of operation, inner core wire (633) may first be advanced to penetrate tissue. Needle cannula (631) may then follow inner core wire (633) after tissue penetration to deliver fluid. In still other examples, needle cannula (631) may first be advanced to abut tissue. Inner core wire (633) may then be advanced to penetrate the tissue. Finally, needle cannula (631) may be advanced again to penetrate the tissue through an opening created by inner core wire (633). Of course, outer cannula (621) and inner core wire (633) may be used in any other suitable sequence as will be apparent to those of ordinary skill in the art in view of the teachings herein. It should also be understood that guide member (36) is omitted from this example, though guide member (36) may instead be included if desired.

Figure 26:
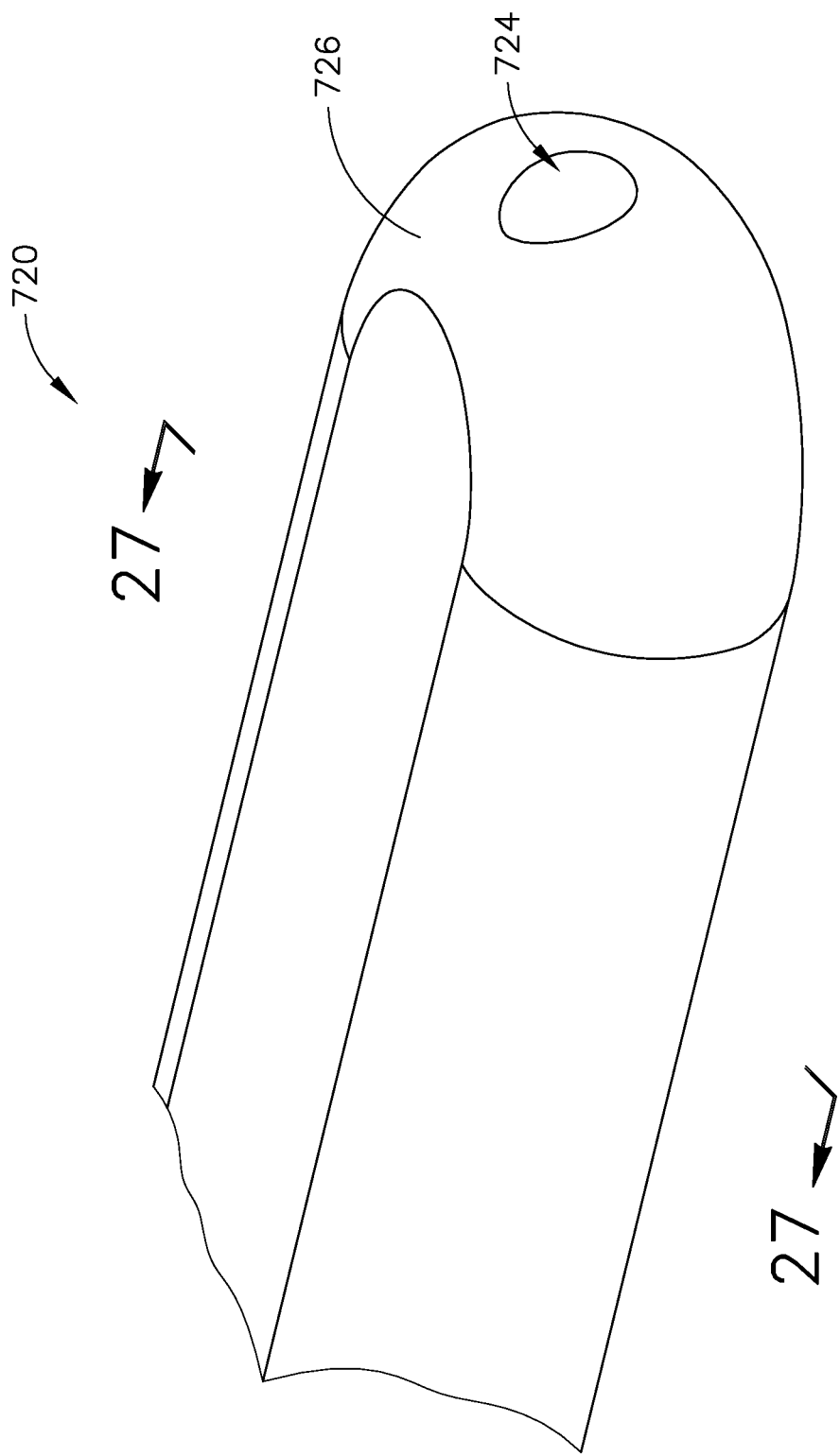
FIG. 26 depicts a perspective view of the distal end of an another exemplary alternative cannula for use with the instrument of FIG. 1.
Figure 27:
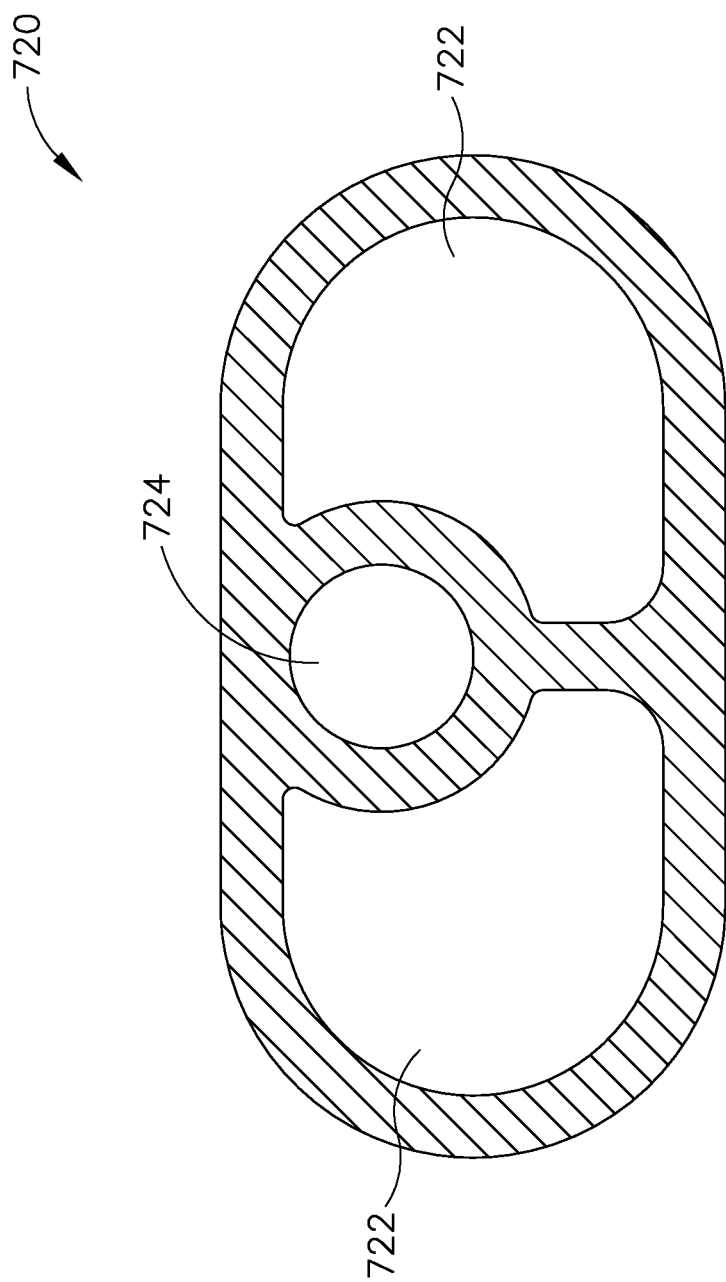
FIG. 27 depicts a cross-sectional view of the cannula of FIG. 26, with the cross-section taken along line 27-27 of FIG. 26.

FIGS. 26 and 27 show yet another exemplary alternative cannula (730) that may be used with instruments (10, 410) described above. Cannula (720) is similar to cannula (20) described above. For instance, like with cannula (20), cannula (720) is flexible enough to conform to the specific structures and contours of a patient's eye, yet cannula (720) is rigid enough to permit advancement without buckling. However, unlike cannula (20), cannula (720) of the present example includes a blunt distal end (726) with a central lumen (724) opening therethough. Blunt distal end (726) may be desirable over other distal ends (26, 526, 626), described herein, to reduce trauma as cannula (720) is advanced within tissue structures of a patient's eye. In particular, blunt distal end (726) is rounded such that cannula (720) includes no corners that may catch tissue as cannula (720) is advanced through tissue of a patient's eye. Although blunt distal end (726) is shown as having particular radii of curvature (i.e., along a vertical dimension and along a horizontal dimension), it should be understood that blunt distal end (726) may be rounded with any suitable radii as will be apparent to those of ordinary skill in the art in view of the teachings herein.

As can be seen in FIG. 27, although blunt distal end (726) includes only central lumen (724) opening therethrough, cannula (720) still includes three lumens (722, 724) similar to cannula (20) described above. In particular, two side lumens (722) extend longitudinally though cannula (720) much like side lumens (22) described above. However, unlike side lumens (22), side lumens (722) are closed at their respective distal ends by blunt distal end (726). Central lumen (724) also extends longitudinally though cannula (720), although as described above central lumen (724) also extends through blunt distal end (726). Central lumen (724), like central lumen (24) described above, is configured to slidably receive a suitable needle similar to needles (30, 530, 630) described herein.

Figure 28:
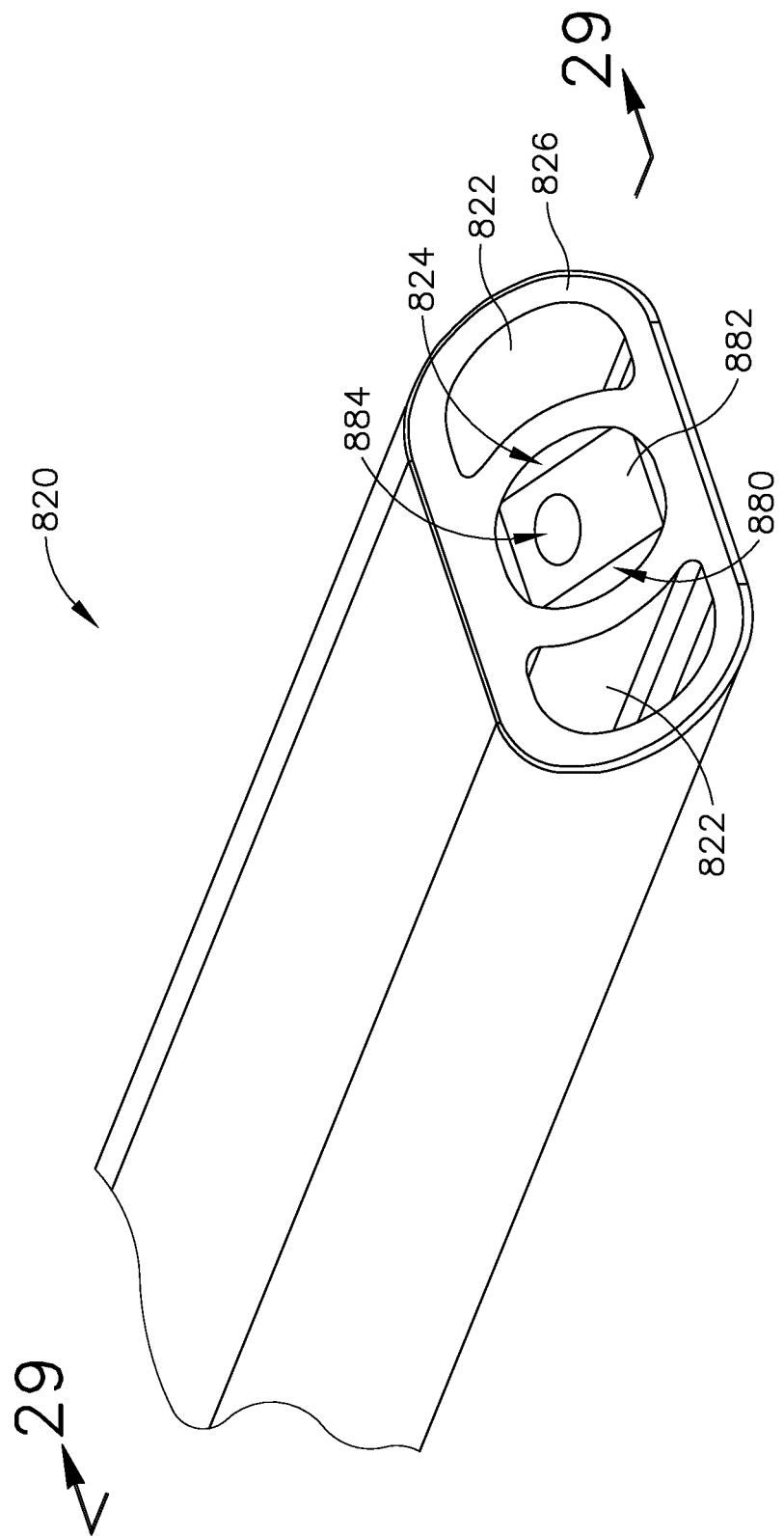
FIG. 28 depicts a perspective view of the distal end of an exemplary alternative cannula for use with the instrument of FIG. 1.
Figure 29:
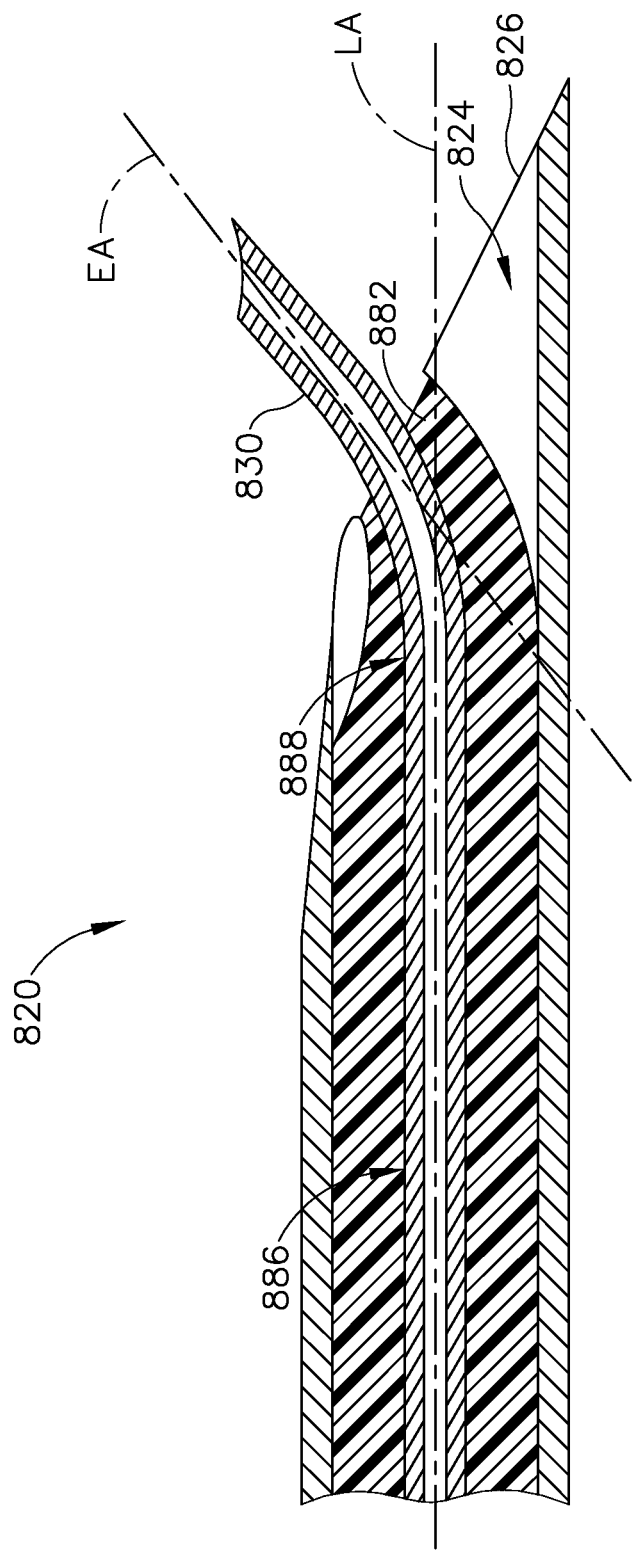
FIG. 29 depicts a cross-sectional view of the cannula of FIG. 28, with the cross-section taken along line 29-29 of FIG. 28.

FIGS. 28 and 29 show an exemplary alternative cannula (820) for use with instruments (10, 410) described above. Cannula (820) is substantially the same as cannula (20) described above. For instance, like with cannula (20), cannula (820) is flexible enough to conform to the specific structures and contours of a patient's eye, yet cannula (820) is rigid enough to permit advancement without buckling. As can be seen in FIG. 28, cannula (820), like cannula (20), comprises two side lumens (822) and a single central lumen (824) extending longitudinally through cannula (820) and terminating at a beveled distal end (826). Lumens (822, 824) and beveled distal end (826) are substantially the same as lumens (22, 24) and beveled distal end (26), described above, such that the particular details of these elements will not be described herein. To maintain the atraumatic nature of beveled distal end (826), needle guide (880) may be disposed within lumen such that a distal face (882) of needle guide (880) is either flush with beveled distal end (826) or slightly proximal to beveled distal end (826).

Unlike cannula (20), cannula (820) includes a needle guide (880) disposed within central lumen (824) and no optical fiber. Needle guide (880) is generally configured to direct a needle (830) upwardly at an angle relative to the longitudinal axis of cannula (820). In the present example, needle guide (880) is comprised of stainless steel, though it should be understood that any other suitable biocompatible material(s) may be used. The shape of needle guide (880) is configured for insertion into central lumen (824). In the present example, needle guide (880) is secured within central lumen (824) by a press or interference fit, although in other examples, adhesives, mechanical locking mechanisms, and/or other structures or techniques may be used to secure needle guide (880).

As can best be seen in FIG. 29, needle guide (880) defines an internal lumen (882) that is configured to slidably receive needle (830). In particular, internal lumen (882) includes a generally straight proximal portion (886) and a curved distal portion (888). Straight proximal portion (886) corresponds to the longitudinal axis of cannula (820), while curved distal portion (888) curves upwardly away from the longitudinal axis (LA) of cannula (820). Curved distal portion (888) of the present example is curved to direct needle (830) along a path that extends distally from cannula (820) along an exit axis (EA) that is at an angle of approximately 7° to approximately 9° relative to the longitudinal axis (LA) of cannula (820). It should be understood that such an angle may be desirable to deflect needle (830) in a direction to ensure penetration of needle into the choroid (306) and to minimize the possibility of needle (830) continuing beneath the choroid (306) through the suprachoroidal space (as opposed to penetrating through the choroid (306)). It should be further understood that such an angle may be desirable to deflect needle (830) in a direction to minimize the risk of needle (830) perforating the retina after entering the suprachoroidal space. For instance in some examples, if such an angle is too steep, needle (830) may have a tendency to perforate the retina (308). If the angle is too shallow, needle (830) may fail to penetrate the choroid (306). By way of further example only, curved distal portion (888) may urge needle (830) to exit cannula (820) along an exit axis (EA) that is oriented at an angle within the range of approximately 5° to approximately 30° relative to the longitudinal axis (LA) of cannula (820); or more particularly within the range of approximately 5° to approximately 20° relative to the longitudinal axis (LA) of cannula (820); or more particularly within the range of approximately 5° to approximately 10° relative to the longitudinal axis (LA) of cannula (820).

In some examples, the desired effect of altering the angle of needle (830) relative to cannula (820) may be achieved without needle guide (880). For instance, in some examples needle (830) may be pre-bent such that needle (830) is resiliently biased to a desired angle (e.g., 20°). In such examples, needle (830) may be constrained to follow a substantially straight path within cannula (820); then advance distally relative to cannula (820) in a position that is angled relative to cannula (820). Still in other examples, cannula (820) itself may be configured to direct needle (830) at an angle using a curved lumen similar to curved distal portion (888) of needle guide (880). Yet in other examples the angle of needle (830) may be altered by any other suitable means as will be apparent to those of ordinary skill in the art in view of the teachings herein.

Figure 31A:
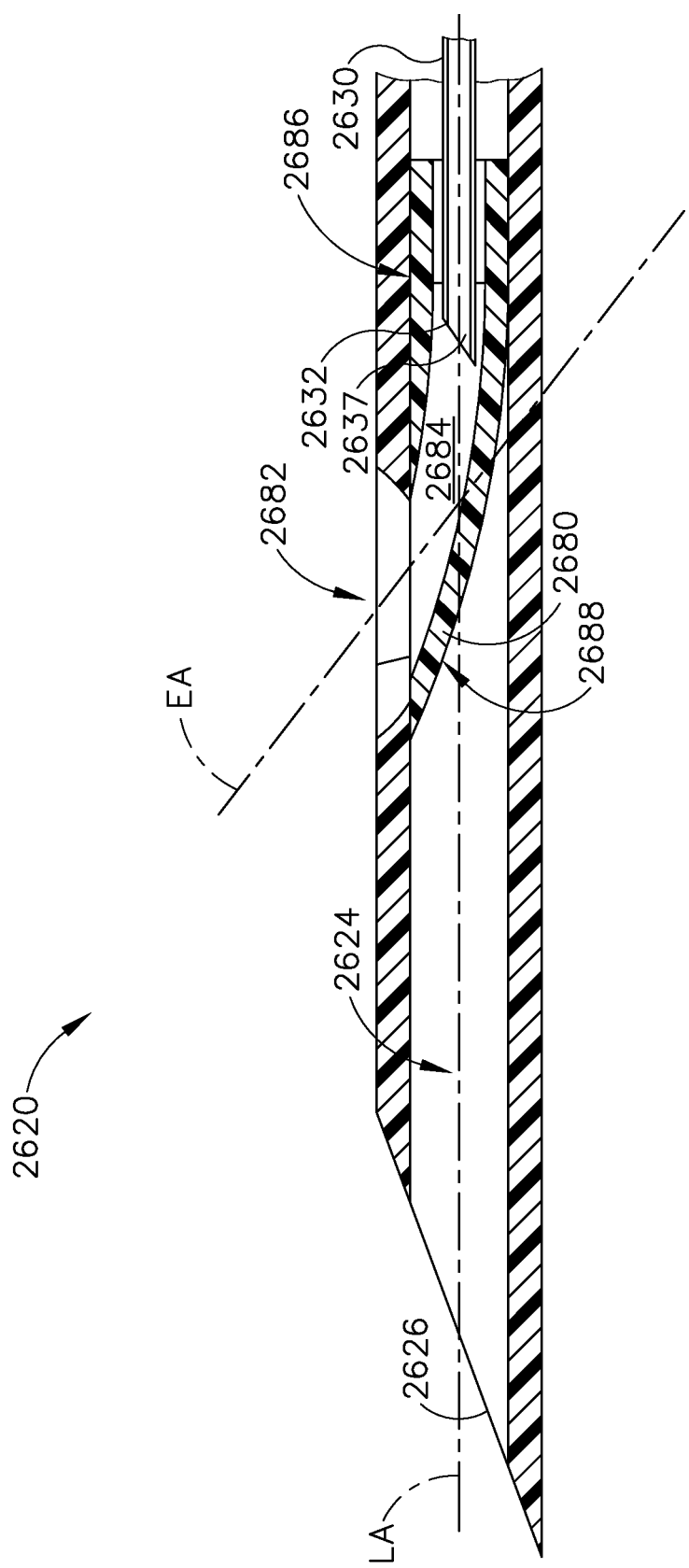
FIG. 31A depicts a cross-sectional view of the cannula of FIG. 30, with the cross-section taken along line 31-31 of FIG. 30.

FIGS. 30 and 31A show an exemplary alternative cannula (2620) for use with instruments (10, 410) described above. Cannula (2620) is substantially the same as cannula (20) described above. For instance, like with cannula (20), cannula (2620) is flexible enough to conform to the specific structures and contours of a patient's eye, yet cannula (2620) is rigid enough to permit advancement without buckling. As can be seen in FIG. 30, cannula (2620), like cannula (20), includes a pair of opposing rounded sides and a pair of opposing flat sides adjacent to the rounded sides and comprises two side lumens (2622) and a single central lumen (2624) extending longitudinally through cannula (2620) and terminating at a beveled distal end (2626). Lumens (2622, 2624) and beveled distal end (2626) are substantially the same as lumens (22, 24) and beveled distal end (26), described above, such that the particular details of these elements will not be described herein. A needle guide (2680) is disposed within lumen (2624) such that needle guide (2680) abuts a separate beveled opening (2682) within cannula (2620) that is laterally oriented on the upper surface of cannula (2620), proximal to beveled distal end (2626).

Unlike cannula (20), cannula (2620) includes a needle guide (2680) disposed within central lumen (2624). Needle guide (2680) is generally configured to direct a needle (2630) upwardly along an exit axis (EA) that is obliquely oriented relative to the longitudinal axis (LA) of cannula (2620) through beveled opening (2682) of cannula (2620). Needle guide (2680) may be formed of plastic, stainless steel, and/or any other suitable biocompatible material(s). The shape of needle guide (2680) is configured for insertion into central lumen (2624). In the present example, needle guide (2680) is secured within central lumen (2624) by a press or interference fit, although in other examples, adhesives and/or mechanical locking mechanisms may be used to secure needle guide (2680).

As can best be seen in FIG. 31A, needle guide (2680) defines an internal lumen (2684) that is configured to slidably receive needle (2630). In particular, internal lumen (2684) includes a generally straight proximal portion (2686) and a curved distal portion (2688). Straight proximal portion (2686) corresponds to the longitudinal axis (LA) of cannula (2620), while curved distal portion (2688) curves upwardly away from the longitudinal axis of cannula (2620). Curved distal portion (2688) of the present example is curved to direct needle (2630) along an exit axis (EA) that extends distally from cannula (2620) at an angle of approximately 7° to approximately 9° relative to the longitudinal axis (LA) of cannula (2620). It should be understood that such an angle may be desirable to deflect needle (2630) in a direction to ensure penetration of needle into the choroid (306) and to minimize the possibility of needle (2630) continuing beneath the choroid (306) through the suprachoroidal space (as opposed to penetrating through the choroid (306)) and the possibility of retinal perforation. By way of further example only, curved distal portion (2688) may urge needle (2630) to exit cannula (2620) along an exit axis (EA) that is oriented at an angle within the range of approximately 5° to approximately 30° relative to the longitudinal axis (LA) of cannula (2620); or more particularly within the range of approximately 5° to approximately 20° relative to the longitudinal axis (LA) of cannula (2620); or more particularly within the range of approximately 5° to approximately 10° relative to the longitudinal axis (LA) of cannula (2620).

Needle (2630) of the present example is substantially the same as needle (30) described above with respect to FIGS. 5A and 5B. In particular, needle (2630) has a sharp distal end (2632). Although not shown, like with distal end (32) described above, distal end (2632) of the present example is a tri-bevel configuration having three separate bevels (not shown) converging with each other to form distal end (2632). Similarly, because needle (2630) is a hypodermic needle, the bevels intersect with an opening (2637) in the distal end of needle (2630). Although needle (2630) is described herein as having three bevels, in other examples distal end (32) may include any other suitable number of bevels having any suitable bevel angle as similarly described above with respect to distal end (2632).

Figure 31B:
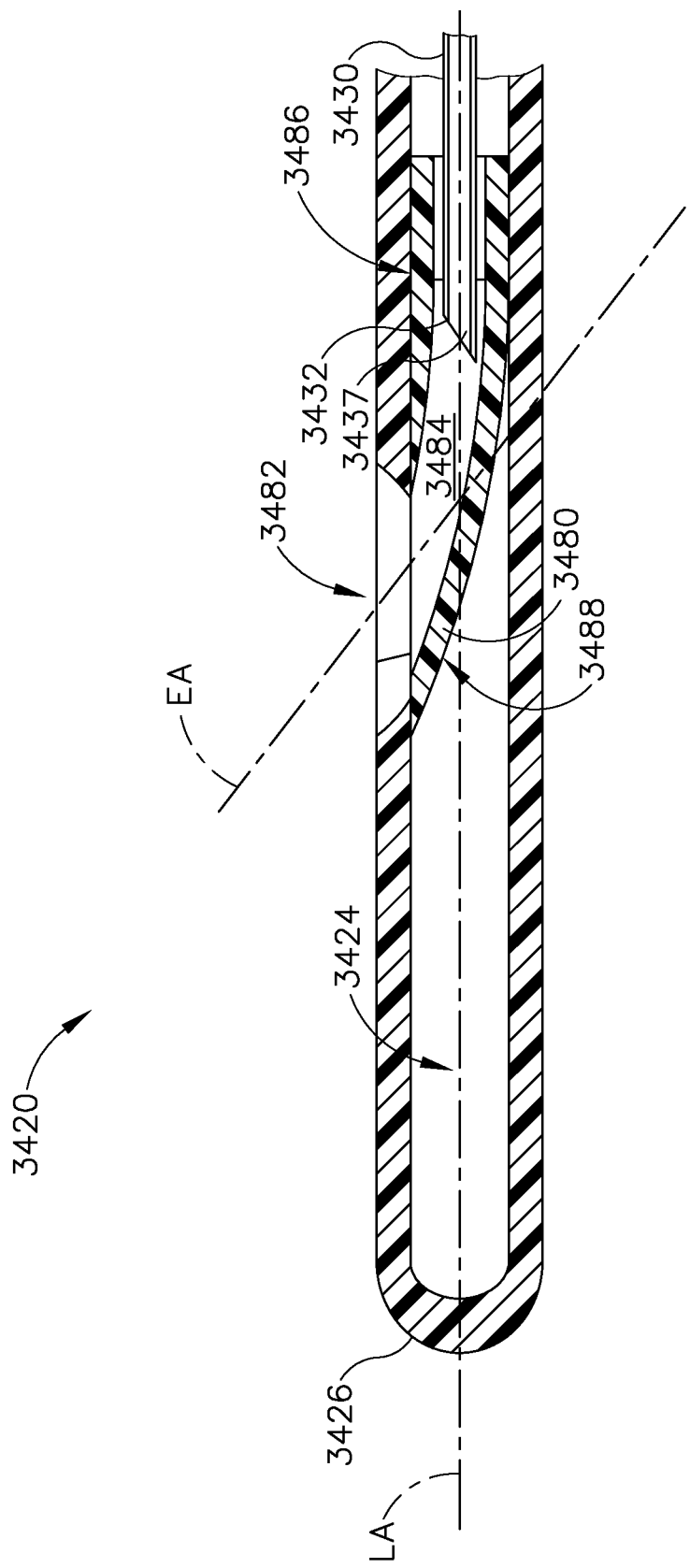
FIG. 31B depicts a cross-sectional view of an exemplary alternative cannula for use with the instrument of FIG. 1.
Figure 31C:
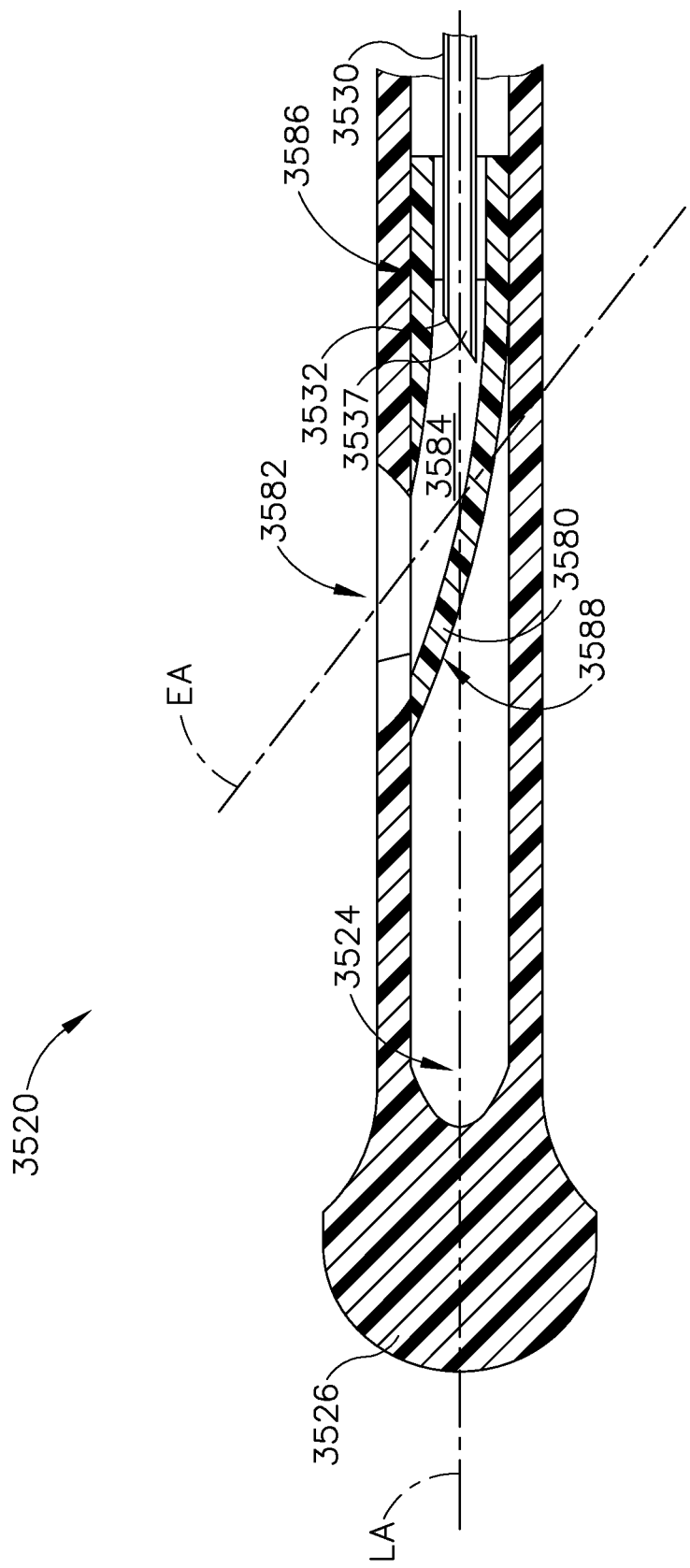
FIG. 31C depicts a cross-sectional view of another exemplary alternative cannula for use with the instrument of FIG. 1.
Figure 31D:
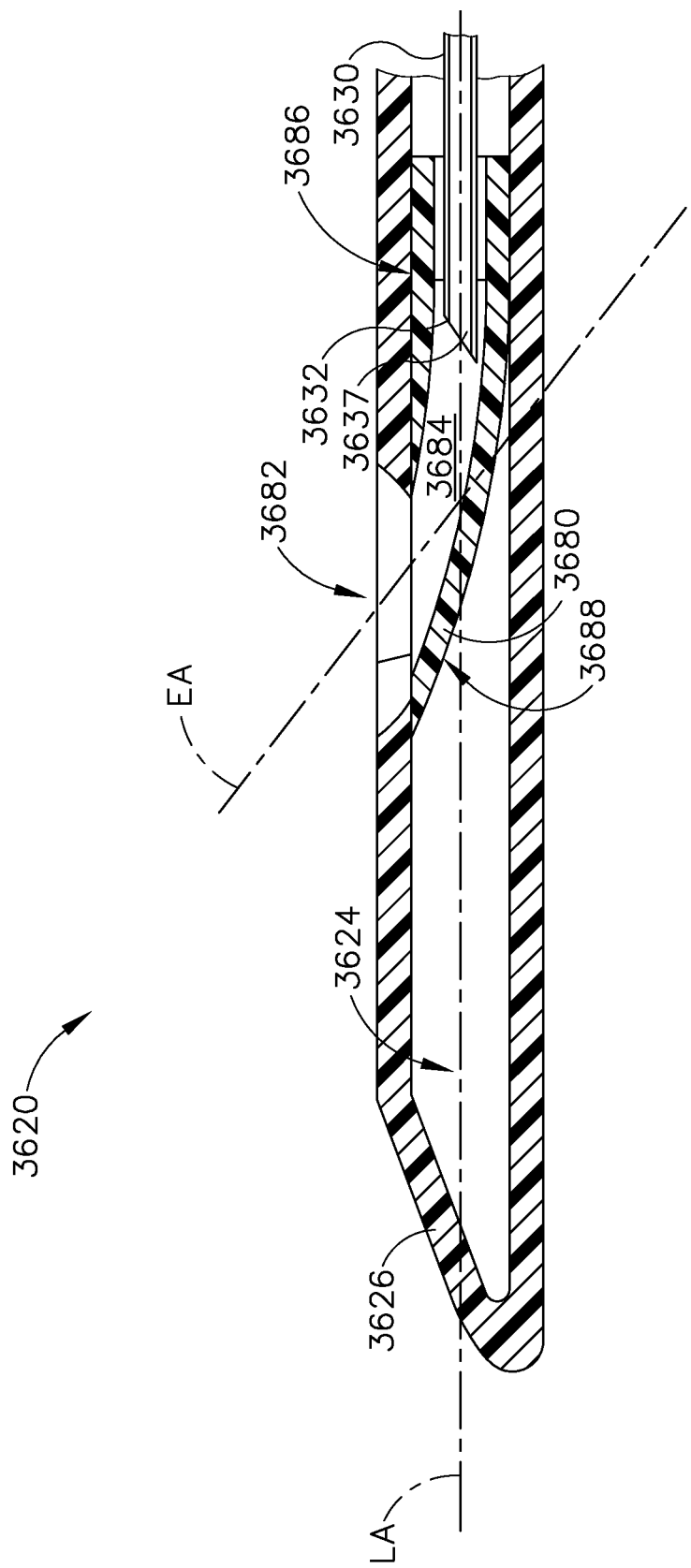
FIG. 31D depicts a cross-sectional view of still another exemplary alternative cannula for use with the instrument of FIG. 1.

FIGS. 31B-31D show various alternative cannulas (3420, 3520, 3620) that may be used in alternative to cannula (2620). Cannulas (3420, 3520, 3620) are substantially the same as cannula (2620) described above except as otherwise noted herein. In particular, like with cannula (2620), each cannula (3420, 3520, 3620) includes a pair of opposing rounded sides and a pair of opposing flat sides adjacent to the rounded sides and comprises a central lumen (3424, 3524, 3624) extending longitudinally through each respective cannula (3420, 3520, 3620) and terminating at a respective distal end (3426, 3526, 3626). A needle guide (2680) is disposed within each lumen (3424, 3524, 3624) such that needle guide each (3480, 3580, 3680) abuts a separate beveled opening (3482, 3582, 3682) within each respective cannula (3420, 3520, 3620) that is laterally oriented on the upper surface of each cannula (3420, 3520, 3620), proximal to each beveled distal end (3426, 3526, 3626).

Each needle guide (3480, 3580, 3680) is generally configured to direct a respective needle (3430, 3530, 3630) upwardly along a respective exit axis (EA) that is obliquely oriented relative to the longitudinal axis (LA) of each cannula (3420, 3520, 3620) through each respective beveled opening (3482, 3582, 3682). Each needle guide (3480, 3580, 3680) defines an internal lumen (3484, 3584, 3684) that is configured to slidably receive each respective needle (3430, 3530, 3630). In particular, each internal lumen (3484, 3584, 3684) includes a generally straight proximal portion (3486, 3586, 3686) and a curved distal portion (3488, 3588, 3688), all of which are similar to proximal portion (2686) and a distal portion (2688) described above.

The general difference between cannulas (3420, 3520, 3620) and cannula (2620) is that each cannula (3420, 3520, 3620) includes an alternative distal tip (3426, 3526, 3626). For instance, as can be seen in FIG. 31B, cannula (3420) includes a generally rounded distal tip (3426). Similarly, as can be seen in FIG. 31C, cannula (3520) includes a bulbous distal tip (3526). It should be understood that bulbous distal tip (3526) may be bulbous along a lateral plane (into and out of the page showing FIG. 31C) and/or along a vertical plane (along the page showing FIG. 31C). For instance, in some versions, distal tip (3526) is only bulbous along a lateral plane (into and out of the page showing FIG. 31C) and simply looks like rounded distal tip (3526) along a vertical plane (along the page showing FIG. 31C). Finally, as can be seen in FIG. 31D, cannula (3620) includes a partially rounded distal tip (3626). It should be understood that each distal tip (3426, 3526, 3626) described herein may provide differing penetration characteristics as each cannula (3420, 3520, 3520) is inserted into an eye of a patient. For instance, rounded or bulbous distal tips (3426, 3526) may provide relatively more atraumatic characteristics, while partially rounded distal tip (3626) may provide intermediate characteristics with penetrating capabilities similar to distal tip (2626) and atraumatic characteristics similar to rounded and bulbous distal tips (3426, 3526). Although certain specific distal tip (2626, 3426, 3526, 3626) are shown and described herein, it should be understood that numerous other suitable distal tips may be used as will be apparent to those of ordinary skill in the art in view of the teachings herein.

C. Exemplary Alternative Suture Measurement Templates

Figure 32:
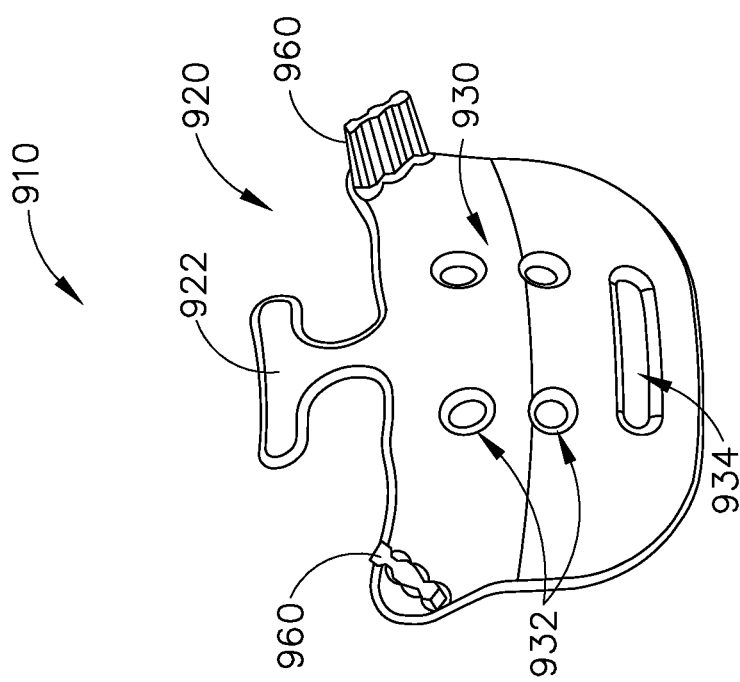
FIG. 32 depicts a perspective view of an exemplary alternative suture measurement template for use in a method for the suprachoroidal administration of a therapeutic agent.
Figure 34:
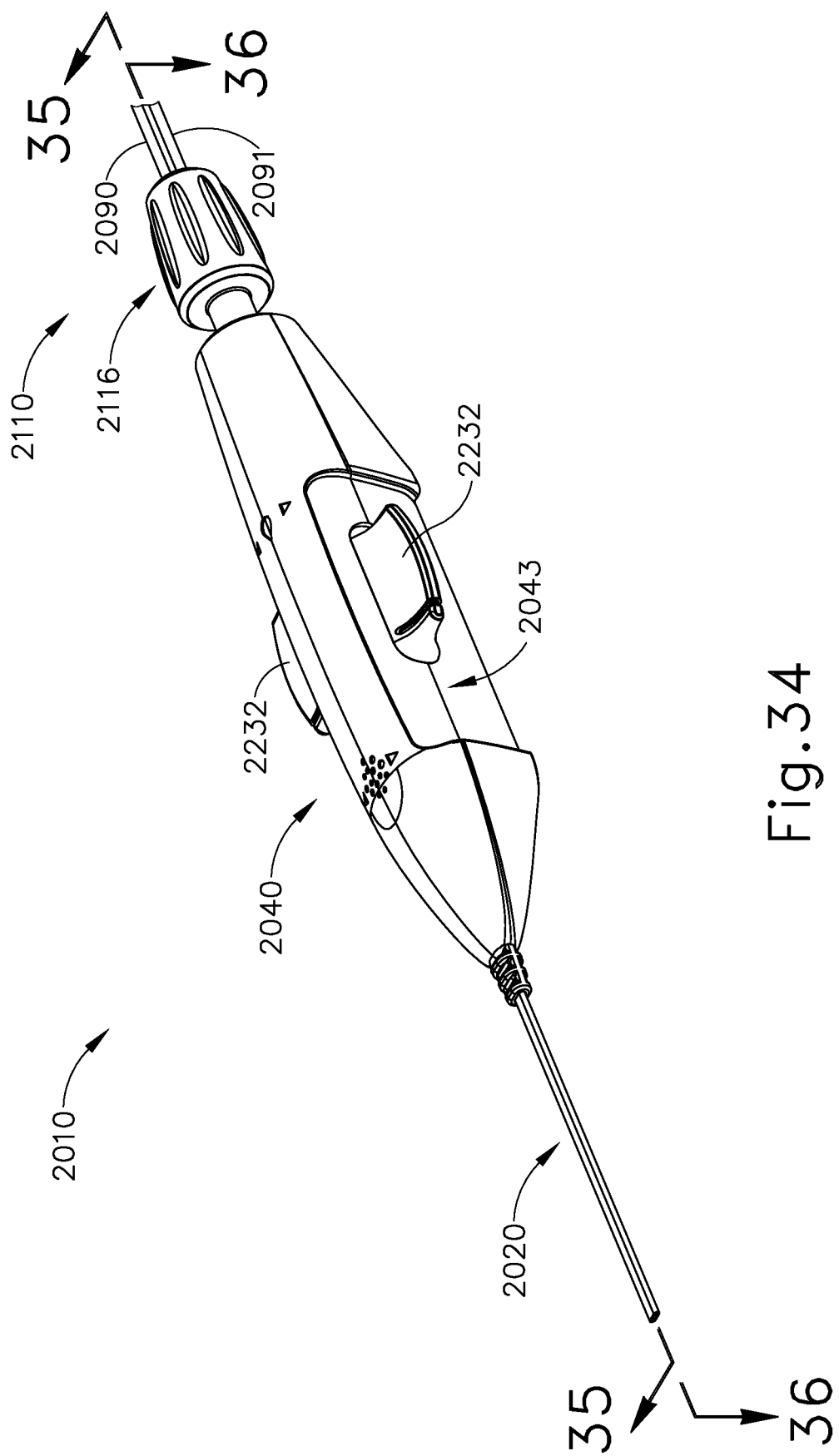
FIG. 34 depicts a perspective view of another exemplary alternative instrument for suprachoroidal administration of a therapeutic agent.

FIG. 32 shows an exemplary alternative suture measurement template (910) that is substantially the same as template (210) described above, except as otherwise noted herein. For instance, template (910) comprises a body (920) that is similar to body (220) described above. However, unlike template (210), template (910) of the present example lacks a shaft. As will be described in greater detail below, body (920) is generally configured to be grasped by forceps in lieu of a shaft. Body (920), like body (220), comprises an upper guide portion (922). Unlike body (220), body (920) of the present example comprises a plurality of openings (930) such that body (920) may be used like a stencil to mark an eye of a patient in lieu of using protrusions (230) to mark the eye as described above.

Upper guide portion (922) is generally semi-circular in shape and is disposed at the top of body (920). The semi-circular shape of upper guide portion (922) has a radius that corresponds to the radius of curvature of an limbus of a patient's eye. As will be described in greater detail below, upper guide portion (922) may be used to position template (910) relative to the limbus of a patient's eye. Accordingly, any pigmentation that may be deposited onto a patient's eye by using template (910) may be positioned relative to the limbus of the patient's eye. Openings (930) are similar to protrusions (230) described above in that openings (930) may be used to mark particular locations of interest on a patient's eye. Openings (930) of the present example comprise four suture loop openings (932) and a single sclerotomy opening (934).

Unlike body (220), body (920) of the present example includes two grasping members (960). Grasping members (960) extend proximally from body (920) and are generally configured to be grasped by a forceps or other instrument. Accordingly, an operator may use a forceps or other surgical instrument to grasp grasping members (960) and manipulate body (920). Although grasping members (960) are shown as elongate rectangles, it should be understood that in other examples any other suitable shape may be used.

In an exemplary use, suture loop openings (932) and sclerotomy openings (934) each correspond to a particular portion of the method described above. In particular, during the method described above, an operator may grasp one or more grasping members (960) with a forceps or other instrument to position body (920) relative to a patient's eye. Once body (920) is positioned, an operator may obtain a pigment pen or other pigment applying device and use the pen to apply pigment within openings (930). Once pigment has been applied, an operator may remove template (910). Once template (910) is removed from an eye of a patient, the pigment applied through openings (930) may remain adhered to the eye to mark particular points of interest, as was described above.

Figure 33:
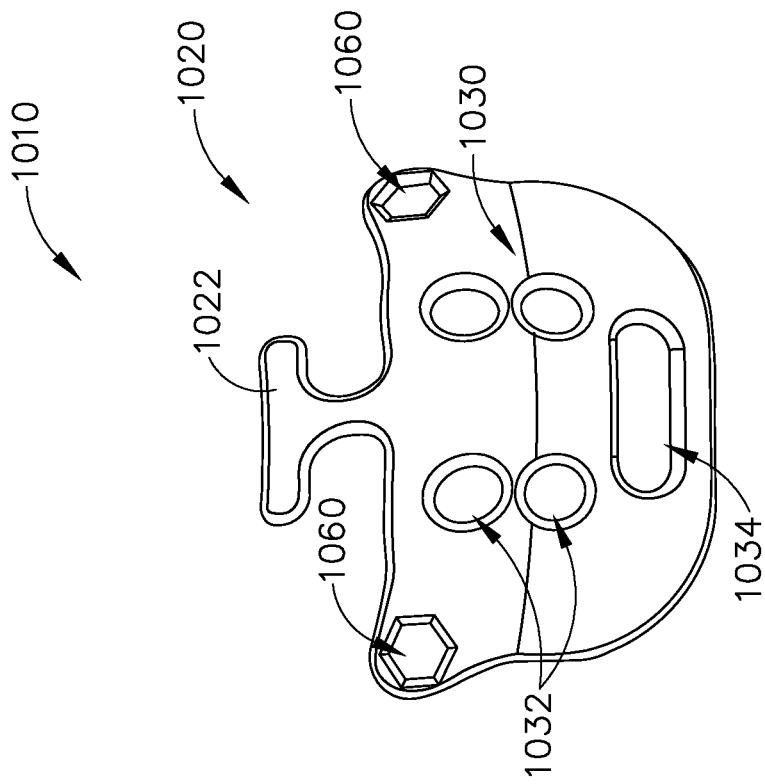
FIG. 33 depicts a perspective view of another exemplary alternative suture measurement template for use in a method for the suprachoroidal administration of a therapeutic agent.

FIG. 33 shows an exemplary alternative suture measurement template (1010) that is substantially the same as template (210) described above, except as otherwise noted herein. For instance, template (1010) comprises a body (1020) that is similar to body (220) described above. However, unlike template (210), template (1010) of the present example lacks a shaft. As will be described in greater detail below, body (1020) is generally configured to be grasped by forceps in lieu of a shaft. Body (1020), like body (220), comprises an upper guide portion (1022). Unlike body (220), body (1020) of the present example comprises a plurality of openings (1030) such that body (1020) may be used like a stencil to mark an eye of a patient in lieu of using protrusions (230) to mark the eye as described above.

Upper guide portion (1022) is generally semi-circular in shape and is disposed at the top of body (1020). The semi-circular shape of upper guide portion (1022) has a radius that corresponds to the radius of curvature of the limbus of a patient's eye. As will be described in greater detail below, upper guide portion (1022) may be used to position template (1010) relative to the limbus of a patient's eye. Accordingly, any pigmentation that may be deposited onto a patient's eye by using template (1010 may be positioned relative to the limbus of the patient's eye. Openings (1030) are similar to protrusions (230) described above in that openings (1030) may be used to mark particular locations of interest on a patient's eye. Openings (1030) of the present example comprise four suture loop openings (1032) and a single sclerotomy opening (1034). In contrast to openings (930) described above, openings (1030) of the present example are enlarged relative to openings (930) such that markings may be more readily made via openings (1030) on an eye of a patient.

Unlike body (220), body (1020) of the present example includes two grasping openings (1060). Grasping openings (1060) are generally configured to be grasped by a forceps or other instrument. Accordingly, an operator may use a forceps or other surgical instrument to grasp grasping openings (1060) and manipulate body (1020). Although grasping openings (1060) are shown as hexagonal openings, it should be understood that in other examples any other suitable shape may be used.

In an exemplary use, suture loop openings (1032) and sclerotomy openings (1034) each correspond to a particular portion of the method described above. In particular, during the method described above, an operator may grasp one or more grasping openings (1060) with a forceps or other instrument to position body (1020) relative to a patient's eye. Once body (1020) is positioned, an operator may obtain a pigment pen or other pigment applying device and use the pen to apply pigment within openings (1030). Once pigment has been applied, an operator may remove template (1010). Once template (1010) is removed from an eye of a patient, the pigment applied through openings (1030) may remain adhered to the eye to mark particular points of interest, as was described above.

D. Exemplary Alternative Instrument with Alternative Rotatable Actuation Feature FIGS. 34-46D show an exemplary alternative instrument (2010) that is similar to instruments (10, 410) described above. Like with instruments (10, 410), instrument (2010) is generally usable in the procedure described above to deliver a therapeutic fluid suprachoroidally to an eye of a patient. It should therefore be understood that instrument (410) may be readily used in place of instrument (10) to perform the medical procedure described above. Like instrument (10), instrument (2010) of this example comprises a cannula (2020), a body (2040), and an actuation assembly (2100). Cannula (2020) includes a Nitinol needle (2030) extending therethrough and is substantially the same as cannula (20) described above. Although cannula (2020) is shown as being substantially similar to cannula (20) described above, it should be understood that in any other cannula described herein may be readily incorporated into instrument (2010). Body (2040) is also similar to body (40) described above, except body (2040) includes a valve actuation recess (2043) as will be described in greater detail below.

The primary difference between instrument (10) and instrument (2010) is that actuation assembly (2100) of instrument (2010) is rotatable instead of being slidable. Additionally, instrument (2010) includes a valve assembly (2200) that operable to change the fluid state of needle (2030). As will be described in greater detail below, actuation assembly (2100) is generally operable to translate valve assembly (2200) longitudinally to thereby translate needle (2030) longitudinally relative to cannula (2020) through rotation of a knob member (2110).

Figure 35:
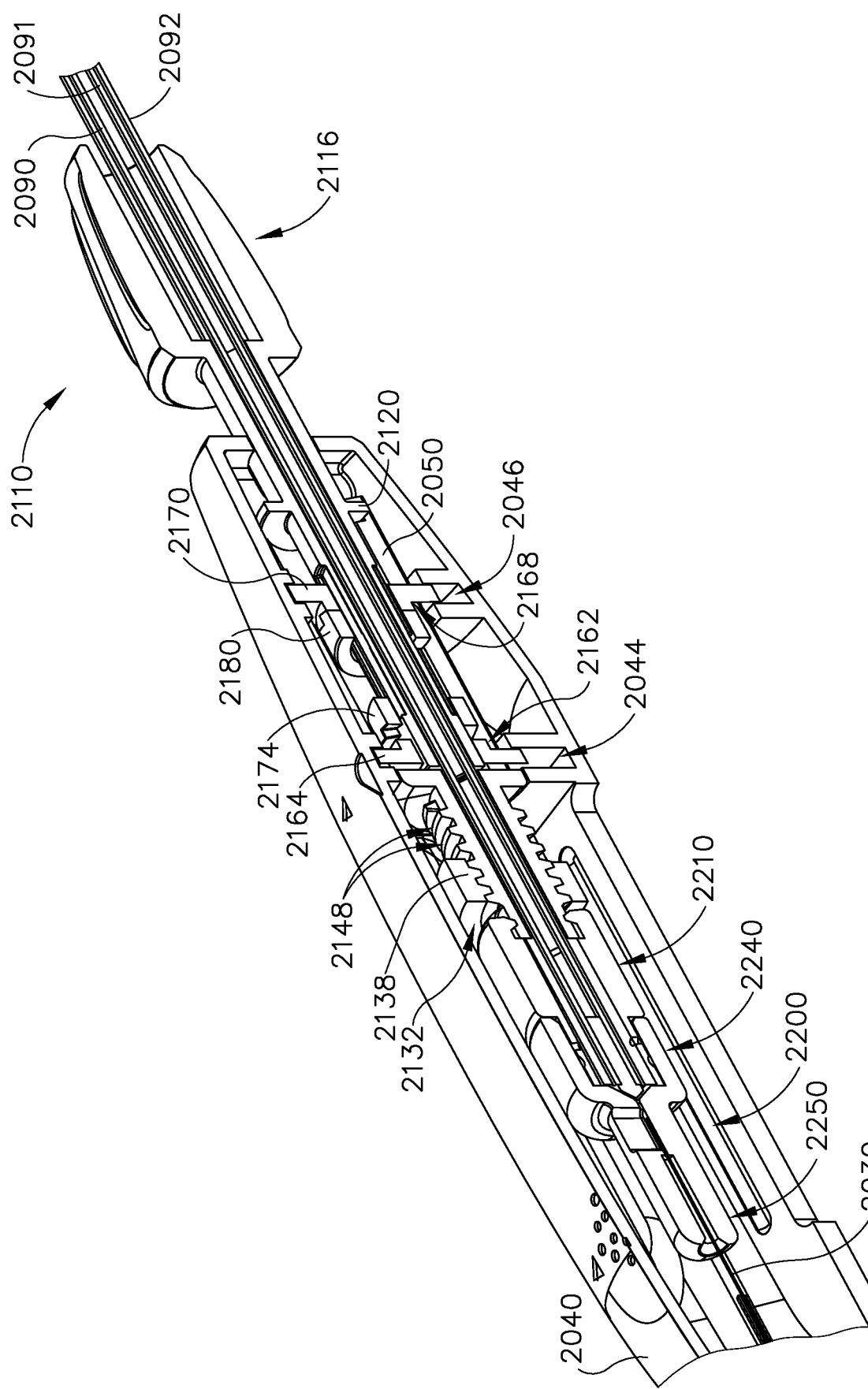
FIG. 35 depicts a perspective cross-sectional view of the instrument of FIG. 34, with the cross-section taken along line 35-35 of FIG. 34.
Figure 36:
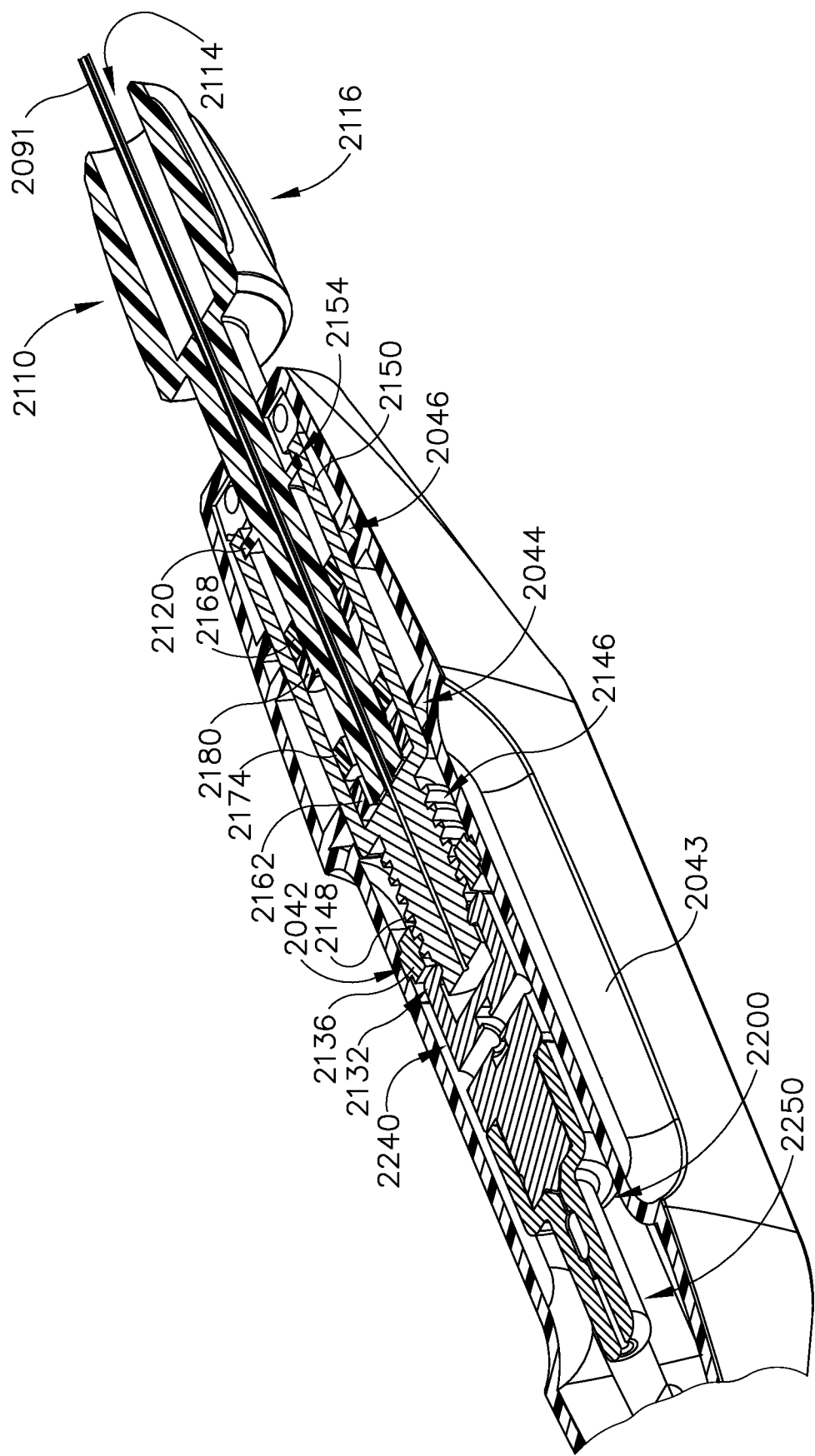
FIG. 36 depicts another perspective cross-sectional view of the instrument of FIG. 34, with the cross-section taken along line 36-36 of FIG. 34.
Figure 38:
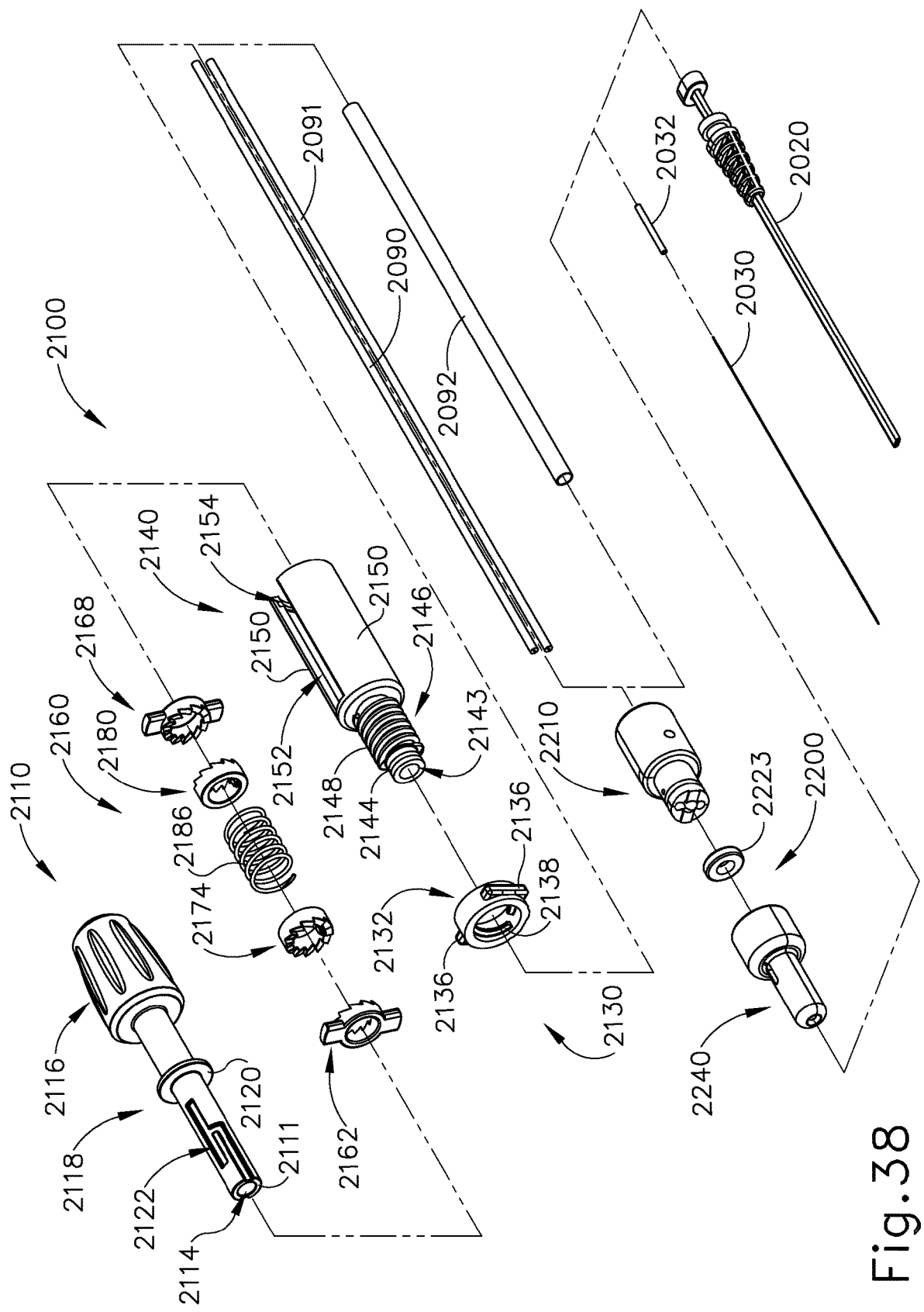
FIG. 38 depicts an exploded perspective view of drive assembly components of the instrument of FIG. 34.
Figure 39:
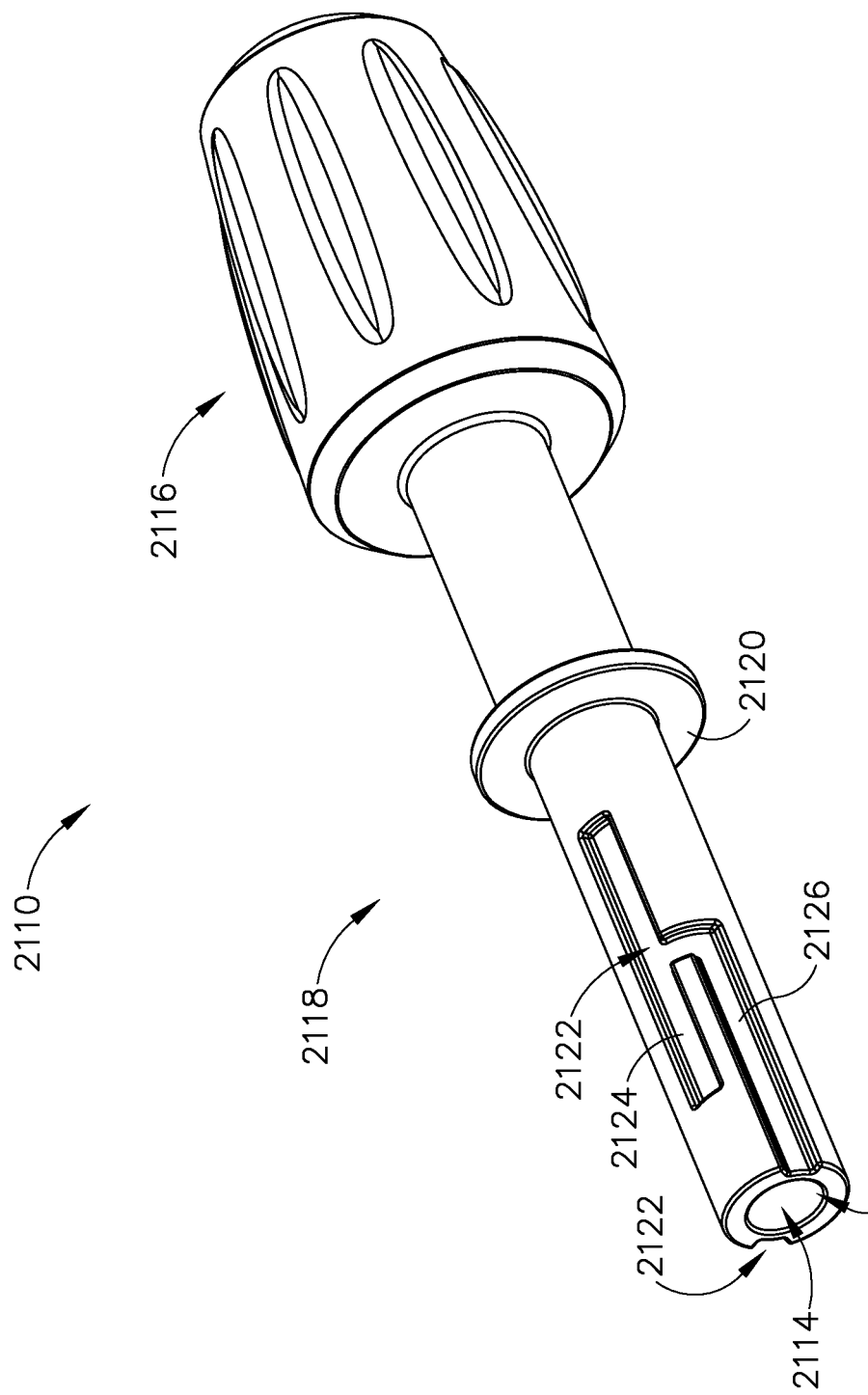
FIG. 39 depicts a perspective view of a knob member of the drive assembly of FIG. 38.

As can be seen in FIGS. 35-36 and 38, actuation assembly (2060) comprises knob member (2110), a translation assembly (2130), and a clutch assembly (2160). As best seen in FIG. 39, knob member (2110) comprises an actuation portion (2116) and an elongate driving portion (2118). Additionally, knob member (2110) comprises openings (2111, 2112) on each end defining a lumen (2114) extending longitudinally through both actuation portion (2116) and driving portion (2118). Actuation portion (2116) is disposed externally of body (2040) and is generally configured to be gripped and rotated by a hand of an operator to actuate actuation assembly (2060).

Driving portion (2118) of knob member (2110) extends distally into body (2040) and is generally operable to drive various components of actuation assembly (2100) as will be described in greater detail below. As can best be seen in FIG. 39, driving portion (2118) comprises an annular flange (2120) and two elongate channels (2122). Annular flange (2120) extends radially outwardly from the outer surface of driving portion (2118). Generally, annular flange (2120) is configured to engage translation assembly (2130) as will be described in greater detail below. Each channel (2122) of driving portion (2118) is recessed into the outer surface of driving portion (2118). Channels (2122) have substantially similar shapes and include a primary portion (2124) and an assembly portion (2126). Primary portion (2124) extends longitudinally along the length of driving portion (2118), terminating proximally of the distal end of driving portion (2118) and distally of annual flange (2120). As will be described in greater detail below, primary portion (2124) is configured to slidably engage clutch assembly (2160). Assembly portion (2126) is L-shaped and intersects with at least a portion of primary portion (2124) and the distal end of driving portion (2118). As will be understood, assembly portion (2126) is merely included for assembly purposes and generally serves no additional functional purposes after instrument (2010) has been assembled. Accordingly, it should be understood that assembly portion (2126) is merely optional and may be omitted in other examples.

Figure 37:
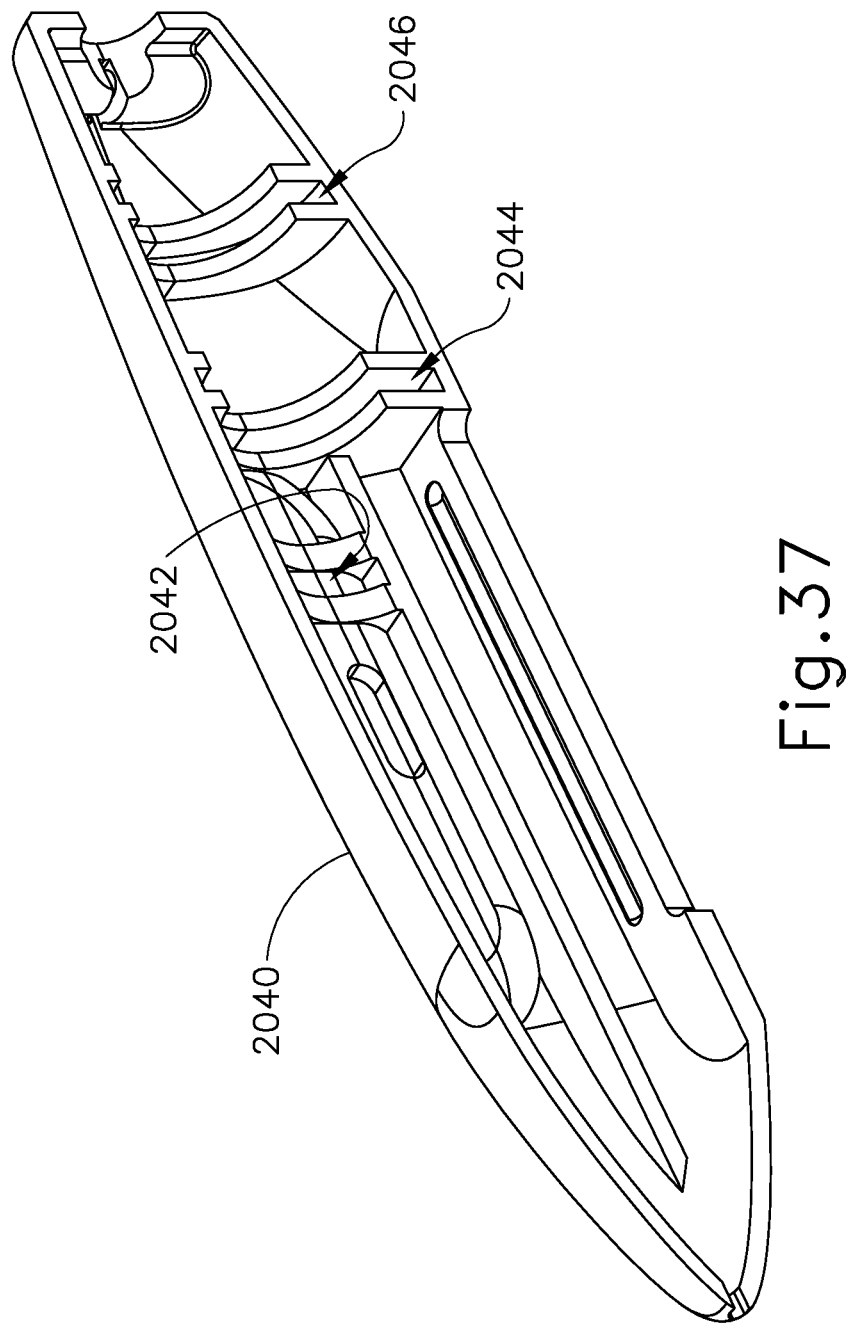
FIG. 37 depicts a cross-sectional view of a body of the instrument of FIG. 34, with the cross-section taken along line 35-35 if FIG. 34.
Figure 40:
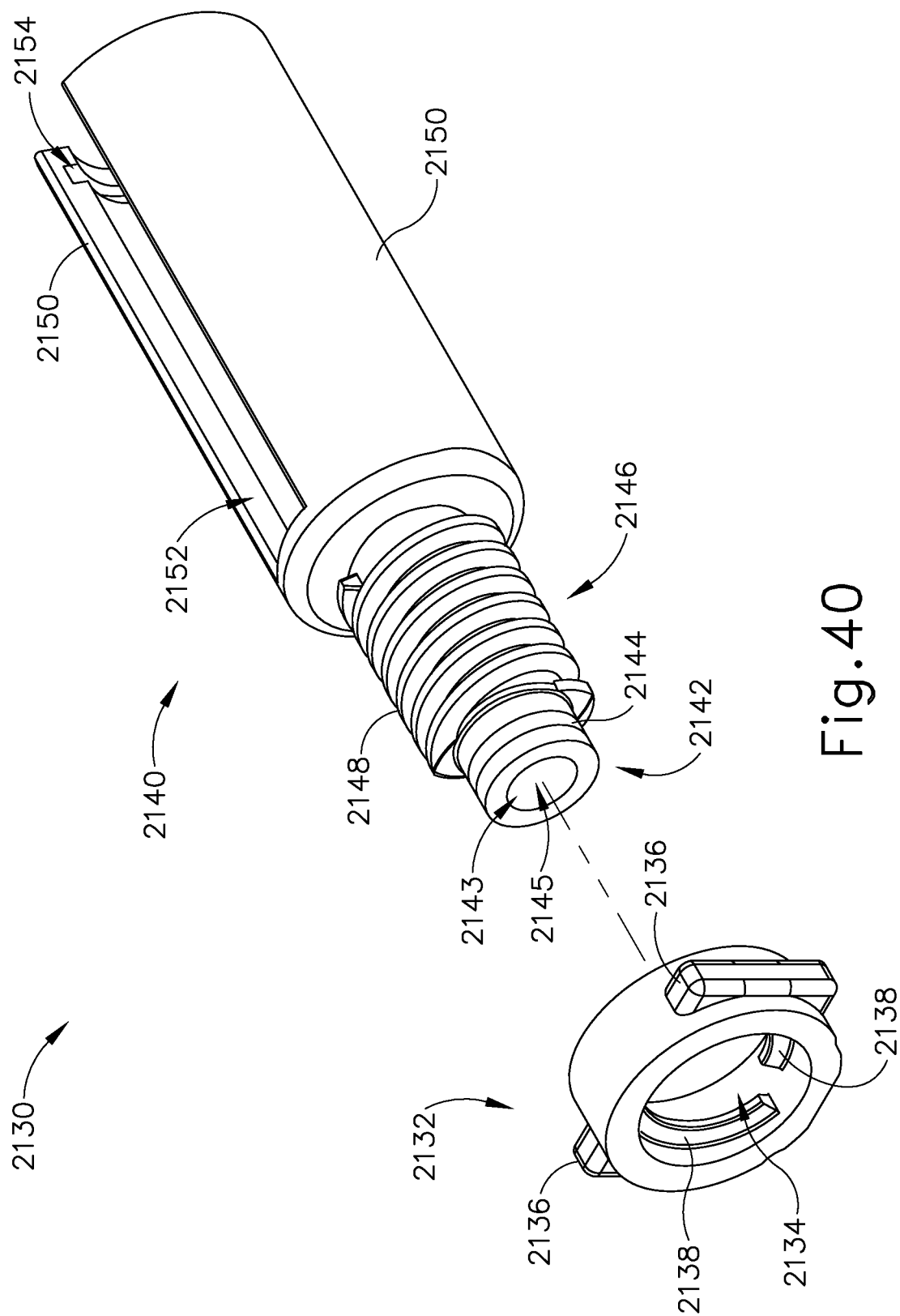
FIG. 40 depicts an exploded perspective view of a lead screw member and a nut member of the drive assembly of FIG. 38.

As can best be seen in FIG. 40, translation assembly (2130) comprises a threaded insert (2132) and a translation member (2140). Threaded insert (2132) is generally round with a bore (2134) extending therethrough. The exterior of threaded insert (2132) includes a pair of outwardly extending tabs (2136). As can best be seen in FIG. 36, tabs (2136) engage a pair of corresponding recesses (2042) formed within body (2040) to translationally and rotationally secure threaded insert (2132) within body (2040). Recess (2042) is also shown in FIG. 37. Referring back to FIG. 40, the interior of threaded insert (2132) includes a pair of thread members (2138) extending radially inwardly into bore (2134). As will be described in greater detail below, thread members (2138) threadingly engage corresponding threading (2148) on the exterior of translation member (2140), such that threaded insert (2132) serves as a nut. As will be understood, threaded insert (2132) is generally operable to provide translation of translation member (2140) relative to body (2040) when translation member (2140) is rotated relative to threaded insert (2132).

Translation member (2140) comprises an attachment portion (2142), a threaded portion (2146), and a pair of longitudinally extending arms (2150). Attachment portion (2142) is generally rounded and includes a distal opening (2143) and an attachment channel (2144) in the form of an annular recess. Distal opening (2143) is generally circular and defines a lumen (2145) extending through translation member (2140). Threaded portion (2146) includes threading (2148) that is configured to engage thread members (2138) described above such that translation member (2140) may be translated relative to body (2040) by rotating translation member (2140) relative to threaded insert (2132). In other words, translation member (2140) serves as a rotating lead screw while threaded insert (2132) serves as a fixed nut.

Arms (2150) have a generally semicircular profile and extend proximally from threaded portion (2146). Each arm (2150) is separated from the other to define two substantially similar elongate channels (2152) between arms (2150). Each arm (2150) includes an annular channel (2154) disposed near the proximal end of each respective arm (2150). Each annular channel (2154) corresponds to the other such that together annular channels (2154) are configured to receive annular flange (2120) of knob member (2110). It should be understood that arms (2150) are relatively rigid such that when annular flange (2120) of knob member (2110) is inserted into annular channels (2154), annular flange (2120) is translationally secured therein. Accordingly, when knob member (2110) is coupled to translation member (2140) via arms (2150), knob member (2110) and translation member (2140) may translate unitarily with each other. However, because of the annular shape of annular channels (2154), knob member (2110) and translation member (2140) may remain free to rotate independently of each other.

Figure 41:
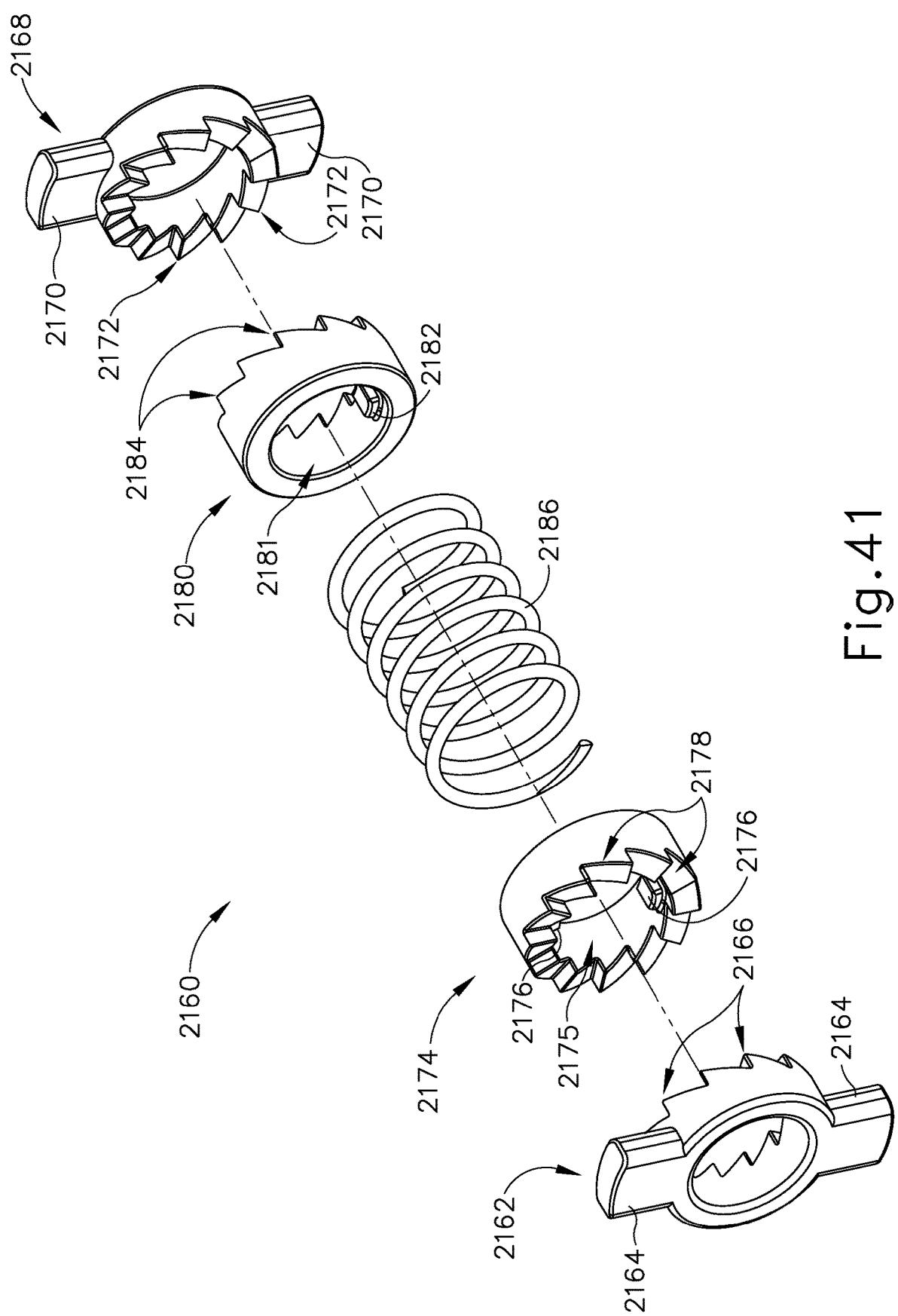
FIG. 41 depicts an exploded perspective view of a clutch assembly of the drive assembly of FIG. 38.
Figure 42:
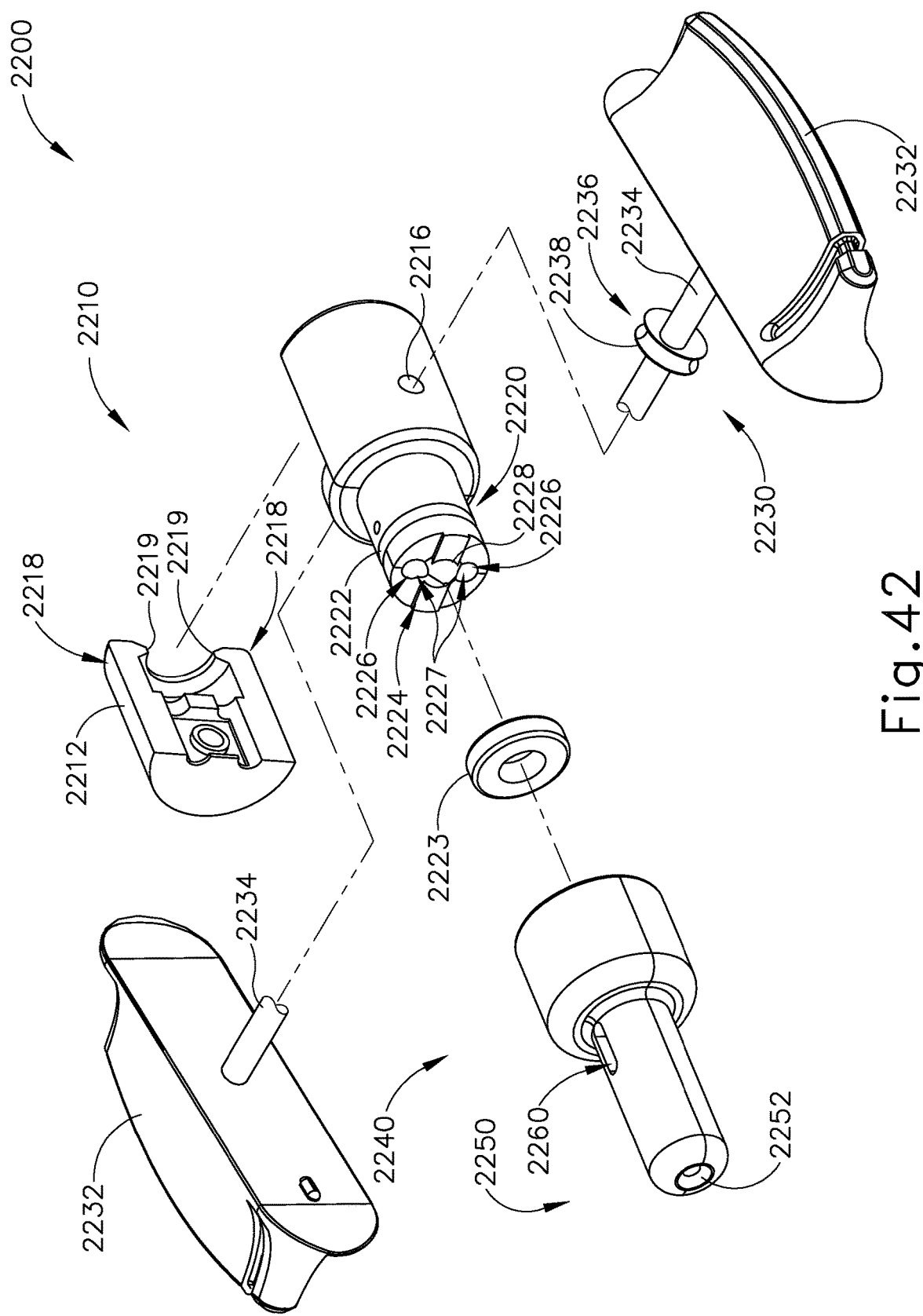
FIG. 42 depicts an exploded perspective view of a valve assembly of the instrument of FIG. 34.
Figure 43:
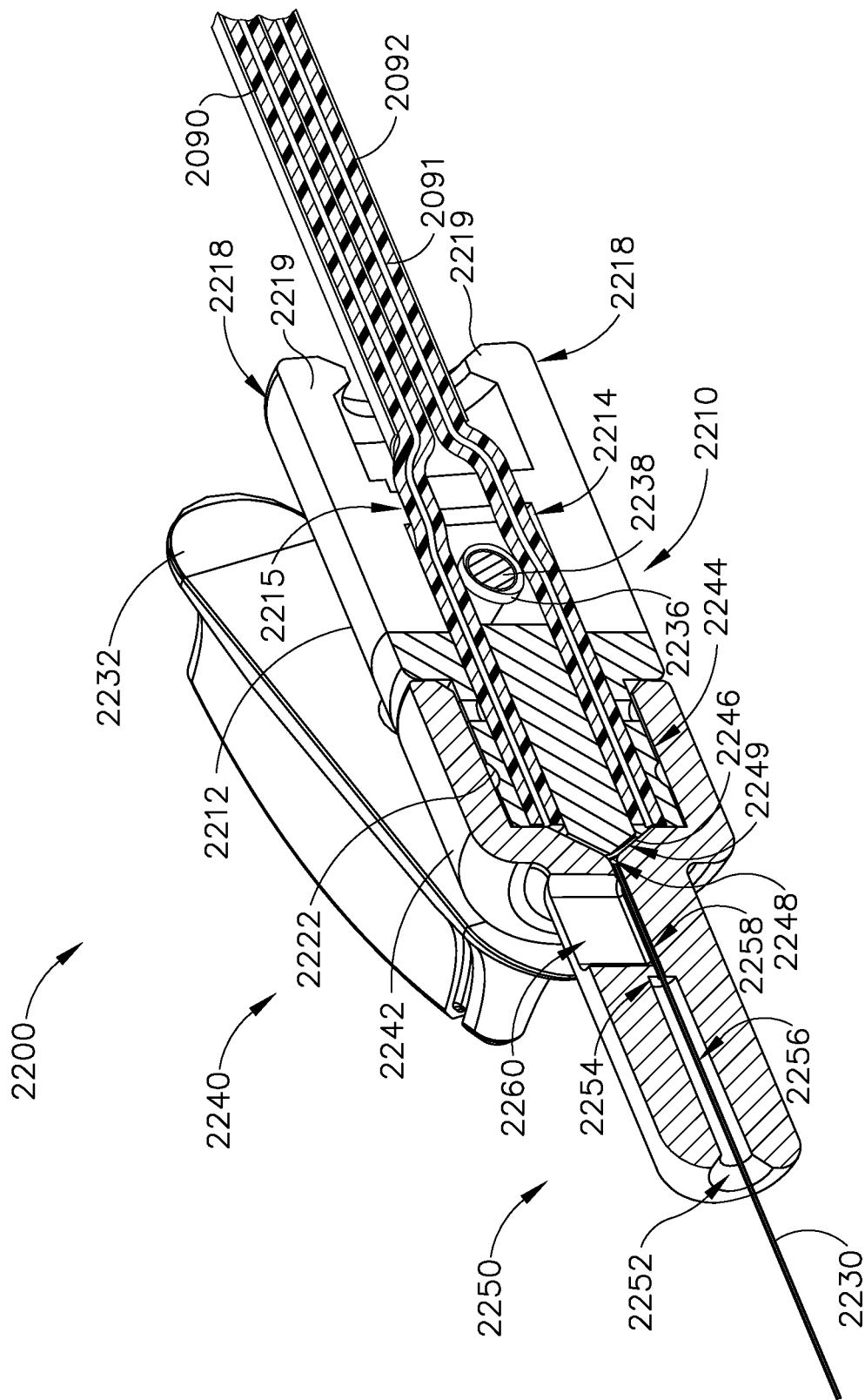
FIG. 43 depicts a perspective cross-sectional view of the valve assembly of FIG. 42.

As can best be seen in FIG. 41, clutch assembly (2160) comprises a first drive gear (2162), a second drive gear (2168), a first clutch gear (2172), a second clutch gear (2178), and a spring (2186) disposed between each clutch gear (2172, 2178). Each drive gear (2162, 2168) is generally circular in shape with a bore (2163, 2169) extending therethrough. Each drive gear (2162, 2168) further comprises a pair of driving protrusions (2164, 2170) and a plurality of gear teeth (2166, 2172). Driving protrusions (2164, 2170) are oriented radially outwardly and are configured to extend through elongate cannels (2152) defined by arms (2150) of translation member (2140). Driving protrusions (2164, 2170) are further configured to be received by corresponding channels (2044, 2046) in body (2040) (see FIGS. 35 and 37) such that driving protrusions (2164, 2170) maintain the longitudinal position of drive gears (2162, 2168), yet permit drive gears (2162, 2168) to freely rotate relative to body (2040) (as seen in FIG. 35). As will be understood, rotation of drive gears (2162, 2168) may cause corresponding rotation of translation member (2140) due to driving protrusions (2164, 2170) acting upon arms (2150) of translation member (2140). It should be understood that translation member rotates with drive gears (2162, 2168) yet translates relative to drive gears (2162, 2168).

Gear teeth (2166) of first drive gear (2162) are oriented to protrude proximally from first drive gear (2162). In contrast, gear teeth (2172) of second drive gear (2168) are oriented to protrude distally from second drive gear (2168). Both sets of gear teeth (2166, 2172) are generally saw-tooth shaped and extend circumferentially around the perimeter of the respective faces of each respective drive gear (2162, 2168). As will be described in greater detail below, each set of gear teeth (2166, 2172) is configured to mesh with a corresponding set of gear teeth (2178, 2184) of each corresponding clutch gear (2174, 2180).

Each clutch gear (2174, 2180) is generally circular in shape with a bore (2175, 2181) extending therethrough. Each clutch gear (2174, 2180) further comprises a pair of protrusions (2176, 2182) and a plurality of gear teeth (2178, 2184) that enable clutch gears (2172, 2180) to operate as coupling elements, as described in greater detail below. Protrusions (2176, 2182) protrude inwardly into each respective bore (2175, 2181). It should be understood that protrusions (2176, 2182) are configured to slidably engage channels (2122) of knob member (2110). As will be described in greater detail below, protrusions (2176, 2182) are configured to rotationally secure each clutch gear (2174, 2180) relative to knob member (2110), while permitting each clutch gear (2174, 2180) to translate along the length of channels (2127). In other words, clutch gears (2174, 2180) rotate with knob member (2110) yet translate relative to knob member (2110).

Gear teeth (2178) of first clutch gear (2174) are oriented to protrude distally from first clutch gear (2174). In contrast, gear teeth (2184) of second clutch gear (2180) are oriented to protrude proximally from second clutch gear (2180). Both sets of gear teeth (2178, 2184) are generally saw-tooth shaped and extend circumferentially around the perimeter of the respective faces of each respective clutch gear (2174, 2180). As was described above, each set of gear teeth (2178, 2184) is configured to mesh with a corresponding set of gear teeth (2166, 2172) of drive gears (2162, 2168).

When each set of gear teeth (2178, 2184) mesh with each respective set of gear teeth (2166, 2172), gear teeth (2178, 2184) are configured to drive or slip relative to gear teeth (2166, 2172) depending on angular rotation in a given direction of each clutch gear (2174, 2180). For instance, because of the orientation of gear teeth (2178) of first clutch gear (2174) relative to the orientation of gear teeth (2166) of first drive gear (2162), rotation of first clutch gear (2174) in a counter clockwise direction (e.g., when viewed from distally from the proximal end of instrument 2010) will drive rotation of first drive gear (2168). In contrast, rotation of first clutch gear (2174) in a clockwise direction will result in slippage of first clutch gear (2174) relative to first drive gear (2168). Similarly, because of the orientation of gear teeth (2184) of second clutch gear (2180) relative to the orientation of gear teeth (2172) of second drive gear (2168), driving of second drive gear (2168) will occur when second clutch gear (2180) is rotated in the counter clockwise direction; and slippage will occur when second clutch gear (2180) is rotated in the clockwise direction. Accordingly, and as will be described in greater detail below, first clutch gear (2174) is operable to drive first drive gear (2162) when first clutch gear (2174) is rotated in a clockwise direction and second clutch gear (2180) is operable to drive second drive gear (2168) when second clutch gear (2180) is rotated in the clockwise direction.

As can best be seen in FIGS. 42-44B, valve assembly (2200) comprises a valve body (2210), a valve actuator (2230), and a needle coupler (2240). In particular, valve body (2210) comprises a valve housing (2212), a cylindrical attachment member (2218) extending proximally from valve housing (2212), and a coupler insert (2220). Valve housing (2212) is generally cylindrical in shape. As can best be seen in FIG. 43, valve housing (2212) defines a chamber (2214) that is configured to receive a pair of supply tubes (2090, 2091) and valve actuator (2230) as will be described in greater detail below. Each side of valve housing (2212) includes a pair of actuator openings (2216), which are configured to rotatably receive valve actuator (2230) through valve housing (2212) and into chamber (2214). In the present example, first supply tube (2090) is configured to couple with a source of bleb fluid (340) (e.g., BSS); while second supply tube (2091) is configured to couple with a source of therapeutic agent (341). It should be understood that each fluid supply tube (2090, 2091) may include a conventional luer feature and/or other structures permitting fluid supply tubes (2090, 2091) to be coupled with respective fluid sources.

The proximal end of valve housing (2212) defines a tube opening (2215) that extends into chamber (2214). As can be seen tube opening (2215) is configured to receive a tube (2092) which houses supply tubes (2090, 2091). As will be described in greater detail below, tube (2092) surrounds supply tubes (2090, 2091) to prevent inadvertent rotation of supply tubes (2090, 2091) by actuation assembly (2100). In the present example, tube opening (2215) is sized such that tube (2092) is secured to valve housing (2212) by a compression or interference fit. In other examples, tube (2092) may alternatively be secured within tube opening (2215) by adhesive bonding, welding, mechanical fasteners, and/or using any other suitable structures or techniques.

Attachment member (2218) is configured to couple with the distal end of translation member (2140). In particular, attachment member (2218) comprises an cylindrical inwardly directed protrusion (2219) that is configured to engage attachment channel (2144) of translation member (2140). It should be understood that in the present example attachment member (2218) merely translationally couples valve assembly (2200) to translation member (2140), while translation member (2140) remains free to rotate relative to valve assembly (2200). In other words, valve assembly (2200) translates with translation member (2140); yet valve assembly (2200) does not rotate with translation member (2140).

Coupler insert (2220) extends distally from valve housing (2212) and is generally configured for insertion into the proximal end of needle coupler (2240) as will be described in greater detail below. Coupler insert (2220) is generally cylindrical in shape and comprises an annular recess (2222) and a distal tip (2224). Annular recess (2222) receives a rubber o-ring (2223) or other sealing device. Distal tip (2224) includes a pair of fluid openings (2226) and a conical protrusion (2228). Fluid openings (2226) open to a pair of tube lumens (2227), which extend through coupler insert (2220). As will be described in greater detail below, tube lumens (2227) are generally configured to receive supply tubes (2090, 2091) such that fluid may be delivered to needle coupler (2240) via fluid openings (2226). As will also be described in greater detail below, conical protrusion (2228) is configured to be received by needle coupler (2240) to direct fluid from fluid openings (2226) and into needle (2030).

Valve actuator (2230) comprises a pair of actuation arms (2232), a connector shaft (2234), and a pinch valve member (2236). Actuator arms (2232) are generally configured to apply a rotational force to connector shaft (2234) to thereby rotate pinch valve member (2236) about the longitudinal axis of connector shaft (2234), as will be described below. In the present example, actuation arms (2232) are generally rectangular in shape. In other examples, actuation arms (2232) may be of any other suitable shape as will be apparent to those of ordinary skill in the art in view of the teachings herein. Connector shaft (2234) is a generally cylindrical shaft that connects each actuation arm (2232) to the other. In the present example, connector shaft (2234) is shown as being integral with actuation arm (2232). It should be understood that in other examples, connection shaft (2234) may be a discrete component of valve actuator (2230) and may be secured to actuation arms (2232) by any suitable connection means such as compression fittings, adhesive bonding, welding, mechanical fastening, etc.

Pinch valve member (2236) is generally oblong in shape and includes an annular recess (2238) extending around the perimeter of valve member (2236). Valve member (2236) is shown as being of integral construction with connector shaft (2234). It should be understood that, in other examples, valve member (2236) may be a discrete component and may be attached to connector shaft (2234) by overmolding, adhesive bonding, welding, etc. Annular recess (2238) has a radius of inner curvature that corresponds to the outer diameter of supply tubes (2090, 2091) such that each supply tube (2090, 2091) may be at least partially disposed within annular recess (2238). Valve member (2236) is eccentrically positioned on connector shaft (2234). As will be described in greater detail below, the generally oblong shape of valve member (2236) and the eccentric mounting of valve member (2236) permit valve member (2236) to pinch and thereby seal supply tubes (2090, 2091) when valve member (2236) is rotated by connector shaft (2234) via actuation arms (2232).

Needle coupler (2240) comprises a valve body receiving portion (2242) and an elongate needle receiving portion (2250). Valve body receiving portion (2242) is generally cylindrical in shape and defines a corresponding cylindrical chamber (2244). Cylindrical chamber (2244) is sized to receive coupler insert (2220) through the proximal end of valve body receiving portion (2242). At the distal end of chamber (2244), valve body receiving portion (2242) defines a conical recess (2246) that corresponds to conical protrusion (2228) of valve body (2210). The distal end of conical recess (2246) includes a single fluid opening (2248). As will be described in greater detail below, fluid opening (2248) is in communication with a needle lumen (2254) to communicate fluid to needle (2030). Although conical recess (2246) corresponds to conical protrusion (2228) of valve body (2210), it should be understood that conical recess (2246) is sized such that there is a fluid cavity (2249) disposed between conical recess (2246) and conical protrusion (2228). Accordingly and as will be described in greater detail below, fluid may pass from supply tubes (2090, 2091) though fluid openings in valve body (2210), into fluid cavity (2249) and through fluid opening (2248) of conical recess (2246) to needle lumen (2254).

Needle receiving portion (2250) is generally cylindrical in shape and extends distally from valve body receiving portion (2242). The distal end of needle receiving portion (2250) comprises a conical opening (2252) that is configured to receive needle (2030) therethrough. In particular, conical opening (2252) is in communication with needle lumen (2254), which extends longitudinally through needle receiving portion (2250). Needle lumen (2254) comprises a distal portion (2256) and a proximal portion (2258). Distal portion (2256) of needle lumen (2254) has a diameter that is large relative to the outer diameter of needle (2030) such that needle (2030) freely disposed within distal portion (2256). Proximal portion (2258) of needle lumen (2254) extends proximally from distal portion (2256) and intersects with fluid opening (2248) of conical recess (2246). Accordingly, needle (2030) extends through proximal portion (2258) such that needle (2030) is in fluid communication with fluid chamber (2249). Proximal portion (2258) is relatively small in comparison to distal portion (2256). In particular, the diameter of distal portion (2256) is near the outer diameter of needle (2030) such that needle (2030) is supported by distal portion (2256). However, it should be understood that the diameter of proximal portion (2258) is large enough to permit needle (2030) to be inserted into proximal portion (2258).

Proximal portion (2258) further intersects with a lateral notch (2260) in needle receiving portion (2250). Lateral notch (2260) provides access to proximal portion (2258) from the exterior of needle receiving portion (2250). Although not shown, it should be understood that in some examples lateral notch (2260) may be filled with an adhesive such as epoxy or similar liquid hardening agents to fixedly secure and seal needle (2030) within proximal portion of needle lumen (2254).

Figure 44A:
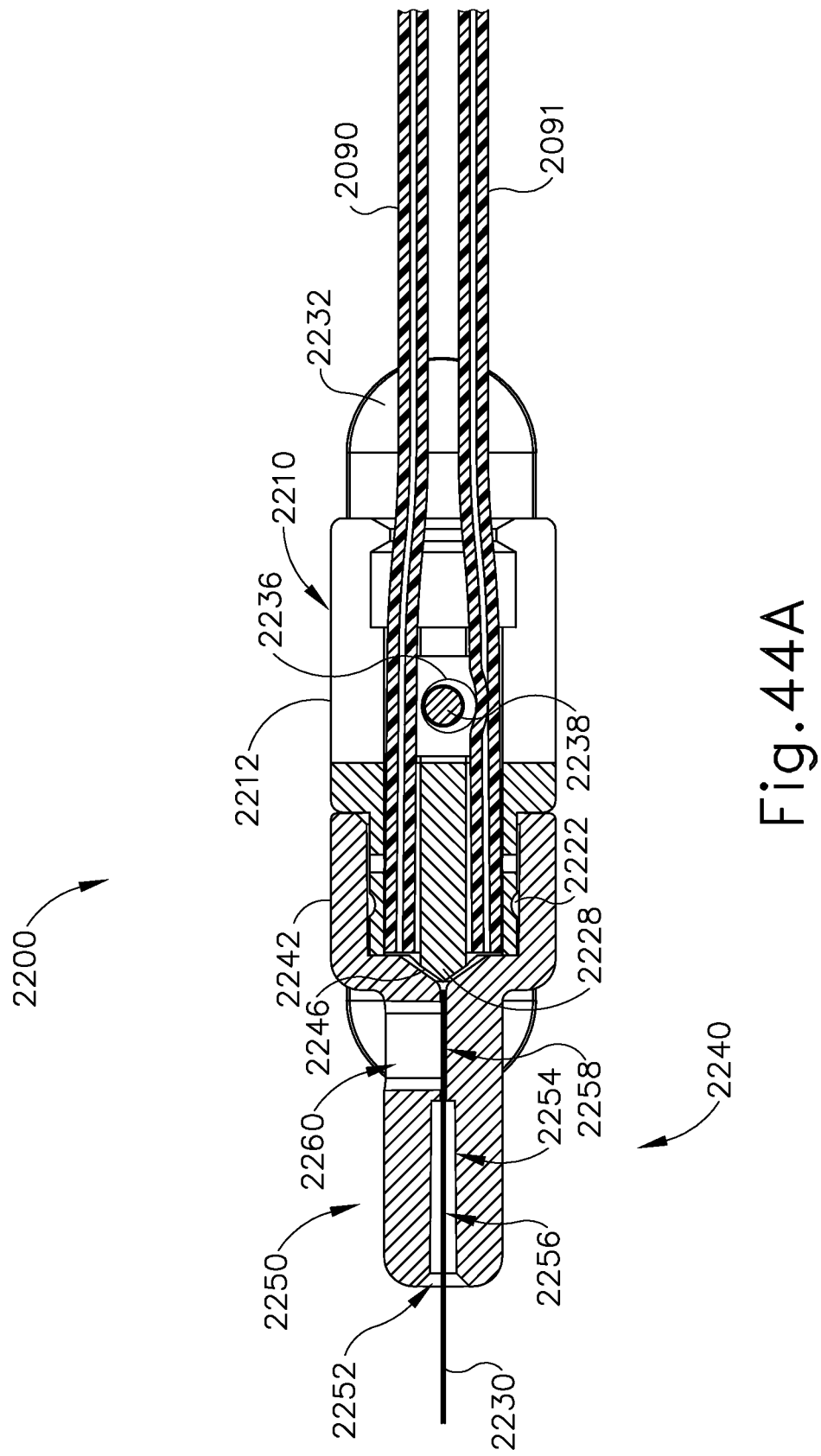
FIG. 44A depicts a cross-sectional side view of the valve assembly of FIG. 42, with the valve assembly in first state.
Figure 44B:
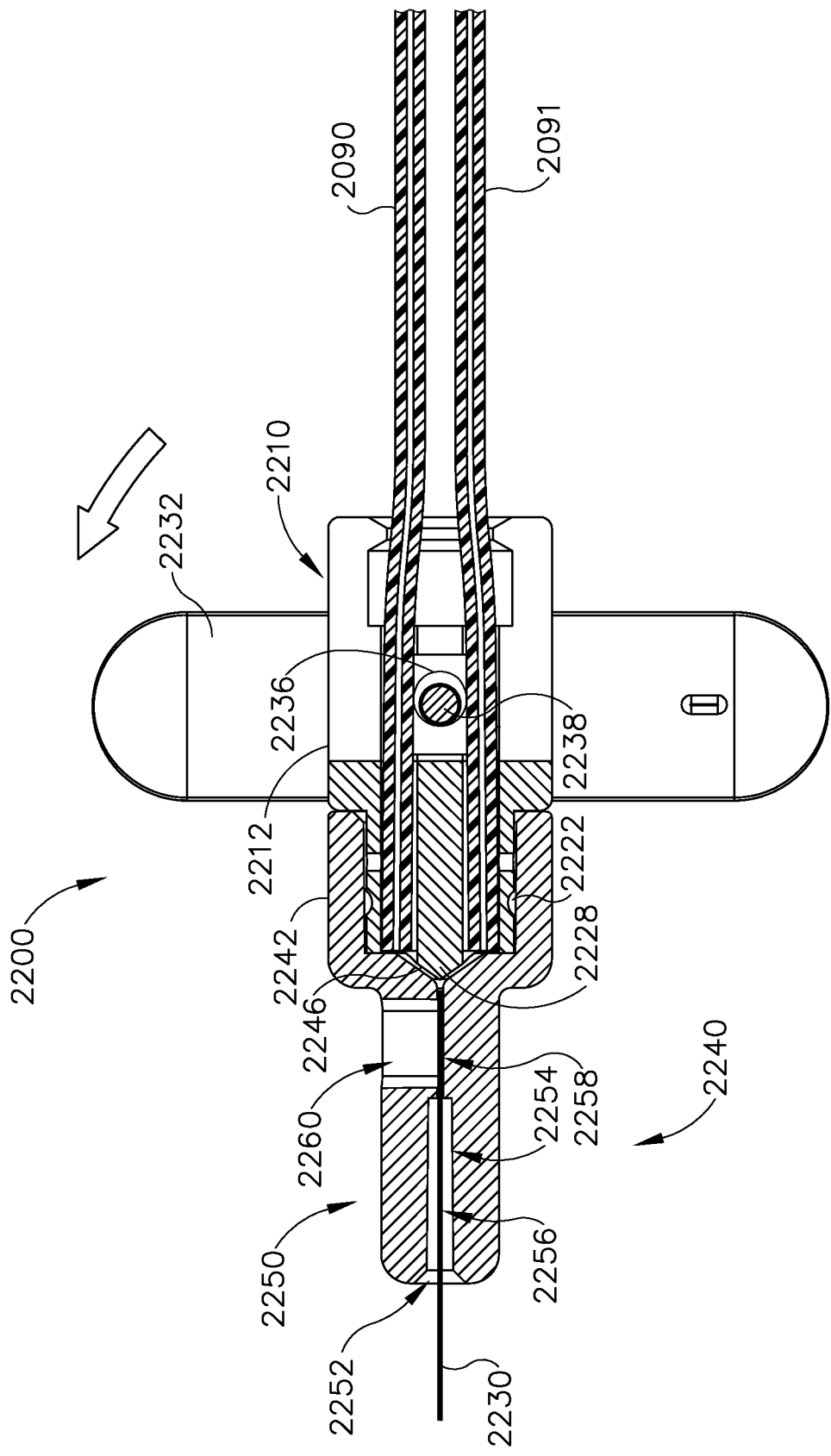
FIG. 44B depicts a cross-sectional side view of the valve assembly of FIG. 42, with the valve assembly in a second state.
Figure 44C:
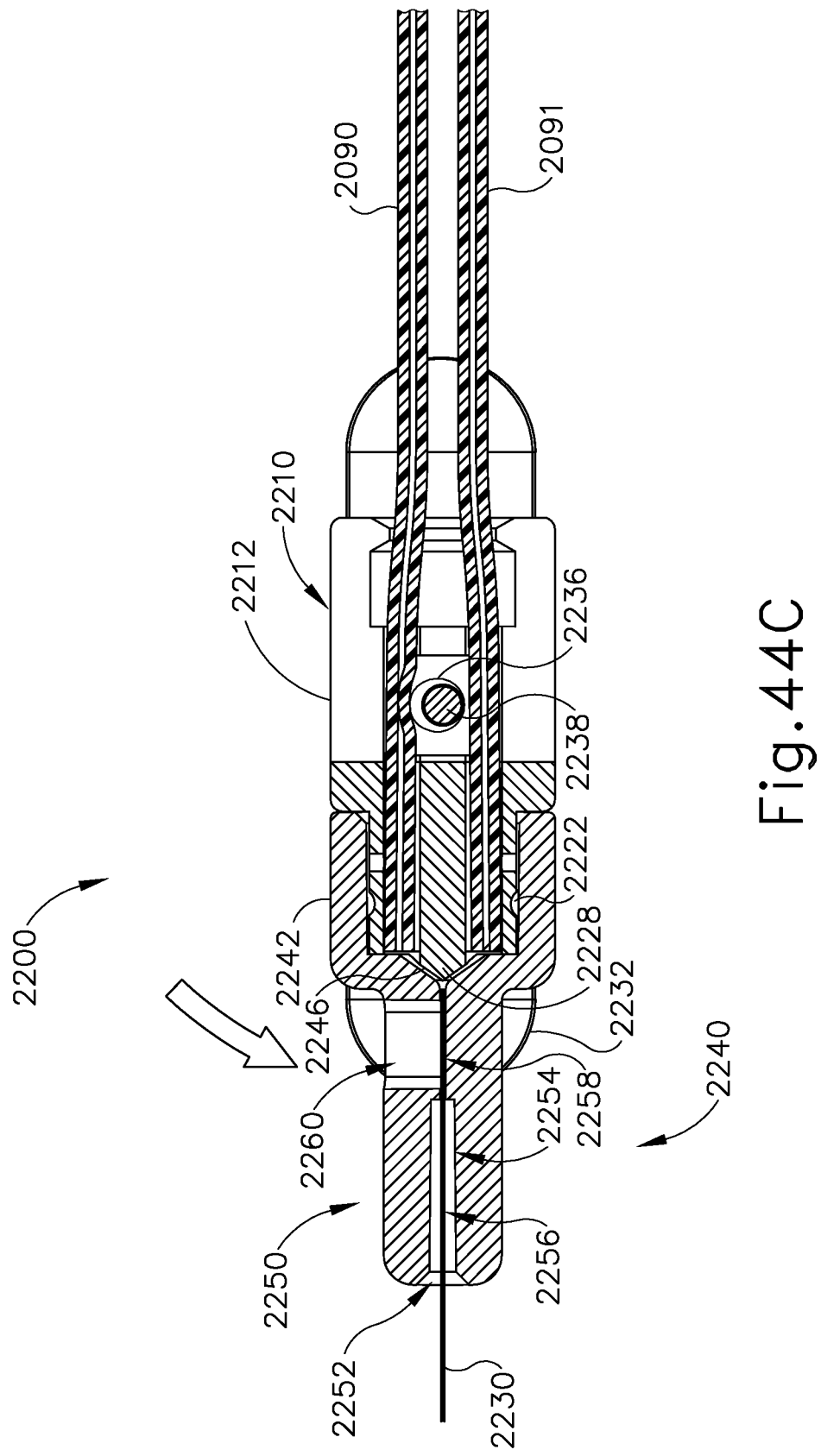
FIG. 44C depicts a cross-sectional side view of the valve assembly of FIG. 42, with the valve assembly in a third state.

An exemplary use of valve assembly (2200) can be seen in FIGS. 44A-44C. As can best be seen in FIG. 44A, actuation arms (2232) initially begin in a first state where actuation arms (2232) are oriented rearwardly along a plane that is parallel to the longitudinal axis of valve assembly (2200). Valve member (2236) is disposed within chamber (2214) of valve housing (2212) such that supply tubes (2090, 2091) are at least partially disposed within annular recess (2238) of valve member (2236). In the first position, first supply tube (2090) is relaxed relative to valve member (2236) such that valve member (2236) does not pinch or exert a significant amount of force, if any at all, on first supply tube (2090). Thus, leading bleb fluid (340) may be freely communicated to needle (2030) via first supply tube (2090). However, as can be seen in FIG. 44A, the valve member (2236) is configured and positioned at this stage such that second supply tube (2091) is pinched or otherwise compressed by valve member (2236). Thus, with valve assembly (2200) in the first position one, first supply tube (2090) is open such that fluid may freely pass through, while second supply tube (2091) is closed such that fluid is prevented from flowing through second supply tube (2091).

To actuate valve assembly (2200) to a second state, an operator may grasp one or both actuation arms (2232) to rotate actuation arms (2232) about the axis of connector shaft (2234). Because of the shape of valve actuation recess (2043) in body (2040), actuation arms (2232) are rotatable distally and upwardly relative to body (2040). Of course, in other examples body (2040) may be configured differently to permit rotation in the opposite direction. As actuation arms (2232) are rotated, valve member (2236) is also rotated by connector shaft (2234). As shown in FIG. 44B, as valve member (2236) reaches an angular position that is approximately 90° relative to the position shown in FIG. 44A, the position and configuration of valve member (2236) relative to supply tubes (2090, 2091) allows fluid to flow through both supply tubes (2090, 2091). Valve assembly (2200) is thus actuated to a fully opened state by rotating actuation arms (2232) approximately 90°, where actuation arms (2232) are oriented along a plane that is perpendicular to the longitudinal axis of valve assembly (2200). It should be understood that, in some alternative versions, valve assembly (2200) is in a fully opened state when actuation arms (2232) are oriented along a plane that is parallel to the longitudinal axis of valve assembly (2200); while valve assembly (2200) is in a partially open state when actuation arms (2232) are oriented along a plane that is perpendicular to the longitudinal axis of valve assembly (2200). Other suitable orientations and relationships will be apparent to those of ordinary skill in the art in view of the teachings herein. It should also be understood that instrument (2010) may be packaged and shipped in the state shown in FIG. 44B, preventing supply tubes (2090, 2091) from experiencing the stress of constant pinching before instrument (2010) is used.

After actuation to the second state, actuation arms (2232) may be actuated to a third state shown in FIG. 44C. As can be seen, actuation arms (2232) are oriented forwardly along a plane that is parallel to the longitudinal axis of valve assembly (2200) when actuation arms (2232) are in the third state. In the third state, second supply tube (2091) is relaxed relative to valve member (2236) such that valve member (2236) does not pinch or exert a significant amount of force, if any at all, on second supply tube (2091). Thus, therapeutic agent (341) may be freely communicated to needle (2030) via second supply tube (2091). However, as can be seen in FIG. 44C, the valve member (2236) is configured and positioned at this stage such that first supply tube (2090) is pinched or otherwise compressed by valve member (2236). It should be understood that regardless of which particular supply tube (2090) is relaxed or pinched, the configuration in the third position is such that the particular supply tube (2090, 2091) that was relaxed in the first state will be pinched in the third state. Similarly, the particular supply tube (2090, 2091) that was pinched in the first state will be relaxed in the third state. Thus, with valve assembly (2200) in the third state, supply tubes (2090, 2091) are in an opposite state relative to the first state.

In use, the first state, second state, and third state may be configured for different portions of the procedure. For instance, valve assembly (2200) may be initially placed and kept in the first state until the operator has dispensed the leading bleb of fluid (340) to the target site as shown in FIGS. 14I, 15F, and 17B and as described above. The operator may then actuate valve assembly (2200) through the second state to the third state. Upon reaching the third state, the operator may begin dispensing therapeutic agent (341) to the target site as shown in FIGS. 14J, 15G, and 17C and as described above. It should be understood that the operator need not necessarily be dispensing any fluid while valve assembly (2200) is at the second state, transitioning to the second state, or transitioning from the second state. Other suitable ways in which valve assembly (2200) may be used will be apparent to those of ordinary skill in the art in view of the teachings herein.

Figure 45A:
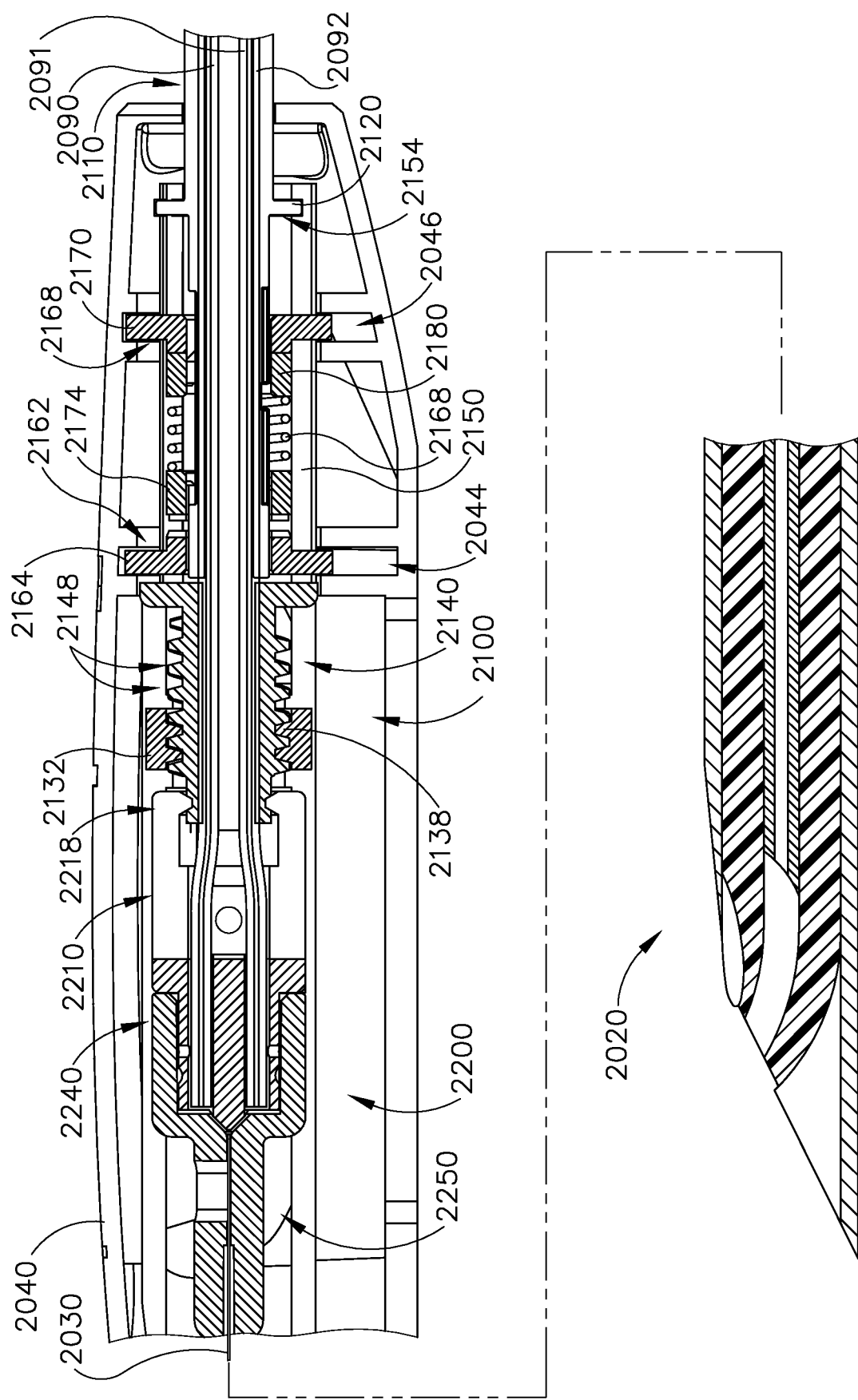
FIG. 45A depicts a partial side cross-sectional view of the instrument of FIG. 34, with the cross-section taken along line 35-35 of FIG. 34 and the drive assembly of FIG. 38 in a non-actuated state.
Figure 45B:
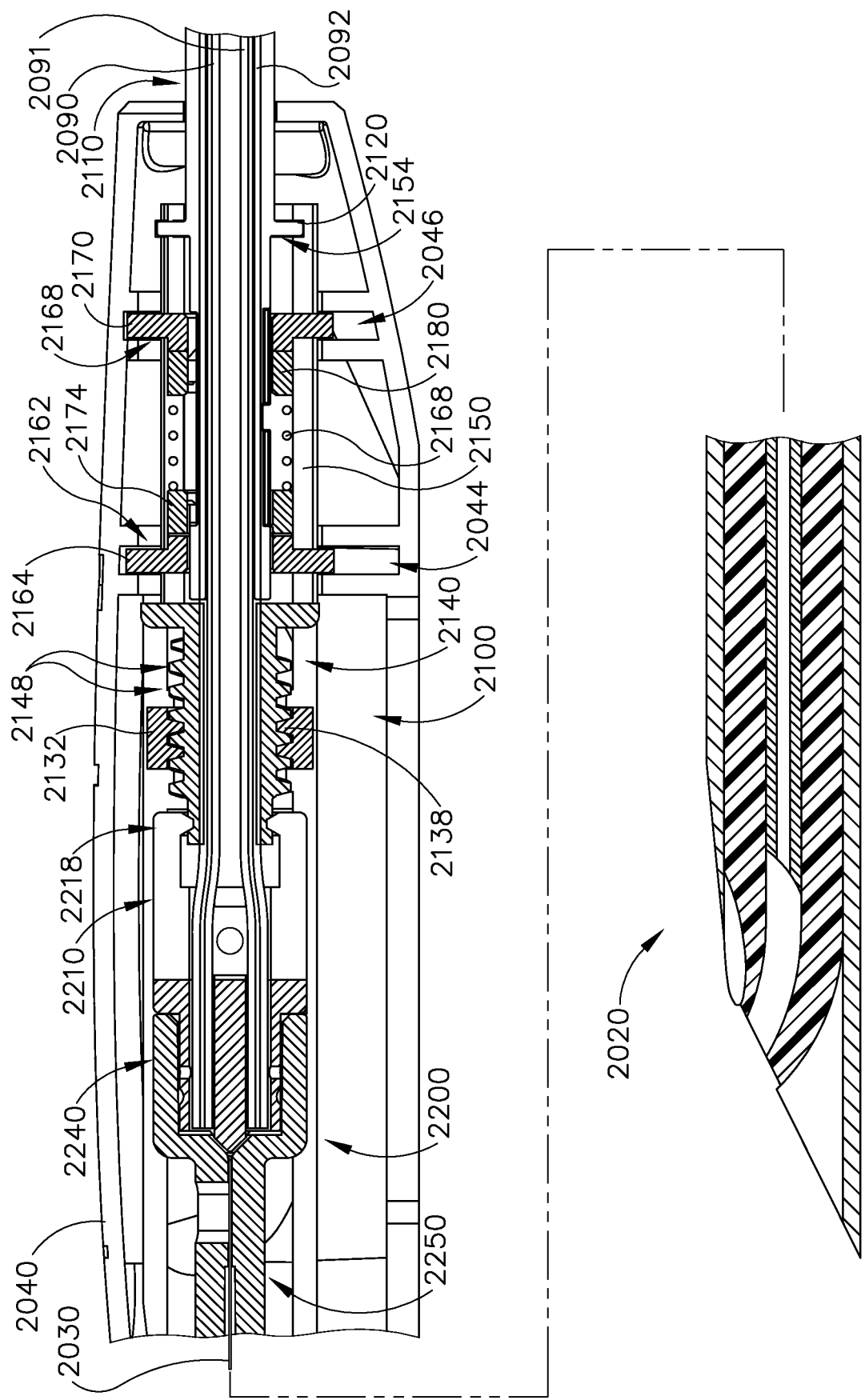
FIG. 45B depicts a partial, cross-sectional side view of the instrument of FIG. 34, with the cross-section taken along line 35-35 of FIG. 34 and the drive assembly of FIG. 38 in a first partially actuated state.
Figure 45D:
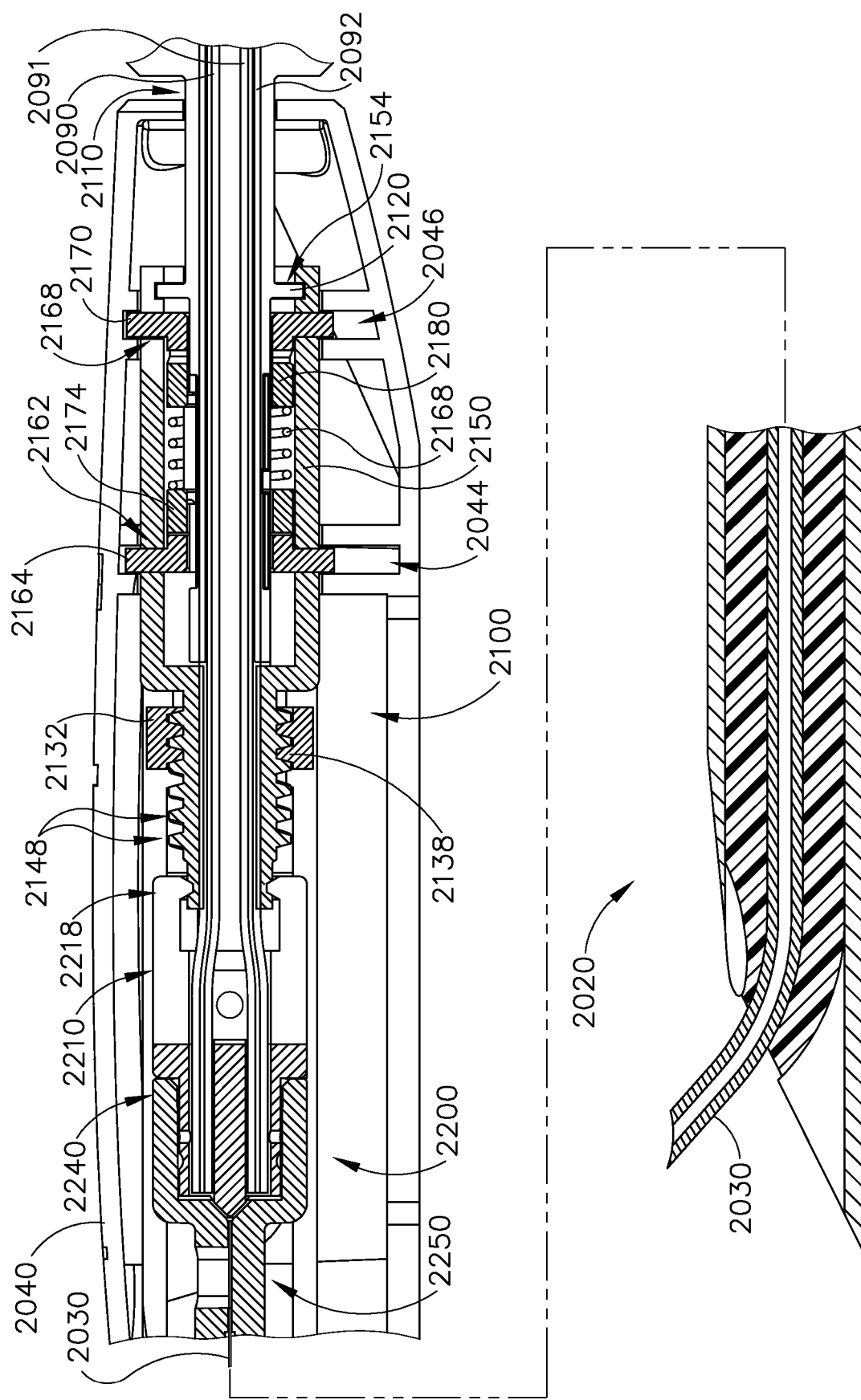
FIG. 45D depicts a partial, cross-sectional side view of the instrument of FIG. 34, with the cross-section taken along line 35-35 of FIG. 34 and the drive assembly of FIG. 38 in a fully actuated state.
Figure 46A:
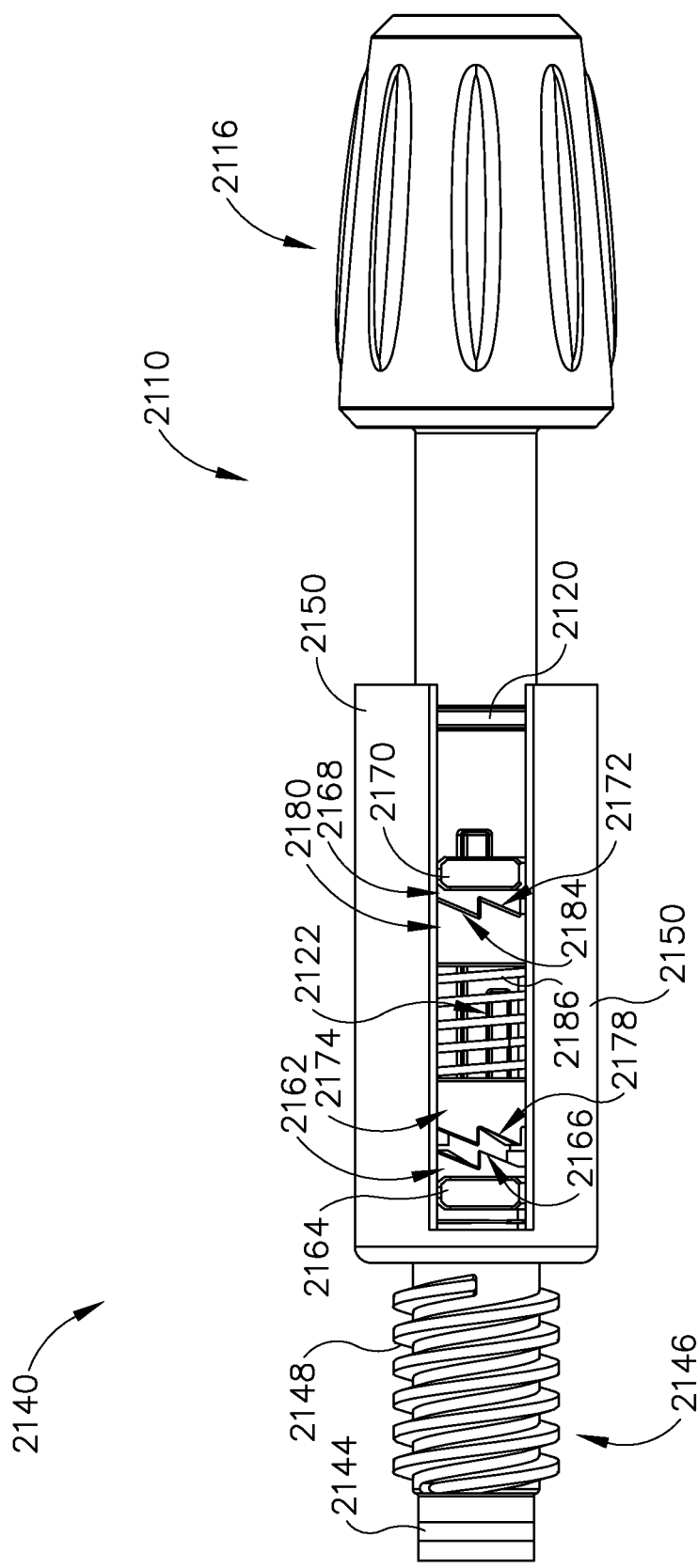
FIG. 46A depicts a partial top plan view of proximal components of the drive assembly of FIG. 38, with the drive assembly in the non-actuated state.
Figure 46B:
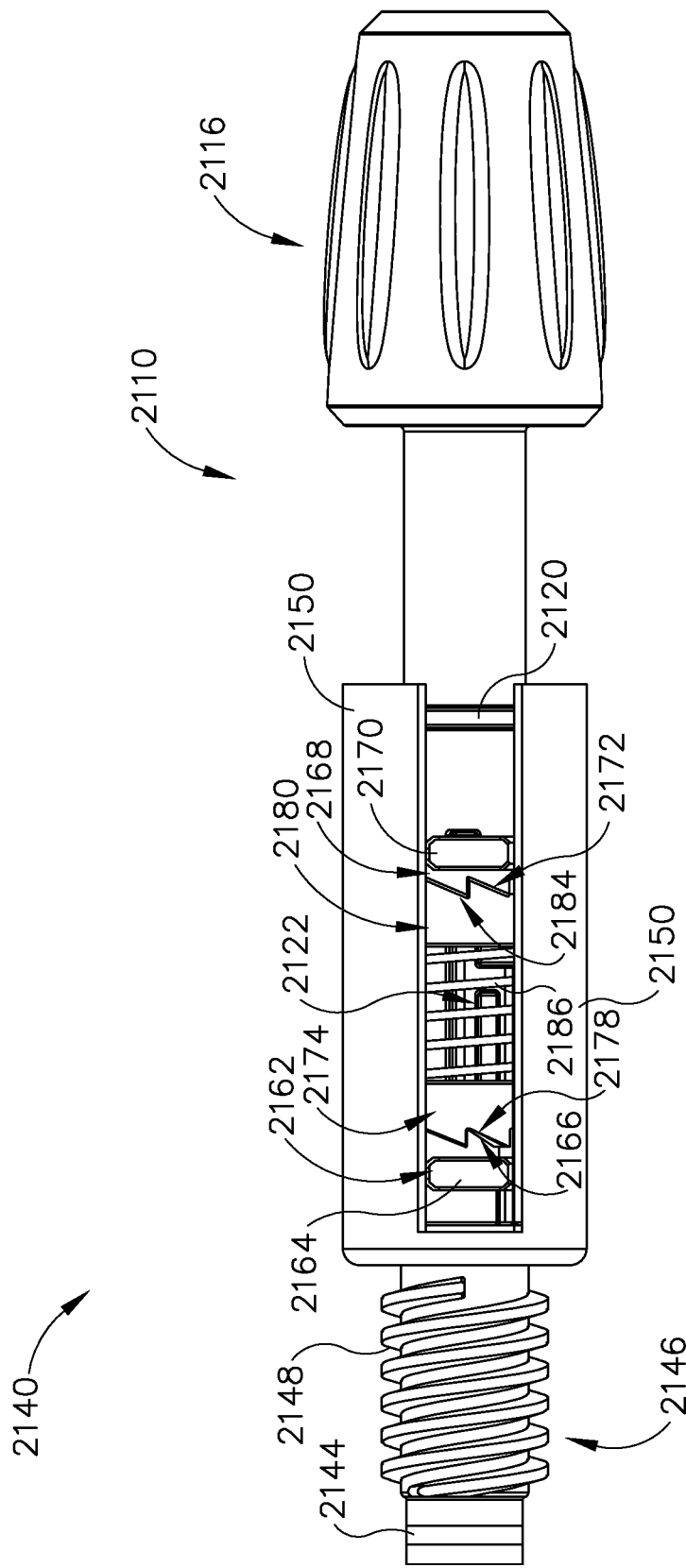
FIG. 46B depicts a partial top plan view of proximal components of the drive assembly of FIG. 38, with the drive assembly in the first partially actuated state.

FIGS. 45A-45D and 46A-46D illustrate an exemplary use of actuation assembly (2100) to drive valve assembly (2200) longitudinally to thereby drive needle (2030) longitudinally. It should be understood that, when instrument (2010) is used in the medical procedure described above, this actuation of actuation assembly (2100) may be initiated at the stages shown in FIGS. 14G and 15D to reach the states shown in FIGS. 14H, 15E, and 17A. As can be seen in FIGS. 45A and 46A, actuation assembly (2100), valve assembly (2100), and needle (2030) are initially in a fully proximal position. In this position, translation member (2140) is disposed in a proximal position relative to threaded insert (2132) such that thread members (2138) engage threading (2148) of translation member (2140) near the distal end of translation member (2140). Because knob member (2110) is translationally fixed relative to translation member (2140), knob member (2110) is also in a proximal position relative to threaded insert (2132). As can best be seen in FIG. 46A, channels (2122) are oriented relative to clutch gears (2174, 2180) such that first clutch gear (2174) is pushed proximally by channels (2122), while second clutch gear (2180) is pushed proximally by spring (2186) to engage second drive gear (2168).

When actuation assembly (2100) is in the proximal position, an operator may rotate knob member (2110) in either a counter clockwise or clockwise direction. If knob member (2110) is rotated in the counter clockwise direction, rotation member (2110) will merely rotate freely. This will occur for two reasons. First, first clutch gear (2174) is spaced proximally away from engagement with first drive gear (2162) by channels (2122) of knob member (2110). Second, because of the configuration of gear teeth (2184) of second clutch gear (2180), second clutch gear (2180) will merely slip relative to second drive gear (2168) when second clutch gear (2180) is rotated counterclockwise by knob member (2110) via channels (2122) of knob member (2110).

To begin advancement of actuation assembly (2100), valve assembly (2200) and needle (2030), an operator may rotate knob member (2110) in the clockwise direction. As described above, gear teeth (2184) of second clutch gear (2180) are configured to drive second drive gear (2168) when second clutch gear (2180) is rotated in the clockwise direction. When second drive gear (2170) is driven by second clutch gear (2180), driving protrusions (2170) of second drive gear (2170) act upon translation member (2140) to initiate clockwise rotation of translation member (2140) as described above. As translation member (2140) rotates clockwise, threading (2148) of translation member (2140) act upon thread members (2138) of threaded insert (2132). Because threaded insert (2132) is fixed relative to body (2040), threaded insert (2132) acts to translate translation member (2140) distally as translation member (2140) rotates clockwise. Because translation member (2140) is translationally fixed relative to knob member (2110), translation member (2140) will act to translate knob member (2110) distally as translation member (2140) translates distally. Similarly, because valve assembly (2200) is translationally fixed relative to translation member (2140), translation member (2140) will also act to translate valve assembly (2200) distally as translation member (2140) translates.

Figure 46C:
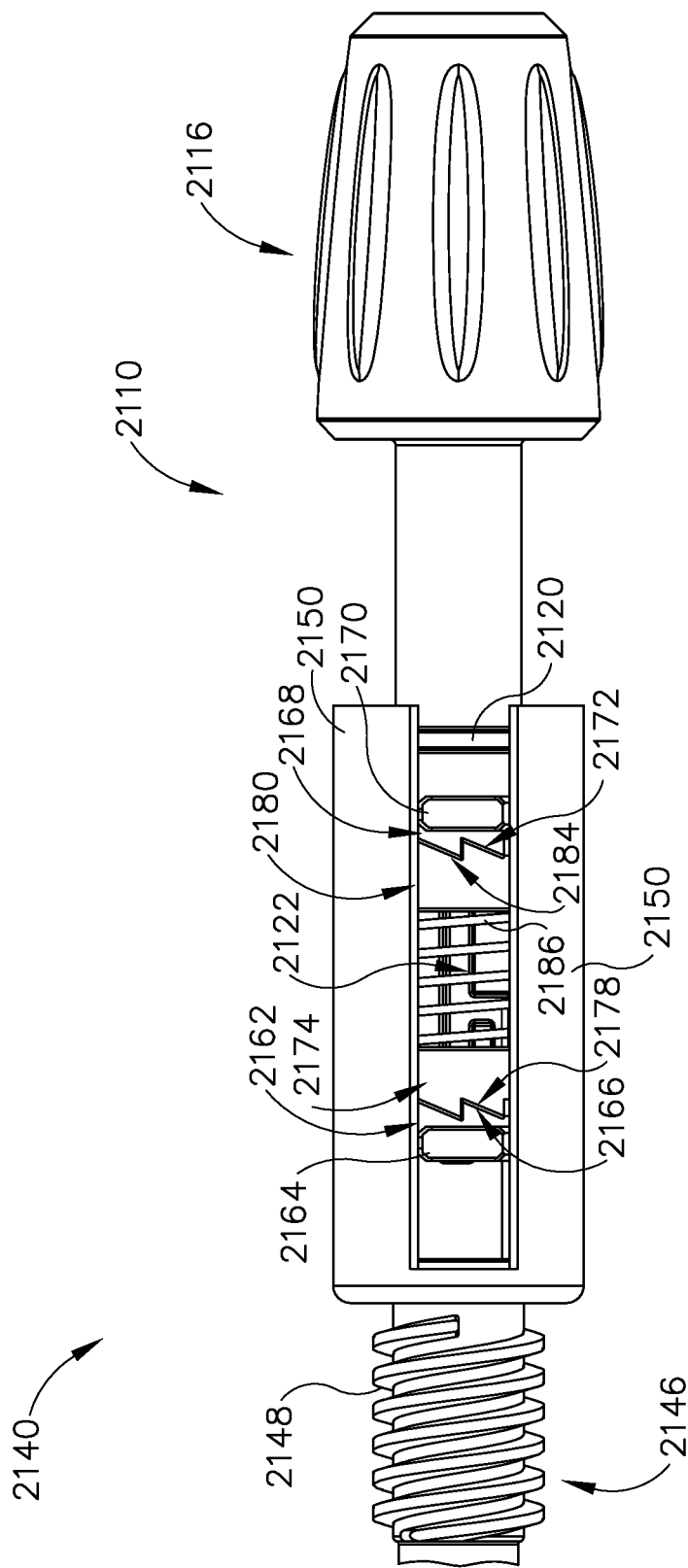
FIG. 46C depicts a partial top plan view of proximal components of the drive assembly of FIG. 38, with the drive assembly in the second partially actuated state.

An operator may continue clockwise rotation of knob member (2110) to drive needle (2030) out of the distal end of cannula (2020). FIGS. 45C and 46C show actuation assembly (2100), valve assembly (2200), and needle (2030) in a position immediately prior to actuation assembly (2100), valve assembly (2200), and needle (2030) being translated to a fully distal position. In this position, both first clutch gear (2174) and second clutch gear (2180) are in engagement with first drive gear (2164) and second drive gear (2170), respectively. Accordingly, in the position shown in FIGS. 45C and 46C, knob member (2110) may be rotated in either the clockwise direction or the counter clockwise direction to drive actuation assembly (2100) distally or proximally, respectively. However, as can best be seen in FIG. 46C, in this position rotation member (2110) is advanced distally to a position such that further advancement will cause channels (2122) of rotation member (2110) to begin to drive second clutch gear (2180) out of engagement with second drive gear (2170) as will be described in greater detail below.

Figure 46D:
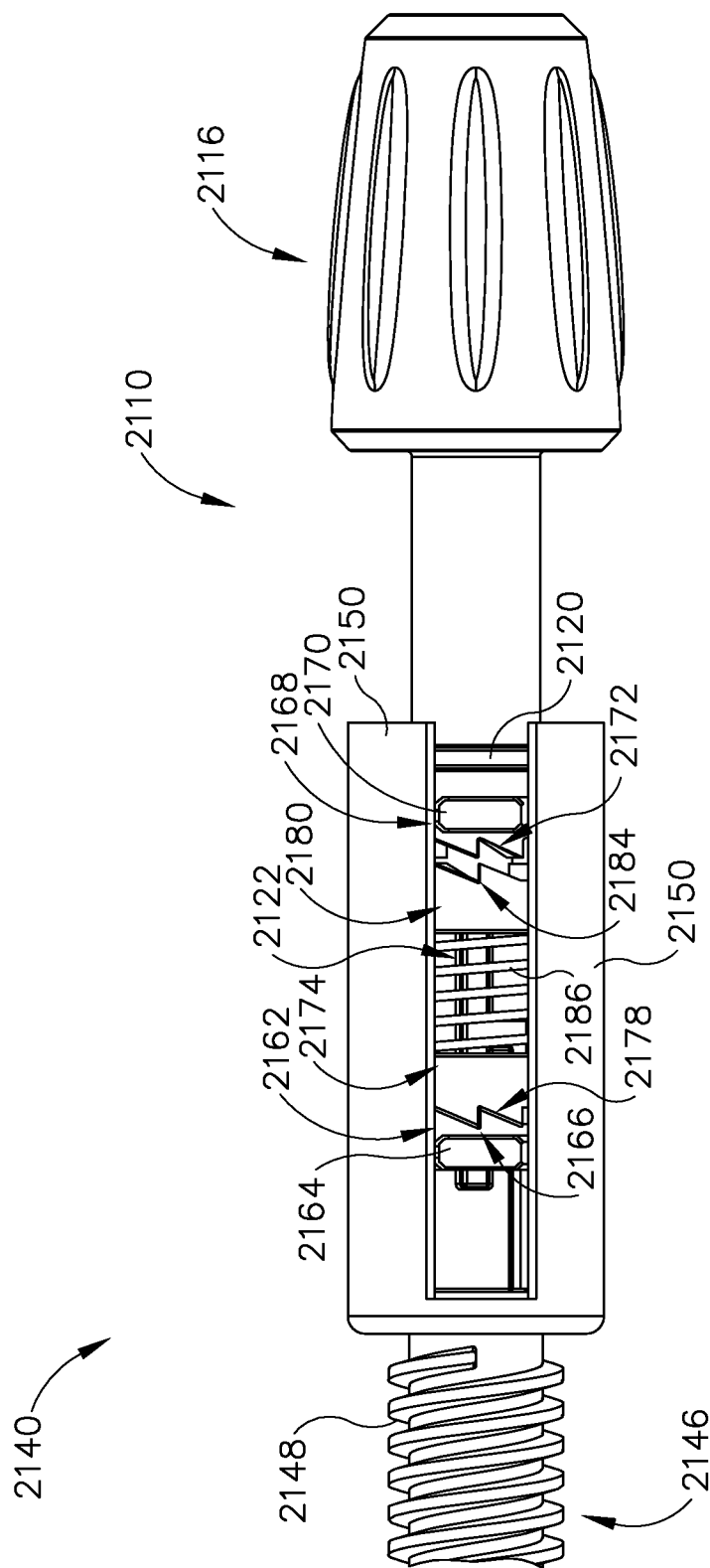
FIG. 46D depicts a partial top plan view of proximal components of the drive assembly of FIG. 38, with the drive assembly in the fully actuated state.

As can be seen in FIGS. 45D and 46D, rotation member (2110) has been rotated clockwise direction to translate actuation assembly slightly distally of the position shown in FIGS. 45C and 46D. In this position, actuation assembly (2100), valve assembly (2200), and needle (2030) are at their furthest distal position relative to body (2040). As can be seen, this position corresponds to needle (2030) being advanced to its furthest distal position relative to the distal end of cannula (2020). In the furthest distal position, translation member (2140) is translated distally such that thread members (2138) of threaded insert (2132) engage threading (2148) of translation member (2140) just distally of the proximal end of threading (2148). Because knob member (2110) is translationally secured relative to translation member (2140), translation member (2140) has translated knob member (2110) to its furthest distal position relative to body (2040). When knob member (2110) is in its furthest distal position, channels (2122) of knob member (2110) are positioned such that channels (2122) drive second clutch gear (2180) out of engagement with second drive gear (2168). Because first clutch gear (2174) merely slips when rotated in the clockwise direction and second clutch gear (2180) is out of engagement with second drive gear (2168) at this stage, it should be understood that further clockwise rotation of knob member (2110) will merely result in free rotation of knob member (2110).

With needle (2030) in the distal position, the operator may then actuate valve assembly (2200) to the open configuration as shown in FIG. 44A to enable the delivery of therapeutic agent via tubes (2090, 2091) and needle (2030). In other words, at this stage instrument (2010) may be used to perform the steps of the medical procedure shown in FIGS. 14I-14J, 15F-15G, and 17B-17C as described above. The operator may then wish to retract needle (2030).

Although channels (2122) of knob member (2110) drive second clutch gear (2180) out of engagement with second drive gear (2168) when knob member (2110) is in the distal position, it should be understood that first clutch gear (2180) remains engaged with first drive gear (2162). Accordingly, while further clockwise rotation of knob member (2110) will cause first clutch gear (2180) to slip relative to first drive gear (2162), counter clockwise rotation of knob member (2110) will cause first clutch gear (2180) to drive first drive gear (2162) in the counter clockwise direction. Rotation of first drive gear (2162) in the counter clockwise direction will rotate translation member (2140) in the counter clockwise direction via driving protrusions (2164) of first drive gear (2162). With translation member (2140) rotated in the counter clockwise direction, threading (2148) will engage threaded insert (2132) to translate translation member (2140) proximally. Thus, counter clockwise rotation of rotation member (2110) in the distal position will cause translation member (2140) to translate proximally thereby retracting actuation assembly (2100), valve assembly (2200), and needle (2030) relative to body (2040).

To return actuation assembly (2100), valve assembly (2200), and needle (2030) to the proximal position shown in FIGS. 45A and 46A, an operator may continue to rotate rotation member (2110) in the counter clockwise direction until channels (2122) of rotation member (2110) push first clutch gear (2174) out of engagement with first drive gear (2162), as described above. Although actuation assembly (2100) is described herein as generally being used to translate valve assembly (2200) and needle (2030) between the proximal position and the distal position, it should be understood that no such limitation is intended. For instance, an operator may use actuation assembly (2100) to translate valve assembly (2200) and needle (2030) to any desirable position. In one merely exemplary use, needle (2030) may only be partially driven distally of cannula (2020). In another exemplary use, an operator may only partially advance needle (2030) to a point prior to needle advancing out of the distal end of cannula (2020). An operator may then desire to abort the procedure or otherwise retract needle (2030) relative to cannula (2020) without ever advancing needle (2030) out of cannula (2020). Of course, any other suitable amount of advancement or retraction may be used as will be apparent to those of ordinary skill in the art in view of the teachings herein.

It should be understood that as actuation assembly (2100) is rotated to actuate valve assembly (2200) and needle (2030), valve assembly (2200) and needle (2030) remain substantially rotationally stationary relative to actuation assembly (2100). As described above, such functionality is facilitated by the coupling between translation member (2140) of actuation assembly (2100) and valve body (2210) of valve assembly (2200). In addition, it should be understood that tube (2092) extends through lumens (2114, 2145) of rotation member (2110) and translation member (2140) to prevent rotation member (2110) and translation member (2140) from applying torque to supply tubes (2090, 2091) that might otherwise cause valve assembly (2200) to rotate. In the present example, it may be desirable to prevent rotation of valve assembly (2200) so that needle (2030) translates but does not rotate. This is because of the geometry of needle (2030) and because of potential interactions of that geometry with tissue. Of course, in other examples needle (2030) may be configured such that rotation is desired. In such examples, features to prevent rotation of valve assembly (2200) may be omitted or modified as will be apparent to those of ordinary skill in the art in view of the teachings herein.

E. Exemplary Alternative Support Assembly

Figure 47:
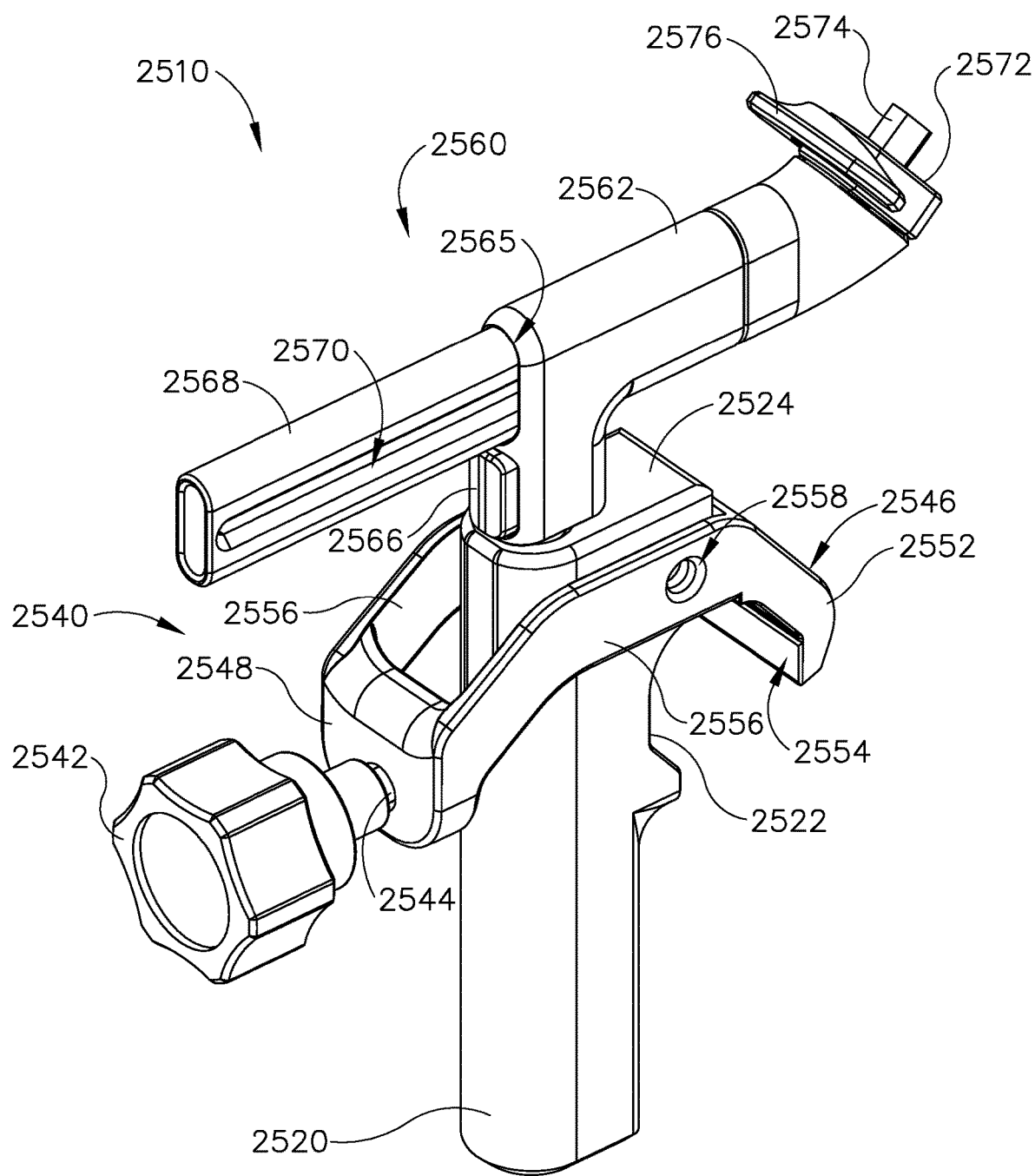
FIG. 47 depicts a perspective view of an exemplary support assembly for use with the instrument of FIG. 34.
Figure 48:
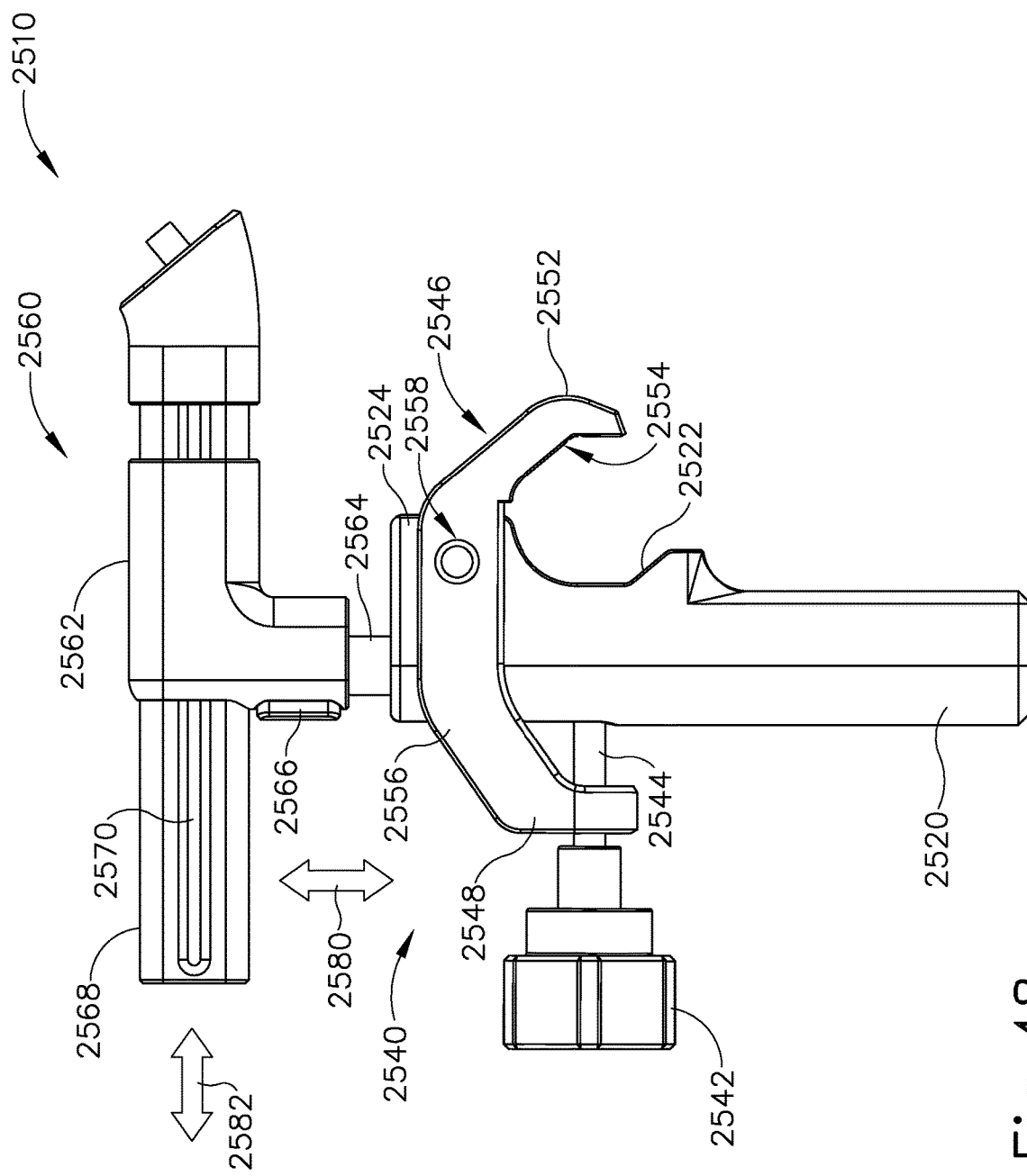
FIG. 48 depicts a side plan view of the support assembly of FIG. 47.
Figure 49:
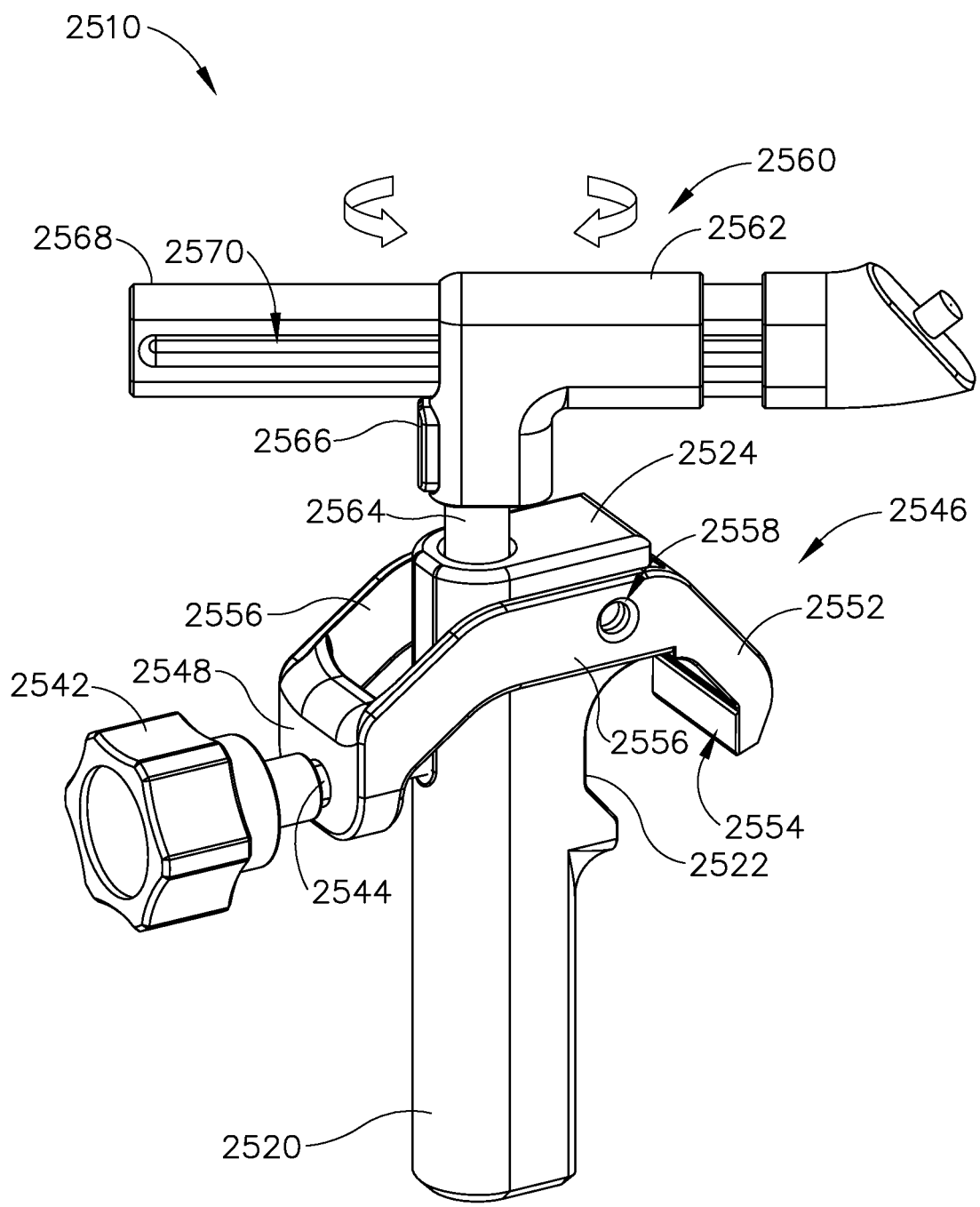
FIG. 49 depicts another perspective view of the support assembly of FIG. 47.

FIGS. 47-49 show an exemplary alternative support assembly (2510) that is similar to support assembly (110) described above. However, unlike support assembly (110), support assembly (2510) comprises a relatively rigid structure and is configured to support instrument (2010) described above. Support assembly (2510) comprises a vertical support arm (2520), a clamp assembly (2540), and a lateral support arm (2560). Vertical support arm (2520) is relatively rigid and generally permits attachment of support assembly (2510) to a conventional ophthalmic surgery wrist rest or other fixture. Vertical support arm (2520) extends upwardly with a generally rectangular cross-section. An integral cradle member (2522) is included near the upper end of support arm (2520). Cradle member (2522) is generally shaped as a partially cylindrical recess such that cradle member (2522) is configured to receive a tubular structure that may be a part of a wrist rest or other fixture. The upper end of support arm (2520) further includes a distally extending protrusion (2524) that is configured to support clamp assembly (2540) as will be described in greater detail. As will also be described in greater detail below, vertical support arm (2520) may include a bore (not shown) to provide attachment of clamp assembly (2540).

Clamp assembly (2540) comprises an actuation knob (2542) and a clamp bracket (2546). Actuation knob (2542) is configured to be rotated by the hand of an operator. A threaded shaft (2544) extends distally from actuation knob (2542). As will be described in greater detail below, actuation knob (2542) is generally configured to be rotated to engage with clamp bracket and vertical support arm (2520) via threaded shaft (2544). Clamp bracket (2546) comprises a proximal portion (2548), a distal portion (2552), and a pair of arms (2556) extending between proximal portion (2548) and distal portion (2552). Proximal portion (2548) includes an opening (2550) centered in proximal portion (2548). Opening (2550) is configured to receive threaded shaft (2544) of actuation knob (2542) to permit threaded shaft (2542) to pass therethrough to vertical support arm (2520). Distal portion (2552) is generally curved in shape to define a generally partially cylindrical recess (2554), which complements cradle member (2522) of vertical support arm (2520). As will be described in greater detail below, cradle member (2522) and distal portion (2552) are operable together to clamp a tubular structure that may be part of a wrist rest or other fixture.

Arms (2556) extend between proximal portion (2548) and distal portion (2552). In particular, arms (2556) are generally curved upwardly as they extend between proximal portion (2548) and distal portion (2552). Such a curvature is configured to permit clamping actuation of clamp assembly (2540) as will be described in greater detail below. Each arm (2556) includes a bore (2558) oriented near distal portion (2552). Bore (2558) permits pivotable attachment of arms (2556) to protrusion (2524) of vertical support arm (2520) via a screw or other fastener.

Lateral support arm (2560) comprises an adjustable collar (2562), a slidable shaft (2568), and an attachment bracket (2572). Adjustable collar (2562) is generally L-shaped and is configured to selectively permit slidable shaft (2568) to slide relative to vertical support arm (2520). In particular, the lower end of adjustable collar (2562) includes an attachment shaft (2564), a distal opening (not shown), a proximal opening (2565), and an adjustment button (2566). Attachment shaft (2564) extends downwardly from adjustable collar (2562) and into vertical support arm (2520). As will be described in greater detail below, attachment shaft (2564) attaches adjustable collar (2562) to vertical support arm (2520) such that adjustable collar (2562) may be selectively rotated and translated relative to vertical support arm (2520).

The distal opening and proximal opening (2565) of adjustable collar (2562) define a lumen (not shown) extending through adjustable collar (2562). Openings (2565) are configured to receive slidable shaft (2568) such that slidable shaft (2568) may extend longitudinally through adjustable collar (2562). As will be described in greater detail below, adjustable collar (2562) is configured to selectively lock and unlock slidable shaft (2568) such that slidable shaft (2568) may be selectively translated within adjustable collar (2562) relative to vertical support arm (2520).

Slidable shaft (2568) is generally ovular in shape and comprises a central channel (2570) extending longitudinally through slidable shaft (2568). In some examples, central channel (2570) may receive pins or other features disposed within the lumen of adjustable collar (2562) to maintain the horizontal position of slidable shaft (2568). Of course, such features are merely optional and may be omitted in some examples.

Attachment bracket (2572) is configured to receive at least a portion of instrument (2010) described above. In particular, attachment bracket comprises (2572) an indexing pin (2574) and a quick release handle (2576). Indexing pin (2574) may engage a corresponding geometry of instrument (2010) to index the position of instrument (2010) relative to attachment bracket (2572). Quick release handle (2576) is in communication with a mechanism within attachment bracket, which may facilitate the release of instrument (2010) from attachment bracket (2572) or attachment bracket (2572) from support assembly (2510). It should be understood that, in some examples, attachment bracket (2572) may include magnets that may engage corresponding magnets in instrument (2010) to permit quick attachment and detachment of instrument (2010) from support assembly (2510), in addition to or in lieu of including quick release handle (2576).

An exemplary use of support assembly (2510) is shown in FIGS. 48 and 49. As can be seen, support assembly (2510) is movable through three separate ranges of motion (e.g., as indicated by arrows (2580, 2582, 2584)). In particular, as can be seen in FIG. 48, support assembly (2510) may first be actuated vertically as indicated by arrow (2580). To permit vertical actuation of support assembly (2510), an operator may press button (2566), which actuates an internal mechanism inside vertical support arm (2520) thereby permitting adjustment through all three ranges of motion. With attachment shaft (2564) free to rotate, an operator may grasp lateral support arm (2560) and move lateral support arm (2560) to a desired height.

Slidable shaft (2568) may also translate laterally relative to vertical support arm (2520) as indicated by arrow (2582). To translate slidable shaft (2568), an operator may press button (2566) to unlock translation of slidable shaft (2568). Although not shown, it should be understood that button (2566) may be in communication with a spring loaded locking feature or other similar apparatus that may be disengaged when button (2566) is pressed. While button (2566) is pressed, an operator may grasp lateral support arm (2560) and move lateral support arm (2560) to a desired lateral position.

As can be seen in FIG. 49, lateral support arm (2560) may also be rotated relative to vertical support arm (2520) as indicated by arrows (2584). Such rotation is initiated by also pressing button (2566) as described above. In particular, pressing button (2566) actuates a mechanism inside vertical support arm (2520) permitting rotation and translation of attachment shaft (2564) within vertical support arm (2520). With attachment shaft (2564) free to rotate, an operator may grasp lateral support arm (2560) and rotate lateral support arm (2560) to a desired angular position. Other suitable ways in which support assembly (2510) may be used will be apparent to those of ordinary skill in the art in view of the teachings herein. Similarly, other suitable ways in which instrument (2010) may be supported will be apparent to those of ordinary skill in the art in view of the teachings herein.

VI. Miscellaneous

Although the procedures and devices described herein are discussed in the context of the treatment of age-related macular degeneration, it should be understood that no such limitation is intended or implied. The procedures and devices described herein may be used to treat various other kinds of medical conditions. By way of example only, the procedures and devices described herein (and variations thereof) may be used to treat retinitis pigmentosa, diabetic retinopathy, wet age-related macular degeneration, and/or other medical conditions. Various suitable medical contexts in which the procedures and devices described herein may be used will be apparent to those of ordinary skill in the art.

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for delivering therapeutic agent to an eye, wherein the apparatus comprises:
   (a) a body;
   (b) a flexible cannula extending distally from the body, wherein the flexible cannula is sized and configured to be insertable between a choroid and a sclera of an eye of a patient, wherein the flexible cannula defines a longitudinal axis, wherein the flexible cannula includes an atraumatic distal end;
   (c) a needle, wherein the needle is slidable relative to the flexible cannula between a retracted position and an extended position; and
   (d) an actuation assembly, wherein the actuation assembly is operable to actuate the needle relative to the flexible cannula to thereby drive a distal portion of the needle along an exit axis that is obliquely oriented relative to the longitudinal axis of the flexible cannula, wherein the exit axis is oriented at an angle between 5° and 30° relative to the longitudinal axis of the flexible cannula, wherein the needle is configured to pierce through the choroid into a subretinal space of the eye when the needle is in the extended position with the flexible cannula inserted between the choroid and the sclera, wherein the flexible cannula has a generally rectangular cross-sectional profile with rounded sides in a plane perpendicular to the longitudinal axis.

2. The apparatus of claim 1, wherein the actuation assembly includes an actuation member that is movable relative to the body to actuate the needle.

3. The apparatus of claim 2, wherein the actuation member is rotatable relative to the body to actuate the needle.

4. The apparatus of claim 3, wherein the actuation assembly includes a threaded member that is associated with the actuation member, wherein the threaded member is configured to engage a threaded bore in the body to actuate the needle when the actuation member is rotated relative to the body.

5. The apparatus of claim 1, wherein the needle includes a sharp distal tip.

6. The apparatus of claim 5, wherein the sharp distal tip of the needle comprises a first bevel, a second bevel, and a third bevel, wherein the first bevel, second bevel, and third bevel are each oriented obliquely relative to each other.

7. The apparatus of claim 1, wherein the exit axis is oriented at an angle between 7° and 9° relative to the longitudinal axis of the flexible cannula.

8. The apparatus of claim 1, wherein the flexible cannula includes a blunt distal tip.

9. The apparatus of claim 1, wherein the flexible cannula includes a beveled distal end, wherein the beveled distal end has a bevel angle, wherein the bevel angle is between 10° and 30°.

10. The apparatus of claim 1, wherein the flexible cannula defines a plurality of lumens extending longitudinally through the length of the flexible cannula, wherein at least one lumen of the plurality of lumens is configured to slidably receive the needle.

11. The apparatus of claim 1, further comprising a needle coupler configured to couple at least two separate fluid sources with the needle.

12. The apparatus of claim 1, wherein the flexible cannula has a bending stiffness between $2.0 \times 10^{-6}$ $Nm^2$ to $6.0 \times 10^{-6}$ $Nm^2$.

13. The apparatus of claim 1, further comprising a valve assembly, wherein the valve assembly is operable to provide a fluid coupling between a fluid source and the needle, wherein the valve assembly is configured to translate with the needle relative to the body.

14. The apparatus of claim 1, wherein a distal portion of the flexible cannula has a distal opening oriented transversely relative to the longitudinal axis of the flexible cannula, wherein the needle is configured to exit the flexible cannula via the distal opening.

15. The apparatus of claim 14, wherein the flexible cannula has a closed distal end, wherein the distal opening is proximal to the closed distal end.

16. The apparatus of claim 14, further comprising a needle guide disposed in the flexible cannula, wherein the needle is slidably disposed in the needle guide, wherein the needle guide is configured to guide the needle toward the distal opening.

17. The apparatus of claim 1, wherein the flexible cannula defines a lumen extending distally from the body toward the atraumatic distal end, wherein the lumen is configured to slidably receive the needle, wherein at least a portion of the lumen terminates proximally relative to the atraumatic distal end.

18. The apparatus of claim 17, wherein the portion of the lumen terminating proximally relative to the atraumatic distal end defines an opening, wherein the needle is configured to exit the flexible cannula via the opening.

19. An apparatus for delivering therapeutic agent to an eye, wherein the apparatus comprises:
(a) a body;
(b) a flexible cannula extending distally from the body, wherein the flexible cannula is sized and configured to be insertable between a choroid and a sclera of an eye of a patient, wherein the flexible cannula defines a longitudinal axis, wherein the flexible cannula has an opening, wherein the flexible cannula includes a rounded, atraumatic distal end, wherein the flexible cannula includes a pair of opposing rounded sides and a pair of opposing flat sides extending between the pair of opposing rounded sides, wherein the pair of opposing flat sides and the pair of opposing rounded sides collectively define an outer periphery of the flexible cannula;
(c) a needle, wherein the needle is slidable relative to the flexible cannula between a retracted position and an extended position; and
(d) an actuation assembly, wherein the actuation assembly is operable to actuate the needle relative to the flexible cannula to thereby drive a distal portion of the needle out through the opening of the flexible cannula and along an exit axis that is obliquely oriented relative to the longitudinal axis of the flexible cannula,
wherein the needle is configured to pierce through the choroid into a subretinal space of the eye when the needle is in the extended position with the flexible cannula inserted between the choroid and the sclera.

20. An apparatus for delivering therapeutic agent to an eye, wherein the apparatus comprises:
(a) a body;
(b) a flexible cannula extending distally from the body, wherein the flexible cannula is sized and configured to be insertable between a choroid and a sclera of an eye of a patient, wherein the flexible cannula defines a longitudinal axis, wherein the flexible cannula comprises:
(i) a pair of opposing rounded sides,
(ii) a pair of opposing flat sides adjacent to the rounded sides, wherein the pair of opposing flat sides and the pair of opposing rounded sides collectively define an outer periphery of the flexible cannula,
(iii) an atraumatic distal end, and
(iv) an opening at or near the distal end;
(c) a needle, wherein the needle is slidable relative to the flexible cannula between a retracted position and an extended position; and
(d) an actuation assembly, wherein the actuation assembly is operable to actuate the needle relative to the flexible cannula to thereby drive a distal portion of the needle out through the opening of the flexible cannula and along an exit axis that is obliquely oriented relative to the longitudinal axis of the flexible cannula,
wherein the needle is configured to pierce through the choroid into a subretinal space of the eye when the needle is in the extended position with the flexible cannula inserted between the choroid and the sclera.

* * * * *